US008962655B2

(12) United States Patent
Yamamoto

(10) Patent No.: US 8,962,655 B2
(45) Date of Patent: Feb. 24, 2015

(54) COMPOSITION FOR TREATMENT OF UNDIFFERENTIATED GASTRIC CANCER

(75) Inventor: Yuji Yamamoto, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 866 days.

(21) Appl. No.: 12/524,754

(22) PCT Filed: Jan. 28, 2008

(86) PCT No.: PCT/JP2008/051697
§ 371 (c)(1),
(2), (4) Date: Jul. 28, 2009

(87) PCT Pub. No.: WO2008/093855
PCT Pub. Date: Aug. 7, 2008

(65) Prior Publication Data
US 2010/0048620 A1 Feb. 25, 2010

Related U.S. Application Data

(60) Provisional application No. 60/887,006, filed on Jan. 29, 2007.

(51) Int. Cl.
A01N 43/42 (2006.01)
A61K 31/47 (2006.01)
C07D 215/00 (2006.01)
C07D 215/22 (2006.01)

(52) U.S. Cl.
CPC .................................. C07D 215/22 (2013.01)
USPC ......................................... 514/312; 546/153

(58) Field of Classification Search
USPC ......................................... 514/312; 546/153
See application file for complete search history.

(56) References Cited

U.S. PATENT DOCUMENTS

| 4,526,988 | A | 7/1985 | Hertel et al. |
|---|---|---|---|
| 4,563,417 | A | 1/1986 | Albarella et al. |
| 4,582,789 | A | 4/1986 | Sheldon, III et al. |
| 4,742,003 | A | 5/1988 | Derynck et al. |
| 4,764,454 | A | 8/1988 | Ichijima et al. |
| 5,180,818 | A | 1/1993 | Cech et al. |
| 5,445,934 | A | 8/1995 | Fodor et al. |
| 5,464,826 | A | 11/1995 | Grindey et al. |
| 5,487,889 | A | 1/1996 | Eckert et al. |
| 5,624,937 | A | 4/1997 | Reel et al. |
| 5,650,376 | A | 7/1997 | Badaye et al. |
| 5,656,454 | A | 8/1997 | Lee et al. |
| 5,658,374 | A | 8/1997 | Glover |
| 5,733,913 | A | 3/1998 | Blankley et al. |
| 5,747,651 | A | 5/1998 | Lemischka |
| 5,750,376 | A | 5/1998 | Weiss et al. |
| 5,770,599 | A | 6/1998 | Gibson |
| 5,792,783 | A | 8/1998 | Tang et al. |
| 5,891,996 | A | 4/1999 | Mateo de Acosta del Rio et al. |
| 5,948,438 | A | 9/1999 | Staniforth et al. |
| 6,027,880 | A | 2/2000 | Cronin et al. |
| 6,057,100 | A | 5/2000 | Heyneker |
| 6,143,764 | A | 11/2000 | Kubo et al. |
| 6,156,501 | A | 12/2000 | McGall et al. |
| 6,156,522 | A | 12/2000 | Keay et al. |
| 6,217,866 | B1 | 4/2001 | Schlessinger et al. |
| 6,261,776 | B1 | 7/2001 | Pirrung et al. |
| 6,346,398 | B1 | 2/2002 | Pavco et al. |
| 6,476,040 | B1 | 11/2002 | Norris et al. |
| 6,524,583 | B1 | 2/2003 | Thorpe et al. |
| 6,534,535 | B1 | 3/2003 | Zhu et al. |
| 6,576,424 | B2 | 6/2003 | Fodor et al. |
| 6,676,941 | B2 | 1/2004 | Thorpe et al. |
| 6,762,180 | B1 | 7/2004 | Roth et al. |
| 6,797,823 | B1 | 9/2004 | Kubo et al. |
| 6,811,779 | B2 | 11/2004 | Rockwell et al. |
| 6,812,341 | B1 | 11/2004 | Conrad |
| 6,821,987 | B2 | 11/2004 | Kubo et al. |

(Continued)

FOREIGN PATENT DOCUMENTS

| CN | 1473041 | | 2/2004 |
|---|---|---|---|
| CN | 1478078 | A | 2/2004 |

(Continued)

OTHER PUBLICATIONS

Ko et al. Cancer supportive care.com, published online Feb. 2003, pp. 1-4.*

(Continued)

Primary Examiner — Samira Jean-Louis
(74) Attorney, Agent, or Firm — Fish & Richardson P.C.

(57) ABSTRACT

Disclosed are: a therapeutic agent, a kit and a treatment method for undifferentiated gastric cancer; and a pharmaceutical composition, a kit and a treatment method which are more effective on a living organism having at least one cell selected from the group consisting of a cell overexpressing FGFR2 and a cell expressing a mutant FGFR2. A combination of a FGFR2 inhibitor and a therapeutic substance for gastric cancer is more effective on undifferentiated gastric cancer. The combination of a FGFR2 inhibitor and a therapeutic substance for gastric cancer is more effective on a living organism having at least one cell selected from the group consisting of a cell overexpressing FGFR2 and a cell expressing a mutant FGFR2.

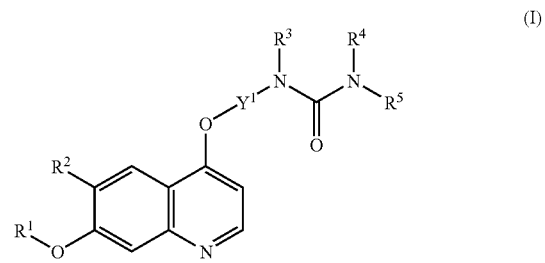

(I)

1 Claim, 9 Drawing Sheets

(56) References Cited

U.S. PATENT DOCUMENTS

| | | |
|---|---|---|
| 7,005,430 B2 | 2/2006 | Ueno et al. |
| 7,101,663 B2 | 9/2006 | Godfrey et al. |
| 7,135,466 B2 | 11/2006 | Sakai et al. |
| 7,169,789 B2 | 1/2007 | Kubo et al. |
| 7,253,286 B2 | 8/2007 | Funahashi et al. |
| 7,435,590 B2 | 10/2008 | Komurasaki |
| 7,485,658 B2 | 2/2009 | Bolger et al. |
| 7,495,104 B2 | 2/2009 | Miwa et al. |
| 7,550,483 B2 | 6/2009 | Sakaguchi et al. |
| 7,612,092 B2 | 11/2009 | Funahashi et al. |
| 7,612,208 B2 | 11/2009 | Matsushima et al. |
| 7,855,290 B2 | 12/2010 | Matsushima et al. |
| 7,973,160 B2 | 7/2011 | Funahashi et al. |
| 8,288,538 B2 | 10/2012 | Matsushima et al. |
| 8,372,981 B2 | 2/2013 | Funahashi et al. |
| 8,377,938 B2 | 2/2013 | Matsushima et al. |
| 2002/0010203 A1 | 1/2002 | Lipson et al. |
| 2002/0040127 A1 | 4/2002 | Jiang et al. |
| 2003/0013208 A1 | 1/2003 | Jendoubi |
| 2003/0087907 A1 | 5/2003 | Kubo et al. |
| 2003/0113713 A1 | 6/2003 | Glezer et al. |
| 2003/0215523 A1 | 11/2003 | Ozawa et al. |
| 2004/0009965 A1 | 1/2004 | Collins et al. |
| 2004/0034026 A1 | 2/2004 | Wood et al. |
| 2004/0053908 A1 | 3/2004 | Funahashi et al. |
| 2004/0086915 A1 | 5/2004 | Lin et al. |
| 2004/0132727 A1 | 7/2004 | Sakai et al. |
| 2004/0152759 A1 | 8/2004 | Abrams et al. |
| 2004/0167134 A1 | 8/2004 | Bruns et al. |
| 2004/0171068 A1 | 9/2004 | Wehland et al. |
| 2004/0191254 A1 | 9/2004 | Fagin |
| 2004/0229876 A1 | 11/2004 | Kubo et al. |
| 2004/0242506 A1 | 12/2004 | Barges Causeret et al. |
| 2004/0253205 A1 | 12/2004 | Yamamoto et al. |
| 2004/0259834 A1 | 12/2004 | Kasprzyk et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0209452 A1 | 9/2005 | Bornsen et al. |
| 2005/0272688 A1 | 12/2005 | Higgins et al. |
| 2005/0277652 A1 | 12/2005 | Matsushima et al. |
| 2006/0004017 A1 | 1/2006 | Stokes et al. |
| 2006/0004029 A1 | 1/2006 | Tsuruoka et al. |
| 2006/0057195 A1 | 3/2006 | Nonomura et al. |
| 2006/0079494 A1 | 4/2006 | Santi et al. |
| 2006/0135486 A1 | 6/2006 | Owa et al. |
| 2006/0160832 A1 | 7/2006 | Funahashi et al. |
| 2006/0189629 A1 | 8/2006 | Bolger et al. |
| 2006/0292192 A1 | 12/2006 | Hasenzahl et al. |
| 2007/0004773 A1 | 1/2007 | Sakaguchi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2007/0214604 A1 | 9/2007 | Yi |
| 2008/0214604 A1 | 9/2008 | Furitsu et al. |
| 2008/0241835 A1 | 10/2008 | Mehraban et al. |
| 2009/0047278 A1 | 2/2009 | Owa et al. |
| 2009/0047365 A1 | 2/2009 | Owa et al. |
| 2009/0053236 A1 | 2/2009 | Yamamoto et al. |
| 2009/0202541 A1 | 8/2009 | Bruns et al. |
| 2009/0247576 A1 | 10/2009 | Kamata et al. |
| 2009/0264464 A1 | 10/2009 | Yamamoto et al. |
| 2009/0304694 A1 | 12/2009 | Oliner et al. |
| 2010/0048503 A1 | 2/2010 | Yamamoto |
| 2010/0048620 A1 | 2/2010 | Yamamoto et al. |
| 2010/0092490 A1 | 4/2010 | Matsui et al. |
| 2010/0105031 A1 | 4/2010 | Matsui et al. |
| 2010/0239688 A1 | 9/2010 | Yamamoto |
| 2010/0324087 A1 | 12/2010 | Yamamoto |
| 2011/0118470 A1 | 5/2011 | Funahashi et al. |
| 2011/0158983 A1 | 6/2011 | Bascomb et al. |
| 2011/0293615 A1 | 12/2011 | Yamamoto |
| 2012/0077842 A1 | 3/2012 | Bando |
| 2012/0207753 A1 | 8/2012 | Yu et al. |
| 2012/0219522 A1 | 8/2012 | Xi |
| 2012/0244209 A1 | 9/2012 | Roth et al. |
| 2012/0263677 A1 | 10/2012 | Eagle et al. |
| 2012/0283206 A1 | 11/2012 | Bruns et al. |
| 2013/0296365 A1 | 11/2013 | Bando |

FOREIGN PATENT DOCUMENTS

| | | |
|---|---|---|
| CN | 10-0589032 | 6/2006 |
| CN | 1890220 | 1/2007 |
| CN | 101001629 | 7/2007 |
| CN | 101029022 | 9/2007 |
| CN | 101198590 | 6/2008 |
| CN | 101316590 | 12/2008 |
| CN | 101454311 | 6/2009 |
| CN | 101616671 | 12/2009 |
| CN | 102470133 | 5/2012 |
| EP | 0 297 580 | 1/1989 |
| EP | 0405425 | 1/1991 |
| EP | 0602851 | 6/1994 |
| EP | 0684820 | 6/1995 |
| EP | 0795556 | 9/1997 |
| EP | 0837063 | 4/1998 |
| EP | 0870842 | 10/1998 |
| EP | 930305 | 7/1999 |
| EP | 930310 | 7/1999 |
| EP | 1029853 | 8/2000 |
| EP | 1044969 | 10/2000 |
| EP | 543942 | 1/2001 |
| EP | 1153920 | 11/2001 |
| EP | 0712863 | 2/2002 |
| EP | 1331005 | 7/2003 |
| EP | 1382604 A1 | 1/2004 |
| EP | 1 411 046 | 4/2004 |
| EP | 1415987 | 5/2004 |
| EP | 1447405 | 1/2005 |
| EP | 1506962 | 2/2005 |
| EP | 1 522 540 | 4/2005 |
| EP | 1 535 910 | 6/2005 |
| EP | 1 552 833 | 7/2005 |
| EP | 1566379 | 8/2005 |
| EP | 1604665 | 12/2005 |
| EP | 1683785 | 7/2006 |
| EP | 1698623 A1 | 9/2006 |
| EP | 1797877 | 6/2007 |
| EP | 1797881 | 6/2007 |
| EP | 1859797 | 11/2007 |
| EP | 1894918 | 3/2008 |
| EP | 1925676 | 5/2008 |
| EP | 1925941 | 5/2008 |
| EP | 1949902 | 7/2008 |
| EP | 1964837 | 9/2008 |
| EP | 2 119 707 | 11/2009 |
| EP | 2116246 | 11/2009 |
| EP | 2133094 | 12/2009 |
| EP | 2133095 | 12/2009 |
| EP | 2218712 | 8/2010 |
| GB | 2253848 | 9/1992 |
| IN | 236500 | 11/2009 |
| JP | S63-028427 | 2/1988 |
| JP | 01-022874 | 1/1989 |
| JP | 02-291295 | 12/1990 |
| JP | 04-341454 | 11/1992 |
| JP | 06-153952 | 6/1994 |
| JP | 07-176103 | 7/1995 |
| JP | 08-045927 | 2/1996 |
| JP | 08-048078 | 2/1996 |
| JP | 09-023885 | 1/1997 |
| JP | 09-234074 | 9/1997 |
| JP | 11-501343 | 2/1999 |
| JP | 11-143429 | 5/1999 |
| JP | 11-158149 | 6/1999 |
| JP | 11-322596 | 11/1999 |
| JP | 3040486 | 3/2000 |
| JP | 3088018 | 7/2000 |
| JP | 2000-328080 | 11/2000 |

(56) References Cited

FOREIGN PATENT DOCUMENTS

| | | |
|---|---|---|
| JP | 2001-131071 | 5/2001 |
| JP | 2002-003365 | 1/2002 |
| JP | 2002-114710 | 4/2002 |
| JP | 2002-536414 | 10/2002 |
| JP | 2003-026576 | 1/2003 |
| JP | 2003012668 A | 1/2003 |
| JP | 3420549 | 4/2003 |
| JP | 2003-525595 | 9/2003 |
| JP | 2004-513964 | 5/2004 |
| JP | 2004-155773 | 6/2004 |
| JP | 2004-531549 | 10/2004 |
| JP | 2005-501074 | 1/2005 |
| JP | 2005-504111 | 2/2005 |
| JP | 2005-520834 | 7/2005 |
| JP | 3712393 | 8/2005 |
| JP | 2005-272474 | 10/2005 |
| JP | 2006-508981 | 3/2006 |
| JP | 2006-515884 | 6/2006 |
| WO | 86/03222 | 6/1986 |
| WO | WO 92/20642 | 11/1992 |
| WO | 94/09010 | 4/1994 |
| WO | WO 95/15758 | 6/1995 |
| WO | WO 95/19774 | 7/1995 |
| WO | WO 96/09294 | 3/1996 |
| WO | WO 96/26997 | 9/1996 |
| WO | 96/30347 | 10/1996 |
| WO | 96/33980 | 10/1996 |
| WO | WO 96/39145 | 12/1996 |
| WO | WO 96/40142 | 12/1996 |
| WO | WO 97/03069 | 1/1997 |
| WO | WO 97/13760 | 4/1997 |
| WO | WO 97/13771 | 4/1997 |
| WO | 97/17329 | 5/1997 |
| WO | WO 97/21437 | 6/1997 |
| WO | WO 97/38984 | 10/1997 |
| WO | 97/48693 | 12/1997 |
| WO | WO 98/00134 | 1/1998 |
| WO | WO 98/02434 | 1/1998 |
| WO | WO 98/02437 | 1/1998 |
| WO | WO 98/02438 | 1/1998 |
| WO | 98/14437 | 4/1998 |
| WO | WO 98/13350 | 4/1998 |
| WO | WO 98/23613 | 6/1998 |
| WO | WO 98/32436 | 7/1998 |
| WO | 98/35958 | 8/1998 |
| WO | WO 98/37079 | 8/1998 |
| WO | WO 98/50346 | 11/1998 |
| WO | WO 98/52558 | 11/1998 |
| WO | WO 99/00357 | 1/1999 |
| WO | 99/35146 | 7/1999 |
| WO | WO 99/32106 | 7/1999 |
| WO | WO 99/32110 | 7/1999 |
| WO | WO 99/32111 | 7/1999 |
| WO | WO 99/32436 | 7/1999 |
| WO | WO 99/35132 | 7/1999 |
| WO | WO 99/43654 | 9/1999 |
| WO | 99/62890 | 12/1999 |
| WO | 00/31048 | 6/2000 |
| WO | 00/42012 | 7/2000 |
| WO | 00/43366 | 7/2000 |
| WO | WO 00/43384 | 7/2000 |
| WO | 00/47212 | 8/2000 |
| WO | WO 00/44728 | 8/2000 |
| WO | WO 00/50405 | 8/2000 |
| WO | WO 00/71097 | 11/2000 |
| WO | 01/02369 | 1/2001 |
| WO | 01/23375 | 4/2001 |
| WO | 01/27081 | 4/2001 |
| WO | 01/32926 | 5/2001 |
| WO | WO 01/36403 | 5/2001 |
| WO | 01/40217 | 6/2001 |
| WO | WO 01/45689 | 6/2001 |
| WO | 01/47890 | 7/2001 |
| WO | WO 01/47931 | 7/2001 |
| WO | 01/60814 | 8/2001 |
| WO | WO 02/16348 | 2/2002 |
| WO | 0232872 A1 | 4/2002 |
| WO | 02/36117 | 5/2002 |
| WO | 02/41882 | 5/2002 |
| WO | WO 02/044156 | 6/2002 |
| WO | 02072578 A2 | 9/2002 |
| WO | 02/080975 | 10/2002 |
| WO | 02/088110 | 11/2002 |
| WO | 02/092091 | 11/2002 |
| WO | 03/006462 | 1/2003 |
| WO | WO 03/013529 | 2/2003 |
| WO | WO 03/024386 | 3/2003 |
| WO | 03/027102 | 4/2003 |
| WO | 03/028711 | 4/2003 |
| WO | 03/033472 | 4/2003 |
| WO | 03033472 A1 | 4/2003 |
| WO | 03/050090 | 6/2003 |
| WO | 03/074045 | 9/2003 |
| WO | 03/079020 | 9/2003 |
| WO | 2004/006862 | 1/2004 |
| WO | 2004/020434 | 3/2004 |
| WO | 2004/032872 | 4/2004 |
| WO | 2004/032937 | 4/2004 |
| WO | WO 2004/035052 | 4/2004 |
| WO | 2004/041308 | 5/2004 |
| WO | 2004/043472 | 5/2004 |
| WO | WO 2004/039782 | 5/2004 |
| WO | 2004/045523 | 6/2004 |
| WO | WO 2004/064730 | 8/2004 |
| WO | 2004/078144 | 9/2004 |
| WO | 2004080462 A1 | 9/2004 |
| WO | WO 2004/080966 | 9/2004 |
| WO | 2004/101526 | 11/2004 |
| WO | 2005/004870 | 1/2005 |
| WO | 2005/021537 | 3/2005 |
| WO | 2005/027972 | 3/2005 |
| WO | 2005/030140 | 4/2005 |
| WO | 2005/044788 | 5/2005 |
| WO | 2005/051366 | 6/2005 |
| WO | 2005/056764 | 6/2005 |
| WO | 2005063713 A1 | 7/2005 |
| WO | 2005/082854 | 9/2005 |
| WO | 2005/092896 | 10/2005 |
| WO | 2005/117887 | 12/2005 |
| WO | 2006/030826 | 3/2006 |
| WO | 2006/030941 | 3/2006 |
| WO | 2006/030947 | 3/2006 |
| WO | 2006/062984 | 6/2006 |
| WO | 2006/090930 | 8/2006 |
| WO | 2006/090931 | 8/2006 |
| WO | 2006/036941 | 12/2006 |
| WO | 2006/137474 | 12/2006 |
| WO | 2007/000347 | 1/2007 |
| WO | 2007/014335 | 2/2007 |
| WO | 2007/015569 | 2/2007 |
| WO | 2007/015578 | 2/2007 |
| WO | 2007/023768 | 3/2007 |
| WO | 2007/040565 | 4/2007 |
| WO | 2007/052849 | 5/2007 |
| WO | 2007/052850 | 5/2007 |
| WO | 2007/061127 | 5/2007 |
| WO | 2007/061130 | 5/2007 |
| WO | 2007/136103 | 11/2007 |
| WO | 2008/023698 | 2/2008 |
| WO | 2008/026748 | 3/2008 |
| WO | 2008/088088 | 7/2008 |
| WO | 2008/093855 | 8/2008 |
| WO | 2009/060945 | 5/2009 |
| WO | 2009/077874 | 6/2009 |
| WO | 2009/096377 | 8/2009 |
| WO | 2009/140549 | 11/2009 |

OTHER PUBLICATIONS

Anonymous, Scientific Discussion, Internet Citation, Jan. 1, 2004, p. 1/61-p. 61/61, XP007918143.
Bastin et al., "Salt Selection and Optimisation for Pharmaceutical New Chemical Entities," Organic Process Research and Development, Cambridge, GB, vol. 4, No. 5, Jan. 1, 2000, p. 427-p. 435, XP002228592.

(56) References Cited

OTHER PUBLICATIONS

Berge et al., Journal of Pharmaceutical Sciences, American Pharmaceutical Association, Washington, US, vol. 66, No. 1, Jan. 1, 1977, p. 1-p. 19, XP002550655.
Gould et al., International Journal of Pharmaceutics, Elsevier, BV, NL, vol. 33, No. 1-3, Nov. 1, 1986, p. 201-p. 217, XP025813036.
Morris et al., "An integrated approach to the selection of optimal salt form for a new drug candidate," International Journal of Pharmaceutics, Elsevier, BV, NL, vol. 105, No. 3, May 9, 1994, p. 209-p. 217, XP023724810.
Ocqueteau et al., "Expression of the CD117 Antigen (C-Kit) on Normal and Myelomatous Plasma cells", British Journal of Haematology, 95:489-493 (1996).
Paz and Zhu, "Development of Angiogenesis Inhibitors to Vascular Endothelial Growth Factor Receptor 2. Current Status and Future Perspectiv", Frontiers in Bioscience 10:1415-1439 (2005).
Pritzker, "Cancer Biomarkers: Easier Said Than Done", Clinical Chemistry 48(8):1147-1150 (2002).
Raimondo et al., "Angiogenic factors in multiple myeloma: higher levels in bone marrow than in peripheral blood", Haematologica, 85:800-805 (2000).
Tong et al., "Vascular Normalization by Vascular Endothelial Growth Factor Receptor 2 Blockade Induces a Pressure Gradient Across the Vasculature and Improves Drug Penetration in Tumors", Cancer Research 64:3731-3736 (2004).
US Office Action directed at U.S. Appl. No. 11/997,543 issued May 19, 2011.
US Office Action directed at U.S. Appl. No. 12/094,492 issued on Mar. 24, 2011.
US Office Action directed at U.S. Appl. No. 12/864,817 issued on May 19, 2011.
Zhu et al., Molecular Targets for Therapy (MTT), "Inhibition of human leukemia in an animal . . . activity", Leukemia 17:604-611 (2003).
Types of Lung Cancer. Accessed on Nov. 12, 2009 at: http://www.lungcancer.org/reading/types.php?printable=true.
Communication pursuant to Article 94(3) EPC mailed Oct. 30, 2009 in European Patent Application No. 04719054.1.
Office communication mailed Aug. 20, 2009 in U.S. Appl. No. 10/797,903.
Hattori et al., "Immunohistochemical Detection of K-sam Protein in Stomach Cancer", Clinical Cancer Research. 2(8), 1373-1381, 1996.
Werner et al., "Gastric adenocarcinoma: pathomorphology and molecular pathology", Journal of Cancer Research and Clinical Oncology. 127, 207-216, 2001.
Itoh et al., "Preferential Alternative splicing in cancer generates a K-sam Messenger RNA with higher transforming activity", Cancer Research. 54, 3237-3241, 1994.
Ueda et al., "Deletion of Carboxyl-Terminal Exons of K-sam/FGFR2 by Short homologymediated recombination, generating preferential expression of specific messenger RNAs", Cancer Research. 59(24), 6080-6086, 1999.
Shimizu et al., "Orally active anti-proliferation agents: novel diphenylamine derivatives as FGF-R2 autophosphorylation inhibitors", Bioorganic and Medicinal Chemistry Letters. 14(4), 875-879, 2004.
Proceeding of the American Association for Cancer Research. 47, 890, 2006.
Salmon et al., Anti-angiogenic treatment of gastrointestinal malignancies, Cancer Investigation, 2005, vol. 23, No. 8, p. 712-726.
Wakui A, Chemotherapy of scirrhous gastric cancer, Japanese Journal of Cancer and Chemotherapy, 1994, vol. 21, No. 14, p. 2398-2406.
Takahashi Y et al., "A case of inoperable scirrhous gastric cancer that responded remarkably to a combination of TS-1 +paclitaxel and showed complete loss of ascites", Japanese Journal of Cancer and Chemotherapy, 2004, vol. 31, No. 7, p. 1093-1095.
Yanagihara K et al., "Development and biological analysis of peritoneal metastasis mouse models for human scirrhous stomach cancer", Cancer Science, 2005, vol. 96; No. 6, p. 323-332.

International Search Report for corresponding PCT/JP2008/051697 mailed Mar. 4, 2008.
Chesi et al., "Activated fibroblast growth factor receptor 3 is an oncogene that contributes to tumor progression in multiple myeloma", Blood 97(3):729-736 (2001).
Search report directed at EP application No. 03791389.4, issued on Jul. 7, 2011, 3 pages.
Carlomagno et al., "ZD6474, an Orally Available Inhibitor of KDR Tyrosine Kinase Activity, Efficiently Blocks Oncogenic RET Kinases", Cancer Research 62:7284-7290 (2002).
Zhang et al., "Overexpression of Platelet-Derived Growth Factor Receptor α in Endothelial Cells of Hepatocellular Carcinoma Associated with High Metastatic Potential", Clinical Cancer Research 11:8557-8563 (2005).
European Search Report, EP Application No. 07806561.2, dated Jan. 19, 2011, 16 pages.
Chinese Office Action directed at application No. 200880003336.6, issued on May 24, 2011, 24 pages (with English translation).
Zhou et al., "Correlation Research on VEGF Testing in Primary Gastric Cancer and Clinical Pathology Factor", Journal of Practical Oncology, 20(2):103-105 (2006) with English translation.
European Search Report for Application No. 04807580.8 dated Apr. 18, 2011 (9 pages).
European Search Report for Application No. 06767145.3 dated May 23, 2011 (7 pages).
US Office Action directed at U.S. Appl. No. 12/301,353 issued on Jan. 24, 2011, 42 pages.
Yu, Lian, "Amorphous pharmaceutical solids: preparation, characterization and stabilization", Adv. Drug Delivery Reviews, Elsevier, Amsterdam, NL, 48(1):27-42 (2001).
Office Action for U.S. Appl. No. 13/205,328 dated Jan. 12, 2012.
Inai et al., "Inhibition of Vascular Endothelial Growth Factor (VEGF) Signaling in Cancer Causes Loss of Endothelial Fenestrations, Regression of Tumor Vessels, and Appearance of Basement Membrane Ghosts", American J. of Pathol. 165(1): 35-52 (2004).
Ohe et al., "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan", Annals of Oncology 18:317-323 (2007).
Asuno-Shinyaku, "The New Drugs of Tomorrow", Update Summary Dec. 2006 with English translation (14 pages).
Agarwal et al., "Binding of Discoidin Domain Receptor 2 to Collagen I: An Atomic Force Microscopy Investigation", Biochemistry 41:11091-11098 (2002).
Plowright et al., "Ectopic expression of fibroblast growth factor receptor 3 promotes myeloma cell proliferation and prevents apoptosis" Neoplasia, Blood, 95(3): 992-998 (2000).
Heinrich et al., "Inhibition of c-kit receptor tyrosine kinase activity by STI 571, a selective tyrosine kinase inhibitor", Hematopoeisis, Blood 96(3):925-932 (2000).
Trudel et al., "Inhibition of fibroblast growth factor receptor 3 induces differentiation and apoptosis in t(4;14) myeloma", Neoplasia, Blood, 103(9): 3521-3528 (2004).
Trudel et al., "CHIR-258, a novel, multitargeted tyrosine kinase inhibitor for the potential treatment of t(4;14) multiple myeloma", Neoplasia, Blood 105(7):2941-2948 (2005).
Paterson et al., "Preclinical studies of fibroblast growth factor receptor 3 as a therapeutic target in multiple myeloma", Blackwell Publishing Ltd, British Journal of Haematology, 124: 595-603 (2004).
Wang et al., "Phase II study of gemcitabine and carboplatin in patients with advanced non-small-cell lung cancer", Cancer Chemother Pharmacol, 60:601-607 (2007).
Baker et al., "Blockade of Vascular Endothelial Growth Factor Receptor and Epidermal Growth Factor Receptor Signaling for Therapy of Metastatic Human Pancreatic Cancer", Cancer Research 62: 1996-2003 (2002).
Lin et al., "The Vascular Endothelias Growth Factor Receptor Tyrosine Kinase Inhibitor PTK787/ZK222584 Inhibits Growth and Migration of Mutiple Myeloma Cells in the Bone Marrow Microenvironment", Cancer Research, 62:5019-5026 (2002).

(56) References Cited

OTHER PUBLICATIONS

Lesueur et al., "Polymorphisms in RET and Its Coreceptors and Ligands as Genetic Modifiers of Multiple Endocrine Neoplasia Type 2A", Cancer Research 66(2):1177-1180 (2006).
Kim et al., "A Phase II Study of Irinotecan Plus Cisplatin for Patients With Advanced Stage IIIB or IV NSCLC Previously Treated With Nonplatinum-Based Chemotherapy", American Cancer Socieity, pp. 799-805 (2006).
Shiang et al., "Mutations in the Transmembrane Domain of FGFR3 Cause the Most Common Genetic Form of Dwarfism, Achondroplasia", Cell 78:335-342 (1994).
Vogel et al., "Sensing extracellular matrix: An update on discoidin domain receptor function", Cellular Signalling 18:1108-1116 (2006).
Zieger et al., "Role of Activating Fibroblast Growth Factor Receptor 3 Mutations in the Development of Bladder Tumors", Clin Cancer Res 11(21):7709-7719 (2005).
Van Oers et al., "A Simple and Fast Method for the Simultaneous Detection of Nine Fibroblast Growth Factor Receptor 3Mutations in Bladder Cancer and Voided Urine", Clin Cancer Res 11(21):7743-7748 (2005).
Santoro et al., "Minireview: RET: Normal and Abnormal Functions", Endocrinology 145(12):5448-5451 (2004).
Jung et al., "Effects of combination anti-vascular endothelial growth factor receptor and anti-epidermal growth factor receptor therapies on the growth of gastric cancer in a nude mouse model", European Journal of Cancer, 38:1133-1140 (2002).
Matsui et al., "146 E7080, a novel multi-targeted tyrosine kinase inhibitor, exhibits anti-angiogenic activity via inhibition of KIT signaling in a small cell lung cancer xenograft model", European Journal of Cancer, Supplement Pergamore Oxford, GB XP004639590 abstract, 2004.
Erber et al., "Combined inhibition ofVEGF- and PDGF-signaling enforces tumor vessel regression by interfering with pericytemediated endothelial cell survival mechanisms", The FASEB Journal published online Dec. 4, 2003 (25 pages).
Haymo et al., "Pericytes in experimental MDA-MB231 tumor angiogenesis", Histochemistry and Cell Biology, 117(6):527-534 (2002).
Logie et al., "Activating mutations of the tyrosine kinase receptor FGFR3 are associated with benign skin tumors in mice and humans", Human Molecular Genetics, 14(9):1153-1160 (2005).
Bruns et al., "Effect of the Vascular Endothelial Growth Factor Receptor-2 Antibody DC101 Plus Gemcitabine on Growth, Metastasis and Angiogenesis of Human Pancreatic Cancer Growing Orthotopically in Nude Mice", Int. J. Cancer 102:101-108 (2002).
Haller, D., "Chemotherapy for Advanced Pancreatic Cancer", Int. J. Radiation Oncology Biol. Phys., 56(4): Supplement, pp. 16-23 (2003).
Alvares et al., "A Novel Germ-Line Point Mutation in RET Exon 8 (Gly$^{533}$Cys) in a Large Kindred with Familial Medullary Thyroid Carcinoma" The Journal of Clinical Endocrinology & Metabolism 88(11):5438-5443, 2003.
Jimenez et al., "Pheochromocytoma and Medullary Thyroid Carcinoma:A New Genotype-Phenotype Correlation of the *RET* Protooncogene 891 Germline Mutation", The Journal of Clinical Endocrinology & Metabolism 89(8):4142-4145 (2004).
Elisei et al., "Identification of a Novel Point Mutation in the RET Gene (Ala883Thr), Which Is Associated with Medullary Thyroid Carcinoma Phenotype Only in Homozygous Condition", The Journal of Clinical Endocrinology & Metabolism 89(11):5823-5827 (2004).
Kim et al., "An Orally Administered Multitarget Tyrosine Kinase Inhibitor, SU11248, Is a Novel Potent Inhibitor of Thyroid Oncogenic RET/Papillary Thyroid Cancer Kinases", The Journal of Clinical Endocrinology & Metabolism 91(10):4070-4075 (2006).
Johnson et al., "Paclitaxel Plus Carboplatin in Advanced Non-Small-Cell Lung Cancer: A Phase II Trial", Journal of Clinical Oncology 14(7):2054-2060 (1996).
Wozniak et al., "Randomized Trial Comparing Cisplatin With Cisplathn Plus Vinorelbine in the Treatment of Advanced Non-Small Cell Lung. Cancer: A Southwest Oncology Group Study", Journal of Clinical Oncology 16(7):2459-2465 (1998).
Sandler et al., "Phase III Trial of Gemcitabine Plus Cisplatin Versus Cisplatin Alone in Patients With Locally Advanced or Metastatic Non-Small-Cell Lung Cancer", Journal of Clinical Oncology 18(1):122-130 (2000).
Gatzemeier et al., "Phase III Comparative Study of High-Dose Cisplatin Versus a Combination of Paclitaxel and Cisplatin in Patients With Advanced Non-Small-Cell Lung Cancer", Journal of Clinical Oncology 18(19):3390-3399 (2000).
Kelly et al., "Randomized Phase III Trial of Paclitaxel Plus Carboplatin Versus Vinorelbine Plus Cisplatin in the Treatment of Patients With Advanced Non—Small-Cell Lung Cancer: A Southwest Oncology Group Trial", Journal of Clinical Oncology 19(13):3210-3218 (2001).
Heinrich et al., "Inhibition of KIT Tyrosine Kinase Activity: A Novel Molecular Approach to the Treatment of KIT-Positive Malignancies", Journal of Oncology 20(6):1692-1703 (2002).
Ozols et al., "Phase III Trial of Carboplatin and Paclitaxel Compared With Cisplatin and Paclitaxel in Patients With Optimally Resected Stage III Ovarian Cancer: A Gynecologic Oncology Group Study", Journal of Oncology 21(17):3194-3200 (2003).
Morgan et al., "Dynamic Contrast-Enhanced Magnetic Resonance Imaging as a Biomarker for the Pharmacological Response of PTK787/ZK 222584, an Inhibitor of the Vascular Endothelial Growth Factor Receptor Tyrosine Kinases, in Patients With Advanced Colorectal Cancer and Liver Metastases: Results From Two Phase I Studies", Journal of Oncology 21(21):3955-3964 (2003).
McCulloch et al., "*Astragalus*-Based Chinese Herbs and Platinum-Based Chemotherapy for Advanced Non—Small-Cell Lung Cancer: Meta-Analysis of Randomized Trials", Journal of Clinical Oncology 24(3):419-430 (2006).
Mologni et al., "Inhibition of RET tyrosine kinase by SU5416", Journal of Mol. Endo., 37:199-212 (2006).
Carlomagno et al., "BAY 43/9006 Inhibition of Oncogenic RET Mutants", Journal of the National Cancer Institute 98(5):326-334 (2006).
Tan et al., "Randomized study of vinorelbine-gemcitabine versus vinorelbine-carboplatin in patients with advanced non-small cell lung cancer", Lung Cancer, 49:233-240 (2005).
McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer", Molecular Cancer Therapeutics, 3(9):1041-1048 (2004).
Zhu et al., "Fibroblast growth factor receptor 3 inhibition by short hairpin RNAs leads to apoptosis in multiple myeloma", Mol Cancer Ther 4(5):787-798 (2005).
Yamada et al., "New Technique for Staining", Monthly Medical Technology, (13 pages), Apr. 1999.
Santoro et al., "Drug Insight: small-molecule inhibitors of protein kinases in the treatment of thyroid cancer", Nature Clinical Practice Endocrinology & Metabolism 2(1):42-52 (2006).
Naski et al., "Graded activation of fibroblast growth factor receptor 3 by mutations causing achondroplasia and thanatophoric dysplasia", Nature Genetics 13:233-237 (1996).
Chesi et al., "Frequent translocation t(4;14)(p16.3;q32.3) in multiple myeloma is associated with increased expression and activating mutations of fibroblast growth factor receptor", Nature Genetics, 3 16:260-264 (1997).
Capellen et al., "Frequent activating mutations of FGFR3 in human bladder and cervix carcinomas", Nature Genetics, 23:18-20 (1999).
Willett et al., "Direct evidence that the VEGF-specific antibody bevacizumab has antivascular effects in human rectal cancer", Nature Medicine 10(2):145-147 (2004).
Hurwitz et al., "Bevacizumab plus Irinotecan, Fluorouracil, and Leucovorin for Metastatic Colorectal Cancer", The New England Journal of Medicine, 350(23):2335-2342 (2004).
Miller et al., "Paclitaxel plus Bevacizumab versus Paclitaxel Alone for Metastatic Breast Cancer", The New England Journal of Medicine, 357:2666-76 (2007).
Jhiang, S., "The RET proto-oncogene in human cancers", Oncogene 19:5590-5597 (2000).

(56) References Cited

OTHER PUBLICATIONS

Chen et al., "FGFR3 as a therapeutic target of the small molecule inhibitor PKC412 in hematopoietic malignancies", Oncogene 24:8259-8267 (2005).
Kashuk et al., "Phenotype—genotype correlation in Hirschsprung disease is illuminated by comparative analysis of the RET protein sequence", PNAS 102(25):8949-8954 (2005).
Morikawa et al., Angiogenesis and Pericytes, Putative Positive Function of Pericytes in Angiogenesis, Course of Cellular Biology, 13 pages, with English translation, (2005).
Benjamin et al., "Selective ablation of immature blood vessels in established human tumors follows vascular endothelial growth factor withdrawal", The J. of Clin. Invest. 103(2):159-165 (1999).
Olaso et al., "DDR2 receptor promotes MMP-2—mediated proliferation and invasion by hepatic stellate cells", The Journal of Clinical Investigation, 108( 9):1369-1378 (2001).
Bergers et al., "Benefits of targeting both pericytes and endothelial cells in the tumor vasculature with kinase inhibitors", The Journal of Clinical Investigation 111(9):1287-1295 (2003).
Inoue et al., "Molecular Target Therapy Targeting Angiogenesis Pathways", The Nishinihon J. Urol., 66:425-432 (2004).
Giles, F., "The Vascular Endothelial Growth Factor (VEGF) Signaling Pathway: A Therapeutic Target in Patients with Hematologic Malignancies", The Oncologists 6(suppl5):32-39 (2001).
Hannequin et al., "Novel 4-Anilinoquinazolines with C-7 Basic Side Chains: Design and Structure Activity Relationship of a Series of Potent, Orally Active, VEGF Receptor Tyrosine Kinase Inhibitors", Journal of Medicine Chemistry 45:1300-1312 (2002).
Micke et al., "Characterization of c-kit expression in small cell lung cancer: prognostic and therapeutic implications", Clinical Cancer Res. 9:188-194(2003).
European Search Report for EP Appl. No. 07743994, May 2010.
European Search Report for EP Appl. No. 06782407, Jul. 23, 2010.
ISR (PCT/JP2006/315563) dated Sep. 5, 2006.
ISR (PCT/JP2006/315698) dated Oct. 17, 2006.
ISR (PCT/JP2006/322514) dated Jan. 23, 2007.
ISR (PCT/JP2006/323881) dated Jan. 23, 2007.
ISR (PCT/JP2007/060560) dated Sep. 11, 2007.
ISR (PCT/JP2007/063525) dated Sep. 4, 2007.
ISR (PCT/JP2007/067088) dated Nov. 20, 2007.
ISR (PCT/JP2008/051024) dated Apr. 1, 2008.
ISR (PCT/JP2008/070321) dated Jan. 20, 2009.
ISR (PCT/JP2009/051244) dated Mar. 24, 2009.
Wang and Schwabacher, "A Convenient Set of Bidentate Pyridine Ligands for Combinatorial Synthesis", Tetrahedron Lett.40, 1999, p. 4779-p. 4782.
Taguchi et al., "A novel orally active inhibitor of VEGF rector tyrosine kinases KRN951: Anti-angiogenic and anti-tumor activity against human solid tumors.", Taguchi E et al., Proceedings of the AACR annual meeting., vol. 45, Mar. 2004, p. 595, XP002536608.
Lev et al., "A Specific Combination of Substrates is Involved in Signal Transduction by the Kit-Encoded Rector", The EMBO Journal,10(3), 1991, p. 647-p. 654.
Li et al., "Abrogation of c-kit/Steel factor-dendent tumorigenesis by kinase defective mutants of the c-kit rector: c-kit kinase defective mutants as candidate tools for cancer gene therapy, Cancer Research vol. 56", Oct. 1, 1996, p. 4343-p. 4346, XP002522473.
Gall-lstok, et al., "Abstract of Acta Chimica Hungarica", Inst. Exp. Med., Hung. Avad. Svi., Budapest, 1983, p. 112(2)-p. 241-7.
Tian, et al., "Activating c-kit Gene Mutations in Human Germ Cell Tumors", American Journal of Pathology, 154(6), 1999, p. 1643-p. 1647.
Okayama, et al., "Activation of Eosinophils with Cytokines Produced by Lung Mast Cells", Int Arch Allergy Immuno1.114:(suppl 1), 1997, p. 75-p. 77.
Blume-Jensen, et al., "Activation of the Human c-kit Product by Ligand-Induced Dimerization Mediates Circular Actin Reorganization and Chemotaxis", The EMBO Journal, 10(13), 1991, p. 4121-p. 4128.
Miyazaki et al., Synthesis, Structure and Biological Activity Relationship of . . . PDGF Receptor, AIMECS 03, 5th AFMC International Medicinal Chem. Symposium, Oct. 2003, Kyoto Japan, 1 page.
Longley, et al., "Altered Metabolism of Mast-Cell Growth Factor (c-kit Ligand) in Cutaneous Mastocytosis", The New England Journal of Medicine, 328(18), 1993, p. 1302-p. 1307.
Hayek, et al., "An in Vivo Model for Study of the Angiogenic Effects of Basic Fibroblast Growth Factor", Biochemical and Biophysical Research Communications, 147(2), 1987, p. 876-p. 880.
Folkman, et al., "Angiogenesis", The Journal of Biological Chemistry, 267(16), 1992, p. 10931-p. 10934.
Gerald B. Dermer, "Another anniversary for the war on cancer", Bio/Technology, vol. 12, 1994, p. 320.
Deplanque, et al., "Anti-Angiogenic Agents: Clinical Trial Design and Therapies in Development", European Journal of Cancer, 36, 2000, p. 1713-p. 1724.
Wedge et al., "AZD2171: A Highly Potent, Orally Bioavailable, Vascular Endothelial Growth Factor Rector-2 Tyrosine Kinase Inhibitor for the Treatment of Cancer", Cancer Res., vol. 65(10), p. 4389-4400, 2005.
Natali, et al., "Breast Cancer is Associated with Loss of the c-kit Oncogene Product", Int. J. Cancer, 52, 1992, p. 713-p. 717.
Trisha Gura, "Cancer Models Systems for Identifying new drugs are often faulty", Science, vol. 278, Nov. 7, 1997, p. 1041-p. 1042.
Wakeling, et al., ZD1839 (Iressa): An Orally Active Inhibitor of Epidermal Growth Factor Signalling with Potential for Cancer Therapy, Cancer Res.,62:5749-5754 ( 2002).
Ikeda, et al., "Changes in Phenotype and Proliferative Potential of Human Acute Myeloblastic Leukemia Cells in Culture with Stem Cell Factor", Experimental Hematology, 21, 1993, p. 1686-p. 1694.
J. Haleblian, Characterization of Habits and Crystalline Modification of Solids and Their Pharmaceutical Applications", Journal of Pharmaceutical Sciences ", 64(8):1269-1288 (1975).
Metcalfe, D., "Classification and Diagnosis of Mastocytosis: Current Status", J. Invest. Dermatol, 96, 1991, p. 2S-p. 4S.
Folkman, et al., "Clinical Applications of Research on Angiogenesis", The New England Journal of Medicine, 333(26), 1995, p. 1757-p. 1763.
Hines, et al., "Coexpression of the c-kit and Stem Cell Factor Genes in Breast Carcinomas", Cell Growth & Differentiation, 6, 1995, p. 769-p. 779.
Hibi, et al., "Coexpression of the Stem Cell Factor and the c-kit Genes in Small-Cell Lung Cancer", Oncogene, 6, 1991, p. 2291-p. 2296.
R. Ian Freshney, Alan R. Liss, "Culture of Animal Cells, A Manual of Basic Technique", New York, 1983, p. 4.
Jakeman, et al., "Developmental Expression of Binding Sites and Messenger Ribonucleic Acid for Vascular Endothelial Growth Factor Suggests a Role for This Protein in Vasculogenesis and Angiogenesis", Endocrinology, 133(2), 1993, p. 848-p. 859.
Matsui et al., "E7080 (ER-203492-00), a Novel VEGF Rector Tyrosine Kinase Inhibitor-I. Characterization as an Angiogenesis Inhibitor.", Abstract # 51, AACR, Toronto, Canada, Apr. 5-9, 2003.
Nakamura et al., "E7080 (ER-203492-00), a Novel VEGF Rector Tyrosine Kinase Inhibitor-II. Effects on Growth of Human Tumor Xenografts and Life Span of Mice in Colon 38 Orthotopic Transplantation Model." Abstract # 52, AACR, Toronto, Canada, Apr. 5-9, 2003.
Yamamoto et al., "A Novel VEGF Receptor Tyrosine Kinase Inhibitor-III. Significant prolongation of life span in mice transplanted with human ovarian carcinoma based on inhibition of VEGF signaling", Abstract # 50, AACR, Toronto, Canada, Apr. 5-9, 2003.
Yamamoto et al., "E7080 a novel multitargeted tyrosine kinase inhibitor, has direct anti-tumor activity via inhibition of KIT signaling in small cell lung cancer", Yamamoto et al., Abstract #4636, AACR, Orlando, FL, Mar. 27-31, 2004.
Matsui et al., "E7080, a novel inhibitor that targets multiple kinases, has potent antitumor activities against stem cell factor producing human small cell lung cancer H146, based on angionenesis inhibition", Int. J. Cancer 122:664-671 (2008).
Matsui et al., "E7080, a novel multi-rector Tyrosine Kinase Inhibitor, inhibited in vitro / in vivo VEGF- and SCF-driven angiogenesis SCLC cell line", Matsui et al., Abstract #146, EORTC-NCI-AACR, Geneva, Switzerland, Sep. 28-Oct. 1, 2004.

(56) References Cited

OTHER PUBLICATIONS

Yamamoto et al., "E7080, an oral multi-targeted tyrosine kinase inhibitor, has direct anti-tumor efficacy via inhibition of KIT signaling in gastrointestinal stromal tumor (GIST)" Abstract #40358, 97th annual meeting AACR, Washington, DC., Apr. 1-5, 2006.

Taniguchi, et al., "Effect of c-kit Mutation on Prognosis of Gastrointestinal Stromal Tumors", Cancer Research, 59, 1999, p. 4297-p. 4300.

Nagata, et al., "Elevated Expression of the Proto-Oncogene c-kit in Patients with Mastocytosis", Leukemia, 12, 1998, p. 175-p. 181.

Kay, et al., "Eosinophils and Eosinophil-Associated Cytokines in Allergic Inflammation", Int. Arch. Allergy Immunol. 113, 1997, p. 196-p. 199.

Ikeda, et al., "Expression and Functional Role of the Proto-Oncogene c-kit in Acute Myeloblastic Leukemia Cells", Blood, 78(11), 1991, p. 2962-p. 2968.

Karl Nocka, et al., "Expression of c-kit gene products in known cellular targets of W mutations in normal and W mutant mice-evidence for an impaired c-kit kinase mutant mice", Genes & Development, Cold Spring Harbor Laboratory Press, 3:816-826, (1989).

Cohen, et al., "Expression of Stem Cell Factor and c-kit in Human Neuroblastoma", Blood, 84(10):3465-3472 (1994).

Strohmeyer, et al., "Expression of the hst-1 and c-kit Protoonocogenes in Human Testicular Germ Cell Tumors", Cancer Research, 51, 1991, p. 1811-p. 1816.

Kanakura, et al., "Expression, Function and Activation of the Proto-Oncogene c-kit Product in Human Leukemia Cells", Leukemia and Lymphorma, 10, 1993, p. 35-p. 41.

Bellone, et al., "Growh Stimulation of Colorectal Carcinoma Cells via the c-kit Rector is Inhibited by TGF-β-1", Journal of Cellular Physiology,172, 1997, p. 1-p. 11.

Okayama, et al., "Human Lung Mast Cells are Enriched in the Capacity to Produce Granulocyte-Macrophage Colony-Stimulating Factor in Response to IgE-Dendent Stimulation", Eur. J. Immunol. 28, 1998, p. 708-p. 715.

Furitsu, et al., "Identification of Mutations in the Coding Sequence of the Proto-Oncogene c-kit in a Human Mast Cell Leukemia Cell Line Causing Ligand-Indendent Activation of c-kit Product", J. Clin. Invest. 92, 1993, p. 1736-p. 1744.

Croom, et al., "Imatinib mesylate in the Treatment of Gastrointestinal Stromal Tumours", Drugs, 63(5), 2003, p. 513-p. 522.

Mendel et al., "In Vivo Antitumor Activity of SU11248, a Novel Tyrosine Kinase Inhibitor Targeting Vascular Endothelial Growth Factor and Platelet-derived Growth Factor Rectors: Determination of a Pharmacokinetic/Pharmacodynamic Relationship" Clin. Cancer Res., 9: 327-337, (2003).

Spacey, et al., "Indolocarbazoles, Potent and Selective Inhibitors of Platelet-Derived Growth Factor Rector Autophosphorylation", Biochemical Pharmacology, 55:261-271, (1998).

Ciardiello, et al., "ZD1839 (IRESSA), An EGFR-Selective Tyrosine Kinase Inhibitor, Enhances Taxane Activity in BCL-2 Overexpressing, Multidrug Resistant MCF-7 ADR Human Breast Cancer Cells", Int. J. Cancer, 98:463-469, (2002).

Naruse, et al., "Antitumor Activity of the Selective Epidermal Growth Factor Receptor-Tyrosine Kinase Inhibitor (EGFR-TKI) IRESSA . . . In Vivo", Int. J. Cancer, 98:310-315, (2002).

International Search Report issued for related PCT application PCT/JP01/09221, Jan. 15, 2002.

International Search Report issued for related PCT application PCT/JP2004/003087, Jul. 13, 2004.

Boissan, et al., "c-Kit and c-kit mutations in mastocytosis and other hematological diseaseas", J. Leukocyte Biol., 67:135-148, (2000).

Nugiel et al., "Synthesis and Evaluation of Indenopyrazoles as Cyclin-Dependent Kinase Inhibitors. 2. Probing the Indeno Ring Substituent Pattern", Journal of Medical Chemistry, 45(24):5224-5232, (2002).

Tonary, et al., "Lack of Expression of c-KIT in Ovarian Cancers is Associated with Poor Prognosis", Int. J. Cancer (Pred. Oncol) 89, 2000, p. 242-p. 250.

Longley, et al., "Classes of c-Kit activating mutations: proposed mechanisms of action and implications for disease classification and therapy", Leukemia Res., 25:571-576, (2001).

Metcalf, et al., "Lineage Commitment in the Progeny of Murine Hematopoietic Prrogenitor Cells: Influence of Thrombopoietin and Interleukin 5", Proc. Nat'l Acad. Sci. USA, 95, 1998, p. 6408-p. 6412.

Metcalfe, et al., "Mast Cells", Physiological Reviews, 77(4), 1997, p. 1033-p. 1079.

Golkar, et al., "Mastocytosis", Lancet, 349, 1997, p. 1379-p. 1385.

Lasota, et al., "Mutations in Exons 9 and 13 of KIT Gene Are Rare Events in Gastrointestinal Stromal Tumors", American Journal of Pathology, 157(4), 2000, p. 1091-p. 1095.

"NCBI GenBank Accession No. NM_000222", Feb. 11, 2008.

Cairns et al., "New antiallergic pyrano[3,2g]quinoline-2,8-dicarboxylic acids with potential for the topical treatment of asthma", Cairns et al, Journal of Medicinal Chemistry 8(12), 1985, p. 1832-p. 1842.

Folkman, J., "New Perspective in Clinical Oncology From Angiogenesis Research", Eur J. Cancer. 32A(14), 1996, p. 2534-p. 2539.

Hogaboam, et al."Novel Role of Transmembrane SCF for Mast Cell Activation and Eotaxin Production in Mast Cell-Fibroblast Interactions", The Journal of Immunology, 160, 1998, p. 6166-p. 6171.

Gardner et al., "In Vitro Activity of Sorghum-Selective Fluorophenyl Urea Herbicides", Pesticide Biochemistry and Physiology, 24(3):285-297, (1985).

Sekido, et al., "Preferential Expression of c-kit Protooncogene Transcripts in Small Cell Lung Cancer", Cancer Research, 51, 1991, p. 2416-p. 2418.

"Proceedings of the American Association for Cancer Research", vol. 45, Mar. 2004, p. 1070-p. 1071.

Kolibaba, et al., "Protein Tyrosine Kinases and Cancer", Biochimica et Biophysica Acta, 1333, 1997, p. F217-p. F248.

Matsui et al., "Quantitative analysis of the profile of tumor vessels may be useful as predictive biomarkers for E7080", Abstract #4631, 98th AACR annual meeting, Los Angeles, CA,, Apr. 14-18, 2007.

Berdel, et al, "Recombinant Human Stem Cell Factor Stimulates Growth of a Human Glioblastoma Cell Line Expressing c-kit Protooncogene", Cancer Research, 52, 1992, p. 3498-p. 3502.

"Redefining the Frontiers of Science 94th Annual Meeting", American Association for Cancer Research, 2003, vol. 44, Washington D.C., USA, Jul. 11-14, 2003.

Kitamura, et al., "Regulation of Development, Survival and Neoplastic Growth of Mast Cells through the c-kit Rector", Int Arch Allergy Immunol., 107, 1995, p. 54-p. 56.

Naclerio, et al., "Rhinitis and Inhalant Allergens", JAMA, 278(22), 1997, p. 1842-p. 1848.

Bussolino, et al, "Role of Soluble Mediators in Angiogenesis", Eur. J. Cancer, 32A(14): , 1996, p. 2401-p. 2412.

Clark et al., "Safety and Pharmacokinetics of the Dual Action Raf Kinase and Vascular Endothelial Growth Factor Rector Inhibitor, BAY43-9006, in Patients with Advanced Refractory Solid Tumors", Clin. Cancer Res. (2005)11:, 2005, p. 5472-p. 5480.

Longley, et al., "Somatic c-KIT Activating Mutation in Urticaria Pigmentosa and Aggressive Mastocytosis: Establishment of Clonality in a Human Mast Cell Neoplasm", Nature Genetics, 12, 1996, p. 312-p. 314.

Furitsu et al., "Stable medicinal compositions of quinolinecarboxamide derivative", Database Caplus Chemical Abstracts Service, Columbus, Ohio, US, 2006, XP002520305.

Lukacs, et al., "Stem Cell Factor (c-kit Ligand) Influences Eosinophil Recruitment and Histamine Levels in Allergic Airway Inflammation", The Journal of Immunology, 156, 1996, p. 3945-p. 3951.

Kotva, et al., "Substances with Antineoplastic Activity, LIII. N-(δ-(4-Pyrrolo[2,3-d]Pyrimidinylthio) Valeryl]} Amino Acids and Analogous Derivatives of Di-and Triglycine", Collection Czechoslov. Chem. Commun. 38, 1973, p. 1438-p. 1444.

Furuta, et al., "Synthesis and Biological Evaluation of Selective Inhibitors of PDGF Rector Auto Phosphorylation", Pharmaceutical Research Laboratories, Kirin Brewery Co., Ltd. Takasaki, Gunma, Japan, Sep. 2003.

(56) References Cited

OTHER PUBLICATIONS

Abuzar, S. et al., "Synthesis of some new 7-chloro-4-substituted quinolines as potential antiparasitic agents", Eur. J. Med. Chem.,vol. 21,No. 1, 1986, p. 5-p. 8.
Miyazaki et al., "Synthesis, Structure and Biological Activity Relationship of E7080 and its Derivatives as Novel and Potent Antiangiogenic Protein Tyrosine Kinase Inhibitors Including the VEGF Rectors, FGFR1 Rector and PDGF Rector." Abstract B-15, AIMECS03, Kyoto, Japan, Oct. 14-17, 2003.
Thomas et al., "The Eosinophil and its Role in Asthma", Gen. Pharmac. 27(4), 1996, p. 593-p. 597.
Wang, et al., "The Expression of the Proto-Oncogene C-Kit in the Blast Cells of Acute Myeloblastic Leukemia", Leukemia, 3(10), 1989, p. 699-p. 702.
Meltzer, E.O., "The Pharmacological Basis for the Treatment of Perennial Allergic Rhinitis and Non-Allergic Rhinitis with Topical Corticosteroids", Allergy, 52, 1997, p. 33-p. 40.
Myers, et al., "The Praration and SAR of 4-(Anilino), 4-(Phenoxy), and 4-(Thiophenoxy)-Quinazolines: Inhibitors of p561ck and EGF-R Tyrosine Kinase Activity", Bioorgan. & Med. Chem. Letters, 7, 1997, p. 417-p. 420.
Hamel, et al., "The Road Less Travelled: c-kit and Stem Cell Factor", Journal of Neuro-Oncology, 35, 1997, p. 327-p. 333.
Takano et al., "Thermal recording materials with improved background stability", Database CA(Online) Chemical Abstracts Service, Columbus, Ohio, US, Feb. 20, 1996, XP002443195.
Scheijen et al."Tryosine Kinase Oncogenes in Normal Hematopoiesis and Hematological Disease", Oncogene, 21, 2002, p. 3314-p. 3333.
Matsui et al., "VEGFRs inhibitor E7080 inhibits lymph node metastasis of human breast carcinoma, by preventing murine lymphatic endothelial cells from lymphangiogenesis.", Abstract # PD12-8, 18th EORTC-NCI-AACR symposium on "Molecular Targets and Cancer Therapeutics", Prague, Czech rublic, Nov. 7-10, 2006.
Folkman, J., "What is the Evidence That Tumors are Angiogenesis Dendent?", Journal of the National Cancer Institute, 82(1), 1990, p. 4-p. 6.
Takeda et al., "AZD2171 shows potent anti-tumor activity against gastric cancer expressing variant K-SAM/FGFR2", Proceeding of the American Association for Cancer Research, 47:890 (2006) #3785.
CN Office Action directed at application No. 200580026468.7 issued on Jun. 26, 2009, 6 pages.
CN Office Action directed at application No. 200710007097.9 issued on Mar. 6, 2009, 5 pages.
EESR directed at application No. 06832529.9 issued on Jul. 29, 2009, 6 pages.
Office Action directed at application No. 4025700.8 issued on Apr. 10, 2006, 3 pages.
Search Report directed at application No. 4719054.1 issued on Apr. 17, 2009, 4 pages.
Search Report directed at application No. 4818213.3 issued on Jul. 30, 2007, 3 pages.
JP Allowance directed at application No. P2005-515330 issued on Apr. 21, 2009, 2 pages.
KR Office Action directed at application No. 10-2006-7013993 issued on Jul. 31, 2007 (with English translation), 9 pages.
US Office Action directed at U.S. Appl. No. 10/577,531 issued on Sep. 23, 2008, 17 pages.
US Office Action directed at U.S. Appl. No. 10/797,903 issued on Dec. 11, 2007, 12 pages.
US Office Action directed at U.S. Appl. No. 11/347,749 issued on Feb. 9, 2009, 6 pages.
US Office Action directed at U.S. Appl. No. 11/997,719 issued on Sep. 3, 2010, 10 pages.
WO IPRP directed at application No. PCT/JP2004/003087 issued on Feb. 23, 2006, 5 pages.
WO IPRP directed at application No. PCT/JP2006/312487 issued on Jan. 10, 2008, 7 pages.
Anderson et al., "Preparation of Water-soluble Compounds through Salt Formation", The Practice of Medicinal Chemistry, Technomics, pp. 347-349, 355-356 (1999).
Japanese Office Action for Application No. 2005-516605, Jun. 1, 2010 (with partial translation).
Traxler et al., "AEE788: A Dual Family Epidermal Growth Factor Receptor/ErbB2 and Vascular Endothelial Growth Factor Receptor Tyrosine Kinase Inhibitor with Antitumor and Antiangiogenic Activity", Cancer Research 64:4931-4941 (2004).
European Search Report for Application No. 06768437.3 dated Oct. 11, 2010 (10 pages).
Vippagunta et al., "Crystalline solids", Advanced Drug Delivery Reviews 48:3-26 (2001).
Juurikivi et al., "Inhibition of c-kit tyrosine kinase by imatinib mesylate induces apoptosis in mast cells in rheumatoid synovia: a potential approach to the treatment of arthritis", Ann. Rheum. Dis., 64:1126-1131 (2005).
US Office Action directed at U.S. Appl. No. 12/092,539 issued on Jan. 7, 2011.
European Search Report for Application No. 06833681.7 dated Nov. 24, 2010, 15 pages.
Sanger et al., "DNA sequencing with chain-terminating inhibitors", Proc. Natl. Acad. Sci. USA 74: 5463 (1977).
Wakui, "Chemotherapy for Scirrhous Gastric Cancer", Japanese Journal of Cancer and Chemotherapy, 21:(14): 2398-2406 (1994) (English translation only).
Takahashi et al., "A Case of Inoperable Scirrhous Gastric Cancer that Responded Remarkably to a Combination . . . Loss of Ascites", Japanese Journal of Cancer and Chemotherapy, 31(7):1093-1095 (2004) (English translation only).
PCT/JP2008/051697 Written Opinion of the International Searching Authority issued on Mar. 4, 2008.
PCT/JP2008/051697 International Preliminary Report on Patentability issued on Aug. 4, 2009.
CN200880003336.6 Response to Office Action filed on Oct. 8, 2011.
Israel 200090 Office Actions issued on Jun. 22, 2010.
Israel 200090 Response to Office Action filed on Oct. 12, 2010.
Chinese Office Action directed at application No. 200880003336.6, issued on May 24, 2011.
European Search Report for Application No. 10015141.4 dated Sep. 9, 2011.
Kleespies et al., Tyrosine kinase inhibitors and gemcitabine: New treatment options in pancreatic cancer?, Drug Resistance Updates 9:1-19 (2006).
Okura et al., "Effects of monoclonal anti-c-kit antibody (ACK2) on melanocytes in newborn mice", J. Invest. Dermatol., 105(3): 322-328 (1995).
US Office Action directed at U.S. Appl. No. 12/439,339 issued Nov. 14, 2011.
US Office Action directed a U.S. Appl. No. 12/523,495 issued on Sep. 27, 2011.
Final Office Action for U.S. Appl. No. 12/523,495 dated Dec. 27, 2011.
Final Office Action for US at U.S. Appl. No. 11/997,719 issued on Apr. 6, 2011.
Office Action for U.S. Appl. No. 13/205,325 dated Jan. 12, 2012.
Final Office Action for U.S. Appl. No. 11/997,543 dated Nov. 9, 2011.
European Search Report for EP 08846814.5 dated Jun. 18, 2012.
Office Action for JP2007-529565 dated Aug. 7, 2012 with English translation.
Noriyuki et al., "Anti-tumor effect of E7080, a novel angiogenesis inhibitor", Database Biosis (online) Biosciences Information Service, Philadelphia, PA, US, Database Accession No. PREV200800475929 (abstract), Aug. 2008, XP002677323.
Submission of Documents re Claim 3 and Figure 3 for KR App. Ser. No. 10-2009-7005657, filed on Jul. 13, 2012.
Official Letter for AU2008211952 dated Jul. 10, 2012.
Response to Office Action for U.S. Appl. No. 12/741,682, filed Jul. 30, 2012.
Communication (Notice of Allowance) for JP2011-527665 dated Jul. 17, 2012 (with English translation).

(56) References Cited

OTHER PUBLICATIONS

Communication (Notice of Allowance) for EP07806561.2 dated Jun. 25, 2012.
Australian Office Action for Application No. AU2006309551 issued on Apr. 28, 2011.
Australian Response to Office Action for Application No. 2006309551 filed on Jan. 21, 2012.
Australian Office Action for Application No. 2006309551 issued on Feb. 2, 2012.
Chinese Office Action for Application No. 200680041355.9 issued on Mar. 5, 2010 with English translation.
Chinese Response to Office Action for Application No. 200680041355.9 filed on Jul. 19, 2010 with English translation.
Chinese Office Action for Application No. 200680041355.9 issued on Aug. 24, 2010 with English translation.
Chinese Response to Office Action for Application No. 200680041355.9 filed on Nov. 8, 2010 with English translation.
Abrams et al., "SU11248 Inhibits KIT and Platelet-derived Growth Factor Receptor Beta in Preclinical Models of Human Small Cell Lung Cancer", Molecular Cancer Therapeutics. 2: 471-478, 2003.
Carter et al., "Inhibition of drug-resistant mutants of ABL, KIT and EGF receptor kinases", Proceedings of the National Academy of Sciences of the United States of America., 102, 11011-11016, 2005.
CN200780032071.8 Office Action issued on Oct. 13, 2010 with English translation.
CN200780032071.8 Response to Office Action filed on Feb. 16, 2011 with English translation.
Corbin et al., "Sensitivity of oncogenic KIT mutants to the kinase inhibitors MLN518 and PD180970", Blood. 104, 3754-3757, 2004.
EP07806561.2 Office Actions issued on Jan. 19 and Feb. 7, 2011.
EP07806561.2 Response to Office Action filed on Aug. 9, 2011.
EP07806561.2 Office Action issued on Dec. 9, 2011.
European Office Action for Application No. 06832529.9 issued on Oct. 15, 2009.
European Response to Office Action for Application No. 06832529.9 filed on Apr. 22, 2010.
European Office Action for Application No. 06832529.9 issued on Sep. 12, 2011.
European Response to Office Action for Application No. 06832529.9 filed on Oct. 4, 2011.
EP Communication under Rule 71(3) EPC for Application No. 06832529.9 issued on Nov. 25, 2011.
Genitourinary Cancers, Prostate Cancer Genitourinary, http://www.merkmanuals.com/professional/print/sec17/ch241/ch241e.html Mar. 16, 2011.
Guo et al., "Expression of gastric cancer-associated MG7 antigen in gastric cancer, precancerous lesions and H. pylori-associated gastric diseases", Word J. Gastroenterol, 8(6):1009-1013 (2002).
Hamby et al., "Structure-Activity Relationships for a Novel Series of Pyrido[2,3-d]pyrimidine Tyrosine Kinase Inhibitors", Journal of Medicinal Chemistry. 40, 2296-2303, 1997.
Huston et al., "Protein engineering of antibody binding sites: Recovery of specific activity in an anti-digoxin single-chain Fv analogue produced in *Escherichia coli*", Proc. Natl. Acad. Sci. USA 85:5879-83, 1988.
Japanese Publication of Patent Application No. H11-322596 with English translation.
Japanese Patent Application No. 2006-230816 (English translation).
Krystal et al., "Indolinone Tyrosine Kinase Inhibitors Block Kit Activation and Growth of Small Cell Lung Cancer Cells", Cancer Research., 61, 3660-3668, 2001.
Leukemias, Hematology and Oncology, http://www.merkmanuals.com/professional/print/sec11/ch142/ch142a.html Mar. 16, 2011.
Nakamura et al., "KRN633: A Selective inhibitor of vascular endothelial growth factor receptor-2 tyrosine kinase that suppresses tumor angiogenesis and growth", Molecular Cancer Therapeutics. 3:1639-49, 2004.
Pandey et al., "Identification of Orally Active, Potent, and Selective 4-Piperazinylquinazolines as Antagonists of the Platelet-Derived Growth Factor Receptor Tyrosine Kinase Family", Journal of Medicinal Chemistry. 45, 3772-3793, 2002.
PCT/JP2006/322514 International Preliminary Report on Patentability issued on May 7, 2008.
PCT/JP2006/322516 International Search Report issued on Jan. 23, 2007.
PCT/JP2006/322516 International Preliminary Report on Patentability issued on May 7, 2008.
Santoro et al., "Molecular Mechanism of RET Activation in Human Cancer", Ann. N.Y. Acad Sci. 963:116-121 (2002).
Shibata et al., "Rapid Communication Association of Epstein-Barr Virus with Undifferentiated Gastric Carcinomas with Intense Lymphoid Infiltration", American Journal of Pahthology 139(3):469-473 (1991).
Thyroid Cancers, Endocrine and Metabolic Disorders, http://www.merkmanuals.com/professional/print/sec12/ch152/ch152j.html Mar. 16, 2011.
Office Action for U.S. Appl. No. 12/092,539 issued on Oct. 29, 2010.
Final Office Action for U.S. Appl. No. 12/092,539 issued on May 9, 2011.
Advisory Action for U.S. Appl. No. 12/092,539 issued on Jun. 28, 2011.
Van Dijk et al. "Induction of Tumor-Cell Lysis by B-Specific Monoclonal Antibodies Recognizing Renal-Cell Carcinoma and CD3 Antigen", Int. J. Cancer 43: 344-9, 1989.
Wisniewski et al.,"Characterization of Potent Inhibitors of the Bcr-Abl and the c-Kit Receptor Tyrosine Kinases", Cancer Research. 62, 4244-4255, 2002.
Wood et al., "PTK787/ZK 222584, a Novel and Potent Inhibitor of Vascular Endothelial Growth Factor Receptor Tyrosine Kinases, Impairs Vascular Endothelial Growth Factor-Induced Responses and Tumor Growth after Oral Administration", Cancer Research. 60, 2178-2189, 2000.
Yigitbasi et al., "Tumor Cell and Endothelial Cell Therapy of Oral Cancer by Dual Tyrosine Kinase Receptor Blockade", Cancer Research, 64, 7977-7984, 2004.
Sun et al., "Synthesis and Biological Evaluations of 3-Substituted Indolin-2-ones: A novel class of Tyrosine kinase inhibitors that exhibit selectivity toward particular receptor tyrosine kinases", Journal of Medicinal Chemistry. 41:2588-2603 (1998).
Sun et al., "Design, synthesis, and evaluations of substituted 3-[(3-or 4-carboxyethylpyrrol-2- yl)methylidenyl]indolin-2-ones as inhibitors of VEGF, FGF, and PDGF receptor tyrosine kinases", Journal of Medicinal Chemistry. 42:5120-5130 (1999).
Sun et al., "Discovery of 5-[5-Fluoro-2-oxo-1,2-dihydroindol-(3Z)-ylidenemethy1]-2,4-dimethyl-1H-pyrrole-3carboxylic acid . . . Tyrosine Kinase", Journal of Medicinal Chemistry. 46:1116-1119 (2003).
Bold et al., "New anilinophthalazines as potent and orally well absorbed inhibitors of the VEGF receptor tyrosine kinases useful as antagonists of tumor-driven angiogenesis", Journal of Medicinal Chemistry. 43:2310-2323 (2000).
Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis", Cancer Research. 64:7099-7109 (2004).
Bankston et al., "A Scaleable synthesis of BAY 43-9006: A Potent Raf Kinase Inhibitor for the Treatment of Cancer", Organic Process Res Dev. 6:777-81 (2002).
Response to the European Search Report for European Application No. 06782407 filed on Nov. 8, 2010.
Office Action issued for European Search Report for European Application No. 06782407 issued on Sep. 29, 2011.
Response to the Office Action for European Application No. 06782407 filed on Jan. 23, 2012.
Office Action issued for Japanese Application No. 2007-529565 issued on Dec. 13, 2011 with English translation.
Response to the Office Action issued for Japanese Application No. 2007-529565 filed on Feb. 3, 2012 with English full translation.
Office Action directed at Israel Application No. 207089 issued on Nov. 13, 2011 (with English translation).

(56) References Cited

OTHER PUBLICATIONS

Written Opinion of the International Searching Authority directed at PCT/JP2009/051244 issued on Mar. 24, 2009 (with English translation).
International Preliminary Report directed at PCT/JP2009/051244 issued on Aug. 31, 2010 (with English translation).
Israel Office Action directed at Appl. No. 205512 issued on Nov. 13, 2011 with English translation.
PCT/JP2008/070321 Written Opinion of the International Searching Authority issued on Jan. 20, 2009 with English translation.
PCT/JP2008/070321 International Preliminary Report on Patentability issued on May 11, 2010 with English translation.
Office Action issued for EP application No. 07806561.2 on Dec. 9, 2011.
Office Action issued for U.S. Appl. No. 10/797,903 on Apr. 1, 2010.
Office Action issued for U.S. Appl. No. 10/797,903 on Sep. 1, 2010.
Office Action (Decision to refuse) issued for EP 04807580.8 on Oct. 25, 2011.
Forbes R T et al., International Journal of Pharmaceutics, Elsevier Science BV, vol. 126, Jun. 1, 1995, pp. 199-208.
Ernst Mutschler et al., Arzneimittel-Wirkungen Lehrbuch Der Pharmakologie Und Toxikologie, Wissenschaftliche Verlagsgesellschaft, Stuttgart, Jan. 1, 1999, pp. 1-5 with Full English translation.
Rudolf Voigt et al., Pharmazeutische Technologie Fuer Studium Und Beruf, Dt. Apotheker-Verl, Stuttgart; DE, Jan. 1, 2000, pp. 40-52, XP008143620 with Full English translation.
Lennartsson et al., "The Stem Cell Factor Receptor/c-Kit as a Drug Target in Cancer", Current Cancer Drug Targets, 6:561-571 (2006).
N. Turner and R. Grose, "Fibroblast growth factor signalling: form development to cancer", Nature Reviews, Cancer, 10:116-129 (2010).
S. Wells and M. Santoro, "Targeting the RET Pathway in Thyroid Cancer", Clinical Cancer Research, 15:7119-7123 (2009).
Giuseppe Di Lorenzo et al., "Targeted Therapy in the Treatment of Metastatic Renal Cell Cancer", Oncology, 77(Suppl.1):122-131 (2010).
Abby B.-Siegel et al., "Sorafenib: Where Do We Go from Here?" Hepatology, 52:360-369 (2010).
Kanai et al., "Development Status and Future Prospects of Novel Molecular Target Drugs for Hepatocellular Carcinoma", Journal of the Japanese Society of Gastroenterology, 106:1727-1735 (2009).
National Institutes of Health, Food and Drug Administration, National Library of Medicine, http://clinicaltrials.gov/ct2/show/study/NCT01136733, May 26, 2010.
Office Action issued for EP application No. 04818213.3 on Feb. 2, 2012.
Kitteringham et al., "A Simple Method for the Synthesis of Unsymmetrical Ureas", Synthetic Communications, 30(11):1937-1943 (2000).
Notice of Allowance issued for U.S. Appl. No. 12/986,638 on Mar. 22, 2012.
International Preliminary Examination Report and Patentability and Written Opinion for International Application No. PCT/2010/063804 dated Mar. 22, 2012.
Restriction Requirement issued for U.S. Appl. No. 11/997,543 dated Feb. 23, 2011.
Restriction Requirement issued for U.S. Appl. No. 12/092,539 dated Oct. 29, 2010.
Restriction Requirement issued for U.S. Appl. No. 12/301,353 dated Oct. 29, 2010.
Restriction Requirement issued for U.S. Appl. No. 12/439,339 dated Jul. 29, 2011.
Restriction Requirement issued for U.S. Appl. No. 12/524,754 Nov. 3, 2011.
Restriction Requirement issued for U.S. Appl. No. 13/083,338 Apr. 12, 2012.
Nishikawa et al., "Cys611Ser mutation in RET proto-oncogene in a kindred with medullary thryroid carcinoma and Hirschsprung's disease", European Journal of Human Genetics, 11,364-368 (2003).
Machens et al., "Genotype-Phenotype Correlations in Hereditary Medullary Thyroid Carcinoma: Oncological Features and Biochemical Properties", Journal of Clinical Endocrinology and Metabolism, 86(3):1104-1109 (2001).
Carniti et al., "The RetC62OR Mutation Affects Renal and Enteric Development in a mouse Model of Hirschprung's Disease", American Journal of Pathology, 168, 1262-1275, (2006).
Asai et al., "Mechanism of Ret Activation by a Mutation of Aspartic Acid 631 Identified in Sporadic Pheochromocytoma", Biochemical and Biophysical Research Communications, 255, 587-590 (1999).
Carlomagno et al., "Point Mutation of the RET Proto-Oncogene in the TT Human Medullary Thyroid Carcinoma cell Line", Biochemical and Biophysical Research Communications, 207, 1022-1028 (1995).
Berndt et al., "A New Hot Spot for Mutations in the ret Protooncogene Causing Familial Medually Thyroid Carcinoma and Multiple Endocrine Neoplasia Type 2A", Journal of Clinical Endocrinology and Metabolism, 83, 770-774 (1998).
Miyauchi et al., "Two Germline Missense Mutations of Codons 804 and 806 of the RET proto-oncogene in the Same 15 Allele in a Patient with Multiple Endocrine Neoplasia Type 2B without Codon 915 Mutation", Japanese Journal of D Cancer Research, 90, 1-5, (1999).
Joao et al., "Somatic trinucleotide change encompassing codons 882 and 883 of the RET proto-oncogene in a patient with sporadic medullary thyroid carcinoma", European Journal of Endocrinology, 142, 573-575, (2000).
Kim et al., "RET Oligonucleotide Microarray for the Detection of RET Mutations in Multiple Endocrine Neoplasia Type 2 Syndromes", Clinical Cancer Research, 8,457-463, (2002).
Salvatore et al., "Molecular profile of hyalinizing trabecular tumours of the thyroid: High prevalence of RET/PTC rearrangements and absence of B-raf and N-raspoint mutations", European Journal of Cancer, 41: 816-821 (2005).
Grieco et al., "PTC is a Novel Rearranged Form of the ret Proto-Oncogene and Is Frequentrly Detected in Vivo in Human Thyroid Papillary Carcinomas", Cell, 60: 557-563 (1990).
Lam et al., "High prevalence of Ret proto-oncogene activation (RET/PTC) in papillary thyroid carcinomas", Eur J Endocrinology, 147: 741-745 (2002).
Klugbauer et al., "Detection of a Novel Type of RET Rearrangement (PTC5) in Thyroid Carcinomas after Chernobyl and Analysis of the Involved RET-fused Gene RFG5", Cancer Research, 58: 198-203 (1998).
Klugbauer and Rabes, "The transcription coactivator HT1 F1 and a related protein are fused to the RET receptor tyrosine kinase in childhood papillary thyroid carcinomas", Oncogene, 18: 4388-4393 (1999).
Salassidis et al., "Translocation t(1 0; 14) (q 11.2; q22.1) Fusing the Kinectin to the RET Gene Creates a Novel Rearranged Form (PTC8) of the RET Proto-Oncogene in Radiation-induced Childhood Papillary Thyroid Carcinomas", Cancer Research, 60: 2786-2789 (2000).
Klugbauer et al., "A Novel Type of RET Rearrangement (PTC8) in Childhood Papillary Thyroid Carcinomas and Characterization of the Involved Gene (RFG8)", Cancer Research, 60: 7028-7032 (2000).
Nakata et al., "Fusion of a Novel Gene, ELKS, to RET Due to Translocation t(1 0; 12) (q11; p13) in a Papillary Thyroid Carcinoma", Genes Chromosomes Cancer, 25: 97-103 (1999).
Corvi et al., "RET/PCM-1: a novel fusion gene in papillary thyroid carcinoma", Oncogene, 19: 4236-4242 (2000).
Written Opinion of the International Searching Authority for PCT/JP2007/060560 mailed on Sep. 11, 2007 with English translation.
International Preliminary Report of Patentability issued for PCT/JP2007/060560 on Nov. 18, 2008 with English translation.
Australian Office Action directed at Appl. No. 2007252506 issued on Nov. 7, 2011.
Australian Response to Office Action directed at Appl. No. 2007252506 filed on Jan. 4, 2012.
Australian Office Action directed at Appl. No. 2007252506 issued on Jan. 13, 2012.
Chinese Office Action directed at Appl. No. 200780017371.9 mailed on Oct. 20, 2010 with English translation.
Chinese Response to Office Action directed at Appl. No. 200780017371.9 filed on Feb. 24, 2011 with English translation.

(56) References Cited

OTHER PUBLICATIONS

European Response to EESR directed at Appl. No. 07743994.1-2123 filed on Nov. 23, 2010.
Israel Office Action directed at Appl. No. 195282 issued on Jan. 26, 2010 with English translation.
Israel Response (IDS List) to Office Action directed at Appl. No. 195282 filed on May 3, 2010 with English translation.
Israel Appl. No. 195282 IDS List filed on Jul. 1, 2010.
Russian Office Action directed at Appl. No. 2008149948/15(065561) issued on May 24, 2011 with English translation.
Russian Response to Office Action directed at Appl. No. 2008149948/15(065561) filed on Jul. 27, 2011 with English translation.
Russian Decision of Grant directed at Appl. No. 2008149948/15(065561) received on Nov. 9, 2011 with English translation.
US Office Action directed at U.S. Appl. No. 12/301,353 issued on Oct. 29, 2010.
US Response to Office Action directed at U.S. Appl. No. 12/301,353, filed Nov. 23, 2010.
Australian Response to Office Action directed at Appl. No. 2007252506 filed on Mar. 2, 2012.
Response to Office Action directed at Australain Appl. No. 2006309551 filed on Mar. 30, 2012.
US Office Action directed at U.S. Appl. No. 13/083,338 dated Jun. 8, 2012.
US Final Office Action for U.S. Appl. No. 12/439,339 dated Mar. 30, 2012.
Zimmermann et al., "Potent and Selective Inhibitors of the ABL-Kinase:Phenylamino-Pyrimidine (PAP) Derivatives", Bioorganic and Medicinal Chemistry Letters 7(2):187-192, 1997.
Zimmermann, "Electrical Breakdown, Electropermeabilization and Electrofusion", Rev. Physiol. Biochem. Pharmacol. 105:176-260 (1986).
"Current Protocols in Molecular Biology", John Wiley & Sons Section 11.4-11.13 (1987).
Antibodies: A Laboratory Manual, E. Harlow and D. Lane, ed. Cold Spring Harbor Laboratory (Cold Spring Harbour, NY, 1988).
First Office Action issued on Mar. 6, 2012 for the corresponding JP application, JP2007-542863, and English translation.
Amendment filed on Apr. 27, 2012 in response to the JP Office Action for JP2007-542863 and English translation.
Heinrich et al., "Kinase Mutations and Imatinib Response in Patients with Metastatic Gastrointestinal Stromal Tumor", Journal of Clinical Oncology, vol. 21, No. 23:4342-4349 (2003).
Paulus, "Preparation and Biomedical Applications of Bispecific Antibodies", Behring Inst. Mitt. 78:118-132 (1985).
Waterman, M., "Computer Analysis of Nucleic Acid Sequences", Methods in Enzymology, 164:765-793 (1988).
Wilbur, W.J. and Lipman, D.J., "Rapid similarity searches of nucleic acid and protein data banks", Natl. Acad. Sci, U.S.A. 80:726-730 (1983).
Altschul et al., "Basic Local Alignment Search Tool", J. Mol. Biol. 215:403-410 (1990).
Pearson, "Rapid and Sensitive Sequence Comparison with FASTP and FASTA", Methods in Enzymology 183:63-98 (1990).
Jang et al., "Mutations in Fibroblast Growth Factor Receptor 2 and Fibroblast Growth Factor Receptor 3 Genes Associated with Human Gastric and Colorectal Cancers", Cancer Research, 61:3541-3543 (2001).
Japanese Classification of Gastric Carcinoma "Igan-Toriatsukai Kiyaku" (Jun. 1999, 13th ed.) and an English translation.
Voluntary Amendment filed on Feb. 17, 2012 for TH patent appl. No. 1201000221 with English translation.
Office Action dated Apr. 11, 2012 for RU patent appl. No. 2012103471 with English translation.
Office Action dated Apr. 27, 2012 for KR patent appl. No. 10-2007-7001347 with English translation.
Office Action dated May 3, 2012 for IN patent appl. No. 383/CHENP/2008.
Examination Report dated May 9, 2012 for PK patent appl. No. 94/2011.
Office Action dated Jun. 5, 2012 for JP patent appl. No. 2009-123432 with English translation.
Response to the OA filed on May 29, 2012 for RU patent appl. No. 2012103471 with English translation.
Examiner's Report dated Sep. 20, 2005 for AU Patent Application No. 2001295986.
Response filed on Apr. 27, 2006 for AU Patent Application No. 2001295986.
Examiner's Report dated May 4, 2006 for AU Patent Application No. 2001295986.
Response filed on Jul. 26, 2006 for AU Patent Application No. 2001295986.
Notice of Acceptance dated Aug. 3, 2006 for AU Patent Application No. 2001295986.
Voluntary Amendment filed on Aug. 30, 2006 for AU Patent Application No. 2006203099.
Examiner's Report dated Feb. 21, 2008 for AU Patent Application No. 2006203099.
Voluntary Amendment filed on Feb. 21, 2007 for AU Patent Application No. 2006203099.
Voluntary Amendment filed on Feb. 27, 2007 for AU Patent Application No. 2006236039.
Examiner's Report dated Mar. 26, 2008 for AU Patent Application No. 2006236039.
Response filed on May 8, 2008 for AU Patent Application No. 2006236039.
Notice of Acceptance dated May 13, 2008 for AU Patent Application No. 2006236039.
Office Action dated Dec. 6, 2007 for CA Patent Application No. 2426461.
Response filed on May 16, 2008 for CA Patent Application No. 2426461.
Office Action dated Nov. 20, 2008 for CA Patent Application No. 2426461.
Response filed on Feb. 23, 2009 for CA Patent Application No. 2426461.
Office Action dated May 8, 2009 for CA Patent Application No. 2426461.
Response filed on Aug. 13, 2009 for CA Patent Application No. 2426461.
Office Action dated Feb. 10, 2010 for CA Patent Application No. 2426461.
Response filed on May 20, 2010 for CA Patent Application No. 2426461.
Voluntary Amendment filed on Aug. 19, 2010 for CA Patent Application No. 2426461.
Notice of Allowance dated Oct. 14, 2010 for CA Patent Application No. 2426461.
Amendment after Allowance filed on Jan. 4, 2011 for CA Patent Application No. 2426461.
Office Letter Confirmation of Amendment After Allowance dated Jan. 11, 2011 for CA Patent Application No. 2426461.
Amendment filed on May 28, 2003 for CN Patent Application No. 01819710.8 with English translation.
Office Action dated May 13, 2005 for CN Patent Application No. 01819710.8 with English translation.
Response filed on Sep. 13, 2005 for CN Patent Application No. 01819710.8 with English translation.
Amendment filed on Sep. 13, 2005 for CN Patent Application No. 01819710.8 with English translation.
Office Action dated Feb. 10, 2006 for CN Patent Application No. 01819710.8 with English translation.
Partial European Search Report for EP Patent Application No. 01976786.2; 20040406.
Supplementary European Search Report for EP Patent Application No. 01976786.2; 20040706.
Invitation to declare maintenance of the application for EP Patent Application No. 01976786.2; 20040712.
Maintenance of the application for EP Patent Application No. 01976786.2; 20040906.

(56) References Cited

OTHER PUBLICATIONS

Amendments received before examination for EP Patent Application No. 01976786.2; 20040910.
Communication from the Examining Division for EP Patent Application No. 01976786.2; 20050817.
Brief communication to applicant for EP Patent Application No. 01976786.2; 20050909.
Reply to communication from the Examining Division for EP Patent Application No. 01976786.2; 20060125.
Communication from the Examining Division for EP Patent Application No. 01976786.2; 20060321.
Reply to communication from the Examining Division for EP Patent Application No. 01976786.2; 20060719.
Communication about intention to grant a European patent for EP Patent Application No. 01976786.2; 20060904.
Decision to grant a European patent for EP Patent Application No. 01976786.2; 20070201.
Communication regarding the expiry of opposition period for EP Patent Application No. 01976786.2; 20080104.
European search report for EP Patent Application No. 04025700.8; 20050113.
Communication from the Examining Division for EP Patent Application No. 04025700.8; 20060410.
Reply to communication from the Examining Division for EP Patent Application No. 04025700.8; 20060912.
Communication from the Examining Division for EP Patent Application No. 04025700.8; 20061023.
Reply to communication from the Examining Division for EP Patent Application No. 04025700.8; 20070126.
Reply to communication from the Examining Division for EP Patent Application No. 04025700.8; 20070215.
Communication about intention to grant a European patent for EP Patent Application No. 04025700.8; 20071015.
Request for amendment of the text intended for grant and translation of claims for EP Patent Application No. 04025700.8; 20080201.
Approval of request for amendments for EP Patent Application No. 04025700.8; 20080313.
Decision to grant a European patent for EP Patent Application No. 04025700.8; 20080605.
Communication regarding the expiry of opposition period for EP Patent Application No. 04025700.8; 20090507.
Deficiencies in sequence listing for EP Patent Application No. 06023078.6; 20061205.
Reply to the invitation to remedy deficiencies for EP Patent Application No. 06023078.6; 20070111.
Request for correction of errors in filed documents for EP Patent Application No. 06023078.6; 20070213.
European Search Report for EP Patent Application No. 06023078.6; 20070316.
Information about decision on request for EP Patent Application No. 06023078.6; 20070321.
Invitation to declare maintenance of the application for EP Patent Application No. 06023078.6; 20070502.
Maintenance of the application for EP Patent Application No. 06023078.6; 20070619.
Communication from Examining Division for EP Patent Application No. 06023078.6; 20070802.
Reply to communication from the Examining Division for EP Patent Application No. 06023078.6; 20070911.
Communication from the Examining Division for EP Patent Application No. 06023078.6; 20070926.
Reply to communication from the Examining Division for EP Patent Application No. 06023078.6; 20080204.
Communication about intention to grant a European patent for EP Patent Application No. 06023078.6; 20080718.
Request for amendment of the text intended for grant and translation of claims for EP Patent Application No. 06023078.6; 20081105.
Decision to grant a European patent for EP Patent Application No. 06023078.6; 20081204.
Communication regarding the expiry of opposition period for EP Patent Application No. 06023078.6; 20091104.
"Notice of Allowance dated Dec. 26, 2007 for IL Patent Application No. 155447 " with English translation.
Japanese Patent Application Laid-Open No. H11-158149 with English translation.
"Office Action dated Jul. 27, 2005 for KR Patent Application No. 10-2003-7005506 " with English translation.
"Amendment filed on Oct. 25, 2005 for KR Patent Application No. 10-2003-7005506 " with English translation.
"Notice of decision for patent dated Jun. 12, 2006 for KR Patent Application No. 10-2003-7005506 " with English translation.
"Office Action dated Dec. 8, 2005 for KR Patent Application No. 10-2005-7020292" with English translation.
"Argument Brief filed on Mar. 8, 2006 for KR Patent Application No. 10-2005-7020292" with English translation.
"Amendment filed on Mar. 8, 2006 for KR Patent Application No. 10-2005-7020292" with English translation.
"Notice of decision for patent dated Apr. 17, 2006 for KR Patent Application No. 10-2005-7020292" with English translation.
"Office Action dated Oct. 4, 2005 for MX Patent Application No. PA/a/2003/003362" with English translation.
"Response filed on Dec. 15, 2005 for MX Patent Application No. PA/a/2003/003362" with English translation.
"Office Action dated Jun. 7, 2006 for MX Patent Application No. PA/a/2003/003362"with English translation.
"Response filed on Aug. 21, 2006 for MX Patent Application No. PA/a/2003/003362" with English translation.
"Notice of Allowance dated Oct. 18, 2006 for MX Patent Application No. PA/a/2003/003362" with English translation.
"Office Action dated Nov. 26, 2007 for MX Patent Application No. PA/a/2005/013764" with English translation.
"Office Action dated Mar. 7, 2007 for NO Patent Application No. 20031731"with English translation.
"Response filed on Sep. 10, 2007 for NO Patent Application No. 20031731"with English translation.
"Office Action dated Oct. 4, 2007 for NO Patent Application No. 20031731"with English translation.
"Response filed on May 7, 2008 for NO Patent Application No. 20031731"with English translation.
"Office Action dated May 16, 2008 for NO Patent Application No. 20031731"with English translation.
"Response filed on Aug. 18, 2008 for NO Patent Application No. 20031731"with English translation.
"Office Action dated Sep. 5, 2008 for NO Patent Application No. 20031731" with English translation.
"Response filed on Oct. 13, 2008 for NO Patent Application No. 20031731"with English translation.
"Notice of Allowance dated Oct. 31, 2008 for NO Patent Application No. 20031731" with English translation.
"Examination Report dated Oct. 13, 2003 for NZ Patent Application No. 525324".
"Response filed on Aug. 26, 2004 for NZ Patent Application No. 525324".
"Examination Report dated Sep. 2, 2004 for NZ Patent Application No. 525324".
"Response filed on Jan. 21, 2005 for NZ Patent Application No. 525324".
"Examination Report dated Feb. 18, 2005 for NZ Patent Application No. 525324".
"Notice of Acceptance of Complete Specification dated Mar. 4, 2005 for NZ Patent Application No. 525324".
"Formality Requirement dated Jun. 18, 2003 for PH Patent Application No. 1-2003-500266".
"Response filed on Aug. 5, 2003 for PH Patent Application No. 1-2003-500266".
"Office Action dated Aug. 8, 2003 for PH Patent Application No. 1-2003-500266".
"Response filed on Sep. 8, 2003 for PH Patent Application No. 1-2003-500266".
"Response filed on Sep. 15, 2003 for PH Patent Application No. 1-2003-500266".

(56) References Cited

OTHER PUBLICATIONS

"Office Action dated Jul. 21, 2006 for PH Patent Application No. 1-2003-500266".
"Response filed on Aug. 14, 2006 for PH Patent Application No. 1-2003-500266".
"Office Action dated Mar. 21, 2007 for PH Patent Application No. 1-2003-500266".
"Response filed on Apr. 17, 2007 for PH Patent Application No. 1-2003-500266".
"Office Action dated Jun. 27, 2007 for PH Patent Application No. 1-2003-500266".
"Response filed on Jul. 31, 2007 for PH Patent Application No. 1-2003-500266".
"Office Action dated Sep. 7, 2007 for PH Patent Application No. 1-2003-500266".
"Response filed on Oct. 15, 2007 for PH Patent Application No. 1-2003-500266".
"Notice of Allowability dated Nov. 28, 2007 for PH Patent Application No. 1-2003-500266".
"Response to the Notice of Allowability filed on Dec. 13, 2007 for PH Patent Application No. 1-2003-500266".
"Notification dated Apr. 25, 2008 for PH Patent Application No. 1-2003-500266".
"Response filed on Apr. 30, 2008 for PH Patent Application No. 1-2003-500266".
"Registered dated Feb. 24, 2009 for PH Patent Application No. 1-2003-500266".
"Office Action dated Jun. 29, 2004 for RU Patent Application No. 2003114740" with English translation.
"Response filed on Nov. 30, 2004 for RU Patent Application No. 2003114740" with English translation.
"Office Action dated Jan. 19, 2005 for RU Patent Application No. 2003114740" with English translation.
"Response filed on Mar. 17, 2005 for RU Patent Application No. 2003114740" with English translation.
"Notice of Allowance dated Apr. 19, 2005 for RU Patent Application No. 2003114740" with English translation.
"Amendment filed on Apr. 17, 2002 for TW Patent Application No. 90125928" with English translation.
"Rejection dated Apr. 26, 2004 for TW Patent Application No. 90125928" with English translation.
"Reexamination filed on Nov. 25, 2004 for TW Patent Application No. 90125928" with English translation.
"Office Action dated Oct. 11, 2007 for TW Patent Application No. 90125928" with English translation.
"Response filed on Dec. 11, 2007 for TW Patent Application No. 90125928" with English translation.
"Notice of Allowance dated Oct. 20, 2008 for TW Patent Application No. 90125928" with English translation.
"Notice of Allowance dated Jun. 3, 2008 for U.S. Appl. No. 11/293,785".
"Notice of Allowance dated Nov. 19, 2008 for U.S. Appl. No. 11/293,785".
"Notice of Allowance dated Feb. 27, 2009 for U.S. Appl. No. 11/293,785".
"Notice of Allowance dated May 18, 2009 for U.S. Appl. No. 11/293,785".
"Preliminary Amendment filed on Apr. 18, 2003 for U.S. Appl. No. 10/420,466".
"Office Action dated Apr. 13, 2005 for U.S. Appl. No. 10/420,466".
"Response filed on Jul. 1, 2005 for U.S. Appl. No. 10/420,466".
"Notice of Allowance dated Sep. 12, 2005 for U.S. Appl. No. 10/420,466".
"Notice of Allowance dated Jun. 13, 2006 for U.S. Appl. No. 10/420,466".
"Notice of Allowance dated Mar. 16, 2007 for U.S. Appl. No. 10/420,466".
Preliminary Amendment filed on Dec. 2, 2005 for U.S. Appl. No. 11/293,785.
"Preliminary Amendment filed on Feb. 3, 2006 for U.S. Appl. No. 11/293,785".
"Office Action dated Sep. 4, 2007 for U.S. Appl. No. 11/293,785".
"Response filed on Feb. 26, 2008 for U.S. Appl. No. 11/293,785".
"Notification of Non-Compliant Amendment filed on Jan. 13, 2005 for U.S. Appl. No. 10/420,466".
"Office Communication concerning dated Sep. 13, 2004 for U.S. Appl. No. 10/420,466".
"Response filed on Oct. 8, 2004 for U.S. Appl. No. 10/420,466".
"Preliminary Amendment filed on Oct. 27, 2003 for U.S. Appl. No. 10/420,517".
Amended description filed after receipt of search report for EP Patent Application No. 10809938.3; 20111208.
"Amendment filed on Dec. 15, 2011 for VN Patent Application No. 10-2011-03484" with English translation.
"Office Action dated Nov. 20, 2009 for CN Patent Application No. 200580026468.7 " with English translation.
Communication regarding the expiry of opposition period for EP Patent Application No. 05783232.1; 20100219.
"Decision to grant a European patent for EP Patent Application No. 05783232.1; 20090319".
"Communication about intention to grant a European patent for Ep Patent Application No. 05783232.1; 20081120".
"Reply to official communication for EP Patent Application No. 05783232.1; 20080430".
Communication from the Examining Division for EP Patent Application No. 05783232.1; 20080207.
Maintainance of the application for EP Patent Application No. 05783232.1; 20071109.
Invitation to declare maintenance of the application for EP Patent Application No. 05783232.1; 20070925.
European Search Report for EP Patent Application No. 05783232.1; 20070907.
"Response filed on Jan. 26, 2011 for IL Patent Application No. 181697" with English translation.
Japanese Patent Application Laid-Open No. S63-028427 with English translation.
Japanese Patent Application Laid-Open No. 2003-026576 with English translation.
WO00/071097 with English translation.
"Office Action dated Sep. 28, 2011 for KR Patent Application No. 10-2007-7001347 " with English translation.
ISR dated Nov. 15, 2005 for International Patent Application No. PCT/JP2005/016941.
IPRP dated Mar. 20, 2007 for International Patent Application No. PCT/JP2005/016941.
Office Action for JP2007-542863 dated May 29, 2012 with English translation.
AU2006309551 Response to Office Action filed on Mar. 28, 2012.
CN Office Action issued for CN 200880002425.9 on Mar. 7, 2012 with English translation.
AU Office Action issued for AU 2008211952 on Apr. 3, 2012.
CN Office Action directed at Appl. No. 200780017371.9 mailed on Mar. 7, 2012 with English translation.
IL Office Action issued for IL 195282 on Feb. 5, 2012 with English translation.
CN Office Action issued for CN 200880115011.7 on Feb. 20, 2012 with English translation.
Response to IL OA directed at Appl. No. 205512 filed on Mar. 11, 2012 with English translation.
Response to IL OA directed at Appl. No. 207089 filed on Mar. 11, 2012 with English translation.
AU Office Action issued for AU 2008205847 on Apr. 11, 2012.
Response to the OA issued for U.S. Appl. No. 11/997,543, filed Mar. 22, 2011.
Response to the OA issued for U.S. Appl. No. 11/997,543, filed Aug. 19, 2011.
Response to the OA issued for U.S. Appl. No. 11/997,543, filed Jan. 9, 2012.
Response to the OA issued for U.S. Appl. No. 11/997,719, filed Dec. 23, 2010.
Response to the Final OA issued for U.S. Appl. No. 11/997,719, filed Jul. 6, 2011.

(56) References Cited

OTHER PUBLICATIONS

U.S. Appl. No. 12/092,539 Response to Office Action filed on Nov. 22, 2010.
U.S. Appl. No. 12/092,539 Response to Office Action filed on Mar. 11, 2011.
U.S. Appl. No. 12/092,539 Response to Final Office Action filed on Jun. 15, 2011.
Response to OA issued for U.S. Appl. No. 13/1205,328, filed Apr. 11, 2012.
Response to Office Action directed at U.S. Appl. No. 12/301,353, filed Nov. 23, 2010.
Response to the OA for U.S. Appl. No. 12/439,339, filed Aug. 10, 2011.
Response to the OA for U.S. Appl. No. 12/439,339, filed Feb. 7, 2012.
Response to the OA for U.S. Appl. No. 12/523,495, filed Dec. 7, 2011.
Response to the OA for U.S. Appl. No. 12/864,817, filed Aug. 9, 2011.
Response to the OA of U.S. Appl. No. 12/864,817, filed Dec. 5, 2011.
Response to the OA for U.S. Appl. No. 12/864,817, filed Dec. 22, 2011.
Asano et al., "Inhibition of Tumor Growth and Metastasis by an Immunoneutralizing Monoclonal Antibody to Human Vascular Endothelial Growth Factor/Vascular Permeability Factor121", Cancer Research. 55, 5296-5301, 1995.
Hori et al., "Suppression of Solid Tumor Growth by Immunoneutralizing Monoclonal Antibody against Human Basic Fibroblast Growth Factor", Cancer Research. 51, 6180-4, 1991.
Gutheil et al., Targeted Antiangiogenic Therapy for Cancer Using Vitaxin: A Humanized Monoclonal Antibody to the Integrin alphavbeta3 1 Clinical Cancer Research., 6, 3056-61, 2000.
Dias et al., "IL-12 Regulates VEGF and MMPs in a Murine Breast Cancer Model", International J. Cancer. 78, 361-5, 1998.
Liu et al., "Structure of Human Methionine Aminopeptidase-2 Complexed with Fumagillin", Science., 282, 1324-1327, 1998.
Wedge et al., "ZD4190: An Orally Active Inhibitor of Vascular Endothelial Growth Factor Signaling with Broad-Spectrum Antitumor Efficacy", Cancer Research. 60, 970-975, 2000.
Hannequin et al., "Design and Structure-Activity Relationship of a New Class of Potent VEGF Receptor Tyrosine Kinase Inhibitors", Journal of Medicinal Chemistry. 42: 5369-5389, 1999.
Fong et al., "SU5416 Is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types", Cancer Research. 59, 99-106, 1999.
Laird et al., "SU6668 Is a Potent Antiangiogenic and Antitumor Agent That Induces Regression of Established Tumorsl", Cancer Research. 60, 4152-4160, 2000.
Gingrich et al., "A New Class of Potent Vascular Endothelial Growth Factor Receptor Tyrosine . . . Clinical Candidate CEP-7055", Journal of Medicinal Chemistry. 46: 5375-88, 2003.
Beebe et al., "Pharmacological Characterization of CP-547,632, a Novel Vascular Endothelial Growth Factor Receptor-2 Tyrosine Kinase Inhibitor for Cancer Therapyl", Cancer Research. 63:7301-9, 2003.
Petti et al., "Temporal quantitation of mutant Kit tyrosine kinase signaling attenuated by a novel thiophene kinase inhibitor OSI-930", Molecular Cancer Therapeutics. 4:1186-1197, 2005.
Guo et al., "In Vitro Pharmacological Characterization of TKI-28, a Broad-Spectrum Tyrosine Kinase Inhibitor with Anti-Tumor and Anti-Angiogenic Effects", Cancer Biol Ther., 4, p. 1125-1132, 2005.
Lee et al., "In vivoTargetModulation and Biological Activity of CHIR-258, aMultitargeted Growth Factor Receptor Kinase Inhibitor, in Colon CancerModels", Clinical Cancer Research. 11, 3633-3641, 2005.
Emanuel et al., "A Vascular Endothelial Growth Factor Receptor-2 Kinase Inhibitor Potentiates the Activity of the Conventional Chemotherapeutic Agents Paclitaxel and Doxorubicin in Tumor Xenograft Models", Molecular Pharmacology. 66, 635-647, 2004.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Models1", Cancer Research. 63, 5978-5991, 2003.
Kubo et al., "Novel Potent Orally Active Selective VEGFR-2 Tyrosine Kinase Inhibitors: . . . ureas", Journal of Medicinal Chemistry. 48, 1359-1366, 2005.
Amino et al., "YM-231146, a Novel Orally Sioavailable Inhibitor of Vascular Endothelial Growth Factor Receptor-2, Is Effective against Paclitaxel Resistant Tumors", Biological and Pharmaceutical Bulletin. 28:2096-2101, 2005.
Podar et al., "GW654652, the pan-inhibitor of VEGF receptors, blocks the growth and migration of multiple myeloma cells in the bone marrow microenvironment", Blood. 103, 3474-3479, 2004.
Bainbridge et al., "A peptide encoded by exon 6 of VEGF (EG3306) inhibits VEGF-induced angiogenesis in vitro and ischaemic retinal neovascularisation in vivo", Biochem Biophys Res Commun. 302, 793-799, 2003.
Ueda et al., "VGA1155, a Novel Binding Antagonist of VEGF, Inhibits Angiogenesis In Vitro and In Vivo", Anticancer Research. 24, 3009-3017, 2004.
Wulff et al., "Luteal Angiogenesis: Prevention and Intervention by Treatment with Vascular Endothelial Growth Factor TrapA40", the Journal of Clinical Endocrinology & Metabolism. 86(7), 3377-3386, 2001.
Mohammadi et al., "Crystal structure of an angiogenesis inhibitor bound to the FGF receptor tyrosine kinase domain", EMBO J., 17, 5896-5904, 1998.
Roberts et al., "Antiangiogenic and Antitumor Activity of a Selective PDGFR Tyrosine Kinase Inhibitor, CP-673,451", Cancer Research. 65, 957-966, 2005.
Kubo et al., "A Novel Series of 4-Phenoxyquinolines: Potent and Highly Selective Inhibitors of PDGF Receptor Autophosphorylation", Bioorganic and Medicinal Chemistry Letters. 7, 2935-2940, 1997.
Wood et al., "A Unique Structure for Epidermal Growth Factor Receptor Bound to GW572016 (Lapatinib): Relationships among Protein Conformation, Inhibitor Off-Rate, and Receptor Activity in Tumor Cells", Cancer Research. 64, 6652-6659. 2004.
Nyati et al., "Radiosensitization by Pan ErbB Inhibitor CI-1033 in Vitro and in Vivo", Clinical Cancer Research. 10:691-700, 2004.
El-Abseri et al., "Chemoprevention of UV Light-Induced Skin Tumorigenesis by Inhibition of the Epidermal Growth Factor Receptor", Cancer Research. 64, 3958-3965, 2004.
Tsou et al., "Optimization of 6,7-Disubstituted-4-(arylamino)quinoline-3-carbonitriles as Orally Active, Irreversible Inhibitors of Human Epidermal Growth Factor Receptor-2 Kinase Activity", Journal of Medicinal Chemistry. 48, 1107-1131, 2005.
Experimental Medicine, Supplementary Volume, "A New Handbook of Genetic Engineering", Section 4, Yodosha, 2003(Japanese).
Cell Technology, Supplementary Volume, "Bio-Experiment Illustrated vol. 5, No Fear of Proteins", Visual Laboratory Notebook Series, Section 6, Immunostaining, pp. 127-163, Shujunsha, Co., Ltd., 1997 (Japanese).
Masferrer et al., "COX-2 Inhibitors A New Class of Antiangiogenic Agents", Annals of N.Y. Acad. Science. 889:84-6, 1999.
Bramhall, S., "The Matrix Metalloproteinases and Their Inhibitors in Pancreatic Cancer", International J. Pancreatol. 21, 1-12, 1997.
AACR American Association Cancer Research, 92nd Annual Meeting, 42:583, Mar. 24-28, 2001, New Orleans, LA, USA, 3126.
AACR American Association Cancer Research., 93nd Annual Meeting, 43:1080, Apr. 6-10, 2002, San Francisco, CA, USA, 5347.
AACR American Association Cancer Research., 96th Annual Meeting, 46, (Abstract 2031), Anaheim, Orange County, CA, USA Apr. 2005.
EORTC-NCI-AACR Symp Mol Targets Cancer Ther., 2, (Abstract 172), 2004.
AACR American Association Cancer Research, 96th Annual Meeting, 46:1407, (Abstract 5981), Anaheim, Orange County CA USA Apr. 16-20, 2005.
AACR American Association Cancer Research, 96th Annual Meeting, 46 (Abstract 3033), Anaheim, Orange County CA USA Apr. 16-20, 2005.

(56) References Cited

OTHER PUBLICATIONS

"Pharmacokinetics (PK) and tolerability of GW786034, a VEGFR tyrosine kinase inhibitor, after daily oral administration to patients with solid tumors.", Proc. Am. Soc. Clin. Oncology, (Abstract 3054), 2004.
ZK304709 (Proceedings of the American Association for Cancer Research, 46, (Abstract 5842), 2005.
EORTC-NCI-AACR Symp Mol Targets Cancer Ther., (Abstract 134), 2004.
EORTC-NCI-AACR Symp Mol Targets Cancer Ther., 2, (Abstract 151), 2004.
Proceedings of the American Association for Cancer Research, 44, 9, (Abstract 39), 2003.
Proceedings of the American Association for Cancer Research, 44, 9, (Abstract 40), 2003.
Proceedings of the American Association for Cancer Research, 45, 694, (Abstract 3005), 2004.
Proceedings of the American Association for Cancer Research, 44, 1479, (Abstract 6454), 2003.
Proc. Am. Soc. Clin. Oncology, (Abstract 776), 2003.
Am. Assoc. Cancer Research, A3394, 2005.
Am. Assoc. Cancer Research, A3405, 2005.
"Recent Results and Ongoing Trials with Panitumumab (ABF-EGF), a Fully Human Anti—Epidermal Growth Factor Receptor Antibody, in Metastatic Colorectal Cancer", Clinical Colorectal Cancer. 2005; 5(1):21-3.
Kim, T., "Technology evaluation: Matuzumab, Merck KGaA", Curr Opin Mol Ther. 2004; 6(1):96-103.
Am. Assoc. Cancer Research, Abstract 5353, 2005.
David et al., "A Phase I Trial of the Epidermal Growth Factor Receptor (EGFR)-Directed Bispecific Antibody (BsAB) MDX-447 in Patients with Solid Tumors. (Meeting abstract).", ASCO 18: 433, Abstract 1999.
The Pharmacology of Monoclonal Antibody, vol. 113, Chapter 11, Rosenburg and Moore ed., Springer Verlag (1994) pp. 269-315.
LeDoussal et al. "Bispecific-Antibody-Mediated Targeting of Radiolabeled Bivalent Haptens: Theoretical, Experimental and Clinical Results", Int. J. Cancer Suppl. 7: 58-62, 1992.
Millstein and Cuello, "Hybrid hybridomas and their use in immunohistochemistry", Nature 305: 537-9, 1983.
Am. Assoc. Cancer Res. Abstract 3399, 2005.
Proceedings of the American Association for Cancer Research, 45, 594, (Abstract 2571), 2004.
Proceedings of the American Association for Cancer Research, 44, 865, (Abstract 3780), 2003.
Decision of Rejection issued on May 29, 2012 for JP No. 2007-542863 with English translation.
Dvorakova et al., "Exon 5 of the RET proto-oncogene: A newly detected risk exon for familial medullary thyroid carcinoma, a novel germ-line mutation Gly321Arg", Journal of Endocrinological Investigation, 28, 905-909, 2005.
Kinlaw et al., "Multiple endocrine neoplasia 2A due to a unique C6095 RET mutation presents with pheochromocytoma and reduced penetrance of medullary thyroid carcinoma", Clin Endocrinol, 69, 676-682, 2005.
Dourisboure et al, "Penetrance and Clinical Manifestations of Non-Hotspot Germ line RET Mutation, C630R, in a Family with Medullary Thyroid Carcinoma", Thyroid, 15, 668-671, 2005.
Kruckeberg et al., "Pyrosequencing Technology as a Method for the Diagnosis of Multiple Endocrine Neoplasia Type 2", Clinical Chemistry, 50, 522-529, 2004.
Bartsch et al., "A RET double mutation in the germline of a kindred with FMTC", Exp. Clin Endocrinol Diabetes, 108, 128-132, 2000.
Fugazzola et al., "Molecular and biochemical analysis of RET/PTC4, a novel oncogenic rearrangement between RET and ELE1 genes, in a post-Chernobyl papillary thyroid cancer", Oncogene, 13, 1093-1097, 1996.
Hara et al., "Amplification of c-myc, K-sam, and c-met in Gastric Cancers: Detection by Fluorescence In Situ Hybridization", Laboratory Investigation, 78, 1143-1153, 1998.

Office Action issued for JP Appl. No. 2007-529565 issued on May 8, 2012 with English translation.
Response to EP OA for EP 07806561.2 filed on Apr. 18, 2012.
Response to CN OA for CN200880003336.6 filed on May 3, 2012.
Response to IL OA for IL 195282 filed on May 28, 2012.
Response to AU OA for AU 2008211952 filed on Jun. 28, 2012.
Heinemann, V., et al., "Comparison of the Cellular Pharmacokinetics and Toxicity . . . 1-beta-d-Arabinofuranosylcytosine", Cancer Research, 48, 4024-4031, 1988.
Hertel LW., et al., "Evaluation of the Antitumor Activity of Gemcitabine (2',2' -Difluoro-2'-deoxycytidine)", Cancer Research, 50, 4417-4422, 1990.
IPRP (PCT/JP2008/051024)dated Jul. 21, 2009, with English translation.
Office Action issued for CN 200880002425.9 on Mar. 2, 2011 with English translation.
Argument and Amendment for CN 200880002425.9 filed on Jul. 18, 2011 with English translation.
Office Action for CN 200880002425.9 issued on Mar. 7, 2012 with English translation.
Office Action for IL 199907 issued on Jun. 17, 2010 with English translation.
Response to Office Action for IL 199907 filed on Oct. 11, 2010 with English translation.
Office Action issued for EP06768437.3 (EPO Form1224) issued on Oct. 28, 2010.
Response to OA for EP10015141 filed on Mar. 5, 2012.
PCT/JP2006/0315563 Written Opinion of the International Searching Authority dated Feb. 5, 2008, with English translation.
PCT/JP2006/315563 International Preliminary Report on Patentability dated Feb. 5, 2008, with English translation.
PCT/JP2006/0315698 Written Opinion of the International Searching Authority, dated Feb. 5, 2008, with English translation.
PCT/JP2006/315698 International Preliminary Report on Patentability with dated Feb. 5, 2008, English translation.
Communication (Notice of Allowance) for EP06782407.8 dated Jun. 20, 2012.
Submission of Documents re UAa201203132, dated May 22, 2012 with English translation.
Office Letter for ZA 2011/08697, dated May 25, 2012.
Response to OA for U.S. Appl. No. 12/439,339, filed Jul. 30, 2012.
Submission of Documents for CO 12-022608 dated Jun. 12, 2012.
Chinese Office Action for CN 200680020317.5 dated Aug. 3, 2012 with English translation.
Sihto, H., "KIT and Platelet-Derived Growth Factor Receptor Alpha Tyrosine Kinase Gene Mutations and KIT Amplifications in Human Solid Tumors", 23 J. Clin. Oncol. 49-57 (Jan. 1, 2005).
European Search Report for EP 08704376.6 dated Jun. 14, 2012.
Response to Office Action for U.S. Appl. No. 13/083,338, filed Sep. 6, 2012.
De Lange et al., "Phase II trial of cisplatin and gemcitabine in patients with advanced gastric cancer", Annals of Oncology, Kluwer, Dordrecht, NL, 15(3): 484-488, Mar. 1, 2004, XP002511249.
Office Action for IL 199907 issued on Apr. 22, 2012 with English translation.
Response to Chinese Office Action filed for CN 200880115011.7 dated Jul. 5, 2012, with English translation.
Japanese Office Action for JP2009-123432 dated Sep. 4, 2012, with English translation.
Response to Chinese Office Action for CN 200680020317.5 dated Sep. 11, 2012, with English translation.
Official Letter for CA Patent Application No. 2627598 dated Sep. 19, 2012.
Schlumberger et al., "A Phase 2 Trial of the Multi-Targeted Kinase Inhibitor Lenvatinib(E7080) In Advanced Medullary Thyroid Cancer (MTC)", 2012 ASCO Annual Meeting, Poster Presentation, Jun. 1-5, 2012.
Funahashi et al., "P-2123, Lenvatinib treatment of differentiated thyroid cancer (DTC): Analysis to identify biomarkers associated with response", The 71st Annual Meeting of the Japanese Cancer Association, p. 339, Sep. 19-21, 2012.

(56) References Cited

OTHER PUBLICATIONS

Tohyama et al., "P-3111, Preclinical effect of lenvatinib on human thyroid cancer targeting angiogenesis and receptor tyrosine kinase signaling", The 71st Annual Meeting of the Japanese Cancer Association, p. 502, Sep. 19-21, 2012.
Chinese Office Action for CN 200880003336.6 dated Sep. 5, 2012, with English translation.
Chinese Office Action for CN 200880115011.7 dated Sep. 5, 2012, with English translation.
Notice of Allowance for U.S. Appl. No. 12/986,638, Sep. 25, 2012.
Response to Chinese Office Action filed for CN 200880003336.6 dated Jul. 11, 2012, with English translation.
Office Action for U.S. Appl. No. 13/322,961 dated Sep. 25, 2012.
Office Action for CN 200780017371.9 dated Sep. 28, 2012 with English translation.
Office Action for JP 2008-516724 dated Oct. 9, 2012 with English translation.
Office Action for IL 200090 dated Oct. 15, 2012 with English translation.
Office Action (Notice of Allowance) for EP 06782407.8 dated Nov. 2, 2012.
Office Action (Notice of Allowance) for EP 07806561.2 dated Nov. 2, 2012.
Office Action for JP 2008-532141 dated Nov. 13, 2012 with English translation.
Examination Report for NZ Patent Application No. 598291 dated Oct. 15, 2012.
Office Action for CN 200980103218.7 dated Sep. 29, 2012 with English translation.
Office Action for EP07743994.1 dated Oct. 10, 2012.
Response to Office Action for CN200880115011.7 dated Nov. 20, 2012 with English translation.
Office Action for U.S. Appl. No. 13/083,338 dated Nov. 23, 2012.
Response to Office Action for JP2011-527665 dated May 10, 2012 with English translation.
Explanation of Circumstances re Accelerated Examination filed for JP2011-527665 dated May 10, 2012 with English translation.
Office Action for IN 1571/CHENP/2007 dated Oct. 30, 2012.
Office Action for AU 2008325608 dated Nov. 24, 2012.
Response to Office Action for IL Patent Application No. 175363 dated Feb. 27, 2013.
Notice of Allowance for AU Application No. 2008325608 dated Feb. 27, 2013.
Communication from Israel Patent Office for IL 175363 dated Jan. 2, 201 (with English translation).
Response to Office Action for Canadian Patent Application No. 2627598 dated Jan. 25, 2013.
Office Action for Australian Patent Application No. 2009210098 dated Jan. 30, 2013.
Response to Office Action for European Application No. 07743994.1 dated Feb. 8, 2013.
Request to amend specification for Australian Patent Application No. 2008325608 dated Feb. 15, 2013.
Response to Office Action for Chinese Patent Application No. 200780017371.9 dated Nov. 30, 2012 (with English translation).
European Search Report for EP 12195436.6 dated Feb. 21, 2013.
Office Action for Israel Patent Application No. 175363 dated Jan. 2, 2013.
Amendment for New Zealand Patent Application No. 598291 dated Jan. 30, 2013.
Amendment for Chinese Patent Application No. 201080030508.6 dated Feb. 7, 2013 (with English translation).
Notice of Allowance for U.S. Appl. No. 12/741,682 dated Feb. 19, 2013.
Response to Office Action for IL Application No. 205512 dated Mar. 14, 2013 (with English translation).
Communication (Notification on Defects in application) for IL Application No. 207089 dated Jan. 6, 2013 (with English translation).
Office Action from CN Patent Application No. 200880115011.7 dated Feb. 25, 2013 (with English translation).
Communication (Notice of Allowance) for CA Patent Application No. 2627598 dated Mar. 8, 2013.
Notice of Acceptance for NZ Application No. 598291 dated Feb. 15, 2013.
Kawano et al., "Presentation Abstract, Abstract Number; 1619,- Combination of VEGFR inhibitor lenvatinib (E7080) and Met/EphB4 inhibitor golvatinib (E7050) overcomes VEGFR inhibitor— resistant I tumor vascular", Annual Meeting 2013, Walter E. Washington Convention Center, Washington, DC, Apr. 6-10, 2013.
Response to Office Action for CN Application No. 200980103218.7 dated Feb. 16, 2013 (with English translation ).
Office Action for U.S. Appl. No. 13/624,278 dated Mar. 29, 2013.
Preliminary Amendment for U.S. Appl. No. 13/624,278, filed Sep. 21, 2012.
Response to Office Action for U.S. Appl. No. 13/083,338, filed Apr. 2, 2013.
Response to Office Action for IL 200090 dated Dec. 23, 2012( with English translation).
European Search Report for EP 10809938.3 dated Jan. 2, 2013.
Office Action for CN 201080030508.6 dated Nov. 30, 2012 (with English translation).
Response to Office Action for EP 08704376.6 dated Jan. 2, 2013.
Response to Office Action for EP 08846814.5 dated Jan. 3, 2013.
Office Action for U.S. Appl. No. 13/083,338 dated Jan. 3, 2013.
Clinical Trial: AMG 706 20040273 Thyroid Cancer Study, Stage 4 Cancer Treatments, Chat w/a Cancer Info Expert About Stage 4 Cancer Treatment Options. Www.CancerCenter.com, Jul. 2005.
Polverino et al., "AMG 706, an Oral, Multikinase Inhibitor that Selectively Targets Vascular Endothelial Growth Factor, Platelet-Derived Growth Factor, and Kit Receptors, Potently Inhibits Angiogenesis and Induces Regression in Tumor Xenografts", Cancer Research, 66(1):8715-8721, Sep. 1, 2006.
Office Action for IL 205512 dated Dec. 20, 2012 (with English translation).
Submission to European Patent Office for EP03791389.4 dated Dec. 20, 2012.
Communication from Israel Patent Office for IL 175363 dated Jan. 2, 2013 . (with English translation).
Amendment submitted for Korean Application No. 10-2009-7017694 dated Jan. 18, 2013 (with English translation).
Response to Office Action for U.S. Appl. No. 13/322,961 dated Jan. 25, 2013.
Decision of Patent Grant for JP2008-516724 dated Jan. 22, 2013 (with English translation).
Office Action for JP2008-556208 dated Jan. 22, 2013 (with English translation).
International Preliminary Report on Patentability for PCT/JP2011/064430 dated Jan. 24, 2013 (with English translation).
Communication from Israel Patent Office for IL 175363 dated Jan. 2, 2013 (with English translation).
Corrected English Translation for Office Action for JP Patent Application No. 2007-529565 dated Aug. 7, 2012.
Bernex et al., "Spatial and temporal patterns of c-kit-expressing cells in WlacZ/+ and WlacZ/WlacZ mouse embryos", Development 122:3023-3033 (1996).
Office Action from CN Patent Application No. 200780017371.9 dated Mar. 14, 2013 (with English translation).
Response to Office Action for IN Patent Application No. 1571/CHENP/2007 dated Apr. 10, 2013.
Office Action for U.S. Appl. No. 11/997,719 dated Apr. 8, 2013.
Office Action for CN Patent Application No. 201080030508.6 dated Apr. 9, 2013 (with English translation).
Office Action for CA Application No. 2652442 dated Apr. 16, 2013.
Office Action for IL Patent Application No. 217197 dated Apr. 11, 2013 (with English translation).
Response to Office Action for IL Application No. 207089 dated Apr. 22, 2013 (with English translation).
Preliminary Amendment for U.S. Appl. No. 13/870,507, filed Apr. 26, 2013.
Communication (Notice of Allowance) for EP Application No. 04818213.3 dated May 6, 2013.

(56) References Cited

OTHER PUBLICATIONS

Request to amend specification for Australian Patent Application No. 2009210098 dated May 9, 2013.
Amendment and RCE for U.S. Appl. No. 12/741,682 dated May 17, 2013.
Supplementary Observation for CN Application No. 200980103218.7 dated Mar. 13, 2013 (with English translation).
Response to Office Action for CN Application No. 200880115011.7 dated Apr. 11, 2013 (with English translation).
Office Action for EP08846814.5 dated Apr. 16, 2013.
Office Action for KR 10-2008-7013685 dated May 20, 2013 (with English translation).
Office Action for JP2008-532141 dated May 21, 2013 (with English translation).
Office Action for U.S. Appl. No. 12/439,339 dated May 23, 2013.
Applicant Interview Summary for U.S. Appl. No. 12/439,339 dated May 23, 2013.
Response to Office Action for CN201080030508.6 dated May 27, 2013 (with English translation).
Request for Substantive Examination for UA a201203132 dated Apr. 15, 2013 (with English translation).
Request for Substantive Examination for ID W-00201201031 dated Jun. 3, 2013 (with English translation).
Notice of Acceptance (Notice of Allowance) for AU2009210098 dated Jun. 4, 2013.
Notice of Allowance for U.S. Appl. No. 13/083,338 dated Jun. 4, 2013.
"Amendment and Response to Office Action Under 37 C.F.R. §1.111" submitted for U.S. Appl. No. 13/624,278, dated Jun. 28, 2013.
Notice of Allowance for CN Patent Application No. 200980103218.7 dated May 27, 2013 (with English translation).
Office Action for IL Application No. 195282 dated Apr. 10, 2013 (with English translation).
Notice of Allowance for U.S. Appl. No. 13/205,328 dated Jun. 10, 2013.
U.S. Appl. No. 13/923,858, filed Jun. 21, 2013.
Koyama et al., "Anti-tumor effect of E7080, a novel angiogenesis inhibitor", Folia Pharmacol. Jpn. 132, Therapeutic Agents Series (28), Molecular Target Drugs-1-1, p. 100-p. 104, Apr. 18, 2008.
Haiyi Jiang, "ZD6474: an Agent That Selectively Targets Both VEGFR Tyrosine Kinase and EGFR Tyrosine Kinase", Japanese Journal of Lung Cancer, vol. 46, No. 3, Jun. 20, 2006, p. 283-p. 288.
Stefan Frings, "New Molecular Targeted Therapeutic Drugs Clinical Results of Bevacizumab in Non-Small Cell Lung Cancer (NSCLC)", Japanese Journal of Lung Cancer, vol.46, No. 3, Jun. 20, 2006, p. 277-p. 281.
Lumi Chikahisa et al., "TSU-68 JDR/flk-inhibitor, can modulate the anti-tumor activity of paclitaxel by the induction of endothelial cell and tumor cell apoptosis", 61st Annual Meeting of Japanese Cancer Association, 2002, vol. 61, No. 1374, 2002, p. 443.
Office Action for JP2009-551518 dated Jun. 18, 2013 (with English translation).
The Argument and the Amendment for JP Patent Application No. 2008-532141 filed on Nov. 29, 2012, (with English translation).
The Argument and the Amendment for JP Patent Application No. 2008-556208 filed on Mar. 21, 2013, (with English translation).
The Argument and the Amendment for JP Patent Application No. 2008-516724 filed on Nov. 28, 2012, (with English translation).
The Explanation of Circumstances Concerning Accelerated Examination and the Amendment filed on May 10, 2012 for JP Patent Application No. 2011-527665 (with English translation).
The Argument and the Amendment for JP Patent Application No. 2009-123432 filed on Jun. 12, 2012, (with English translation).
The Argument and the Amendment for JP Patent Application No. 2009-529019 filed on Jul. 3, 2012, (with English translation).
Response to Office Action for CN Application No. 200780017371.9 dated May 29, 2013 (with English translation).
Response to Office Action for U.S. Appl. No. 11/997,719, filed Jul. 3, 2013.
Office Action for JP Application No. 2009-540099 dated Jul. 2, 2013 (with English translation).
Notice of Allowance for CN Patent Application No. 201080030508.6 dated Jul. 4, 2013 (with English translation).
Notice of Allowance for JP Patent Application No. P2008-0556208 dated Jul. 9, 2013 (with English translation).
Matsui et al., "Extracellular matrix of linitis plastica as possible new therapeutic target", Surgical treatment 89(3):301-306 (Sep. 1, 2013) (with English translation).
Amendment for Application No. IL Patent Application No. 195282 dated Jul. 11, 2013 (with English translation).
Amended Claims for KR Patent Application 10-2010-7011023 dated Jul. 17, 2013 (with English translation).
Communication for EP Patent Application No. 10809938.3 dated Jul. 19, 2013.
Notice of Allowance for EP Patent Application No. 10015141.4 dated Jul. 1, 2013.
Response to Office Action for IL Patent Application No. 217197 dated Jul. 31, 2013 (with English translation).
Response to Communication for EP Patent Application No. 08846814.5 dated Aug. 1, 2013.
Office Action for CN Patent Application No. 200780017371.9 dated Jul. 3, 2013 (with English translation).
Office Action for MX Patent Application No. MX/a/2012/002011 dated Jul. 17, 2013 (with English translation).
Amendment (amending specification) for AU Patent Application No. 2012246490 dated Aug. 2, 2013.
Response to Office Action for EP Application No. 11798224.9 dated Aug. 2, 2013.
Nishio et al., "Phase 1 study of lenvatinib combined with carboplatin and paclitaxel in patients with non-small-cell lung cancer", British Journal of Cancer (2013), 109:538-544.
Amendment submitted for Korean Application No. 10-2008-7013685 dated Jul. 5, 2013 (with English translation).
Voluntary amendment for CA Patent Application No. 2704000 dated Aug. 6, 2013.
Amendment filed for JP Patent Application 2008-532141 dated Jul. 5, 2013 (with English translation).
Demand for Appeal Trial for JP Patent Application 2008-532141 dated Jul. 5, 2013 (with English translation).
Notice of Allowance for IL Patent Application No. 175363 dated Aug. 13, 2013 (with English translation).
Amendment filed for EP Application No. 12774278.1 dated Aug. 13, 2013.
Office Action for IL Patent Application No. 200090 dated Jul. 24, 2013 (with English translation).
Response to Office Action for U.S. Appl. No. 12/439,339 dated Aug. 22, 2013.
Communication to the Patent Office for CL Application No. 2012-00412 dated Aug. 31, 2012 (with English translation).
Communication to the Patent Office for AR Application No. P110100513 dated Aug. 27, 2013 (with English translation).
Notice of Allowance for U.S. Appl. No. 12/741,682 dated Jun. 19, 2013.
RCE and IDS filed for U.S. Appl. No. 13/083,338, filed Aug. 28, 2013.
Office Action for U.S. Appl. No. 13/238,085 dated Sep. 6, 2013.
Response to Office Action for MX Patent Application No. MX/a/2012/002011 dated Aug. 29, 2013 (with English Translation).
Final Office Action for U.S. Appl. No. 12/039,381 dated Sep. 12, 2013.
Preliminary Amendment for U.S. Appl. No. 14/002,018, filed Aug. 28, 2013.
Amended Claims for RU Patent Application No. 2013140169 dated Aug. 29, 2013 (with English translation).
Notice of Allowance for CN Application No. 200880115011.7 dated Aug. 5, 2013 (with English translation).
Amendment filed for JP Patent Application No. 2009-551518 dated Aug. 6, 2013 (with English translation).
Argument filed for JP Patent Application No. 2009-551518 dated Aug. 6, 2013 (partial English translation).
Response to Office Action for CA Patent Application No. 2652442 dated Sep. 5, 2013.

(56) References Cited

OTHER PUBLICATIONS

Amendment to claims for IN Patent Application No. 7026/CHENP/2013 dated Sep. 5, 2013.
Amendment filed for JP Patent Application No. 2009-540099 dated Aug. 13, 2013 (with English translation).
Argument filed for JP Patent Application No. 2009-540099 dated Aug. 13, 2013 (with partial English translation).
Preliminary Amendment filed for U.S. Appl. No. 13/805,826 dated Sep. 9, 2013.
Request for Continued Examination and Information Disclosure Statement for U.S. Appl. No. 13/205,328 dated Sep. 10, 2013.
Notice of Allowance for JP Patent Application No. P2008-532141 dated Sep. 10, 2013 (with English translation).
Amendments for CN Patent Application No. 201280010898.X dated Aug. 29, 2013 (with English translation).
Notice of Allowance for U.S. Appl. No. 13/624,278 dated Sep. 16, 2013.
Notice of Allowance for EP Patent Application No. 04818213.3 dated Sep. 19, 2013.
Request for Continued Examination and Information Disclosure Statement for U.S. Appl. No. 12/741,682, filed Sep. 19, 2013.
Amendment of Specification for AU Patent Application No. 2011270165 dated Sep. 23, 2013.
Office Action for PH Application No. 1-2011-502441 dated Oct. 1, 2013.
Amendment for IN Patent Application No. 10502/CHENP/2012 dated Oct. 1, 2013.
Response to Opposition for CL Patent Application No. 2012-00412 dated Oct. 2, 2013 (with English translation).
Office Action for KR 10-2008-7029472 dated Sep. 30, 2013 (in Korean).
Office Action for KR 10-2008-7029472 dated Sep. 30, 2013 (with English translation).
Ezzat et al., "Dual Inhibition of RET and FGFR4 Restraints Medullary Thyroid Cancer Cell Growth", Clinical Cancer Research, 11:1336-1341 (2005).
Sattler et al., "Targeting c-Kit mutations: basic science to novel therapies", Leukemia Research, 28S1:S11-S20 (2004).
Office Action for KR10-2009-7005657 dated Sep. 30, 2013 (in English).
Office Action for KR10-2009-7005657 dated Sep. 30, 2013 (in Korean).
Notice of Allowance for U.S. Appl. No. 13/205,328 dated Oct. 3, 2013.
Response to Restriction Requirement for U.S. Appl. No. 13/238,085, filed Oct. 4, 2013.
Amendment for KR Patent Application No. 10-2012-7033886 dated Sep. 27, 2013 (with English translation).
Office Action for U.S. Appl. No. 11/997,543 dated Sep. 30, 2013.
Office Action for CO Patent Application No. 12/022,608 dated Oct. 7, 2013 (with English translation).
Notice of Allowance for U.S. Appl. No. 13/083,338 dated Sep. 26, 2013.
Amendment for IL Patent Application No. 200090 dated Oct. 2, 2013 in English.
St. Bernard et al., "Fibroblast Growth Factor Receptors as Molecular Targets in Thyroid Carcinoma", Endocrinology, 146(3):1145-1153 (2005).
Amendment filed for CA Patent Application No. 2828946 dated Aug. 30, 2013.
Notice of Allowance for U.S. Appl. No. 11/997,719 dated Sep. 13, 2013.
Amendment filed for RU Patent Application No. 2012158142 dated Oct. 17, 2013 (with English translation).
Amendment filed for MX Patent Application No. MX/a/2012/014776 dated Oct. 21, 2013.
Office Action for IN Application No. 6415/CHENP/2008 dated Oct. 3, 2013.
Request for Re-examination for CN Patent Application No. 200780017371.9 dated Oct. 11, 2013 (with English translation).
Office Action for MX Patent Application No. MX/a/2010/008187 dated Aug. 21, 2013 (with English translation).
Request for Examination and Voluntary Amendment for CA Patent Application No. 2713930 dated Oct. 21, 2013.
Notice of Allowance for U.S. Appl. No. 12/741,682 dated Oct. 21, 2013.
Response to Office Action for IN Application No. 1571/CHENP/2007 dated Oct. 30, 2013.
Request for Continued Examination and Response to Final Office Action for U.S. Appl. No. 12/039,381 dated Oct. 23, 2013.
Response to Office Action for MX Patent Application No. MX/a/2010/008187 dated Nov. 4, 2013 (with English Translation).
Response to Office Action for PH Application No. 1-2011-502441 dated Nov. 4, 2013.
IPRP for PCT/JP2012/060279 dated Oct. 31, 2013.
Notice of Allowance for U.S. Appl. No. 12/439,339 dated Nov. 7, 2013.
Notice of Allowance for JP Patent Application No. P2009-551518 dated Oct. 22, 2013 (with English translation).
Office Action for U.S. Appl. No. 13/238,085 dated Nov. 12, 2013.
Office Action for CA Patent Application No. 2652442 dated Oct. 4, 2013.
Response to Office Action for CO Patent Application No. 12-022608 dated Nov. 13, 2013 (with English translation).
Amendment for BR Patent Application No. 112012032462-4 dated Nov. 4, 2013 (with English translation).
Wang, Y., "Drugs of Today, Everolimus in renal cell carcinoma", Journals of the Web, 46(8):Abstract, Aug. 2010.
Office Action for CN Patent Application No. 201180030568.2 dated Oct. 12, 2013 (with English translation).
Office Action for in Patent Application No. 1571/CHENP/2007 dated Oct. 23, 2013.
Office Action for IL Patent Application No. 205512 dated Oct. 28, 2013 (with English translation).
Preliminary Amendment filed for U.S. Appl. No. 14/117, 276, filed Nov. 12, 2013.
Preliminary Amendment filed for EP Patent Application No. 12786619.2 dated Nov. 13, 2013.
Voluntary amendment filed for CA Patent Application No. 2802644 dated Nov. 22, 2013.
Amendment filed for KR Patent Application No. 10-2008-7029472 dated Nov. 20, 2013 (with English translation).
Amendment filed for EP Application No. 12793322.4 dated Nov. 28, 2013.
Request for Continuted Examination and Information Disclosure Statement filed for U.S. Appl. No. 13/083,338 dated Dec. 2, 2013.
Amendment for KR Patent Application No. 10-2013-7020616 dated Nov. 22, 2013 (with English translation).
IPRP of International Patent Application No. PCT-JP2012-062509 dated Nov. 28, 2013.
Decision of Patent Grant for KR Patent Application No. 10-2008-7013685 dated Nov. 29, 2013 (with English translation).
Office Action for IN Patent Application No. 1571/CHENP/2007 dated Dec. 9, 2013.
Preliminary Amendment filed for U.S. Appl. No. 14/122,339 dated Nov. 26, 2013.
Response filed for KR Application No. 10-2009-7005657 dated Nov. 21, 2013 (with English translation).
Notice of Allowance for IL Patent Application No. 200090 dated Nov. 18, 2013 (with English translation).
Office Action for MX Patent Application No. MX/a/2012/002011 dated Nov. 21, 2013 (with English translation).
Office Action for CN Patent Application No. 200680020317.5 dated Nov. 28, 2013 (with English translation).
Request for Continued Examination filed for U.S. Appl. No. 11/997,719 dated Dec. 11, 2013.
Request for Continued Examination filed for U.S. Appl. No. 13/624,278 dated Dec. 13, 2013.
Response to Office Action and Information Disclosure Statement filed for U.S. Appl. No. 11/997,543 dated Dec. 19, 2013.
Office Action of MX Patent Application No. MX-a-2010-008187 dated Dec. 5, 2013 (with English translation).

(56) References Cited

OTHER PUBLICATIONS

Office Action of CO Patent Application No. 12-022608 Dec. 17, 2013 (with English translation).
Office Action of IL Patent Application No. 207089 dated Nov. 25, 2013 (with English translation).
Request for Continued Examination filed for U.S. Appl. No. 13/205,328 dated Dec. 30, 2013.
Office Action for VN Application No. 1-2011-03484 dated Dec. 31, 2013 (with English translation).
Response to Office Action for CA Patent Application No. 2652442 dated Jan. 8, 2014.
Office Action for U.S. Appl. No. 12/039,381 dated Jan. 9, 2014.
Request for Continued Examination for U.S. Appl. No. 12/741,682 dated Jan. 17, 2014.
Response filed for IN Patent Application No. 6415/CHENP/2008 dated Jan. 17, 2014.
Response filed on Apr. 11, 2006 for CN Patent Application No. 01819710.8 with English translation.
Amendment filed on Apr. 11, 2006 for CN Patent Application No. 01819710.8 with English translation.
Office Action dated Aug. 11, 2006 for CN Patent Application No. 01819710.8 with English translation.
Response filed on Oct. 9, 2006 for CN Patent Application No. 01819710.8.
Amendment filed on Oct. 9, 2006 for CN Patent Application No. 01819710.8.
Notice of Allowance dated Dec. 15, 2006 for CN Patent Application No. 01819710.8 with.
Office Action dated Jul. 24, 2009 for CN Patent Application No. 200710007096.4.
Office Action dated Mar. 6, 2009 for CN Patent Application No. 200710007097.9.
Response filed on Jul. 2, 2009 for CN Patent Application No. 200710007097.9.
Amendment filed on Jul. 2, 2009 for CN Patent Application No. 200710007097.9.
Office Action dated Sep. 11, 2009 for CN Patent Application No. 200710007097.9 with.
Response filed on Nov. 19, 2009 for CN Patent Application No. 200710007097.9 with English translation.
Amendment filed on Nov. 19, 2009 for CN Patent Application No. 200710007097.9 with English translation.
Office Action dated Dec. 25, 2009 for CN Patent Application No. 200710007097.9 with English translation.
Response filed on Jan. 26, 2010 for CN Patent Application No. 200710007097.9 with English translation.
Amendment filed on Jan. 26, 2010 for CN Patent Application No. 200710007097.9 with English translation.
Office Action dated Apr. 27, 2010 for CN Patent Application No. 200710007097.9 with English translation.
Response filed on Jun. 22, 2010 for CN Patent Application No. 200710007097.9 with English translation.
Amendment filed on Jun. 22, 2010 for CN Patent Application No. 200710007097.9 with English translation.
Voluntary Amendment filed on Aug. 11, 2010 for CN Patent Application No. 200710007097.9 with English translation.
Notice of Allowance dated Oct. 9, 2010 for CN Patent Application No. 200710007097.9 with English translation.
Partial European Search Report for EP Patent Application No. 01976786.2; 20040406, 2004.
Supplementary European Search Report for EP Patent Application No. 01976786.2; 20040706, 2004.
Invitation to declare maintenance of the application for EP Patent Application No. 01976786.2; 20040712, 2004.
Maintenance of the application for EP Patent Application No. 01976786.2; 20040906, 2004.
Amendments received before examination for EP Patent Application No. 01976786.2; 20040910, 2004.
Communication from the Examining Division for EP Patent Application No. 01976786.2; 20050817, 2005.
Brief communication to applicant for EP Patent Application No. 01976786.2; 20050909, 2005.
Communication from the Examining Division for EP Patent Application No. 01976786.2; 20050919.
Reply to communication from the Examining Division for EP Patent Application No. 01976786.2; 20060125, 2006.
Communication from the Examining Division for EP Patent Application No. 01976786.2; 20060321, 2006.
Reply to communication from the Examining Division for EP Patent Application No. 01976786.2; 20060719, 2006.
Communication about intention to grant a European patent for EP Patent Application No. 01976786.2; 20060904, 2006.
Decision to grant a European patent for EP Patent Application No. 01976786.2; 20070201, 2007.
Communication regarding the expiry of opposition period for EP Patent Application No. 01976786.2; 20080104, 2008.
European search report for EP Patent Application No. 04025700.8; 20050113, 2005.
Communication from the Examining Division for EP Patent Application No. 04025700.8; 20060410, 2006.
Reply to communication from the Examining Division for EP Patent Application No. 04025700.8; 20060912, 2006.
Communication from the Examining Division for EP Patent Application No. 04025700.8; 20061023, 2006.
Reply to communication from the Examining Division for EP Patent Application No. 04025700.8; 20070126, 2007.
Reply to communication from the Examining Division for EP Patent Application No. 04025700.8; 20070215, 2007.
Communication about intention to grant a European patent for EP Patent Application No. 04025700.8; 20071015, 2007.
Request for amendment of the text intended for grant and translation of claims for EP Patent Application No. 04025700.8; 20080201, 2008.
Approval of request for amendments for EP Patent Application No. 04025700.8; 20080313, 2008.
Decision to grant a European patent for EP Patent Application No. 04025700.8; 20080605, 2008.
Communication regarding the expiry of opposition period for EP Patent Application No. 04025700.8; 20090507, 2009.
Deficiencies in sequence listing for EP Patent Application No. 06023078.6; 20061205, 2006.
Reply to the invitation to remedy deficiencies for EP Patent Application No. 06023078.6; 20070111, 2007.
Request for correction of errors in filed documents for EP Patent Application No. 06023078.6; 20070213, 2007.
European Search Report for EP Patent Application No. 06023078.6; 20070316, 2007.
Information about decision on request for EP Patent Application No. 06023078.6; 20070321, 2007.
Invitation to declare maintenance of the application for EP Patent Application No. 06023078.6; 20070502, 2007.
Maintenance of the application for EP Patent Application No. 06023078.6; 20070619, 2007.
Communication from Examining Division for EP Patent Application No. 06023078.6; 20070802, 2007.
Reply to communication from the Examining Division for EP Patent Application No. 06023078.6; 20070911, 2007.
Communication from the Examining Division for EP Patent Application No. 06023078.6; 20070926, 2007.
Reply to communication from the Examining Division for EP Patent Application No. 06023078.6; 20080204, 2008.
Communication about intention to grant a European patent for EP Patent Application No. 06023078.6; 20080718, 2008.
Request for amendment of the text intended for grant and translation of claims for EP Patent Application No. 06023078.6; 20081105, 2008.
Decision to grant a European patent for EP Patent Application No. 06023078.6; 20081204, 2008.
Communication regarding the expiry of opposition period for EP Patent Application No. 06023078.6; 20091104, 2009.
"Voluntary Amendment filed on Sep. 10, 2010 for HU Patent Application No. P0302603" with English translation.

(56) References Cited

OTHER PUBLICATIONS

"Office Action dated Oct. 16, 2007 for IL Patent Application No. 155447" with English translation.
"Response filed on Dec. 4, 2007 for IL Patent Application No. 155447" with English translation.
"Notice of Allowance dated Dec. 26, 2007 for IL Patent Application No. 155447" with English translation.
"Notice Prior to Examination dated Jun. 29, 2008 for IL Patent Application No. 189677" with English translation.
"Response to Notice Prior to Examination filed on Jan. 11, 2009 for IL Patent Application No. 189677" with English translation.
"Office Action dated Feb. 18, 2009 for IL Patent Application No. 189677" with English translation.
"Response filed on May 13, 2009 for IL Patent Application No. 189677"with English translation.
"Notice of Allowance dated Mar. 14, 2010 for IL Patent Application No. 189677" with English translation.
"Amendment filed on Mar. 7, 2005 for JP Patent Application No. 2002-536056" with English translation.
"Office Action dated Apr. 11, 2005 for JP Patent Application No. 2002-536056" with English translation.
"Argument filed on Apr. 19, 2005 for JP Patent Application No. 2002-536056" with English translation.
"Amendment filed on Apr. 19, 2005 for JP Patent Application No. 2002-536056" with English translation.
"Notice of Allowance dated Aug. 2, 2005 for JP Patent Application No. 2002-536056" with English translation.
"Office Action dated Jan. 27, 2009 for JP Patent Application No. 2005-124034" with English translation.
Japanese Patent Application Laid-Open No. H11-158149 with English translation, 1999.
"Argument filed on Mar. 23, 2009 for JP Patent Application No. 2005-124034"with English translation.
"Amendment filed on Mar. 23, 2009 for JP Patent Application No. 2005-124034"with English translation.
"Office Action dated Apr. 28, 2009 for JP Patent Application No. 2005-124034"with English translation.
"Argument filed on May 21, 2009 for JP Patent Application No. 2005-124034"with English translation.
"Amendment filed on May 21, 2009 for JP Patent Application No. 2005-124034"with English translation.
"Notice of Allowance dated Jul. 21, 2009 for JP Patent Application No. 2005-124034" with English translation.
"Written Amendment filed on Jun. 16, 2009 for JP Patent Application No. 2009-123432" with English translation.
"Written Statement filed on Jun. 16, 2009 for JP Patent Application No. 2009-123432" with English translation.
"Preliminary Amendment filed on May 23, 2003 for KR Patent Application No. 10-2003-7005506" with English translation.
"Office Action dated Jul. 27, 2005 for KR Patent Application No. 10-2003-7005506" with English translation.
"Argument Brief filed on Oct. 25, 2005 for KR Patent Application No. 10-2003-7005506" with English translation.
"Amendment filed on Oct. 25, 2005 for KR Patent Application No. 10-2003-7005506" with English translation.
"Office Action dated Jan. 5, 2006 for KR Patent Application No. 10-2003-7005506" with English translation.
"Argument Brief filed on Mar. 6, 2006 for KR Patent Application No. 10-2003-7005506" with English translation.
"Amendment filed on Mar. 6, 2006 for KR Patent Application No. 10-2003-7005506" with English translation.
ISR dated Jan. 15, 2002 for International Patent Application No. PCT/JP01/09221.
IPRP dated Jan. 8, 2003 for International Patent Application No. PCT/JP01/09221.
Amendment filed on Aug. 4, 2004 for ZA Patent Application No. 2003/3567.
Notice of Acceptance dated Aug. 10, 2004 for ZA Patent Application No. 2003/3567.
Amendment filed on Aug. 17, 2004 for ZA Patent Application No. 2003/3567.
Amended description filed after receipt of search report for EP Patent Application No. 10809938.3; 20111208, 2011.
"Amendment filed on Dec. 12, 2011 for JO Patent Application No. 55/2011" with English translation.
"Written Amendment filed on Sep. 21, 2011 for JP Patent Application No. 2011-527665" with English translation.
"Written Statement filed on Sep. 21, 2011 for JP Patent Application No. 2011-527665" with English translation.
Amendment filed on Oct. 28, 2011 for LB Patent Application No. 9292.
Amendment filed on Feb. 9, 2011 for TW Patent Application No. 100104281.
"Amendment filed on Dec. 15, 2011 for VN Patent Application No. 1-2011-03484" with English translation.
"ISR dated Sep. 14, 2010 for International Patent Application No. PCT/JP2010/063804".
"IPRP dated Mar. 13, 2012 for International Patent Application No. PCT/JP2010/063804".
Amendment filed on Dec. 22, 2011 for ZA Patent Application No. 2011/08697.
"Voluntary Amendment filed on Feb. 9, 2010 for AU Patent Application No. 2005283422".
"Notice of Allowance dated Apr. 29, 2010 for AU Patent Application No. 2005283422".
"Voluntary Amendment filed on Jul. 6, 2010 for AU Patent Application No. 2005283422".
"Office Action dated Jul. 15, 2011 for CA Patent Application No. 2579810".
"Response filed on Sep. 21, 2011 for CA Patent Application No. 2579810".
"Notice of Allowance dated Oct. 17, 2011 for CA Patent Application No. 2579810".
"Office Action dated Jun. 26, 2009 for CN Patent Application No. 200580026468.7" with English translation.
"Response filed on Sep. 23, 2009 for CN Patent Application No. 200580026468.7" with English translation.
"Amendment filed on Sep. 23, 2009 for CN Patent Application No. 200580026468.7" with English translation.
"Office Action dated Nov. 20, 2009 for CN Patent Application No. 200580026468.7" with English translation.
"Response filed on Jan. 11, 2010 for CN Patent Application No. 200580026468.7" with English translation.
"Amendment filed on Jan. 11, 2010 for CN Patent Application No. 200580026468.7" with English translation.
"Notice of Allowance dated Feb. 5, 2010 for CN Patent Application No. 200580026468.7" with English translation.
Communication regarding the expiry of opposition period for EP Patent Application No. 05783232.1; 20100219, 2010.
"Decision to grant a European patent for EP Patent Application No. 05783232.1; 20090319", 2009.
"Communication about intention to grant a European patent for EP Patent Application No. 05783232.1; 20081120", 2008.
"Reply to official communication for EP Patent Application No. 05783232.1; 20080430", 2008.
Communication from the Examining Division for EP Patent Application No. 05783232.1; 20080207, 2008.
Maintainance of the application for EP Patent Application No. 05783232.1; 20071109, 2007.
Invitation to declare maintenance of the application for EP Patent Application No. 05783232.1; 20070925, 2007.
European Search Report for EP Patent Application No. 05783232.1; 20070907, 2007.
Notice Prior to Examination dated Mar. 9, 2009 for IL Patent Application No. 181697 with English translation.
"Response to Notice Prior to Examination filed on Apr. 22, 2009 for IL Patent Application No. 181697" with English translation.
"Office Action dated Dec. 20, 2010 for IL Patent Application No. 181697" with English translation.
"Response filed on Jan. 26, 2011 for IL Patent Application No. 181697" with English translation.

(56) References Cited

OTHER PUBLICATIONS

"Notice of Allowance dated Nov. 14, 2011 for IL Patent Application No. 181697" with English translation.
"Notice of Allowance dated Sep. 20, 2011 for JP Patent Application No. 2006-535174" with English translation.
Japanese Patent Application Laid-Open No. S63-028427 with English translation, 1988.
Japanese Patent Application Laid-Open No. 2003-026576 with English translation, 2003.
WO00/071097 with English translation, 2000.
"Office Action dated Sep. 28, 2011 for KR Patent Application No. 10-2007-7001347" with English translation.
"Amendment filed on Nov. 24, 2011 for KR Patent Application No. 10-2007-7001347" with English translation.
Argument Brief filed on Nov. 24, 2011 for KR Patent Application No. 10-2007-7001347 with English translation.
Almarsson et al., "High-Throughput Surveys of Cyrstal Form Diversity of Highly Polymorphic Pharmaceutical Compounds", Crystal Growth & Design, pp. 927-933 (2003).
Amendment for CO Application No. 12-022608 dated Jan. 28, 2014 (with English translation).
Amendment for in Patent Application No. 1571/CHENP/2007 dated Jan. 23, 2014.
Amendment to Specification for KR Patent Application No. 10-2009-7017694 dated Feb. 28, 2014 (with English translation).
Argument for KR Patent Application No. 10-2009-7017694 dated Feb. 28, 2014 (with English translation).
European Search Report for EP 11798224.9 dated Mar. 4, 2014.
Final Office Action for U.S. Appl. No. 11/997,543 dated Mar. 11, 2014.
International Preliminary Report (IPRP) for PCT/US2012/040183 dated Apr. 3, 2014.
Notice of Allowance for CA Application No. 2652442 dated Apr. 16, 2014.
Notice of Allowance for U.S. Appl. No. 12/439,339 dated Apr. 1, 2014.
Notice of Allowance for U.S. Appl. No. 13/205,328 dated Jan. 30, 2014.
Notice of Allowance for UA Patent Application No. a201203132 dated Mar. 21, 2014 (with English translation).
Notice of Allowance for U.S. Appl. No. 12/741,682 dated Feb. 7, 2014.
Notice of Allowance for U.S. Appl. No. 13/083,338 dated Feb. 6, 2014.
Notice of Allowance for VN Application No. 1-2011-03484 dated Apr. 28, 2014 (with English translation).
Office Action for CA Application No. 2676796 dated Dec. 30, 2013.
Office Action for CN Application No. 200680020317.5 dated Mar. 4, 2014 (with English translation).
Office Action for CN Application No. 201180030568.2 dated Mar. 24, 2014 (with English translation).
Office Action for EP Application No. 04807580.8 dated Mar. 18, 2014.
Office Action for European Patent Application No. 08704376.6 dated Feb. 24, 2014.
Office Action for JP Application No. P2009-540099 dated Mar. 25, 2014 (with English translation).
Office Action for KR Application No. 10-2008-7029472 dated Mar. 28, 2014 (with English translation).
Office Action for KR Application No. 10-2009-7005657 dated Mar. 28, 2014 (with English translation).
Office Action for KR Application No. 10-2009-7017694 dated Jan. 29, 2014 (with English translation).
Office Action for PH Application No. 1-2011-502441 dated Feb. 19, 2014.
Office Action for U.S. Appl. No. 13/805,826 dated Apr. 2, 2014.
Office Action for U.S. Appl. No. 13/923,858 dated Apr. 18, 2014.
Office Action for U.S. Appl. No. 14/002,018 dated Apr. 14, 2014.
Office Action for U.S. Appl. No. 11/662,425 dated Feb. 27, 2014.
O'Reilly et al., "Hydrolysis of tert-Butyl Methyl Ether(MTBE) in Dilute—Aqueous Acid", Environ.Sci.Technol; 35, 2001, p. 3954-p. 3961.
Patel et al., "The effect of excipients on the stability of levothyroxine sodium pentahydrate tables", International Journal of Pharmaceutics; 264, p. 35-p. 43 (2003).
Request for Continued Examination for U.S. Appl. No. 12/439,339 dated Jan. 27, 2014.
Response to CN Application No. 201180030568.2 dated Jan. 13, 2014 (with English translation).
Response to Office Action for CN 2006800203175 filed on Jan. 9, 2014 (with English translation).
Response to Office Action for EP Application No. 08704376.6 dated Apr. 30, 2014.
Response to Office Action for MX Patent Application No. MX/a/2010008187 dated Feb. 17, 2014 (with English translation).
Response to Office Action for MX-a-2012-002011 dated Jan. 16, 2014 (with English translation).
Response to Office Action for Philippines Patent Application No. 1-2011-502441 dated Feb. 28, 2014.
Response to Office Action for U.S. Appl. No. 12/039,381 dated Apr. 3, 2014.
Search Report for EP Patent Application No. 11798224.9 dated Mar. 21, 2014.
Stahl and Wermuth, Handbook of Pharmaceutical Salts: Properties, Selection and Use, pp. 117-122 (2002).
Submission for VN Application No. 1-2011-03484 dated Feb. 28, 2014 (with English translation).
Winkler et al., "Kinetics of vascular normalization by VEGFR2 blockade governs brain tumor response to radiation: Role of oxygenation, angiopoietin-1, and matrix metalloproteinases", Cancer Cell vol. 6:553-563 (2004).
Zhang et al. "Synergic antiproliferative effect of DNA methyltransferase inhibitor in combination with anticancer drugs in gastric carcinoma", Cancer Science, vol. 97, No. 9, Sep. 2006, p. 938-p. 944.
Official Letter for SG 201108602-2 dated Aug. 8, 2012.
Office Action for U.S. Appl. No. 13/083,338 dated Jun. 8, 2012.

\* cited by examiner

COMPOSITION FOR TREATMENT OF UNDIFFERENTIATED GASTRIC CANCER

FIELD OF THE INVENTION

The present invention relates to a therapeutic agent, a kit and a therapeutic method for undifferentiated gastric cancer. The therapeutic agent comprises a combination of a substance having the activity of inhibiting the kinase activity of a fibroblast growth factor receptor 2 (hereinafter also referred to as "FGFR2") and a therapeutic substance for gastric cancer or a FGFR2 inhibitor different from the former FGFR2 inhibitor. The substance having such inhibitory activity is hereinafter also referred to as a "FGFR2 inhibitor". The present invention relates to use of a FGFR2 inhibitor for producing the therapeutic agent and to a FGFR2 inhibitor for the therapeutic agent.

In addition, the present invention relates to a pharmaceutical composition and a kit comprising a combination of a FGFR2 inhibitor for administration to a living organism comprising at least one selected from the group consisting of a cell overexpressing FGFR2 and a cell expressing mutant FGFR2 and a therapeutic substance for gastric cancer or a FGFR2 inhibitor different from the former FGFR2 inhibitor, to a therapeutic method for a disease characterized by administering effective dosages of a FGFR2 inhibitor and a therapeutic substance for gastric cancer or a FGFR2 inhibitor different from the former FGFR2 inhibitor to the living organism, to use of a FGFR2 inhibitor for producing the pharmaceutical composition and to a FGFR2 inhibitor for the pharmaceutical composition.

BACKGROUND OF THE INVENTION

Gastric cancer is one of the major cancers that cause death. Gastric cancers are histopathologically classified into differentiated gastric cancers and undifferentiated gastric cancers, where the latter includes poorly differentiated adenocarcinoma, signet-ring cell carcinoma, mucinous carcinoma and the like.

In the case of undifferentiated gastric cancer, cancer cells are likely to diffuse and also likely to develop fibrosis that leads to scirrhous gastric cancer. Undifferentiated gastric cancer is commonly observed in young people, and is known to cause invasive proliferation and metastasis, indicating a poor prognosis[1].

FGFR2 (also referred to as "K-sam") is amplified in diffuse-type gastric cancer, namely, undifferentiated gastric cancer and is known to be involved in malignant alteration of cancer[1,2]. FGFR2 gene is reported to be amplified in 33% of patients with undifferentiated gastric cancer[2], and FGFR2 is reported to be positive in about 50% of patients with undifferentiated gastric cancer[1]. FGFR2 gene induces transformation of NIH3T3 cell, and the transformed cell is reported to show tumorigenicity in nude mice[3]. Furthermore, FGFR2 truncated at C-terminal is reported to have a strong transformation activity and predominantly expressed in undifferentiated gastric cancer cell line[1,3]. For example, FGFR2 having residues downstream from tyrosine at 769 deleted is reported to have a high transformation activity[3].

It is also reported that FGFR2 gene is amplified in poorly differentiated gastric cancer, particularly scirrhous gastric cancer, while FGFR2 protein having C-terminal (including tyrosine residues 780, 784 and 813) deleted is specifically expressed in scirrhous gastric cancer[4]. Amplification of activated FGFR2 is reported to cause tumor growth in scirrhous gastric cancer[4].

Examples of conventionally-used chemotherapeutic substances for gastric cancer include 5-fluorouracil analogs and paclitaxel analogs. None of them, however, have satisfactory anti-tumor effect and thus there has been a strong need for development of a novel anti-tumor agent.

A FGFR2 inhibitor, diphenylamine derivative, is recently reported to dose-dependently suppress cell growth of a human scirrhous gastric cell line and show anti-tumor effect on a subcutaneous transplanted (xenograft) model of human scirrhous gastric cell line[5].

A FGFR2 inhibitor, 4-[(4-fluoro-2-methylindol-5-yl)oxy]-6-methoxy-7-[3-(pyrrolidin-1-yl)propoxy]quinazoline, is suggested to be effective on gastric cancer overexpressing K-sam[6].

Accordingly, a FGFR2 inhibitor is suggested to show anti-proliferative action and anti-tumor effect on undifferentiated gastric cancers, preferably poorly differentiated adenocarcinoma, signet-ring cell carcinoma, mucinous carcinoma and scirrhous gastric cancer.

Here, a compound represented by General Formula (I) is known as an antiangiogenic substance[7-9]. However, there is no report that the compound represented by General Formula (I) has a FGFR2 inhibitory activity.

Moreover, there has been no report as to whether a combination of these compounds will bring any effect.

REFERENCES (1) Clinical Cancer Research. 2(8), 1373-1381, 1996.
(2) Journal of Cancer Research and Clinical Oncology. 127, 207-216, 2001.
(3) Cancer Research. 54, 3237-3241, 1994.
(4) Cancer Research. 59(24), 6080-6086, 1999.
(5) Bioorganic and Medicinal Chemistry Letters. 14(4), 875-879, 2004.
(6) Proceeding of the American Association for Cancer Research. 47, 890, 2006.
(7) International Publication No. WO02/32872
(8) International Publication No. WO2004/080462
(9) International Publication No. WO2005/063713

DISCLOSURE OF THE INVENTION

The present invention was achieved regarding the circumstances described above and the problems to be solved by the invention are to provide a therapeutic agent, a kit and a therapeutic method for undifferentiated gastric cancer, and to provide a pharmaceutical composition, a kit and a therapeutic method which are more effective on a living organism comprising at least one selected from the group consisting of a cell overexpressing FGFR2 and a cell expressing mutant FGFR2.

In order to solve the above problems, the inventors have gone through keen examination, as a result of which the inventors found that a compound represented by General formula (I), a pharmacologically acceptable salt thereof or a solvate thereof has a FGFR2 inhibitory activity. The inventors also found that a compound represented by General formula (I), a pharmacologically acceptable salt thereof or a solvate thereof is more effective on undifferentiated gastric cancer. Furthermore, the inventors found that a compound represented by General formula (I), a pharmacologically acceptable salt thereof or a solvate thereof is more effective on a living organism comprising at least one selected from the group consisting of a cell overexpressing FGFR2 and a cell expressing mutant FGFR2. As a result of further research based on these findings, the inventors found that a compound represented by General formula (I), a pharmacologically acceptable salt thereof or a solvate thereof has a superior anti-tumor effect when used in combination with a therapeutic substance for gastric cancer as compared with that obtained with the therapeutic substance for gastric cancer alone in subcutaneous transplanted (xenograft) models (in vivo) of human scirrhous gastric cancer cell lines. Hence, a FGFR2 inhibitor, for example, a compound represented by General formula (I), a pharmacologically acceptable salt thereof or a solvate thereof appears to show an excellent anti-tumor effect when used in combination with a therapeutic substance for gastric cancer and thus found that a combination of a FGFR2 inhibitor and a therapeutic substance for gastric cancer may be used as an effective therapeutic agent and kit for undifferentiated gastric cancer, and for undifferentiated gastric cancer.

Thus, the present invention relates to the followings.

(1) A therapeutic agent for undifferentiated gastric cancer comprising a compound represented by General Formula (I), a pharmacologically acceptable salt thereof or a solvate thereof in combination with a therapeutic substance for gastric cancer or a FGFR2 inhibitor.

(2) A pharmaceutical composition for administration to a living organism comprising at least one selected from the group consisting of a cell overexpressing FGFR2 and a cell expressing mutant FGFR2, the pharmaceutical composition comprising a compound represented by General Formula (I), a pharmacologically acceptable salt thereof or a solvate thereof in combination with a therapeutic substance for gastric cancer or a FGFR2 inhibitor.

(3) A method for treating undifferentiated gastric cancer, characterized by administering effective dosages of a compound represented by General Formula (I), a pharmacologically acceptable salt thereof or a solvate thereof and a therapeutic substance for gastric cancer or a FGFR2 inhibitor to a living organism.

(4) A method for treating a disease, characterized by administering effective dosages of a compound represented by General Formula (I), a pharmacologically acceptable salt thereof or a solvate thereof and a therapeutic substance for gastric cancer or a FGFR2 inhibitor to a living organism comprising at least one selected from the group consisting of a cell overexpressing FGFR2 and a cell expressing mutant FGFR2.

(5) Use of a compound represented by General Formula (I), a pharmacologically acceptable salt thereof or a solvate thereof for producing a therapeutic agent for undifferentiated gastric cancer in combination with a therapeutic substance for gastric cancer or a FGFR2 inhibitor.

(6) Use of a compound represented by General Formula (I), a pharmacologically acceptable salt thereof or a solvate thereof for producing a pharmaceutical composition in combination with a therapeutic substance for gastric cancer or a FGFR2 inhibitor for administration to a living organism comprising at least one selected from the group consisting of a cell overexpressing FGFR2 and a cell expressing mutant FGFR2.

(7) A compound represented by General Formula (I), a pharmacologically acceptable salt thereof or a solvate thereof for treating undifferentiated gastric cancer in combination with a therapeutic substance for gastric cancer or a FGFR2 inhibitor.

(8) A compound represented by General Formula (I), a pharmacologically acceptable salt thereof or a solvate thereof for administration in combination with a therapeutic substance for gastric cancer or a FGFR2 inhibitor to a living organism comprising at least one selected from the group consisting of a cell overexpressing FGFR2 and a cell expressing mutant FGFR2.

(9) A kit comprising:

(a) at least one selected from the group consisting of a packaging container, an instruction and a package insert describing use of a compound represented by General Formula (I), a pharmacologically acceptable salt thereof or a solvate thereof in combination with a therapeutic substance for gastric cancer or a FGFR2 inhibitor; and (b) a therapeutic agent for undifferentiated gastric cancer comprising a compound represented by General Formula (I), a pharmacologically acceptable salt thereof or a solvate thereof.

(10) A kit comprising:

(a) at least one selected from the group consisting of a packaging container, an instruction and a package insert describing use of a compound represented by General Formula (I), a pharmacologically acceptable salt thereof or a solvate thereof in combination with a therapeutic substance for gastric cancer or a FGFR2 inhibitor; and (b) a pharmaceutical composition comprising a compound represented by General Formula (I), a pharmacologically acceptable salt thereof or a solvate thereof for administration to a living organism comprising at least one selected from the group consisting of a cell overexpressing FGFR2 and a cell expressing mutant FGFR2.

(11) A kit characterized by a set of a therapeutic agent for undifferentiated gastric cancer comprising a compound represented by General Formula (I), a pharmacologically acceptable salt thereof or a solvate thereof and a formulation comprising a therapeutic substance for gastric cancer or a FGFR2 inhibitor.

(12) A kit used for administration to a living organism comprising at least one selected from the group consisting of a cell overexpressing FGFR2 and a cell expressing mutant FGFR2, the kit characterized by a set of a formulation comprising a compound represented by General Formula (I), a pharmacologically acceptable salt thereof or a solvate thereof and a formulation comprising a therapeutic substance for gastric cancer or a FGFR2 inhibitor.

(13) A therapeutic agent for undifferentiated gastric cancer comprising a compound represented by General Formula (I), a pharmacologically acceptable salt thereof or a solvate thereof, characterized by administration to a living organism with a therapeutic substance for gastric cancer or a FGFR2 inhibitor.

(14) A pharmaceutical composition for administration to a living organism comprising at least one selected from the group consisting of a cell overexpressing FGFR2 and a cell expressing mutant FGFR2, the pharmaceutical composition comprising a compound represented by General Formula (I), a pharmacologically acceptable salt thereof or a solvate thereof, characterized by administration to the living organism with a therapeutic substance for gastric cancer or a FGFR2 inhibitor.

Furthermore, the present invention preferably relates to the followings.

(15) A therapeutic agent for undifferentiated gastric cancer comprising 4-(3-chloro-4-(cyclopropylaminocarbonyl)aminophenoxy)-7-methoxy-6-quinolinecarboxamide, a pharmacologically acceptable salt thereof or a solvate thereof in combination with a therapeutic substance for gastric cancer or a FGFR2 inhibitor.

(16) A pharmaceutical composition for administration to a living organism comprising at least one selected from the group consisting of a cell overexpressing FGFR2 and a cell expressing mutant FGFR2, the pharmaceutical composition comprising 4-(3-chloro-4-(cyclopropylaminocarbonyl)aminophenoxy)-7-methoxy-6-quinolinecarboxamide, a pharmacologically acceptable salt thereof or a solvate thereof in combination with a therapeutic substance for gastric cancer or a FGFR2 inhibitor.

(17) A method for treating undifferentiated gastric cancer, characterized by administering effective dosages of 4-(3-chloro-4-(cyclopropylaminocarbonyl)aminophenoxy)-7-methoxy-6-quinolinecarboxamide, a pharmacologically acceptable salt thereof or a solvate thereof and a therapeutic substance for gastric cancer or a FGFR2 inhibitor to a living organism.

(18) A method for treating a disease, characterized by administering effective dosages of 4-(3-chloro-4-(cyclopropylaminocarbonyl)aminophenoxy)-7-methoxy-6-quinolinecarboxamide, a pharmacologically acceptable salt thereof or a solvate thereof and a therapeutic substance for gastric cancer or a FGFR2 inhibitor to a living organism comprising at least one selected from the group consisting of a cell overexpressing FGFR2 and a cell expressing mutant FGFR2.

(19) Use of 4-(3-chloro-4-(cyclopropylaminocarbonyl)aminophenoxy)-7-methoxy-6-quinolinecarboxamide, a pharmacologically acceptable salt thereof or a solvate thereof for producing a therapeutic agent for undifferentiated gastric cancer in combination with a therapeutic substance for gastric cancer or a FGFR2 inhibitor.

(20) Use of 4-(3-chloro-4-(cyclopropylaminocarbonyl)aminophenoxy)-7-methoxy-6-quinolinecarboxamide, a pharmacologically acceptable salt thereof or a solvate thereof for producing a pharmaceutical composition in combination with a therapeutic substance for gastric cancer or a FGFR2 inhibitor for administration to a living organism comprising at least one selected from the group consisting of a cell overexpressing FGFR2 and a cell expressing mutant FGFR2.

(21) 4-(3-Chloro-4-(cyclopropylaminocarbonyl)aminophenoxy)-7-methoxy-6-quinolinecarboxamide, a pharmacologically acceptable salt thereof or a solvate thereof for treating undifferentiated gastric cancer in combination with a therapeutic substance for gastric cancer or a FGFR2 inhibitor.

(22) 4-(3-Chloro-4-(cyclopropylaminocarbonyl)aminophenoxy)-7-methoxy-6-quinolinecarboxamide, a pharmacologically acceptable salt thereof or a solvate thereof for administration in combination with a therapeutic substance for gastric cancer or a FGFR2 inhibitor to a living organism comprising at least one selected from the group consisting of a cell overexpressing FGFR2 and a cell expressing mutant FGFR2.

(23) A kit comprising:
(a) at least one selected from the group consisting of a packaging container, an instruction and a package insert describing use of 4-(3-chloro-4-(cyclopropylaminocarbonyl)aminophenoxy)-7-methoxy-6-quinolinecarboxamide, a pharmacologically acceptable salt thereof or a solvate thereof in combination with a therapeutic substance for gastric cancer or a FGFR2 inhibitor; and
(b) a therapeutic agent for undifferentiated gastric cancer comprising 4-(3-chloro-4-(cyclopropylaminocarbonyl)aminophenoxy)-7-methoxy-6-quinolinecarboxamide, a pharmacologically acceptable salt thereof or a solvate thereof.

(24) A kit comprising:
(a) at least one selected from the group consisting of a packaging container, an instruction and a package insert describing use of 4-(3-chloro-4-(cyclopropylaminocarbonyl)aminophenoxy)-7-methoxy-6-quinolinecarboxamide, a pharmacologically acceptable salt thereof or a solvate thereof in combination with a therapeutic substance for gastric cancer or a FGFR2 inhibitor; and
(b) a pharmaceutical composition comprising 4-(3-chloro-4-(cyclopropylaminocarbonyl)aminophenoxy)-7-methoxy-6-quinolinecarboxamide, a pharmacologically acceptable salt thereof or a solvate thereof for administration to a living organism comprising at least one selected from the group consisting of a cell overexpressing FGFR2 and a cell expressing mutant FGFR2.

(25) A kit characterized by a set of a therapeutic agent for undifferentiated gastric cancer comprising 4-(3-chloro-4-(cyclopropylaminocarbonyl)aminophenoxy)-7-methoxy-6-quinolinecarboxamide, a pharmacologically acceptable salt thereof or a solvate thereof and a formulation comprising a therapeutic substance for gastric cancer or a FGFR2 inhibitor.

(26) A kit used for administration to a living organism comprising at least one selected from the group consisting of a cell overexpressing FGFR2 and a cell expressing mutant FGFR2, the kit characterized by a set of a formulation comprising 4-(3-chloro-4-(cyclopropylaminocarbonyl)aminophenoxy)-7-methoxy-6-quinolinecarboxamide, a pharmacologically acceptable salt thereof or a solvate thereof and a formulation comprising a therapeutic substance for gastric cancer or a FGFR2 inhibitor.

(27) A therapeutic agent for undifferentiated gastric cancer comprising 4-(3-chloro-4-(cyclopropylaminocarbonyl)aminophenoxy)-7-methoxy-6-quinolinecarboxamide, a pharmacologically acceptable salt thereof or a solvate thereof, characterized by administration to a living organism with a therapeutic substance for gastric cancer or a FGFR2 inhibitor.

(28) A pharmaceutical composition for administration to a living organism comprising at least one selected from the group consisting of a cell overexpressing FGFR2 and a cell expressing mutant FGFR2, the pharmaceutical composition comprising 4-(3-chloro-4-(cyclopropylaminocarbonyl)aminophenoxy)-7-methoxy-6-quinolinecarboxamide, a pharmacologically acceptable salt thereof or a solvate thereof, characterized by administration to the living organism with a therapeutic substance for gastric cancer or a FGFR2 inhibitor.

The present invention also relates to the followings.

(29) A therapeutic agent for undifferentiated gastric cancer comprising a FGFR2 inhibitor in combination with a therapeutic substance for gastric cancer.

(30) A pharmaceutical composition for administration to a living organism comprising at least one selected from the group consisting of a cell overexpressing FGFR2 and a cell expressing mutant FGFR2, the pharmaceutical composition comprising a FGFR2 inhibitor in combination with a therapeutic substance for gastric cancer.

(31) A method for treating undifferentiated gastric cancer, characterized by administering effective dosages of a FGFR2 inhibitor and a therapeutic substance for gastric cancer to a living organism.

(32) A method for treating a disease, characterized by administering effective dosages of a FGFR2 inhibitor and a therapeutic substance for gastric cancer to a living organism comprising at least one selected from the group consisting of a cell overexpressing FGFR2 and a cell expressing mutant FGFR2.

(33) Use of a FGFR2 inhibitor or a therapeutic substance for gastric cancer for producing a therapeutic agent for undifferentiated gastric cancer in combination with a therapeutic substance for gastric cancer or a FGFR2 inhibitor.

(34) Use of a FGFR2 inhibitor or a therapeutic substance for gastric cancer for producing a pharmaceutical composition in combination with a therapeutic substance for gastric cancer or a FGFR2 inhibitor for administration to a living organism comprising at least one selected from the group consisting of a cell overexpressing FGFR2 and a cell expressing mutant FGFR2.

(35) A FGFR2 inhibitor or a therapeutic substance for gastric cancer for treating undifferentiated gastric cancer in combination with a therapeutic substance for gastric cancer or a FGFR2 inhibitor.

(36) A FGFR2 inhibitor or a therapeutic substance for gastric cancer for administration in combination with a therapeutic substance for gastric cancer or a FGFR2 inhibitor to a living organism comprising at least one selected from the group consisting of a cell overexpressing FGFR2 and a cell expressing mutant FGFR2.

(37) A kit comprising:

(a) at least one selected from the group consisting of a packaging container, an instruction and a package insert describing combination use of a FGFR2 inhibitor and a therapeutic substance for gastric cancer; and (b) a therapeutic agent for undifferentiated gastric cancer comprising a FGFR2 inhibitor or a therapeutic agent for gastric cancer comprising a therapeutic substance for gastric cancer.

(38) A kit comprising:

(a) at least one selected from the group consisting of a packaging container, an instruction and a package insert describing combination use of a FGFR2 inhibitor and a therapeutic substance for gastric cancer; and (b) a pharmaceutical composition comprising a FGFR2 inhibitor or a therapeutic substance for gastric cancer for administration to a living organism comprising at least one selected from the group consisting of a cell overexpressing FGFR2 and a cell expressing mutant FGFR2.

(39) A kit characterized by a set of a therapeutic agent for undifferentiated gastric cancer comprising a FGFR2 inhibitor and a formulation comprising a therapeutic substance for gastric cancer.

(40) A kit used for administration to a living organism comprising at least one selected from the group consisting of a cell overexpressing FGFR2 and a cell expressing mutant FGFR2, the kit characterized by a set of a formulation comprising a FGFR2 inhibitor and a formulation comprising a therapeutic substance for gastric cancer.

(41) A therapeutic agent for undifferentiated gastric cancer comprising a FGFR2 inhibitor or a therapeutic agent for gastric cancer comprising a therapeutic substance for gastric cancer, characterized by administration to a living organism with a therapeutic substance for gastric cancer or a FGFR2 inhibitor.

(42) A pharmaceutical composition for administration to a living organism comprising at least one selected from the group consisting of a cell overexpressing FGFR2 and a cell expressing mutant FGFR2, the pharmaceutical composition comprising a FGFR2 inhibitor or a therapeutic substance for gastric cancer characterized by administration to the living organism with a therapeutic substance for gastric cancer or a FGFR2 inhibitor.

More specifically, the present invention relates to the followings.

[1] A therapeutic agent for undifferentiated gastric cancer comprising a compound represented by General Formula (I) below, a pharmacologically acceptable salt thereof or a solvate thereof in combination with a therapeutic substance for gastric cancer or a FGFR2 inhibitor:

General Formula (I)

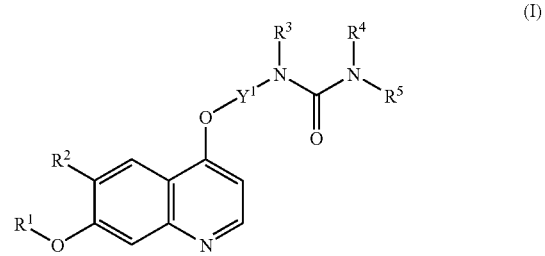

[wherein, $R^1$ represents a group represented by Formula —$V^1$—$V^2$—$V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula —$CONR^6$—, a group represented by Formula —$SO_2NR^6$—, a group represented by Formula —$NR^6SO_2$—, a group represented by Formula —$NR^6CO$— or a group represented by Formula —$NR^6$— (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

$R^2$ represents a cyano group, an optionally substituted $C_{1-6}$ alkoxy group, a carboxyl group, an optionally substituted $C_{2-7}$ alkoxycarbonyl group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

$Y^1$ represents a group represented by either one of the following formulae

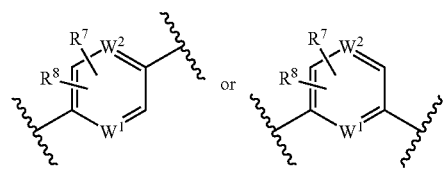

(wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —$CONV^{d1}V^{d2}$ (wherein, $V^{d1}$ and $V^{d2}$ each independently represent a hydrogen atom or an optionally substituted $C_{1-6}$ alkyl group);

$W^1$ and $W^2$ each independently represent an optionally substituted carbon atom or nitrogen atom);

$R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group].

[2] A therapeutic agent according to [1], wherein $R^1$ is a $C_{1-6}$ alkyl group (provided that $R^1$ may have at least one substituent selected from the group consisting of a 3-10-membered nonaromatic heterocyclic group, a hydroxyl group, a $C_{1-6}$ alkoxy group, an amino group, a mono-$C_{1-6}$ alkylamino group and a di-$C_{1-6}$ alkylamino group which may have a $C_{1-6}$ alkyl group).

[3] A therapeutic agent according to [1], wherein $R^1$ is a methyl group or a group represented by any one of the following formulae

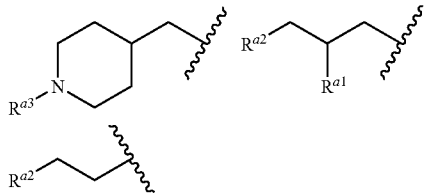

(wherein, $R^{a3}$ represents a methyl group; $R^{a1}$ represents a hydrogen atom or a hydroxyl group; $R^{a2}$ represents a methoxy group, an ethoxy group, a 1-pyrrolidinyl group, a 1-piperidinyl group, a 4-morpholinyl group, a dimethylamino group or a diethylamino group).

[4] A therapeutic agent according to [1], wherein $R^1$ is a methyl group or a 2-methoxyethyl group.

[5] A therapeutic agent according to [1], wherein $R^2$ is a cyano group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group).

[6] A therapeutic agent according to [1], wherein $R^2$ is a cyano group or a group represented by Formula —$CONHV^{a16}$ (wherein, $V^{a16}$ represents a hydrogen atom, a $C_{1-6}$ alkyl group, a $C_{3-8}$ cycloalkyl group, a $C_{1-6}$ alkoxy group or a $C_{3-8}$ cycloalkoxy group, provided that $V^{a16}$ may have at least one substituent selected from the group consisting of a halogen atom, a cyano group, a hydroxyl group and a $C_{1-6}$ alkoxy group).

[7] A therapeutic agent according to [1], wherein $R^2$ is a group represented by Formula —$CONHV^{a17}$ (wherein, $V^{a17}$ represents a hydrogen atom, a $C_{1-6}$ alkyl group or a $C_{1-6}$ alkoxy group).

[8] A therapeutic agent according to [1], wherein $R^2$ is a group represented by Formula —$CONHV^{a18}$ (wherein, $V^{a18}$ represents a hydrogen atom, a methyl group or a methoxy group).

[9] A therapeutic agent according to [1], wherein $Y^1$ is a group represented by the following formula

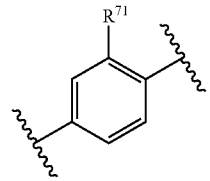

(wherein, $R^{71}$ represents a hydrogen atom or a halogen atom).

[10] A therapeutic agent according to [1], wherein $R^3$ and $R^4$ are hydrogen atoms.

[11] A therapeutic agent according to [1], wherein $R^5$ is a hydrogen atom, a $C_{1-6}$ alkyl group, a $C_{3-8}$ cycloalkyl group or a $C_{6-10}$ aryl group (provided that $R^5$ may have at least one substituent selected from the group consisting of a halogen atom and a methanesulfonyl group).

[12] A therapeutic agent according to [1], wherein $R^5$ is a methyl group, an ethyl group or a cyclopropyl group.

[13] A therapeutic agent according to [1], wherein the compound represented by General Formula (I), a pharmacologically acceptable salt thereof or a solvate thereof is at least one compound selected from the group consisting of:

N-(4-(6-cyano-7-(2-methoxyethoxy)-4-quinolyl)oxy-2-fluorophenyl)-N'-(4-fluorophenyl)urea;

N-(2-chloro-4-((6-cyano-7-((1-methyl-4-piperidyl)methoxy)-4-quinolyl)oxy)phenyl)-N'-cyclopropyl urea;

N-(4-((6-cyano-7-(((2R)-3-(diethylamino)-2-hydroxypropyl)oxy)-4-quinolyl)oxy)phenyl)-N'-(4-fluorophenyl)urea;

N-(4-((6-cyano-7-(((2R)-2-hydroxy-3-(1-pyrrolidino)propyl)oxy)-4-quinolyl)oxy)phenyl)-N'-(4-fluorophenyl)urea;

4-(3-chloro-4-(cyclopropylaminocarbonyl)aminophenoxy)-7-methoxy-6-quinolinecarboxamide;

4-(3-chloro-4-(cyclopropylaminocarbonyl)aminophenoxy)-7-(2-methoxyethoxy)-6-quinolinecarboxamide;

N6-cyclopropyl-4-(3-chloro-4-(((cyclopropylamino)carbonyl)amino)phenoxy)-7-methoxy-6-quinolinecarboxamide;

N6-(2-methoxyethyl)-4-(3-chloro-4-(((cyclopropylamino)carbonyl)amino)phenoxy)-7-methoxy-6-quinolinecarboxamide;

N6-(2-fluoroethyl)-4-(3-chloro-4-(((cyclopropylamino)carbonyl)amino)phenoxy)-7-methoxy-6-quinolinecarboxamide;
N6-methoxy-4-(3-chloro-4-(((cyclopropylamino)carbonyl)amino)phenoxy)-7-methoxy-6-quinolinecarboxamide;
N6-methyl-4-(3-chloro-4-(((cyclopropylamino)carbonyl)amino)phenoxy)-7-methoxy-6-quinolinecarboxamide;
N6-ethyl-4-(3-chloro-4-(((cyclopropylamino)carbonyl)amino)phenoxy)-7-methoxy-6-quinolinecarboxamide;
4-(3-fluoro-4-(cyclopropylaminocarbonyl)aminophenoxy)-7-(2-methoxyethoxy)-6-quinolinecarboxamide;
4-(3-chloro-4-(cyclopropylaminocarbonyl)aminophenoxy)-7-(2-hydroxyethoxy)-6-quinolinecarboxamide;
4-(3-chloro-4-(cyclopropylaminocarbonyl)aminophenoxy)-7-((2S)-2,3-dihydroxypropyl)oxy-6-quinolinecarboxamide;
4-(3-chloro-4-(methylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6-methoxy-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-ethoxyethoxy)-6-quinolinecarboxamide;
4-(4-((cyclopropylamino)carbonyl)aminophenoxy)-7-(2-methoxyethoxy)-6-quinolinecarboxamide;
N-(2-fluoro-4-((6-carbamoyl-7-methoxy-4-quinolyl)oxy)phenyl)-N'-cyclopropyl urea;
N6-(2-hydroxyethyl)-4-(3-chloro-4-(((cyclopropylamino)carbonyl)amino)phenoxy)-7-methoxy-6-quinolinecarboxamide;
4-(3-chloro-4-(1-propylaminocarbonyl)aminophenoxy)-7-methoxy-6-quinolinecarboxamide;
4-(3-chloro-4-(cis-2-fluoro-cyclopropylaminocarbonyl)aminophenoxy)-7-methoxy-6-quinolinecarboxamide;
N6-methyl-4-(3-chloro-4-(((cyclopropylamino)carbonyl)amino)phenoxy)-7-(2-methoxyethoxy)-6-quinolinecarboxamide;
N6-methyl-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-(4-morpholino)ethoxy)-6-quinolinecarboxamide;
4-(3-chloro-4-(2-fluoroethylaminocarbonyl)aminophenoxy)-7-methoxy-6-quinolinecarboxamide;
N6-((2R)tetrahydro-2-furanylmethyl)-4-(3-chloro-4-(((methylamino)carbonyl)amino)phenoxy)-7-methoxy-6-quinolinecarboxamide;
4-(3-fluoro-4-(ethylaminocarbonyl)aminophenoxy)-7-methoxy-6-quinolinecarboxamide;
4-(3-chloro-4-(((cyclopropylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-((2R)-3-diethylamino-2-hydroxypropoxy)-6-quinolinecarboxamide;
N6-methyl-4-(3-chloro-4-(((ethylamino)carbonyl)amino)phenoxy)-7-((2R)-3-diethylamino-2-hydroxypropoxy)-6-quinolinecarboxamide;
N6-methyl-4-(3-chloro-4-(((methylamino)carbonyl)amino)phenoxy)-7-((2R)-2-hydroxy-3-(1-pyrrolidino)propoxy)-6-quinolinecarboxamide;
N6-methyl-4-(3-chloro-4-(((ethylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-((1-methyl-4-piperidyl)methoxy)-6-quinolinecarboxamide;
N6-methyl-4-(3-chloro-4-(((ethylamino)carbonyl)amino)phenoxy)-7-((1-methyl-4-piperidyl)methoxy)-6-quinolinecarboxamide;
N-(4-(6-cyano-7-(2-methoxyethoxy)-4-quinolyl)oxy-2-fluorophenyl)-N'-cyclopropyl urea;
N-(4-(6-cyano-7-(3-(4-morpholino)propoxy)-4-quinolyl)oxyphenyl)-N'-(3-(methylsulfonyl)phenyl)urea;
4-(4-((cyclopropylamino)carbonyl)aminophenoxy)-7-methoxy-6-quinolinecarboxamide;
4-(3-fluoro-4-((2-fluoroethylamino)carbonyl)aminophenoxy)-7-methoxy-6-quinolinecarboxamide;
N6-(2-ethoxyethyl)-4-(3-chloro-4-(((methylamino)carbonyl)amino)phenoxy)-7-methoxy-6-quinolinecarboxamide;
4-(4-(3-ethylureido)-3-fluoro-phenoxy)-7-methoxyquinoline-6-carboxylic acid (2-cyanoethyl)amide; and
N-(4-(6-(2-cyanoethyl)carbamoyl-7-methoxy-4-quinolyl)oxy-2-fluorophenyl)-N'-cyclopropyl urea,
a pharmacologically acceptable salt thereof or a solvate thereof.

[14] A therapeutic agent according to [1], wherein the compound represented by General Formula (I), a pharmacologically acceptable salt thereof or a solvate thereof is at least one compound selected from the group consisting of:
4-(3-chloro-4-(cyclopropylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6-methoxy-4-(3-chloro-4-(((cyclopropylamino)carbonyl)amino)phenoxy)-7-methoxy-6-quinolinecarboxamide;
4-(3-chloro-4-(methylaminocarbonyl)aminophenoxy)-7-methoxy-6-quinolinecarboxamide; and
N6-methoxy-4-(3-chloro-4-(((ethylamino)carbonyl)amino)phenoxy)-7-methoxy-6-quinolinecarboxamide,
a pharmacologically acceptable salt thereof or a solvate thereof.

[15] A therapeutic agent according to [1], wherein the compound represented by General Formula (I), a pharmacologically acceptable salt thereof or a solvate thereof is 4-(3-chloro-4-(cyclopropylaminocarbonyl)aminophenoxy)-7-methoxy-6-quinolinecarboxamide, a pharmacologically acceptable salt thereof or a solvate thereof.

[16] A therapeutic agent according to [1], wherein the compound represented by General Formula (I), a pharmacologically acceptable salt thereof or a solvate thereof is methanesulfonate of 4-(3-chloro-4-(cyclopropylaminocarbonyl)aminophenoxy)-7-methoxy-6-quinolinecarboxamide.

[17] A therapeutic agent according to any one of [1] to [1,6], wherein the therapeutic substance for gastric cancer is at least one selected from the group consisting of irinotecan, paclitaxel, carboquone, nimustine, 5-fluorouracil, tegafur, UFT, doxifluridine, carmofur, S-1, doxorubicin, mitomycin C, aclarubicin, pirarubicin, epirubicin, docetaxel and cis-platinum.

[18] A therapeutic agent according to any one of [1] to [1,6], wherein the therapeutic substance for gastric cancer is irinotecan, 5-fluorouracil or paclitaxel.

[19] A therapeutic agent according to any one of [1] to [16], wherein the FGFR2 inhibitor is at least one compound selected from the group consisting of:
N-(3-trifluoromethyl-4-chlorophenyl)-N'-(4-(2-methylcarbamoylpyridine-4-yl)oxyphenyl)urea;
6-[2-(methylcarbamoyl)phenylsulfanyl]-3-E-[2-(pyridine-2-yl)ethenyl]indazole;

5-(5-fluoro-2-oxo-1,2-dihydroindole-3-ylidenemethyl)-2,4-dimethyl-1H-pyrrole-3-carboxylic acid(2-diethylaminoethyl)amide; and N-{2-chloro-4-[(6,7-dimethoxy-4-quinolyl)oxy]phenyl}-N'-(5-methyl-3-isoxazolyl)urea, a pharmacologically acceptable salt thereof or a solvate thereof.

[20] A therapeutic agent according to [1], wherein the undifferentiated gastric cancer comprises at least one selected from the group consisting of a cell overexpressing FGFR2 and a cell expressing mutant FGFR2.

[21] A therapeutic agent according to [20], wherein the mutant FGFR2 comprises a mutation site where amino acids downstream from at least position 813 are deleted in the amino acid sequence 22-822 among the amino acid sequence represented by SEQ ID NO:2.

[22] A therapeutic agent according to [1], wherein the undifferentiated gastric cancer is at least one gastric cancer selected from the group consisting of poorly differentiated adenocarcinoma, signet-ring cell carcinoma, mucinous carcinoma and scirrhous gastric cancer.

[23] A pharmaceutical composition for administration to a living organism comprising at least one selected from the group consisting of a cell overexpressing FGFR2 and a cell expressing mutant FGFR2, the pharmaceutical composition comprising a compound represented by General Formula (I) below, a pharmacologically acceptable salt thereof or a solvate thereof in combination with a therapeutic substance for gastric cancer or a FGFR2 inhibitor:

General Formula (I)

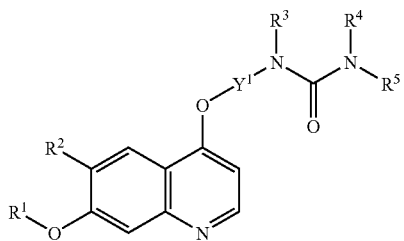

(I)

[wherein, $R^1$ represents a group represented by Formula —$V^1$—$V^2$—$V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula —CONR$^6$—, a group represented by Formula —SO$_2$NR$^6$—, a group represented by Formula —NR$^6$SO$_2$—, a group represented by Formula —NR$^6$CO— or a group represented by Formula —NR$^6$— (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

$R^2$ represents a cyano group, an optionally substituted $C_{1-6}$ alkoxy group, a carboxyl group, an optionally substituted $C_{2-7}$ alkoxycarbonyl group or a group represented by Formula —CONV$^{a11}$V$^{a12}$ (wherein, V$^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; V$^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

$Y^1$ represents a group represented by either one of the following formulae

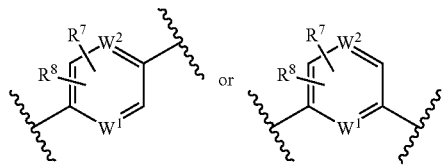

(wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —CONV$^{d1}$V$^{d2}$ (wherein, V$^{d1}$ and V$^{d2}$ each independently represent a hydrogen atom or an optionally substituted $C_{1-6}$ alkyl group);

$W^1$ and $W^2$ each independently represent an optionally substituted carbon atom or nitrogen atom);

$R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group].

[24] A pharmaceutical composition according to [23], wherein $R^1$ is a $C_{1-6}$ alkyl group (provided that $R^1$ may have at least one substituent selected from the group consisting of a 3-10-membered nonaromatic heterocyclic group, a hydroxyl group, a $C_{1-6}$ alkoxy group, an amino group, a mono-$C_{1-6}$ alkylamino group and a di-$C_{1-6}$ alkylamino group which may have a $C_{1-6}$ alkyl group).

[25] A pharmaceutical composition according to [23], wherein $R^1$ is a methyl group or a group represented by any one of the following formulae

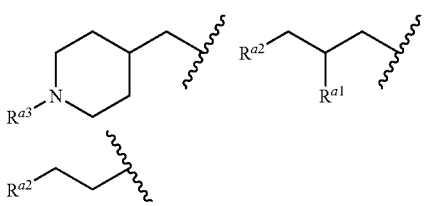

(wherein, $R^{a3}$ represents a methyl group; $R^{a1}$ represents a hydrogen atom or a hydroxyl group; $R^{a2}$ represents a methoxy group, an ethoxy group, a 1-pyrrolidinyl group, a 1-piperidinyl group, a 4-morpholinyl group, a dimethylamino group or a diethylamino group).

[26] A pharmaceutical composition according to [23], wherein $R^1$ is a methyl group or a 2-methoxyethyl group.

[27] A pharmaceutical composition according to [23], wherein $R^2$ is a cyano group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group).

[28] A pharmaceutical composition according to [23], wherein $R^2$ is a cyano group or a group represented by Formula —$CONHV^{a16}$ (wherein, $V^{a16}$ represents a hydrogen atom, a $C_{1-6}$ alkyl group, a $C_{3-8}$ cycloalkyl group, a $C_{1-6}$ alkoxy group or a $C_{3-8}$ cycloalkoxy group, provided that $V^{a16}$ may have at least one substituent selected from the group consisting of a halogen atom, a cyano group, a hydroxyl group and a $C_{1-6}$ alkoxy group).

[29] A pharmaceutical composition according to [23], wherein $R^2$ is a group represented by Formula —$CONHV^{a17}$ (wherein, $V^{a17}$ represents a hydrogen atom, a $C_{1-6}$ alkyl group or a $C_{1-6}$ alkoxy group).

[30] A pharmaceutical composition according to [23], wherein $R^2$ is a group represented by Formula —$CONHV^{a18}$ (wherein, $V^{a18}$ represents a hydrogen atom, a methyl group or a methoxy group).

[31] A pharmaceutical composition according to [23], wherein $Y^1$ is a group represented by the following formula

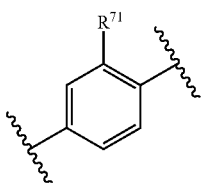

(wherein, $R^{71}$ represents a hydrogen atom or a halogen atom).

[32] A pharmaceutical composition according to [23], wherein $R^3$ and $R^4$ are hydrogen atoms.

[33] A pharmaceutical composition according to [23], wherein $R^5$ is a hydrogen atom, a $C_{1-6}$ alkyl group, a $C_{3-8}$ cycloalkyl group or a $C_{6-10}$ aryl group (provided that $R^5$ may have at least one substituent selected from the group consisting of a halogen atom and a methanesulfonyl group).

[34] A pharmaceutical composition according to [23], wherein $R^2$ is a methyl group, an ethyl group or a cyclopropyl group.

[35] A pharmaceutical composition according to [23], wherein the compound represented by General Formula (I), a pharmacologically acceptable salt thereof or a solvate thereof is at least one compound selected from the group consisting of:

N-(4-(6-cyano-7-(2-methoxyethoxy)-4-quinolyl)oxy-2-fluorophenyl)-N'-(4-fluorophenyl)urea;

N-(2-chloro-4-((6-cyano-7-((1-methyl-4-piperidyl)methoxy)-4-quinolyl)oxy)phenyl)-N'-cyclopropyl urea;

N-(4-((6-cyano-7-(((2R)-3-(diethylamino)-2-hydroxypropyl)oxy)-4-quinolyl)oxy)phenyl)-N'-(4-fluorophenyl) urea;

N-(4-((6-cyano-7-(((2R)-2-hydroxy-3-(1-pyrrolidino)propyl)oxy)-4-quinolyl)oxy)phenyl)-N'-(4-fluorophenyl) urea;

4-(3-chloro-4-(cyclopropylaminocarbonyl)aminophenoxy)-7-methoxy-6-quinolinecarboxamide;

4-(3-chloro-4-(cyclopropylaminocarbonyl)aminophenoxy)-7-(2-methoxyethoxy)-6-quinolinecarboxamide;

N6-cyclopropyl-4-(3-chloro-4-(((cyclopropylamino)carbonyl)amino)phenoxy)-7-methoxy-6-quinolinecarboxamide;

N6-(2-methoxyethyl)-4-(3-chloro-4-(((cyclopropylamino)carbonyl)amino)phenoxy)-7-methoxy-6-quinolinecarboxamide;

N6-(2-fluoroethyl)-4-(3-chloro-4-(((cyclopropylamino)carbonyl)amino)phenoxy)-7-methoxy-6-quinolinecarboxamide;

N6-methoxy-4-(3-chloro-4-(((cyclopropylamino)carbonyl)amino)phenoxy)-7-methoxy-6-quinolinecarboxamide;

N6-methyl-4-(3-chloro-4-(((cyclopropylamino)carbonyl)amino)phenoxy)-7-methoxy-6-quinolinecarboxamide;

N6-ethyl-4-(3-chloro-4-(((cyclopropylamino)carbonyl)amino)phenoxy)-7-methoxy-6-quinolinecarboxamide;

4-(3-fluoro-4-(cyclopropylaminocarbonyl)aminophenoxy)-7-(2-methoxyethoxy)-6-quinolinecarboxamide;

4-(3-chloro-4-(cyclopropylaminocarbonyl)aminophenoxy)-7-(2-hydroxyethoxy)-6-quinolinecarboxamide;

4-(3-chloro-4-(cyclopropylaminocarbonyl)aminophenoxy)-7-((2S)-2,3-dihydroxypropyl)oxy-6-quinolinecarboxamide;

4-(3-chloro-4-(methylaminocarbonyl)aminophenoxy)-7-methoxy-6-quinolinecarboxamide;

4-(3-chloro-4-(ethylaminocarbonyl)aminophenoxy)-7-methoxy-6-quinolinecarboxamide;

N6-methoxy-4-(3-chloro-4-(((ethylamino)carbonyl)amino)phenoxy)-7-methoxy-6-quinolinecarboxamide;

4-(3-chloro-4-(cyclopropylaminocarbonyl)aminophenoxy)-7-(2-ethoxyethoxy)-6-quinolinecarboxamide;

4-(4-((cyclopropylamino)carbonyl)aminophenoxy)-7-(2-methoxyethoxy)-6-quinolinecarboxamide;

N-(2-fluoro-4-((6-carbamoyl-7-methoxy-4-quinolyl)oxy)phenyl)-N'-cyclopropyl urea;

N6-(2-hydroxyethyl)-4-(3-chloro-4-(((cyclopropylamino)carbonyl)amino)phenoxy)-7-methoxy-6-quinolinecarboxamide;

4-(3-chloro-4-(1-propylaminocarbonyl)aminophenoxy)-7-methoxy-6-quinolinecarboxamide;
4-(3-chloro-4-(cis-2-fluoro-cyclopropylaminocarbonyl) aminophenoxy)-7-methoxy-6-quinolinecarboxamide;
N6-methyl-4-(3-chloro-4-(((cyclopropylamino)carbonyl) amino)phenoxy)-7-(2-methoxyethoxy)-6-quinolinecarboxamide;
N6-methyl-4-(3-chloro-4-(((ethylamino)carbonyl)amino) phenoxy)-7-methoxy-6-quinolinecarboxamide;
4-(3-chloro-4-(cyclopropylaminocarbonyl)aminophenoxy)-7-(2-(4-morpholino)ethoxy)-6-quinolinecarboxamide;
4-(3-chloro-4-(2-fluoroethylaminocarbonyl)aminophenoxy)-7-methoxy-6-quinolinecarboxamide;
N6-((2R)tetrahydro-2-furanylmethyl)-4-(3-chloro-4-(((methylamino)carbonyl)amino)phenoxy)-7-methoxy-6-quinolinecarboxamide;
4-(3-fluoro-4-(ethylaminocarbonyl)aminophenoxy)-7-methoxy-6-quinolinecarboxamide;
4-(3-chloro-4-(((cyclopropylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino) phenoxy)-7-((2R)-3-diethylamino-2-hydroxypropoxy)-6-quinolinecarboxamide;
N6-methyl-4-(3-chloro-4-(((ethylamino)carbonyl)amino) phenoxy)-7-((2R)-3-diethylamino-2-hydroxypropoxy)-6-quinolinecarboxamide;
N6-methyl-4-(3-chloro-4-(((methylamino)carbonyl)amino) phenoxy)-7-((2R)-2-hydroxy-3-(1-pyrrolidino)propoxy)-6-quinolinecarboxamide;
N6-methyl-4-(3-chloro-4-(((ethylamino)carbonyl)amino) phenoxy)-7-((2R)-2-hydroxy-3-(1-pyrrolidino)propoxy)-6-quinolinecarboxamide;
N6-methyl-4-(3-chloro-4-(((methylamino)carbonyl)amino) phenoxy)-7-((1-methyl-4-piperidyl)methoxy)-6-quinolinecarboxamide;
N6-methyl-4-(3-chloro-4-(((ethylamino)carbonyl)amino) phenoxy)-7-((1-methyl-4-piperidyl)methoxy)-6-quinolinecarboxamide;
N-(4-(6-cyano-7-(2-methoxyethoxy)-4-quinolyl)oxy-2-fluorophenyl)-N'-cyclopropyl urea;
N-(4-(6-cyano-7-(3-(4-morpholino)propoxy)-4-quinolyl) oxyphenyl)-N'-(3-(methylsulfonyl)phenyl)urea;
4-(4-((cyclopropylamino)carbonyl)aminophenoxy)-7-methoxy-6-quinolinecarboxamide;
4-(3-fluoro-4-((2-fluoroethylamino)carbonyl)aminophenoxy)-7-methoxy-6-quinolinecarboxamide;
N6-(2-ethoxyethyl)-4-(3-chloro-4-(((methylamino)carbonyl)amino)phenoxy)-7-methoxy-6-quinolinecarboxamide;
4-(4-(3-ethylureido)-3-fluoro-phenoxy)-7-methoxyquinoline-6-carboxylic acid (2-cyanoethyl)amide; and
N-(4-(6-(2-cyanoethyl)carbamoyl-7-methoxy-4-quinolyl) oxy-2-fluorophenyl)-N'-cyclopropyl urea,
a pharmacologically acceptable salt thereof or a solvate thereof.

[36] A pharmaceutical composition according to [23], wherein the compound represented by General Formula (I), a pharmacologically acceptable salt thereof or a solvate thereof is at least one compound selected from the group consisting of:
4-(3-chloro-4-(cyclopropylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6-methoxy-4-(3-chloro-4-(((cyclopropylamino)carbonyl) amino)phenoxy)-7-methoxy-6-quinolinecarboxamide;
4-(3-chloro-4-(methylaminocarbonyl)aminophenoxy)-7-methoxy-6-quinolinecarboxamide; and
N6-methoxy-4-(3-chloro-4-(((ethylamino)carbonyl)amino) phenoxy)-7-methoxy-6-quinolinecarboxamide,
a pharmacologically acceptable salt thereof or a solvate thereof.

[37] A pharmaceutical composition according to [23], wherein the compound represented by General Formula (I), a pharmacologically acceptable salt thereof or a solvate thereof is 4-(3-chloro-4-(cyclopropylaminocarbonyl)aminophenoxy)-7-methoxy-6-quinolinecarboxamide, a pharmacologically acceptable salt thereof or a solvate thereof.

[38] A pharmaceutical composition according to [23], wherein the compound represented by General Formula (I), a pharmacologically acceptable salt thereof or a solvate thereof is methanesulfonate of 4-(3-chloro-4-(cyclopropylaminocarbonyl)aminophenoxy)-7-methoxy-6-quinolinecarboxamide.

[39] A pharmaceutical composition according to any one of [23] to [38], wherein the therapeutic substance for gastric cancer is at least one selected from the group consisting of irinotecan, paclitaxel, carboquone, nimustine, 5-fluorouracil, tegafur, UFT, doxifluridine, carmofur, S-1, doxorubicin, mitomycin C, aclarubicin, pirarubicin, epirubicin, docetaxel and cis-platinum.

[40] A pharmaceutical composition according to any one of [23] to [38], wherein the therapeutic substance for gastric cancer is irinotecan, 5-fluorouracil or paclitaxel.

[41] A pharmaceutical composition according to any one of [23] to [38], wherein the FGFR2 inhibitor is at least one compound selected from the group consisting of:
N-(3-trifluoromethyl-4-chlorophenyl)-N'-(4-(2-methylcarbamoylpyridine-4-yl)oxyphenyl)urea;
6-[2-(methylcarbamoyl)phenylsulfanyl]-3-E-[2-(pyridine-2-yl)ethenyl]indazole;
5-(5-fluoro-2-oxo-1,2-dihydroindole-3-ylidenemethyl)-2,4-dimethyl-1H-pyrrole-3-carboxylic acid(2-diethylaminoethyl)amide; and
N-{2-chloro-4-[(6,7-dimethoxy-4-quinolyl)oxy]phenyl}-N'-(5-methyl-3-isoxazolyl)urea,
a pharmacologically acceptable salt thereof or a solvate thereof.

[42] A pharmaceutical composition according to [23], wherein the mutant FGFR2 comprises a mutation site where amino acids downstream from at least position 813 are deleted in the amino acid sequence 22-822 among the amino acid sequence represented by SEQ ID NO:2.

[43] A pharmaceutical composition according to [23], wherein the living organism is a patient suffering from undifferentiated gastric cancer.

[44] A pharmaceutical composition according to [43], wherein the undifferentiated gastric cancer is at least one gastric cancer selected from the group consisting of poorly differentiated adenocarcinoma, signet-ring cell carcinoma, mucinous carcinoma and scirrhous gastric cancer.

[45] A method for treating undifferentiated gastric cancer, characterized by administering effective dosages of a compound represented by General Formula (I) below, a pharmacologically acceptable salt thereof or a solvate thereof and a therapeutic substance for gastric cancer or a FGFR2 inhibitor to a living organism:

General Formula (I)

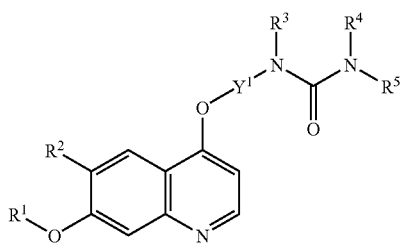

[wherein, $R^8$ represents a group represented by Formula —$V^1$—$V^2V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula —$CONR^6$—, a group represented by Formula —$SO_2NR^6$—, a group represented by Formula —$NR^6SO_2$—, a group represented by Formula —$NR^6$— or a group represented by Formula —$NR^6$— (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

$R^2$ represents a cyano group, an optionally substituted $C_{1-6}$ alkoxy group, a carboxyl group, an optionally substituted $C_{2-7}$ alkoxycarbonyl group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

$Y^1$ represents a group represented by either one of the following formulae

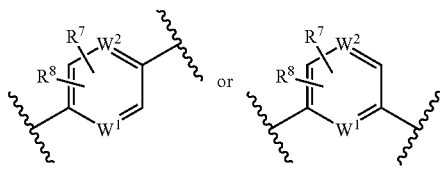

(wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —$CONV^{d1}V^{d2}$ (wherein, $V^{d1}$ and $V^{d2}$ each independently represent a hydrogen atom or an optionally substituted $C_{1-6}$ alkyl group);

$W^1$ and $W^2$ each independently represent an optionally substituted carbon atom or nitrogen atom);

$R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group].

[46] A therapeutic method according to [45], wherein $R^1$ is a $C_{1-6}$ alkyl group (provided that $R^1$ may have at least one substituent selected from the group consisting of a 3-10-membered nonaromatic heterocyclic group, a hydroxyl group, a $C_{1-6}$ alkoxy group, an amino group, a mono-$C_{1-6}$ alkylamino group and a di-$C_{1-6}$ alkylamino group which may have a $C_{1-6}$ alkyl group).

[47] A therapeutic method according to [45], wherein $R^1$ is a methyl group or a group represented by any one of the following formulae

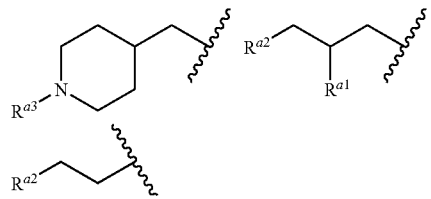

(wherein, $R^{a3}$ represents a methyl group; $R^{a1}$ represents a hydrogen atom or a hydroxyl group; $R^{a2}$ represents a methoxy group, an ethoxy group, a 1-pyrrolidinyl group, a 1-piperidinyl group, a 4-morpholinyl group, a dimethylamino group or a diethylamino group).

[48] A therapeutic method according to [45], wherein $R^1$ is a methyl group or a 2-methoxyethyl group.

[49] A therapeutic method according to [45], wherein $R^2$ is a cyano group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group).

[50] A therapeutic method according to [45], wherein $R^2$ is a cyano group or a group represented by Formula —CONHV$^{a16}$ (wherein, V$^{a16}$ represents a hydrogen atom, a $C_{1-6}$ alkyl group, a $C_{3-8}$ cycloalkyl group, a $C_{1-6}$ alkoxy group or a $C_{3-8}$ cycloalkoxy group, provided that V$^{a16}$ may have at least one substituent selected from the group consisting of a halogen atom, a cyano group, a hydroxyl group and a $C_{1-6}$ alkoxy group).

[51] A therapeutic method according to [45], wherein $R^2$ is a group represented by Formula —CONHV$^{a17}$ (wherein, V$^{a17}$ represents a hydrogen atom, a $C_{1-6}$ alkyl group or a $C_{1-6}$ alkoxy group).

[52] A therapeutic method according to [45], wherein $R^2$ is a group represented by Formula —CONHV$^{a18}$ (wherein, V$^{a18}$ represents a hydrogen atom, a methyl group or a methoxy group).

[53] A therapeutic method according to [45], wherein $Y^1$ is a group represented by the following formula

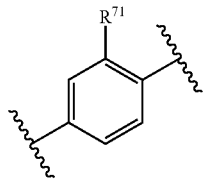

(wherein, $R^{71}$ represents a hydrogen atom or a halogen atom).

[54] A therapeutic method according to [45], wherein $R^3$ and $R^4$ are hydrogen atoms.

[55] A therapeutic method according to [45], wherein $R^5$ is a hydrogen atom, a $C_{1-6}$ alkyl group, a $C_{3-8}$ cycloalkyl group or a $C_{6-10}$ aryl group (provided that $R^5$ may have at least one substituent selected from the group consisting of a halogen atom and a methanesulfonyl group).

[56] A therapeutic method according to [45], wherein $R^5$ is a methyl group, an ethyl group or a cyclopropyl group.

[57] A therapeutic method according to [45], wherein the compound represented by General Formula (I), a pharmacologically acceptable salt thereof or a solvate thereof is at least one compound selected from the group consisting of:

N-(4-(6-cyano-7-(2-methoxyethoxy)-4-quinolyl)oxy-2-fluorophenyl)-N'-(4-fluorophenyl)urea;

N-(2-chloro-4-((6-cyano-7-((1-methyl-4-piperidyl)methoxy)-4-quinolyl)oxy)phenyl)-N'-cyclopropyl urea;

N-(4-((6-cyano-7-(((2R)-3-(diethylamino)-2-hydroxypropyl)oxy)-4-quinolyl)oxy)phenyl)-N'-(4-fluorophenyl) urea;

N-(4-((6-cyano-7-(((2R)-2-hydroxy-3-(1-pyrrolidino)propyl)oxy)-4-quinolyl)oxy)phenyl)-N'-(4-fluorophenyl) urea;

4-(3-chloro-4-(cyclopropylaminocarbonyl)aminophenoxy)-7-methoxy-6-quinolinecarboxamide;

4-(3-chloro-4-(cyclopropylaminocarbonyl)aminophenoxy)-7-(2-methoxyethoxy)-6-quinolinecarboxamide;

N6-cyclopropyl-4-(3-chloro-4-(((cyclopropylamino)carbonyl)amino)phenoxy)-7-methoxy-6-quinolinecarboxamide;

N6-(2-methoxyethyl)-4-(3-chloro-4-(((cyclopropylamino)carbonyl)amino)phenoxy)-7-methoxy-6-quinolinecarboxamide;

N6-(2-fluoroethyl)-4-(3-chloro-4-(((cyclopropylamino)carbonyl)amino)phenoxy)-7-methoxy-6-quinolinecarboxamide;

N6-methoxy-4-(3-chloro-4-(((cyclopropylamino)carbonyl)amino)phenoxy)-7-methoxy-6-quinolinecarboxamide;

N6-methyl-4-(3-chloro-4-(((cyclopropylamino)carbonyl)amino)phenoxy)-7-methoxy-6-quinolinecarboxamide;

N6-ethyl-4-(3-chloro-4-(((cyclopropylamino)carbonyl)amino)phenoxy)-7-methoxy-6-quinolinecarboxamide;

4-(3-fluoro-4-(cyclopropylaminocarbonyl)aminophenoxy)-7-(2-methoxyethoxy)-6-quinolinecarboxamide;

4-(3-chloro-4-(cyclopropylaminocarbonyl)aminophenoxy)-7-(2-hydroxyethoxy)-6-quinolinecarboxamide;

4-(3-chloro-4-(cyclopropylaminocarbonyl)aminophenoxy)-7-((2S)-2,3-dihydroxypropyl)oxy-6-quinolinecarboxamide;

4-(3-chloro-4-(methylaminocarbonyl)aminophenoxy)-7-methoxy-6-quinolinecarboxamide;

4-(3-chloro-4-(ethylaminocarbonyl)aminophenoxy)-7-methoxy-6-quinolinecarboxamide;

N6-methoxy-4-(3-chloro-4-(((ethylamino)carbonyl)amino)phenoxy)-7-methoxy-6-quinolinecarboxamide;

4-(3-chloro-4-(cyclopropylaminocarbonyl)aminophenoxy)-7-(2-ethoxyethoxy)-6-quinolinecarboxamide;

4-(4-((cyclopropylamino)carbonyl)aminophenoxy)-7-(2-methoxyethoxy)-6-quinolinecarboxamide;

N-(2-fluoro-4-((6-carbamoyl-7-methoxy-4-quinolyl)oxy) phenyl)-N'-cyclopropyl urea;

N6-(2-hydroxyethyl)-4-(3-chloro-4-(((cyclopropylamino)carbonyl)amino)phenoxy)-7-methoxy-6-quinolinecarboxamide;

4-(3-chloro-4-(1-propylaminocarbonyl)aminophenoxy)-7-methoxy-6-quinolinecarboxamide;

4-(3-chloro-4-(cis-2-fluoro-cyclopropylaminocarbonyl) aminophenoxy)-7-methoxy-6-quinolinecarboxamide;

N6-methyl-4-(3-chloro-4-(((cyclopropylamino)carbonyl)amino)phenoxy)-7-(2-methoxyethoxy)-6-quinolinecarboxamide;

N6-methyl-4-(3-chloro-4-(((ethylamino)carbonyl)amino) phenoxy)-7-methoxy-6-quinolinecarboxamide;

4-(3-chloro-4-(cyclopropylaminocarbonyl)aminophenoxy)-7-(2-(4-morpholino)ethoxy)-6-quinolinecarboxamide;

4-(3-chloro-4-(2-fluoroethylaminocarbonyl)aminophenoxy)-7-methoxy-6-quinolinecarboxamide;

N6-((2R)tetrahydro-2-furanylmethyl)-4-(3-chloro-4-(((methylamino)carbonyl)amino)phenoxy)-7-methoxy-6-quinolinecarboxamide;

4-(3-fluoro-4-(ethylaminocarbonyl)aminophenoxy)-7-methoxy-6-quinolinecarboxamide;

4-(3-chloro-4-(((cyclopropylamino)carbonyl)amino)phenoxy)-7-((2R)-2-hydroxy-3-(1-pyrrolidino)propoxy)-6-quinolinecarboxamide;

N6-methyl-4-(3-chloro-4-(((methylamino)carbonyl)amino) phenoxy)-7-((2R)-3-diethylamino-2-hydroxypropoxy)-6-quinolinecarboxamide;

N6-methyl-4-(3-chloro-4-(((ethylamino)carbonyl)amino) phenoxy)-7-((2R)-3-diethylamino-2-hydroxypropoxy)-6-quinolinecarboxamide;

N6-methyl-4-(3-chloro-4-(((methylamino)carbonyl)amino) phenoxy)-7-((2R)-2-hydroxy-3-(1-pyrrolidino)propoxy)-6-quinolinecarboxamide;

N6-methyl-4-(3-chloro-4-(((ethylamino)carbonyl)amino) phenoxy)-7-((2R)-2-hydroxy-3-(1-pyrrolidino)propoxy)-6-quinolinecarboxamide;

N6-methyl-4-(3-chloro-4-(((methylamino)carbonyl)amino) phenoxy)-7-((1-methyl-4-piperidyl)methoxy)-6-quinolinecarboxamide;

N6-methyl-4-(3-chloro-4-(((ethylamino)carbonyl)amino) phenoxy)-7-((1-methyl-4-piperidyl)methoxy)-6-quinolinecarboxamide;

N-(4-(6-cyano-7-(2-methoxyethoxy)-4-quinolyl)oxy-2-fluorophenyl)-N'-cyclopropyl urea;

N-(4-(6-cyano-7-(3-(4-morpholino)propoxy)-4-quinolyl)oxyphenyl)-N'-(3-(methylsulfonyl)phenyl)urea;

4-(4-(((cyclopropylamino)carbonyl)aminophenoxy)-7-methoxy-6-quinolinecarboxamide;

4-(3-fluoro-4-((2-fluoroethylamino)carbonyl)aminophenoxy)-7-methoxy-6-quinolinecarboxamide;

N6-(2-ethoxyethyl)-4-(3-chloro-4-(((methylamino)carbonyl)amino)phenoxy)-7-methoxy-6-quinolinecarboxamide;

4-(4-(3-ethylureido)-3-fluoro-phenoxy)-7-methoxyquinoline-6-carboxylic acid (2-cyanoethyl)amide; and N-(4-(6-(2-cyanoethyl)carbamoyl-7-methoxy-4-quinolyl)oxy-2-fluorophenyl)-N'-cyclopropyl urea, a pharmacologically acceptable salt thereof or a solvate thereof.

[58] A therapeutic method according to [45], wherein the compound represented by General Formula (I), a pharmacologically acceptable salt thereof or a solvate thereof is at least one compound selected from the group consisting of:

4-(3-chloro-4-(cyclopropylaminocarbonyl)aminophenoxy)-7-methoxy-6-quinolinecarboxamide;

4-(3-chloro-4-(ethylaminocarbonyl)aminophenoxy)-7-methoxy-6-quinolinecarboxamide;

N6-methoxy-4-(3-chloro-4-(((cyclopropylamino)carbonyl)amino)phenoxy)-7-methoxy-6-quinolinecarboxamide;

4-(3-chloro-4-(methylaminocarbonyl)aminophenoxy)-7-methoxy-6-quinolinecarboxamide; and N6-methoxy-4-(3-chloro-4-(((ethylamino)carbonyl)amino)phenoxy)-7-methoxy-6-quinolinecarboxamide, a pharmacologically acceptable salt thereof or a solvate thereof.

[59] A therapeutic method according to [45], wherein the compound represented by General Formula (I), a pharmacologically acceptable salt thereof or a solvate thereof is 4-(3-chloro-4-(cyclopropylaminocarbonyl)aminophenoxy)-7-methoxy-6-quinolinecarboxamide, a pharmacologically acceptable salt thereof or a solvate thereof.

[60] A therapeutic method according to [45], wherein the compound represented by General Formula (I), a pharmacologically acceptable salt thereof or a solvate thereof is methanesulfonate of 4-(3-chloro-4-(cyclopropylaminocarbonyl)aminophenoxy)-7-methoxy-6-quinolinecarboxamide.

[61] A therapeutic method according to any one of [45] to [60], wherein the therapeutic substance for gastric cancer is at least one selected from the group consisting of irinotecan, paclitaxel, carboquone, nimustine, 5-fluorouracil, tegafur, UFT, doxifluridine, carmofur, S-1, doxorubicin, mitomycin C, aclarubicin, pirarubicin, epirubicin, docetaxel and cis-platinum.

[62] A therapeutic method according to any one of [45] to [60], wherein the therapeutic substance for gastric cancer is irinotecan, 5-fluorouracil or paclitaxel.

[63] A therapeutic method according to any one of [45] to [60], wherein the FGFR2 inhibitor is at least one compound selected from the group consisting of:

N-(3-trifluoromethyl-4-chlorophenyl)-N'-(4-(2-methylcarbamoylpyridine-4-yl)oxyphenyl)urea;

6-[2-(methylcarbamoyl)phenylsulfanyl]-3-E-[2-(pyridine-2-yl)ethenyl]indazole;

5-(5-fluoro-2-oxo-1,2-dihydroindole-3-ylidenemethyl)-2,4-dimethyl-1H-pyrrole-3-carboxylic acid(2-diethylaminoethyl)amide; and N-{2-chloro-4-[(6,7-dimethoxy-4-quinolyl)oxy]phenyl}-N'-(5-methyl-3-isoxazolyl)urea, a pharmacologically acceptable salt thereof or a solvate thereof.

[64] A therapeutic method according to [45], wherein the mutant FGFR2 comprises a mutation site where amino acids downstream from at least position 813 are deleted in the amino acid sequence 22-822 among the amino acid sequence represented by SEQ ID NO:2.

[65] A therapeutic method according to [45], wherein the living organism is a patient suffering from undifferentiated gastric cancer.

[66] A therapeutic method according to [65], wherein the undifferentiated gastric cancer is at least one gastric cancer selected from the group consisting of poorly differentiated adenocarcinoma, signet-ring cell carcinoma, mucinous carcinoma and scirrhous gastric cancer.

[67] A method for treating a disease, characterized by administering effective dosages of a compound represented by General Formula (I) below, a pharmacologically acceptable salt thereof or a solvate thereof and a therapeutic substance for gastric cancer or a FGFR2 inhibitor to a living organism comprising at least one selected from the group consisting of a cell overexpressing FGFR2 and a cell expressing mutant FGFR2:

General Formula (I)

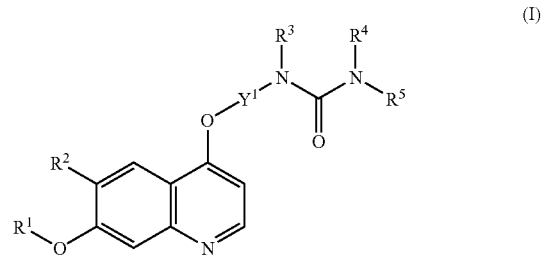

[wherein, $R^1$ represents a group represented by Formula —$V^1$—$V^2$—$V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula —$CONR^6$—, a group represented by Formula —$SO_2NR^6$—, a group represented by Formula —$NR^6SO_2$—, a group represented by Formula —$NR^6CO$— or a group represented by Formula —$NR^6$— (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

$R^2$ represents a cyano group, an optionally substituted $C_{1-6}$ alkoxy group, a carboxyl group, an optionally substituted $C_{2-7}$ alkoxycarbonyl group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

$Y^1$ represents a group represented by either one of the following formulae

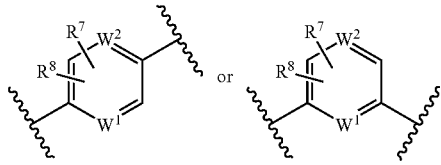

(wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —$CONV^{d1}V^{d2}$ (wherein, $V^{d1}$ and $V^{d2}$ each independently represent a hydrogen atom or an optionally substituted $C_{1-6}$ alkyl group);

$W^1$ and $W^2$ each independently represent an optionally substituted carbon atom or nitrogen atom);

$R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group].

[68] A therapeutic method according to [67], wherein $R^1$ is a $C_{1-6}$ alkyl group (provided that $R^1$ may have at least one substituent selected from the group consisting of a 3-10-membered nonaromatic heterocyclic group, a hydroxyl group, a $C_{1-6}$ alkoxy group, an amino group, a mono-$C_{1-6}$ alkylamino group and a di-$C_{1-6}$ alkylamino group which may have a $C_{1-6}$ alkyl group).

[69] A therapeutic method according to [67], wherein $R^1$ is a methyl group or a group represented by any one of the following formulae

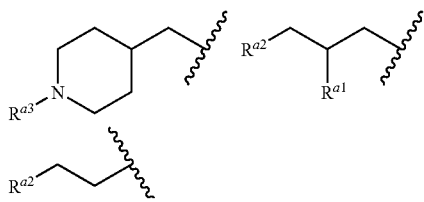

(wherein, $R^{a3}$ represents a methyl group; $R^{a1}$ represents a hydrogen atom or a hydroxyl group; $R^{a2}$ represents a methoxy group, an ethoxy group, a 1-pyrrolidinyl group, a 1-piperidinyl group, a 4-morpholinyl group, a dimethylamino group or a diethylamino group).

[70] A therapeutic method according to [67], wherein $R^1$ is a methyl group or a 2-methoxyethyl group.

[71] A therapeutic method according to [67], wherein $R^2$ is a cyano group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group).

[72] A therapeutic method according to [67], wherein $R^2$ is a cyano group or a group represented by Formula —$CONHV^{a16}$ (wherein, $V^{a16}$ represents a hydrogen atom, a $C_{1-6}$ alkyl group, a $C_{3-8}$ cycloalkyl group, a $C_{1-6}$ alkoxy group or a $C_{3-8}$ cycloalkoxy group, provided that $V^{a16}$ may have at least one substituent selected from the group consisting of a halogen atom, a cyano group, a hydroxyl group and a $C_{1-6}$ alkoxy group).

[73] A therapeutic method according to [67], wherein $R^2$ is a group represented by Formula —$CONHV^{a17}$ (wherein, $V^{a17}$ represents a hydrogen atom, a $C_{1-6}$ alkyl group or a $C_{1-6}$ alkoxy group).

[74] A therapeutic method according to [67], wherein $R^2$ is a group represented by Formula —$CONHV^{a18}$ (wherein, $V^{a18}$ represents a hydrogen atom, a methyl group or a methoxy group).

[75] A therapeutic method according to [67], wherein $Y^1$ is a group represented by the following formula

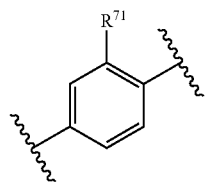

(wherein, $R^{71}$ represents a hydrogen atom or a halogen atom).

[76] A therapeutic method according to [67], wherein $R^3$ and $R^4$ are hydrogen atoms.

[77] A therapeutic method according to [67], wherein $R^5$ is a hydrogen atom, a $C_{1-6}$ alkyl group, a $C_{3-8}$ cycloalkyl group or a $C_{6-10}$ aryl group (provided that $R^5$ may have at least one substituent selected from the group consisting of a halogen atom and a methanesulfonyl group).

[78] A therapeutic method according to [67], wherein $R^5$ is a methyl group, an ethyl group or a cyclopropyl group.

[79] A therapeutic method according to [67], wherein the compound represented by General Formula (I), a pharmacologically acceptable salt thereof or a solvate thereof is at least one compound selected from the group consisting of:

N-(4-(6-cyano-7-(2-methoxyethoxy)-4-quinolyl)oxy-2-fluorophenyl)-N'-(4-fluorophenyl)urea;

N-(2-chloro-4-((6-cyano-7-((1-methyl-4-piperidyl)methoxy)-4-quinolyl)oxy)phenyl)-N'-cyclopropyl urea;

N-(4-((6-cyano-7-(((2R)-3-(diethylamino)-2-hydroxypropyl)oxy)-4-quinolyl)oxy)phenyl)-N'-(4-fluorophenyl)urea;

N-(4-((6-cyano-7-(((2R)-2-hydroxy-3-(1-pyrrolidino)propyl)oxy)-4-quinolyl)oxy)phenyl)-N'-(4-fluorophenyl)urea;

4-(3-chloro-4-(cyclopropylaminocarbonyl)aminophenoxy)-7-methoxy-6-quinolinecarboxamide;

4-(3-chloro-4-(cyclopropylaminocarbonyl)aminophenoxy)-7-(2-methoxyethoxy)-6-quinolinecarboxamide;

N6-cyclopropyl-4-(3-chloro-4-(((cyclopropylamino)carbonyl)amino)phenoxy)-7-methoxy-6-quinolinecarboxamide;

N6-(2-methoxyethyl)-4-(3-chloro-4-(((cyclopropylamino)carbonyl)amino)phenoxy)-7-methoxy-6-quinolinecarboxamide;

N6-(2-fluoroethyl)-4-(3-chloro-4-(((cyclopropylamino)carbonyl)amino)phenoxy)-7-methoxy-6-quinolinecarboxamide;

N6-methoxy-4-(3-chloro-4-(((cyclopropylamino)carbonyl)amino)phenoxy)-7-methoxy-6-quinolinecarboxamide;

N6-methyl-4-(3-chloro-4-(((cyclopropylamino)carbonyl)amino)phenoxy)-7-methoxy-6-quinolinecarboxamide;

N6-ethyl-4-(3-chloro-4-(((cyclopropylamino)carbonyl)amino)phenoxy)-7-methoxy-6-quinolinecarboxamide;

4-(3-fluoro-4-(cyclopropylaminocarbonyl)aminophenoxy)-7-(2-methoxyethoxy)-6-quinolinecarboxamide;

4-(3-chloro-4-(cyclopropylaminocarbonyl)aminophenoxy)-7-(2-hydroxyethoxy)-6-quinolinecarboxamide;

4-(3-chloro-4-(cyclopropylaminocarbonyl)aminophenoxy)-7-((2S)-2,3-dihydroxypropyl)oxy-6-quinolinecarboxamide;

4-(3-chloro-4-(methylaminocarbonyl)aminophenoxy)-7-methoxy-6-quinolinecarboxamide;

4-(3-chloro-4-(ethylaminocarbonyl)aminophenoxy)-7-methoxy-6-quinolinecarboxamide;

N6-methoxy-4-(3-chloro-4-(((ethylamino)carbonyl)amino)phenoxy)-7-methoxy-6-quinolinecarboxamide;

4-(3-chloro-4-(cyclopropylaminocarbonyl)aminophenoxy)-7-(2-ethoxyethoxy)-6-quinolinecarboxamide;

4-(4-((cyclopropylamino)carbonyl)aminophenoxy)-7-(2-methoxyethoxy)-6-quinolinecarboxamide;

N-(2-fluoro-4-((6-carbamoyl-7-methoxy-4-quinolyl)oxy)phenyl)-N'-cyclopropyl urea;

N6-(2-hydroxyethyl)-4-(3-chloro-4-(((cyclopropylamino)carbonyl)amino)phenoxy)-7-methoxy-6-quinolinecarboxamide;

4-(3-chloro-4-(1-propylaminocarbonyl)aminophenoxy)-7-methoxy-6-quinolinecarboxamide;

4-(3-chloro-4-(cis-2-fluoro-cyclopropylaminocarbonyl)aminophenoxy)-7-methoxy-6-quinolinecarboxamide;

N6-methyl-4-(3-chloro-4-(((cyclopropylamino)carbonyl)amino)phenoxy)-7-(2-methoxyethoxy)-6-quinolinecarboxamide;

N6-methyl-4-(3-chloro-4-(((ethylamino)carbonyl)amino)phenoxy)-7-methoxy-6-quinolinecarboxamide;

4-(3-chloro-4-(cyclopropylaminocarbonyl)aminophenoxy)-7-(2-(4-morpholino)ethoxy)-6-quinolinecarboxamide;

4-(3-chloro-4-(2-fluoroethylaminocarbonyl)aminophenoxy)-7-methoxy-6-quinolinecarboxamide;

N6-((2R)tetrahydro-2-furanylmethyl)-4-(3-chloro-4-(((methylamino)carbonyl)amino)phenoxy)-7-methoxy-6-quinolinecarboxamide;

4-(3-fluoro-4-(ethylaminocarbonyl)aminophenoxy)-7-methoxy-6-quinolinecarboxamide;

4-(3-chloro-4-(((cyclopropylamino)carbonyl)amino)phenoxy)-7-((2R)-2-hydroxy-3-(1-pyrrolidino)propoxy)-6-quinolinecarboxamide;

N6-methyl-4-(3-chloro-4-(((methylamino)carbonyl)amino)phenoxy)-7-((2R)-3-diethylamino-2-hydroxypropoxy)-6-quinolinecarboxamide;

N6-methyl-4-(3-chloro-4-(((ethylamino)carbonyl)amino)phenoxy)-7-((2R)-3-diethylamino-2-hydroxypropoxy)-6-quinolinecarboxamide;

N6-methyl-4-(3-chloro-4-(((methylamino)carbonyl)amino)phenoxy)-7-((2R)-2-hydroxy-3-(1-pyrrolidino)propoxy)-6-quinolinecarboxamide;

N6-methyl-4-(3-chloro-4-(((ethylamino)carbonyl)amino)phenoxy)-7-((2R)-2-hydroxy-3-(1-pyrrolidino)propoxy)-6-quinolinecarboxamide;

N6-methyl-4-(3-chloro-4-(((methylamino)carbonyl)amino)phenoxy)-7-((1-methyl-4-piperidyl)methoxy)-6-quinolinecarboxamide;

N6-methyl-4-(3-chloro-4-(((ethylamino)carbonyl)amino)phenoxy)-7-((1-methyl-4-piperidyl)methoxy)-6-quinolinecarboxamide;

N-(4-(6-cyano-7-(2-methoxyethoxy)-4-quinolyl)oxy-2-fluorophenyl)-N'-cyclopropyl urea;

N-(4-(6-cyano-7-(3-(4-morpholino)propoxy)-4-quinolyl)oxyphenyl)-N'-(3-(methylsulfonyl)phenyl)urea;

4-(4-((cyclopropylamino)carbonyl)aminophenoxy)-7-methoxy-6-quinolinecarboxamide;

4-(3-fluoro-4-((2-fluoroethylamino)carbonyl)aminophenoxy)-7-methoxy-6-quinolinecarboxamide;

N6-(2-ethoxyethyl)-4-(3-chloro-4-(((methylamino)carbonyl)amino)phenoxy)-7-methoxy-6-quinolinecarboxamide;

4-(4-(3-ethylureido)-3-fluoro-phenoxy)-7-methoxyquinoline-6-carboxylic acid (2-cyanoethyl)amide; and N-(4-(6-(2-cyanoethyl)carbamoyl-7-methoxy-4-quinolyl)oxy-2-fluorophenyl)-N'-cyclopropyl urea, a pharmacologically acceptable salt thereof or a solvate thereof.

[80] A therapeutic method according to [67], wherein the compound represented by General Formula (I), a pharmacologically acceptable salt thereof or a solvate thereof is at least one compound selected from the group consisting of:

4-(3-chloro-4-(cyclopropylaminocarbonyl)aminophenoxy)-7-methoxy-6-quinolinecarboxamide;

4-(3-chloro-4-(ethylaminocarbonyl)aminophenoxy)-7-methoxy-6-quinolinecarboxamide;

N6-methoxy-4-(3-chloro-4-(((cyclopropylamino)carbonyl)amino)phenoxy)-7-methoxy-6-quinolinecarboxamide;

4-(3-chloro-4-(methylaminocarbonyl)aminophenoxy)-7-methoxy-6-quinolinecarboxamide; and N6-methoxy-4-(3-chloro-4-(((ethylamino)carbonyl)amino)phenoxy)-7-methoxy-6-quinolinecarboxamide, a pharmacologically acceptable salt thereof or a solvate thereof.

[81] A therapeutic method according to [67], wherein the compound represented by General Formula (I), a pharmacologically acceptable salt thereof or a solvate thereof is 4-(3-chloro-4-(cyclopropylaminocarbonyl)aminophenoxy)-7-methoxy-6-quinolinecarboxamide, a pharmacologically acceptable salt thereof or a solvate thereof.

[82] A therapeutic method according to [67], wherein the compound represented by General Formula (I), a pharmacologically acceptable salt thereof or a solvate thereof is methanesulfonate of 4-(3-chloro-4-(cyclopropylaminocarbonyl)aminophenoxy)-7-methoxy-6-quinolinecarboxamide.

[83] A therapeutic method according to any one of [67] to [82], wherein the therapeutic substance for gastric cancer is at least one selected from the group consisting of irinotecan, paclitaxel, carboquone, nimustine, 5-fluorouracil, tegafur, UFT, doxifluridine, carmofur, S-1, doxorubicin, mitomycin C, aclarubicin, pirarubicin, epirubicin, docetaxel and cis-platinum.

[84] A therapeutic method according to any one of [67] to [82], wherein the therapeutic substance for gastric cancer is irinotecan, 5-fluorouracil or paclitaxel.

[85] A therapeutic method according to any one of [67] to [82], wherein the FGFR2 inhibitor is at least one compound selected from the group consisting of:
N-(3-trifluoromethyl-4-chlorophenyl)-N'-(4-(2-methylcarbamoylpyridine-4-yl)oxyphenyl)urea;
6-[2-(methylcarbamoyl)phenylsulfanyl]-3-E-[2-(pyridine-2-yl)ethenyl] indazole;
5-(5-fluoro-2-oxo-1,2-dihydroindole-3-ylidenemethyl)-2,4-dimethyl-1H-pyrrole-3-carboxylic acid(2-diethylaminoethyl)amide; and
N-{2-chloro-4-[(6,7-dimethoxy-4-quinolyl)oxy]phenyl}-N'-(5-methyl-3-isoxazolyl)urea,
a pharmacologically acceptable salt thereof or a solvate thereof.

[86] A therapeutic method according to [67], wherein the mutant FGFR2 comprises a mutation site where amino acids downstream from at least position 813 are deleted in the amino acid sequence 22-822 among the amino acid sequence represented by SEQ ID NO:2.

[87] A therapeutic method according to [67], wherein the living organism is a patient suffering from undifferentiated gastric cancer.

[88] A therapeutic method according to [87], wherein the undifferentiated gastric cancer is at least one gastric cancer selected from the group consisting of poorly differentiated adenocarcinoma, signet-ring cell carcinoma, mucinous carcinoma and scirrhous gastric cancer.

[89] Use of a compound represented by General Formula (I) below, a pharmacologically acceptable salt thereof or a solvate thereof for producing a therapeutic agent for undifferentiated gastric cancer in combination with a therapeutic substance for gastric cancer or a FGFR2 inhibitor:

General Formula (I)

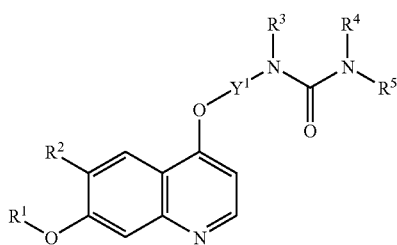

(I)

[wherein, $R^1$ represents a group represented by Formula —$V^1$—$V^2$—$V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula —$CONR^6$—, a group represented by Formula —$SO_2NR^6$—, a group represented by Formula —$NR^6SO_2$—, a group represented by Formula —$NR^6CO$— or a group represented by Formula —$NR^6$— (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

$R^2$ represents a cyano group, an optionally substituted $C_{1-6}$ alkoxy group, a carboxyl group, an optionally substituted $C_{2-7}$ alkoxycarbonyl group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

$Y^1$ represents a group represented by either one of the following formulae

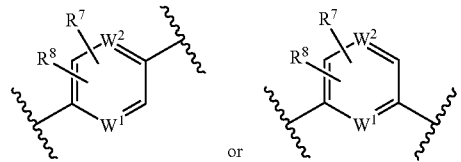

or (wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —$CONV^{d1}V^{d2}$ (wherein, $V^{d1}$ and $V^{d2}$ each independently represent a hydrogen atom or an optionally substituted $C_{1-6}$ alkyl group);

$W^1$ and $W^2$ each independently represent an optionally substituted carbon atom or nitrogen atom);

$R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group].

[90] Use according to [89], wherein $R^1$ is a $C_{1-6}$ alkyl group (provided that $R^1$ may have at least one substituent selected from the group consisting of a 3-10-membered nonaromatic heterocyclic group, a hydroxyl group, a $C_{1-6}$ alkoxy group, an amino group, a mono-$C_{1-6}$ alkylamino group and a di-$C_{1-6}$ alkylamino group which may have a $C_{1-6}$ alkyl group).

[91] Use according to [89], wherein $R^1$ is a methyl group or a group represented by any one of the following formulae

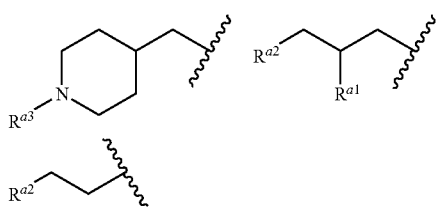

(wherein, $R^{a3}$ represents a methyl group; $R^{a1}$ represents a hydrogen atom or a hydroxyl group; $R^{a2}$ represents a methoxy group, an ethoxy group, a 1-pyrrolidinyl group, a 1-piperidinyl group, a 4-morpholinyl group, a dimethylamino group or a diethylamino group).

[92] Use according to [89], wherein $R^1$ is a methyl group or a 2-methoxyethyl group.

[93] Use according to [89], wherein $R^2$ is a cyano group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group).

[94] Use according to [89], wherein $R^2$ is a cyano group or a group represented by Formula —$CONHV^{a16}$ (wherein, $V^{a16}$ represents a hydrogen atom, a $C_{1-6}$ alkyl group, a $C_{3-8}$ cycloalkyl group, a $C_{1-6}$ alkoxy group or a $C_{3-8}$ cycloalkoxy group, provided that $V^{a16}$ may have at least one substituent selected from the group consisting of a halogen atom, a cyano group, a hydroxyl group and a $C_{1-6}$ alkoxy group).

[95] Use according to [89], wherein $R^2$ is a group represented by Formula —$CONHV^{a17}$ (wherein, $V^{a17}$ represents a hydrogen atom, a $C_{1-6}$ alkyl group or a $C_{1-6}$ alkoxy group).

[96] Use according to [89], wherein $R^2$ is a group represented by Formula —$CONHV^{a18}$ (wherein, $V^{a18}$ represents a hydrogen atom, a methyl group or a methoxy group).

[97] Use according to [89], wherein $Y^1$ is a group represented by the following formula

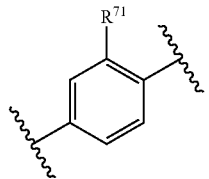

(wherein, $R^{71}$ represents a hydrogen atom or a halogen atom).

[98] Use according to [89], wherein $R^3$ and $R^4$ are hydrogen atoms.

[99] Use according to [89], wherein $R^5$ is a hydrogen atom, a $C_{1-6}$ alkyl group, a $C_{3-8}$ cycloalkyl group or a $C_{6-10}$ aryl group (provided that $R^5$ may have at least one substituent selected from the group consisting of a halogen atom and a methanesulfonyl group).

[100] Use according to [89], wherein $R^5$ is a methyl group, an ethyl group or a cyclopropyl group.

[101] Use according to [89], wherein the compound represented by General Formula (I), a pharmacologically acceptable salt thereof or a solvate thereof is at least one compound selected from the group consisting of:
N-(4-(6-cyano-7-(2-methoxyethoxy)-4-quinolyl)oxy-2-fluorophenyl)-N'-(4-fluorophenyl)urea;
N-(2-chloro-4-((6-cyano-7-((1-methyl-4-piperidyl)methoxy)-4-quinolyl)oxy)phenyl)-N'-cyclopropyl urea;
N-(4-((6-cyano-7-(((2R)-3-(diethylamino)-2-hydroxypropyl)oxy)-4-quinolyl)oxy)phenyl)-N'-(4-fluorophenyl) urea;
N-(4-((6-cyano-7-(((2R)-2-hydroxy-3-(1-pyrrolidino)propyl)oxy)-4-quinolyl)oxy)phenyl)-N'-(4-fluorophenyl) urea;
4-(3-chloro-4-(cyclopropylaminocarbonyl)aminophenoxy)-7-methoxy-6-quinolinecarboxamide;
4-(3-chloro-4-(cyclopropylaminocarbonyl)aminophenoxy)-7-(2-methoxyethoxy)-6-quinolinecarboxamide;
N6-cyclopropyl-4-(3-chloro-4-(((cyclopropylamino)carbonyl)amino)phenoxy)-7-methoxy-6-quinolinecarboxamide;
N6-(2-methoxyethyl)-4-(3-chloro-4-(((cyclopropylamino)carbonyl)amino)phenoxy)-7-methoxy-6-quinolinecarboxamide;
N6-(2-fluoroethyl)-4-(3-chloro-4-(((cyclopropylamino)carbonyl)amino)phenoxy)-7-methoxy-6-quinolinecarboxamide;
N6-methoxy-4-(3-chloro-4-(((cyclopropylamino)carbonyl)amino)phenoxy)-7-methoxy-6-quinolinecarboxamide;
N6-methyl-4-(3-chloro-4-(((cyclopropylamino)carbonyl)amino)phenoxy)-7-methoxy-6-quinolinecarboxamide;
N6-ethyl-4-(3-chloro-4-(((cyclopropylamino)carbonyl)amino)phenoxy)-7-methoxy-6-quinolinecarboxamide;
4-(3-fluoro-4-(cyclopropylaminocarbonyl)aminophenoxy)-7-(2-methoxyethoxy)-6-quinolinecarboxamide;
4-(3-chloro-4-(cyclopropylaminocarbonyl)aminophenoxy)-7-(2-hydroxyethoxy)-6-quinolinecarboxamide;
4-(3-chloro-4-(cyclopropylaminocarbonyl)aminophenoxy)-7-((2S)-2,3-dihydroxypropyl)oxy-6-quinolinecarboxamide;
4-(3-chloro-4-(methylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6-methoxy-4-(3-chloro-4-(((ethylamino)carbonyl)amino)phenoxy)-7-methoxy-6-quinolinecarboxamide;

4-(3-chloro-4-(cyclopropylaminocarbonyl)aminophenoxy)-7-(2-ethoxyethoxy)-6-quinolinecarboxamide;
4-(4-((cyclopropylamino)carbonyl)aminophenoxy)-7-(2-methoxyethoxy)-6-quinolinecarboxamide;
N-(2-fluoro-4-((6-carbamoyl-7-methoxy-4-quinolyl)oxy)phenyl)-N'-cyclopropyl urea;
N6-(2-hydroxyethyl)-4-(3-chloro-4-(((cyclopropylamino)carbonyl)amino)phenoxy)-7-methoxy-6-quinolinecarboxamide;
4-(3-chloro-4-(1-propylaminocarbonyl)aminophenoxy)-7-methoxy-6-quinolinecarboxamide;
4-(3-chloro-4-(cis-2-fluoro-cyclopropylaminocarbonyl)aminophenoxy)-7-methoxy-6-quinolinecarboxamide;
N6-methyl-4-(3-chloro-4-(((cyclopropylamino)carbonyl)amino)phenoxy)-7-(2-methoxyethoxy)-6-quinolinecarboxamide;
N6-methyl-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-(4-morpholino)ethoxy)-6-quinolinecarboxamide;
4-(3-chloro-4-(2-fluoroethylaminocarbonyl)aminophenoxy)-7-methoxy-6-quinolinecarboxamide;
N6-((2R)tetrahydro-2-furanylmethyl)-4-(3-chloro-4-(((methylamino)carbonyl)amino)phenoxy)-7-methoxy-6-quinolinecarboxamide;
4-(3-fluoro-4-(ethylaminocarbonyl)aminophenoxy)-7-methoxy-6-quinolinecarboxamide;
4-(3-chloro-4-(((cyclopropylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-((2R)-3-diethylamino-2-hydroxypropoxy)-6-quinolinecarboxamide;
N6-methyl-4-(3-chloro-4-(((ethylamino)carbonyl)amino)phenoxy)-7-((2R)-3-diethylamino-2-hydroxypropoxy)-6-quinolinecarboxamide;
N6-methyl-4-(3-chloro-4-(((methylamino)carbonyl)amino)phenoxy)-7-((2R)-2-hydroxy-3-(1-pyrrolidino)propoxy)-6-quinolinecarboxamide;
N6-methyl-4-(3-chloro-4-(((ethylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-((1-methyl-4-piperidyl)methoxy)-6-quinolinecarboxamide;
N6-methyl-4-(3-chloro-4-(((ethylamino)carbonyl)amino)phenoxy)-7-((1-methyl-4-piperidyl)methoxy)-6-quinolinecarboxamide;
N-(4-(6-cyano-7-(2-methoxyethoxy)-4-quinolyl)oxy-2-fluorophenyl)-N'-cyclopropyl urea;
N-(4-(6-cyano-7-(3-(4-morpholino)propoxy)-4-quinolyl)oxyphenyl)-N'-(3-(methylsulfonyl)phenyl)urea;
4-(4-((cyclopropylamino)carbonyl)aminophenoxy)-7-methoxy-6-quinolinecarboxamide;
4-(3-fluoro-4-((2-fluoroethylamino)carbonyl)aminophenoxy)-7-methoxy-6-quinolinecarboxamide;
N6-(2-ethoxyethyl)-4-(3-chloro-4-(((methylamino)carbonyl)amino)phenoxy)-7-methoxy-6-quinolinecarboxamide;
4-(4-(3-ethylureido)-3-fluoro-phenoxy)-7-methoxyquinoline-6-carboxylic acid (2-cyanoethyl)amide; and
N-(4-(6-(2-cyanoethyl)carbamoyl-7-methoxy-4-quinolyl)oxy-2-fluorophenyl)-N'-cyclopropyl urea,
a pharmacologically acceptable salt thereof or a solvate thereof.

[102] Use according to [89], wherein the compound represented by General Formula (I), a pharmacologically acceptable salt thereof or a solvate thereof is at least one compound selected from the group consisting of:
4-(3-chloro-4-(cyclopropylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6-methoxy-4-(3-chloro-4-(((cyclopropylamino)carbonyl)amino)phenoxy)-7-methoxy-6-quinolinecarboxamide;
4-(3-chloro-4-(methylaminocarbonyl)aminophenoxy)-7-methoxy-6-quinolinecarboxamide; and
N6-methoxy-4-(3-chloro-4-(((ethylamino)carbonyl)amino)phenoxy)-7-methoxy-6-quinolinecarboxamide,
a pharmacologically acceptable salt thereof or a solvate thereof.

[103] Use according to [89], wherein the compound represented by General Formula (I), a pharmacologically acceptable salt thereof or a solvate thereof is 4-(3-chloro-4-(cyclopropylaminocarbonyl)aminophenoxy)-7-methoxy-6-quinolinecarboxamide, a pharmacologically acceptable salt thereof or a solvate thereof.

[104] Use according to [89], wherein the compound represented by General Formula (I), a pharmacologically acceptable salt thereof or a solvate thereof is methanesulfonate of 4-(3-chloro-4-(cyclopropylaminocarbonyl)aminophenoxy)-7-methoxy-6-quinolinecarboxamide.

[105] Use according to any one of [89] to [104], wherein the therapeutic substance for gastric cancer is at least one selected from the group consisting of irinotecan, paclitaxel, carboquone, nimustine, 5-fluorouracil, tegafur, UFT, doxifluridine, carmofur, S-1, doxorubicin, mitomycin C, aclarubicin, pirarubicin, epirubicin, docetaxel and cis-platinum.

[106] Use according to any one of [89] to [104], wherein the therapeutic substance for gastric cancer is irinotecan, 5-fluorouracil or paclitaxel.

[107] Use according to any one of [89] to [104], wherein the FGFR2 inhibitor is at least one compound selected from the group consisting of:
N-(3-trifluoromethyl-4-chlorophenyl)-N'-(4-(2-methylcarbamoylpyridine-4-yl)oxyphenyl)urea;
6-[2-(methylcarbamoyl)phenylsulfanyl]-3-E-[2-(pyridine-2-yl)ethenyl]indazole;
5-(5-fluoro-2-oxo-1,2-dihydroindole-3-ylidenemethyl)-2,4-dimethyl-1H-pyrrole-3-carboxylic acid(2-diethylaminoethyl)amide; and
N-{2-chloro-4-[(6,7-dimethoxy-4-quinolyl)oxy]phenyl}-N'-(5-methyl-3-isoxazolyl)urea,
a pharmacologically acceptable salt thereof or a solvate thereof.

[108] Use according to [89], wherein the undifferentiated gastric cancer comprises at least one selected from the group consisting of a cell overexpressing FGFR2 and a cell expressing mutant FGFR2.

[109] Use according to [108], wherein the mutant FGFR2 comprises a mutation site where amino acids downstream from at least position 813 are deleted in the amino acid sequence 22-822 among the amino acid sequence represented by SEQ ID NO:2.

[110] Use according to [89], wherein the undifferentiated gastric cancer is at least one gastric cancer selected from the group consisting of poorly differentiated adenocarcinoma, signet-ring cell carcinoma, mucinous carcinoma and scirrhous gastric cancer.

[111] Use of a compound represented by General Formula (I) below, a pharmacologically acceptable salt thereof or a solvate thereof for producing a pharmaceutical composition in combination with a therapeutic substance for gastric cancer or a FGFR2 inhibitor for administration to a living organism comprising at least one selected from the group consisting of a cell overexpressing FGFR2 and a cell expressing mutant FGFR2:

General Formula (I)

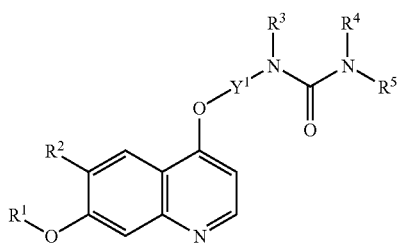
(I)

[wherein, $R^1$ represents a group represented by Formula $-V^1-V^2-V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula $-CONR^6-$, a group represented by Formula $-SO_2NR^6$, a group represented by Formula $-NR^6SO_2-$, a group represented by Formula $-NR^6CO-$ or a group represented by Formula $-NR^6-$ (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

$R^2$ represents a cyano group, an optionally substituted $C_{1-6}$ alkoxy group, a carboxyl group, an optionally substituted $C_{2-7}$ alkoxycarbonyl group or a group represented by Formula $-CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

$Y^1$ represents a group represented by either one of the following formulae

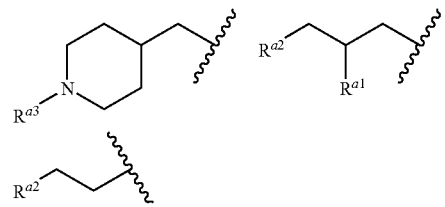

(wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula $-CONV^{d1}V^{d2}$ (wherein, $V^{d1}$ and $V^{d2}$ each independently represent a hydrogen atom or an optionally substituted $C_{1-6}$ alkyl group);

$W^1$ and $W^2$ each independently represent an optionally substituted carbon atom or nitrogen atom);

$R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group].

[112] Use according to [111], wherein $R^1$ is a $C_{1-6}$ alkyl group (provided that $R^1$ may have at least one substituent selected from the group consisting of a 3-10-membered nonaromatic heterocyclic group, a hydroxyl group, a $C_{1-6}$ alkoxy group, an amino group, a mono-$C_{1-6}$ alkylamino group and a di-$C_{1-6}$ alkylamino group which may have a $C_{1-6}$ alkyl group).

[113] Use according to [111], wherein $R^1$ is a methyl group or a group represented by any one of the following formulae

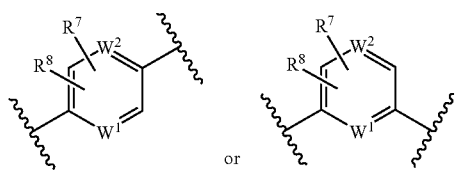

(wherein, $R^{a3}$ represents a methyl group; $R^{a1}$ represents a hydrogen atom or a hydroxyl group; $R^{a2}$ represents a methoxy group, an ethoxy group, a 1-pyrrolidinyl group, a 1-piperidinyl group, a 4-morpholinyl group, a dimethylamino group or a diethylamino group).

[114] Use according to [111], wherein $R^1$ is a methyl group or a 2-methoxyethyl group.

[115] Use according to [111], wherein $R^2$ is a cyano group or a group represented by Formula $-CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group).

[116] Use according to [111], wherein $R^2$ is a cyano group or a group represented by Formula —CONHV$^{a16}$ (wherein, V$^{a16}$ represents a hydrogen atom, a $C_{1-6}$ alkyl group, a $C_{3-8}$ cycloalkyl group, a $C_{1-6}$ alkoxy group or a $C_{3-8}$ cycloalkoxy group, provided that V$^{a16}$ may have at least one substituent selected from the group consisting of a halogen atom, a cyano group, a hydroxyl group and a $C_{1-6}$ alkoxy group).

[117] Use according to [111], wherein $R^2$ is a group represented by Formula —CONHV$^{a17}$ (wherein, V$^{a17}$ represents a hydrogen atom, a $C_{1-6}$ alkyl group or a $C_{1-6}$ alkoxy group).

[118] Use according to [111], wherein $R^2$ is a group represented by Formula —CONHV$^{a18}$ (wherein, V$^{a18}$ represents a hydrogen atom, a methyl group or a methoxy group).

[119] Use according to [111], wherein $Y^1$ is a group represented by the following formula

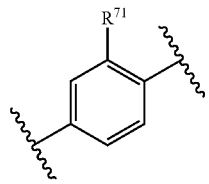

(wherein, $R^{71}$ represents a hydrogen atom or a halogen atom).

[120] Use according to [111], wherein $R^3$ and $R^4$ are hydrogen atoms.

[121] Use according to [111], wherein $R^5$ is a hydrogen atom, a $C_{1-6}$ alkyl group, a $C_{3-8}$ cycloalkyl group or a $C_{6-10}$ aryl group (provided that $R^5$ may have at least one substituent selected from the group consisting of a halogen atom and a methanesulfonyl group).

[122] Use according to [111], wherein $R^5$ is a methyl group, an ethyl group or a cyclopropyl group.

[123] Use according to [111], wherein the compound represented by General Formula (I), a pharmacologically acceptable salt thereof or a solvate thereof is at least one compound selected from the group consisting of:
N-(4-(6-cyano-7-(2-methoxyethoxy)-4-quinolyl)oxy-2-fluorophenyl)-N'-(4-fluorophenyl)urea;
N-(2-chloro-4-((6-cyano-7-((1-methyl-4-piperidyl)methoxy)-4-quinolyl)oxy)phenyl)-N'-cyclopropyl urea;
N-(4-((6-cyano-7-(((2R)-3-(diethylamino)-2-hydroxypropyl)oxy)-4-quinolyl)oxy)phenyl)-N'-(4-fluorophenyl)urea;
N-(4-((6-cyano-7-(((2R)-2-hydroxy-3-(1-pyrrolidino)propyl)oxy)-4-quinolyl)oxy)phenyl)-N'-(4-fluorophenyl)urea;
4-(3-chloro-4-(cyclopropylaminocarbonyl)aminophenoxy)-7-methoxy-6-quinolinecarboxamide;
4-(3-chloro-4-(cyclopropylaminocarbonyl)aminophenoxy)-7-(2-methoxyethoxy)-6-quinolinecarboxamide;
N6-cyclopropyl-4-(3-chloro-4-(((cyclopropylamino)carbonyl)amino)phenoxy)-7-methoxy-6-quinolinecarboxamide;
N6-(2-methoxyethyl)-4-(3-chloro-4-(((cyclopropylamino)carbonyl)amino)phenoxy)-7-methoxy-6-quinolinecarboxamide;
N6-(2-fluoroethyl)-4-(3-chloro-4-(((cyclopropylamino)carbonyl)amino)phenoxy)-7-methoxy-6-quinolinecarboxamide;
N6-methoxy-4-(3-chloro-4-(((cyclopropylamino)carbonyl)amino)phenoxy)-7-methoxy-6-quinolinecarboxamide;
N6-methyl-4-(3-chloro-4-(((cyclopropylamino)carbonyl)amino)phenoxy)-7-methoxy-6-quinolinecarboxamide;
N6-ethyl-4-(3-chloro-4-(((cyclopropylamino)carbonyl)amino)phenoxy)-7-methoxy-6-quinolinecarboxamide;
4-(3-fluoro-4-(cyclopropylaminocarbonyl)aminophenoxy)-7-(2-methoxyethoxy)-6-quinolinecarboxamide;
4-(3-chloro-4-(cyclopropylaminocarbonyl)aminophenoxy)-7-(2-hydroxyethoxy)-6-quinolinecarboxamide;
4-(3-chloro-4-(cyclopropylaminocarbonyl)aminophenoxy)-7-((2S)-2,3-dihydroxypropyl)oxy-6-quinolinecarboxamide;
4-(3-chloro-4-(methylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6-methoxy-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-ethoxyethoxy)-6-quinolinecarboxamide;
4-(4-((cyclopropylamino)carbonyl)aminophenoxy)-7-(2-methoxyethoxy)-6-quinolinecarboxamide;
N-(2-fluoro-4-((6-carbamoyl-7-methoxy-4-quinolyl)oxy)phenyl)-N'-cyclopropyl urea;
N6-(2-hydroxyethyl)-4-(3-chloro-4-(((cyclopropylamino)carbonyl)amino)phenoxy)-7-methoxy-6-quinolinecarboxamide;
4-(3-chloro-4-(1-propylaminocarbonyl)aminophenoxy)-7-methoxy-6-quinolinecarboxamide;
4-(3-chloro-4-(cis-2-fluoro-cyclopropylaminocarbonyl)aminophenoxy)-7-methoxy-6-quinolinecarboxamide;
N6-methyl-4-(3-chloro-4-(((cyclopropylamino)carbonyl)amino)phenoxy)-7-(2-methoxyethoxy)-6-quinolinecarboxamide;
N6-methyl-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-(4-morpholino)ethoxy)-6-quinolinecarboxamide;
4-(3-chloro-4-(2-fluoroethylaminocarbonyl)aminophenoxy)-7-methoxy-6-quinolinecarboxamide;
N6-((2R)tetrahydro-2-furanylmethyl)-4-(3-chloro-4-(((methylamino)carbonyl)amino)phenoxy)-7-methoxy-6-quinolinecarboxamide;
4-(3-fluoro-4-(ethylaminocarbonyl)aminophenoxy)-7-methoxy-6-quinolinecarboxamide;
4-(3-chloro-4-(((cyclopropylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-((2R)-3-diethylamino-2-hydroxypropoxy)-6-quinolinecarboxamide;
N6-methyl-4-(3-chloro-4-(((ethylamino)carbonyl)amino)phenoxy)-7-((2R)-3-diethylamino-2-hydroxypropoxy)-6-quinolinecarboxamide;
N6-methyl-4-(3-chloro-4-(((methylamino)carbonyl)amino)phenoxy)-7-((2R)-2-hydroxy-3-(1-pyrrolidino)propoxy)-6-quinolinecarboxamide;
N6-methyl-4-(3-chloro-4-(((ethylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-((1-methyl-4-piperidyl)methoxy)-6-quinolinecarboxamide;

N6-methyl-4-(3-chloro-4-(((ethylamino)carbonyl)amino) phenoxy)-7-((1-methyl-4-piperidyl)methoxy)-6-quinolinecarboxamide;
N-(4-(6-cyano-7-(2-methoxyethoxy)-4-quinolyl)oxy-2-fluorophenyl)-N'-cyclopropyl urea;
N-(4-(6-cyano-7-(3-(4-morpholino)propoxy)-4-quinolyl) oxyphenyl)-N'-(3-(methylsulfonyl)phenyl)urea;
4-(4-(((cyclopropylamino)carbonyl)aminophenoxy)-7-methoxy-6-quinolinecarboxamide;
4-(3-fluoro-4-((2-fluoroethylamino)carbonyl)aminophenoxy)-7-methoxy-6-quinolinecarboxamide;
N6-(2-ethoxyethyl)-4-(3-chloro-4-(((methylamino)carbonyl)amino)phenoxy)-7-methoxy-6-quinolinecarboxamide;
4-(4-(3-ethylureido)-3-fluoro-phenoxy)-7-methoxyquinoline-6-carboxylic acid (2-cyanoethyl)amide; and
N-(4-(6-(2-cyanoethyl)carbamoyl-7-methoxy-4-quinolyl) oxy-2-fluorophenyl)-N'-cyclopropyl urea,
a pharmacologically acceptable salt thereof or a solvate thereof.

[124] Use according to [111], wherein the compound represented by General Formula (I), a pharmacologically acceptable salt thereof or a solvate thereof is at least one compound selected from the group consisting of:
4-(3-chloro-4-(cyclopropylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6-methoxy-4-(3-chloro-4-(((cyclopropylamino)carbonyl) amino)phenoxy)-7-methoxy-6-quinolinecarboxamide;
4-(3-chloro-4-(methylaminocarbonyl)aminophenoxy)-7-methoxy-6-quinolinecarboxamide; and
N6-methoxy-4-(3-chloro-4-(((ethylamino)carbonyl)amino) phenoxy)-7-methoxy-6-quinolinecarboxamide,
a pharmacologically acceptable salt thereof or a solvate thereof.

[125] Use according to [111], wherein the compound represented by General Formula (I), a pharmacologically acceptable salt thereof or a solvate thereof is 4-(3-chloro-4-(cyclopropylaminocarbonyl)aminophenoxy)-7-methoxy-6-quinolinecarboxamide, a pharmacologically acceptable salt thereof or a solvate thereof.

[126] Use according to [111], wherein the compound represented by General Formula (I), a pharmacologically acceptable salt thereof or a solvate thereof is methanesulfonate of 4-(3-chloro-4-(cyclopropylaminocarbonyl) aminophenoxy)-7-methoxy-6-quinolinecarboxamide.

[127] Use according to any one of [111] to [116], wherein the therapeutic substance for gastric cancer is at least one selected from the group consisting of irinotecan, paclitaxel, carboquone, nimustine, 5-fluorouracil, tegafur, UFT, doxifluridine, carmofur, S-1, doxorubicin, mitomycin C, aclarubicin, pirarubicin, epirubicin, docetaxel and cisplatinum.

[128] Use according to any one of [111] to [116], wherein the therapeutic substance for gastric cancer is irinotecan, 5-fluorouracil or paclitaxel.

[129] Use according to any one of [111] to [116], wherein the FGFR2 inhibitor is at least one compound selected from the group consisting of:
N-(3-trifluoromethyl-4-chlorophenyl)-N'-(4-(2-methylcarbamoylpyridine-4-yl)oxyphenyl)urea;
6-[2-(methylcarbamoyl)phenylsulfanyl]-3-E-[2-(pyridine-2-yl)ethenyl]indazole;
5-(5-fluoro-2-oxo-1,2-dihydroindole-3-ylidenemethyl)-2,4-dimethyl-1H-pyrrole-3-carboxylic acid(2-diethylaminoethyl)amide; and
N-{2-chloro-4-[(6,7-dimethoxy-4-quinolyl)oxy]phenyl}-N'-(5-methyl-3-isoxazolyl)urea,
a pharmacologically acceptable salt thereof or a solvate thereof.

[130] Use according to [111], wherein the undifferentiated gastric cancer comprises at least one selected from the group consisting of a cell overexpressing FGFR2 and a cell expressing mutant FGFR2.

[131] Use according to [130], wherein the mutant FGFR2 comprises a mutation site where amino acids downstream from at least position 813 are deleted in the amino acid sequence 22-822 among the amino acid sequence represented by SEQ ID NO:2.

[132] Use according to [111], wherein the undifferentiated gastric cancer is at least one gastric cancer selected from the group consisting of poorly differentiated adenocarcinoma, signet-ring cell carcinoma, mucinous carcinoma and scirrhous gastric cancer.

[133] A compound represented by General Formula (I) below, a pharmacologically acceptable salt thereof or a solvate thereof for treating undifferentiated gastric cancer in combination with a therapeutic substance for gastric cancer or a FGFR2 inhibitor:

General Formula (I)

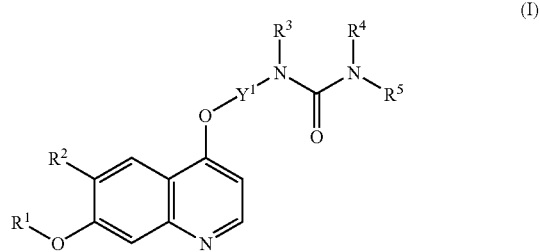

(I)

[wherein, $R^1$ represents a group represented by Formula —$V^1$—$V^2$—$V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula —$CONR^6$—, a group represented by Formula —$SO_2NR^6$—, a group representes by Formula —$NR^6SO_2$—, a group represented by Formula —$NR^6CO$— or a group represented by Formula —$NR^6$— (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

$R^2$ represents a cyano group, an optionally substituted $C_{1-6}$ alkoxy group, a carboxyl group, an optionally substituted $C_{2-7}$ alkoxycarbonyl group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

$Y^1$ represents a group represented by either one of the following formulae

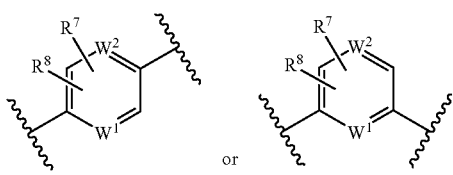

or (wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —$CONV^{d1}V^{d2}$ (wherein, $V^{d1}$ and $V^{d2}$ each independently represent a hydrogen atom or an optionally substituted $C_{1-6}$ alkyl group);

$W^1$ and $W^2$ each independently represent an optionally substituted carbon atom or nitrogen atom);

$R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group].

[134] A compound according to [133], a pharmacologically acceptable salt thereof or a solvate thereof, wherein $R^1$ is a $C_{1-6}$ alkyl group (provided that $R^1$ may have at least one substituent selected from the group consisting of a 3-10-membered nonaromatic heterocyclic group, a hydroxyl group, a $C_{1-6}$ alkoxy group, an amino group, a mono-$C_{1-6}$ alkylamino group and a di-$C_{1-6}$ alkylamino group which may have a $C_{1-6}$ alkyl group).

[135] A compound according to [133], a pharmacologically acceptable salt thereof or a solvate thereof, wherein $R^1$ is a methyl group or a group represented by any one of the following formulae

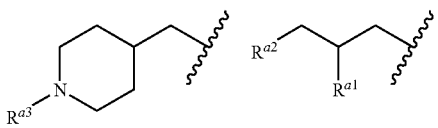

(wherein, $R^{a3}$ represents a methyl group; $R^{a1}$ represents a hydrogen atom or a hydroxyl group; $R^{a2}$ represents a methoxy group, an ethoxy group, a 1-pyrrolidinyl group, a 1-piperidinyl group, a 4-morpholinyl group, a dimethylamino group or a diethylamino group).

[136] A compound according to [133], a pharmacologically acceptable salt thereof or a solvate thereof, wherein $R^1$ is a methyl group or a 2-methoxyethyl group.

[137] A compound according to [133], a pharmacologically acceptable salt thereof or a solvate thereof, wherein $R^2$ is a cyano group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group).

[138] A compound according to [133], a pharmacologically acceptable salt thereof or a solvate thereof, wherein $R^2$ is a cyano group or a group represented by Formula —$CONHV^{a16}$ (wherein, $V^{a16}$ represents a hydrogen atom, a $C_{1-6}$ alkyl group, a $C_{3-8}$ cycloalkyl group, a $C_{1-6}$ alkoxy group or a $C_{3-8}$ cycloalkoxy group, provided that $V^{a16}$ may have at least one substituent selected from the group consisting of a halogen atom, a cyano group, a hydroxyl group and a $C_{1-6}$ alkoxy group).

[139] A compound according to [133], a pharmacologically acceptable salt thereof or a solvate thereof, wherein $R^2$ is a group represented by Formula —$CONHV^{a17}$ (wherein, $V^{a17}$ represents a hydrogen atom, a $C_{1-6}$ alkyl group or a $C_{1-6}$ alkoxy group).

[140] A compound according to [133], a pharmacologically acceptable salt thereof or a solvate thereof, wherein $R^2$ is a group represented by Formula —$CONHV^{a18}$ (wherein, $V^{a18}$ represents a hydrogen atom, a methyl group or a methoxy group).

[141] A compound according to [133], a pharmacologically acceptable salt thereof or a solvate thereof, wherein $Y^1$ is a group represented by the following formula

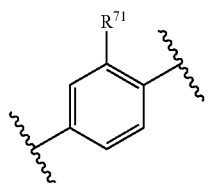

(wherein, $R^{71}$ represents a hydrogen atom or a halogen atom).

[142] A compound according to [133], a pharmacologically acceptable salt thereof or a solvate thereof, wherein $R^3$ and $R^4$ are hydrogen atoms.

[143] A compound according to [133], a pharmacologically acceptable salt thereof or a solvate thereof, wherein $R^5$ is a hydrogen atom, a $C_{1-6}$ alkyl group, a $C_{3-8}$ cycloalkyl group or a $C_{6-10}$ aryl group (provided that $R^5$ may have at least one substituent selected from the group consisting of a halogen atom and a methanesulfonyl group).

[144] A compound according to [133], a pharmacologically acceptable salt thereof or a solvate thereof, wherein $R^5$ is a methyl group, an ethyl group or a cyclopropyl group.

[145] A compound according to [133], a pharmacologically acceptable salt thereof or a solvate thereof, wherein the compound represented by General Formula (I), a pharmacologically acceptable salt thereof or a solvate thereof is at least one compound selected from the group consisting of:
N-(4-(6-cyano-7-(2-methoxyethoxy)-4-quinolyl)oxy-2-fluorophenyl)-N'-(4-fluorophenyl)urea;
N-(2-chloro-4-((6-cyano-7-((1-methyl-4-piperidyl)methoxy)-4-quinolyl)oxy)phenyl)-N'-cyclopropyl urea;
N-(4-((6-cyano-7-(((2R)-3-(diethylamino)-2-hydroxypropyl)oxy)-4-quinolyl)oxy)phenyl)-N'-(4-fluorophenyl) urea;
N-(4-((6-cyano-7-(((2R)-2-hydroxy-3-(1-pyrrolidino)propyl)oxy)-4-quinolyl)oxy)phenyl)-N'-(4-fluorophenyl) urea;
4-(3-chloro-4-(cyclopropylaminocarbonyl)aminophenoxy)-7-methoxy-6-quinolinecarboxamide;
4-(3-chloro-4-(cyclopropylaminocarbonyl)aminophenoxy)-7-(2-methoxyethoxy)-6-quinolinecarboxamide;
N6-cyclopropyl-4-(3-chloro-4-(((cyclopropylamino)carbonyl)amino)phenoxy)-7-methoxy-6-quinolinecarboxamide;
N6-(2-methoxyethyl)-4-(3-chloro-4-(((cyclopropylamino)carbonyl)amino)phenoxy)-7-methoxy-6-quinolinecarboxamide;
N6-(2-fluoroethyl)-4-(3-chloro-4-(((cyclopropylamino)carbonyl)amino)phenoxy)-7-methoxy-6-quinolinecarboxamide;
N6-methoxy-4-(3-chloro-4-(((cyclopropylamino)carbonyl)amino)phenoxy)-7-methoxy-6-quinolinecarboxamide;
N6-methyl-4-(3-chloro-4-(((cyclopropylamino)carbonyl)amino)phenoxy)-7-methoxy-6-quinolinecarboxamide;
N6-ethyl-4-(3-chloro-4-(((cyclopropylamino)carbonyl)amino)phenoxy)-7-methoxy-6-quinolinecarboxamide;
4-(3-fluoro-4-(cyclopropylaminocarbonyl)aminophenoxy)-7-(2-methoxyethoxy)-6-quinolinecarboxamide;
4-(3-chloro-4-(cyclopropylaminocarbonyl)aminophenoxy)-7-(2-hydroxyethoxy)-6-quinolinecarboxamide;
4-(3-chloro-4-(cyclopropylaminocarbonyl)aminophenoxy)-7-((2S)-2,3-dihydroxypropyl)oxy-6-quinolinecarboxamide;
4-(3-chloro-4-(methylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6-methoxy-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-ethoxyethoxy)-6-quinolinecarboxamide;
4-(4-((cyclopropylamino)carbonyl)aminophenoxy)-7-(2-methoxyethoxy)-6-quinolinecarboxamide;
N-(2-fluoro-4-((6-carbamoyl-7-methoxy-4-quinolyl)oxy)phenyl)-N'-cyclopropyl urea;
N6-(2-hydroxyethyl)-4-(3-chloro-4-(((cyclopropylamino)carbonyl)amino)phenoxy)-7-methoxy-6-quinolinecarboxamide;
4-(3-chloro-4-(1-propylaminocarbonyl)aminophenoxy)-7-methoxy-6-quinolinecarboxamide;
4-(3-chloro-4-(cis-2-fluoro-cyclopropylaminocarbonyl)aminophenoxy)-7-methoxy-6-quinolinecarboxamide;
N6-methyl-4-(3-chloro-4-(((cyclopropylamino)carbonyl)amino)phenoxy)-7-(2-methoxyethoxy)-6-quinolinecarboxamide;
N6-methyl-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-(4-morpholino)ethoxy)-6-quinolinecarboxamide;
4-(3-chloro-4-(2-fluoroethylaminocarbonyl)aminophenoxy)-7-methoxy-6-quinolinecarboxamide;
N6-((2R)tetrahydro-2-furanylmethyl)-4-(3-chloro-4-(((methylamino)carbonyl)amino)phenoxy)-7-methoxy-6-quinolinecarboxamide;
4-(3-fluoro-4-(ethylaminocarbonyl)aminophenoxy)-7-methoxy-6-quinolinecarboxamide;
4-(3-chloro-4-(((cyclopropylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-((2R)-3-diethylamino-2-hydroxypropoxy)-6-quinolinecarboxamide;
N6-methyl-4-(3-chloro-4-(((ethylamino)carbonyl)amino)phenoxy)-7-((2R)-3-diethylamino-2-hydroxypropoxy)-6-quinolinecarboxamide;
N6-methyl-4-(3-chloro-4-(((methylamino)carbonyl)amino)phenoxy)-7-((2R)-2-hydroxy-3-(1-pyrrolidino)propoxy)-6-quinolinecarboxamide;
N6-methyl-4-(3-chloro-4-(((ethylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-((1-methyl-4-piperidyl)methoxy)-6-quinolinecarboxamide;
N6-methyl-4-(3-chloro-4-(((ethylamino)carbonyl)amino)phenoxy)-7-((1-methyl-4-piperidyl)methoxy)-6-quinolinecarboxamide;
N-(4-(6-cyano-7-(2-methoxyethoxy)-4-quinolyl)oxy-2-fluorophenyl)-N'-cyclopropyl urea;
N-(4-(6-cyano-7-(3-(4-morpholino)propoxy)-4-quinolyl)oxyphenyl)-N'-(3-(methylsulfonyl)phenyl)urea;
4-(4-((cyclopropylamino)carbonyl)aminophenoxy)-7-methoxy-6-quinolinecarboxamide;
4-(3-fluoro-4-((2-fluoroethylamino)carbonyl)aminophenoxy)-7-methoxy-6-quinolinecarboxamide;
N6-(2-ethoxyethyl)-4-(3-chloro-4-(((methylamino)carbonyl)amino)phenoxy)-7-methoxy-6-quinolinecarboxamide;
4-(4-(3-ethylureido)-3-fluoro-phenoxy)-7-methoxyquinoline-6-carboxylic acid (2-cyanoethyl)amide; and
N-(4-(6-(2-cyanoethyl)carbamoyl-7-methoxy-4-quinolyl)oxy-2-fluorophenyl)-N'-cyclopropyl urea,
a pharmacologically acceptable salt thereof or a solvate thereof.

[146] A compound according to [133], a pharmacologically acceptable salt thereof or a solvate thereof, wherein the compound represented by General Formula (I), a pharmacologically acceptable salt thereof or a solvate thereof is at least one compound selected from the group consisting of:
4-(3-chloro-4-(cyclopropylaminocarbonyl)aminophenoxy)-7-methoxy-6-quinolinecarboxamide;

4-(3-chloro-4-(ethylaminocarbonyl)aminophenoxy)-7-methoxy-6-quinolinecarboxamide;

N6-methoxy-4-(3-chloro-4-(((cyclopropylamino)carbonyl)amino)phenoxy)-7-methoxy-6-quinolinecarboxamide;

4-(3-chloro-4-(methylaminocarbonyl)aminophenoxy)-7-methoxy-6-quinolinecarboxamide; and N6-methoxy-4-(3-chloro-4-(((ethylamino)carbonyl)amino)phenoxy)-7-methoxy-6-quinolinecarboxamide, a pharmacologically acceptable salt thereof or a solvate thereof.

[147] A compound according to [133], a pharmacologically acceptable salt thereof or a solvate thereof, wherein the compound represented by General Formula (I), a pharmacologically acceptable salt thereof or a solvate thereof is 4-(3-chloro-4-(cyclopropylaminocarbonyl)aminophenoxy)-7-methoxy-6-quinolinecarboxamide, a pharmacologically acceptable salt thereof or a solvate thereof.

[148] A compound according to [133], a pharmacologically acceptable salt thereof or a solvate thereof, wherein the compound represented by General Formula (I), a pharmacologically acceptable salt thereof or a solvate thereof is methanesulfonate of 4-(3-chloro-4-(cyclopropylaminocarbonyl)aminophenoxy)-7-methoxy-6-quinolinecarboxamide.

[149] A compound according to any one of [133] to [148], a pharmacologically acceptable salt thereof or a solvate thereof, wherein the therapeutic substance for gastric cancer is at least one selected from the group consisting of irinotecan, paclitaxel, carboquone, nimustine, 5-fluorouracil, tegafur, UFT, doxifluridine, carmofur, S-1, doxorubicin, mitomycin C, aclarubicin, pirarubicin, epirubicin, docetaxel and cis-platinum.

[150] A compound according to any one of [133] to [148], a pharmacologically acceptable salt thereof or a solvate thereof, wherein the therapeutic substance for gastric cancer is irinotecan, 5-fluorouracil or paclitaxel.

[151] A compound according to any one of [133] to [148], a pharmacologically acceptable salt thereof or a solvate thereof, wherein the FGFR2 inhibitor is at least one compound selected from the group consisting of:

N-(3-trifluoromethyl-4-chlorophenyl)-N'-(4-(2-methylcarbamoylpyridine-4-yl)oxyphenyl)urea;

6-[2-(methylcarbamoyl)phenylsulfanyl]-3-E-[2-(pyridine-2-yl)ethenyl]indazole;

5-(5-fluoro-2-oxo-1,2-dihydroindole-3-ylidenemethyl)-2,4-dimethyl-1H-pyrrole-3-carboxylic acid(2-diethylaminoethyl)amide; and N-{2-chloro-4-[(6,7-dimethoxy-4-quinolyl)oxy]phenyl}-N'-(5-methyl-3-isoxazolyl)urea, a pharmacologically acceptable salt thereof or a solvate thereof.

[152] A compound according to [133], a pharmacologically acceptable salt thereof or a solvate thereof, wherein the undifferentiated gastric cancer comprises at least one selected from the group consisting of a cell overexpressing FGFR2 and a cell expressing mutant FGFR2.

[153] A compound according to [152], a pharmacologically acceptable salt thereof or a solvate thereof, wherein the mutant FGFR2 comprises a mutation site where amino acids downstream from at least position 813 are deleted in the amino acid sequence 22-822 among the amino acid sequence represented by SEQ ID NO:2.

[154] A compound according to [133], a pharmacologically acceptable salt thereof or a solvate thereof, wherein the undifferentiated gastric cancer is at least one gastric cancer selected from the group consisting of poorly differentiated adenocarcinoma, signet-ring cell carcinoma, mucinous carcinoma and scirrhous gastric cancer.

[155] A compound represented by General Formula (I) below, a pharmacologically acceptable salt thereof or a solvate thereof for administration in combination with a therapeutic substance for gastric cancer or a FGFR2 inhibitor to a living organism comprising at least one selected from the group consisting of a cell overexpressing FGFR2 and a cell expressing mutant FGFR2:

General Formula (I)

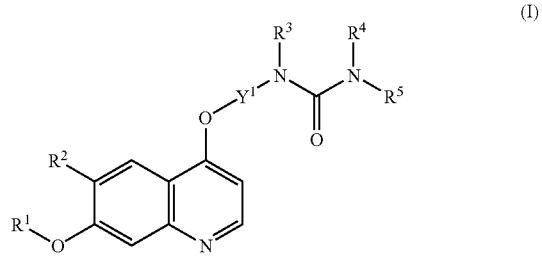

[wherein, $R^1$ represents a group represented by Formula —$V^1$—$V^2$—$V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula —$CONR^6$—, a group represented by Formula —$SO_2NR^6$—, a group represented by Formula —$NR^6SO_2$—, a group represented by Formula —$NR^6CO$— or a group represented by Formula —$NR^6$— (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

$R^2$ represents a cyano group, an optionally substituted $C_{1-6}$ alkoxy group, a carboxyl group, an optionally substituted $C_{2-7}$ alkoxycarbonyl group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

$Y^1$ represents a group represented by either one of the following formulae

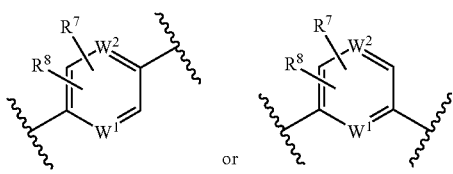

(wherein, R[7] and R[8] each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —$CONV^{d1}V^{d2}$ (wherein, $V^{d1}$ and $V^{d2}$ each independently represent a hydrogen atom or an optionally substituted $C_{1-6}$ alkyl group);

$W^1$ and $W^2$ each independently represent an optionally substituted carbon atom or nitrogen atom);

$R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group].

[156] A compound according to [155], a pharmacologically acceptable salt thereof or a solvate thereof, wherein $R^1$ is a $C_{1-6}$ alkyl group (provided that $R^1$ may have at least one substituent selected from the group consisting of a 3-10-membered nonaromatic heterocyclic group, a hydroxyl group, a $C_{1-6}$ alkoxy group, an amino group, a mono-$C_{1-6}$ alkylamino group and a di-$C_{1-6}$ alkylamino group which may have a $C_{1-6}$ alkyl group).

[157] A compound according to [155], a pharmacologically acceptable salt thereof or a solvate thereof, wherein $R^1$ is a methyl group or a group represented by any one of the following formulae

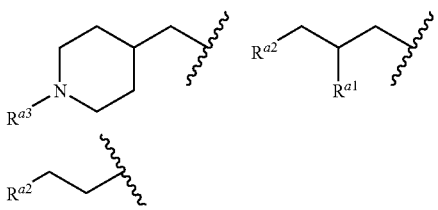

(wherein, $R^{a3}$ represents a methyl group; $R^{a1}$ represents a hydrogen atom or a hydroxyl group; $R^{a2}$ represents a methoxy group, an ethoxy group, a 1-pyrrolidinyl group, a 1-piperidinyl group, a 4-morpholinyl group, a dimethylamino group or a diethylamino group).

[158] A compound according to [155], a pharmacologically acceptable salt thereof or a solvate thereof, wherein $R^1$ is a methyl group or a 2-methoxyethyl group.

[159] A compound according to [155], a pharmacologically acceptable salt thereof or a solvate thereof, wherein $R^2$ is a cyano group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group).

[160] A compound according to [155], a pharmacologically acceptable salt thereof or a solvate thereof, wherein $R^2$ is a cyano group or a group represented by Formula —$CONHV^{a16}$ (wherein, $V^{a16}$ represents a hydrogen atom, a $C_{1-6}$ alkyl group, a $C_{3-8}$ cycloalkyl group, a $C_{1-6}$ alkoxy group or a $C_{3-8}$ cycloalkoxy group, provided that $V^{a16}$ may have at least one substituent selected from the group consisting of a halogen atom, a cyano group, a hydroxyl group and a $C_{1-6}$ alkoxy group).

[161] A compound according to [155], a pharmacologically acceptable salt thereof or a solvate thereof, wherein $R^2$ is a group represented by Formula —$CONHV^{a17}$ (wherein, $V^{a17}$ represents a hydrogen atom, a $C_{1-6}$ alkyl group or a $C_{1-6}$ alkoxy group).

[162] A compound according to [155], a pharmacologically acceptable salt thereof or a solvate thereof, wherein $R^2$ is a group represented by Formula —$CONHV^{a18}$ (wherein, $V^{a18}$ represents a hydrogen atom, a methyl group or a methoxy group).

[163] A compound according to [155], a pharmacologically acceptable salt thereof or a solvate thereof, wherein $Y^1$ is a group represented by the following formula

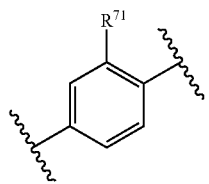

(wherein, $R^{71}$ represents a hydrogen atom or a halogen atom).

[164] A compound according to [155], a pharmacologically acceptable salt thereof or a solvate thereof, wherein $R^3$ and $R^4$ are hydrogen atoms.

[165] A compound according to [155], a pharmacologically acceptable salt thereof or a solvate thereof, wherein $R^5$ is a hydrogen atom, a $C_{1-6}$ alkyl group, a $C_{3-8}$ cycloalkyl group or a $C_{6-10}$ aryl group (provided that $R^5$ may have at least one substituent selected from the group consisting of a halogen atom and a methanesulfonyl group).

[166] A compound according to [155], a pharmacologically acceptable salt thereof or a solvate thereof, wherein $R^5$ is a methyl group, an ethyl group or a cyclopropyl group.

[167] A compound according to [155], a pharmacologically acceptable salt thereof or a solvate thereof, wherein the compound represented by General Formula (I), a pharmacologically acceptable salt thereof or a solvate thereof is at least one compound selected from the group consisting of:

N-(4-(6-cyano-7-(2-methoxyethoxy)-4-quinolyl)oxy-2-fluorophenyl)-N'-(4-fluorophenyl)urea;
N-(2-chloro-4-((6-cyano-7-((1-methyl-4-piperidyl)methoxy)-4-quinolyl)oxy)phenyl)-N'-cyclopropyl urea;
N-(4-((6-cyano-7-(((2R)-3-(diethylamino)-2-hydroxypropyl)oxy)-4-quinolyl)oxy)phenyl)-N'-(4-fluorophenyl)urea;
N-(4-((6-cyano-7-(((2R)-2-hydroxy-3-(1-pyrrolidino)propyl)oxy)-4-quinolyl)oxy)phenyl)-N'-(4-fluorophenyl)urea;
4-(3-chloro-4-(cyclopropylaminocarbonyl)aminophenoxy)-7-methoxy-6-quinolinecarboxamide;
4-(3-chloro-4-(cyclopropylaminocarbonyl)aminophenoxy)-7-(2-methoxyethoxy)-6-quinolinecarboxamide;
N6-cyclopropyl-4-(3-chloro-4-(((cyclopropylamino)carbonyl)amino)phenoxy)-7-methoxy-6-quinolinecarboxamide;
N6-(2-methoxyethyl)-4-(3-chloro-4-(((cyclopropylamino)carbonyl)amino)phenoxy)-7-methoxy-6-quinolinecarboxamide;
N6-(2-fluoroethyl)-4-(3-chloro-4-(((cyclopropylamino)carbonyl)amino)phenoxy)-7-methoxy-6-quinolinecarboxamide;
N6-methoxy-4-(3-chloro-4-(((cyclopropylamino)carbonyl)amino)phenoxy)-7-methoxy-6-quinolinecarboxamide;
N6-methyl-4-(3-chloro-4-(((cyclopropylamino)carbonyl)amino)phenoxy)-7-methoxy-6-quinolinecarboxamide;
N6-ethyl-4-(3-chloro-4-(((cyclopropylamino)carbonyl)amino)phenoxy)-7-methoxy-6-quinolinecarboxamide;
4-(3-fluoro-4-(cyclopropylaminocarbonyl)aminophenoxy)-7-(2-methoxyethoxy)-6-quinolinecarboxamide;
4-(3-chloro-4-(cyclopropylaminocarbonyl)aminophenoxy)-7-(2-hydroxyethoxy)-6-quinolinecarboxamide;
4-(3-chloro-4-(cyclopropylaminocarbonyl)aminophenoxy)-7-((2S)-2,3-dihydroxypropyl)oxy-6-quinolinecarboxamide;
4-(3-chloro-4-(methylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6-methoxy-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-ethoxyethoxy)-6-quinolinecarboxamide;
4-(4-((cyclopropylamino)carbonyl)aminophenoxy)-7-(2-methoxyethoxy)-6-quinolinecarboxamide;
N-(2-fluoro-4-((6-carbamoyl-7-methoxy-4-quinolyl)oxy)phenyl)-N'-cyclopropyl urea;
N6-(2-hydroxyethyl)-4-(3-chloro-4-(((cyclopropylamino)carbonyl)amino)phenoxy)-7-methoxy-6-quinolinecarboxamide;
4-(3-chloro-4-(1-propylaminocarbonyl)aminophenoxy)-7-methoxy-6-quinolinecarboxamide;
4-(3-chloro-4-(cis-2-fluoro-cyclopropylaminocarbonyl)aminophenoxy)-7-methoxy-6-quinolinecarboxamide;
N6-methyl-4-(3-chloro-4-(((cyclopropylamino)carbonyl)amino)phenoxy)-7-(2-methoxyethoxy)-6-quinolinecarboxamide;
N6-methyl-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-(4-morpholino)ethoxy)-6-quinolinecarboxamide;
4-(3-chloro-4-(2-fluoroethylaminocarbonyl)aminophenoxy)-7-methoxy-6-quinolinecarboxamide;
N6-((2R)tetrahydro-2-furanylmethyl)-4-(3-chloro-4-(((methylamino)carbonyl)amino)phenoxy)-7-methoxy-6-quinolinecarboxamide;
4-(3-fluoro-4-(ethylaminocarbonyl)aminophenoxy)-7-methoxy-6-quinolinecarboxamide;
4-(3-chloro-4-(((cyclopropylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-((2R)-3-diethylamino-2-hydroxypropoxy)-6-quinolinecarboxamide;
N6-methyl-4-(3-chloro-4-(((ethylamino)carbonyl)amino)phenoxy)-7-((2R)-3-diethylamino-2-hydroxypropoxy)-6-quinolinecarboxamide;
N6-methyl-4-(3-chloro-4-(((methylamino)carbonyl)amino)phenoxy)-7-((2R)-2-hydroxy-3-(1-pyrrolidino)propoxy)-6-quinolinecarboxamide;
N6-methyl-4-(3-chloro-4-(((ethylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-((1-methyl-4-piperidyl)methoxy)-6-quinolinecarboxamide;
N6-methyl-4-(3-chloro-4-(((ethylamino)carbonyl)amino)phenoxy)-7-((1-methyl-4-piperidyl)methoxy)-6-quinolinecarboxamide;
N-(4-(6-cyano-7-(2-methoxyethoxy)-4-quinolyl)oxy-2-fluorophenyl)-N'-cyclopropyl urea;
N-(4-(6-cyano-7-(3-(4-morpholino)propoxy)-4-quinolyl)oxyphenyl)-N'-(3-(methylsulfonyl)phenyl)urea;
4-(4-((cyclopropylamino)carbonyl)aminophenoxy)-7-methoxy-6-quinolinecarboxamide;
4-(3-fluoro-4-((2-fluoroethylamino)carbonyl)aminophenoxy)-7-methoxy-6-quinolinecarboxamide;
N6-(2-ethoxyethyl)-4-(3-chloro-4-(((methylamino)carbonyl)amino)phenoxy)-7-methoxy-6-quinolinecarboxamide;
4-(4-(3-ethylureido)-3-fluoro-phenoxy)-7-methoxyquinoline-6-carboxylic acid (2-cyanoethyl)amide; and
N-(4-(6-(2-cyanoethyl)carbamoyl-7-methoxy-4-quinolyl)oxy-2-fluorophenyl)-N'-cyclopropyl urea,
a pharmacologically acceptable salt thereof or a solvate thereof.

[168] A compound according to [155], a pharmacologically acceptable salt thereof or a solvate thereof, wherein the compound represented by General Formula (I), a pharmacologically acceptable salt thereof or a solvate thereof is at least one compound selected from the group consisting of:
4-(3-chloro-4-(cyclopropylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6-methoxy-4-(3-chloro-4-(((cyclopropylamino)carbonyl)amino)phenoxy)-7-methoxy-6-quinolinecarboxamide;
4-(3-chloro-4-(methylaminocarbonyl)aminophenoxy)-7-methoxy-6-quinolinecarboxamide; and
N6-methoxy-4-(3-chloro-4-(((ethylamino)carbonyl)amino)phenoxy)-7-methoxy-6-quinolinecarboxamide,
a pharmacologically acceptable salt thereof or a solvate thereof.

[169] A compound according to [155], a pharmacologically acceptable salt thereof or a solvate thereof, wherein the compound represented by General Formula (I), a pharmacologically acceptable salt thereof or a solvate thereof is 4-(3-chloro-4-(cyclopropylaminocarbonyl)aminophenoxy)-7-methoxy-6-quinolinecarboxamide, a pharmacologically acceptable salt thereof or a solvate thereof.

[170] A compound according to [155], a pharmacologically acceptable salt thereof or a solvate thereof, wherein the compound represented by General Formula (I), a pharmacologically acceptable salt thereof or a solvate thereof is methanesulfonate of 4-(3-chloro-4-(cyclopropylaminocarbonyl)aminophenoxy)-7-methoxy-6-quinolinecarboxamide.

[171] A compound according to any one of [155] to [170], a pharmacologically acceptable salt thereof or a solvate thereof, wherein the therapeutic substance for gastric cancer is at least one selected from the group consisting of irinotecan, paclitaxel, carboquone, nimustine, 5-fluorouracil, tegafur, UFT, doxifluridine, carmofur, S-1, doxorubicin, mitomycin C, aclarubicin, pirarubicin, epirubicin, docetaxel and cis-platinum.

[172] A compound according to any one of [155] to [170], a pharmacologically acceptable salt thereof or a solvate thereof, wherein the therapeutic substance for gastric cancer is irinotecan, 5-fluorouracil or paclitaxel.

[173] A compound according to any one of [155] to [170], a pharmacologically acceptable salt thereof or a solvate thereof, wherein the FGFR2 inhibitor is at least one compound selected from the group consisting of:

N-(3-trifluoromethyl-4-chlorophenyl)-N'-(4-(2-methylcarbamoylpyridine-4-yl)oxyphenyl)urea;

6-[2-(methylcarbamoyl)phenylsulfanyl]-3-E-[2-(pyridine-2-yl)ethenyl]indazole;

5-(5-fluoro-2-oxo-1,2-dihydroindole-3-ylidenemethyl)-2,4-dimethyl-1H-pyrrole-3-carboxylic acid(2-diethylaminoethyl)amide; and N-{2-chloro-4-[(6,7-dimethoxy-4-quinolyl)oxy]phenyl}-N'-(5-methyl-3-isoxazolyl)urea, a pharmacologically acceptable salt thereof or a solvate thereof.

[174] A compound according to [155], a pharmacologically acceptable salt thereof or a solvate thereof, wherein the undifferentiated gastric cancer comprises at least one selected from the group consisting of a cell overexpressing FGFR2 and a cell expressing mutant FGFR2.

[175] A compound according to [174], a pharmacologically acceptable salt thereof or a solvate thereof, wherein the mutant FGFR2 comprises a mutation site where amino acids downstream from at least position 813 are deleted in the amino acid sequence 22-822 among the amino acid sequence represented by SEQ ID NO:2.

[176] A compound according to [155], a pharmacologically acceptable salt thereof or a solvate thereof, wherein the undifferentiated gastric cancer is at least one gastric cancer selected from the group consisting of poorly differentiated adenocarcinoma, signet-ring cell carcinoma, mucinous carcinoma and scirrhous gastric cancer.

[177] A kit comprising:

(a) at least one selected from the group consisting of a packaging container, an instruction and a package insert describing use of a compound represented by General Formula (I), a pharmacologically acceptable salt thereof or a solvate thereof in combination with a therapeutic substance for gastric cancer or a FGFR2 inhibitor; and (b) a therapeutic agent for undifferentiated gastric cancer comprising a compound represented by General Formula (I), a pharmacologically acceptable salt thereof or a solvate thereof:

General Formula (I)

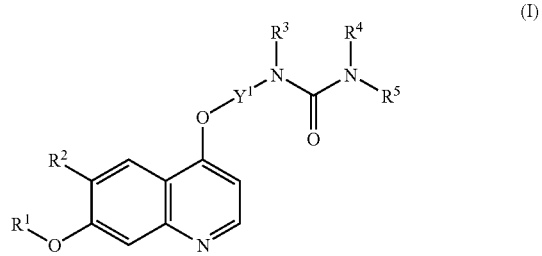

[wherein, $R^1$ represents a group represented by Formula —$V^1$—$V^2$—$V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula —$CONR^6$—, a group represented by Formula —$SO_2NR^6$—, a group represented by Formula —$NR^6SO_2$—, a group represented by Formula —$NR^6CO$— or a group represented by Formula —$NR^6$— (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

$R^2$ represents a cyano group, an optionally substituted $C_{1-6}$ alkoxy group, a carboxyl group, an optionally substituted $C_{2-7}$ alkoxycarbonyl group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

$Y^1$ represents a group represented by either one of the following formulae

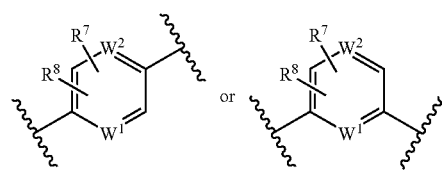

(wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —CONV$^{d1}$V$^{d2}$ (wherein, V$^{d1}$ and V$^{d2}$ each independently represent a hydrogen atom or an optionally substituted $C_{1-6}$ alkyl group);

W$^1$ and W$^2$ each independently represent an optionally substituted carbon atom or nitrogen atom);

R$^3$ and R$^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and R$^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group].

[178] A kit comprising:
(a) at least one selected from the group consisting of a packaging container, an instruction and a package insert describing use of a compound represented by General Formula (I), a pharmacologically acceptable salt thereof or a solvate thereof in combination with a therapeutic substance for gastric cancer or a FGFR2 inhibitor; and
(b) a pharmaceutical composition comprising a compound represented by General Formula (I), a pharmacologically acceptable salt thereof or a solvate thereof for administration to a living organism comprising at least one selected from the group consisting of a cell overexpressing FGFR2 and a cell expressing mutant FGFR2:

General Formula (I)

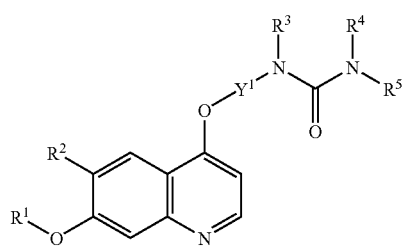

[wherein, R$^1$ represents a group represented by Formula —V$^1$—V$^2$—V$^3$ (wherein, V$^1$ represents an optionally substituted $C_{1-6}$ alkylene group; V$^2$ represents a single bond, an oxygen atom, a sulfur atom, a carbonyl group, a sulfinyl group, a sulfonyl group, a group represented by Formula —CONR$^6$—, a group represented by Formula —SO$_2$NR$^6$—, a group represented by Formula —NR$^6$SO$_2$—, a group represented by Formula —NR$^6$CO— or a group represented by Formula —NR$^6$— (wherein, R$^6$ represents a hydrogen atom, an optionally substituted $C_{1-6}$ alkyl group or an optionally substituted $C_{3-8}$ cycloalkyl group); V$^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

R$^2$ represents a cyano group, an optionally substituted $C_{1-6}$ alkoxy group, a carboxyl group, an optionally substituted $C_{2-7}$ alkoxycarbonyl group or a group represented by Formula —CONV$^{a11}$V$^{a12}$ (wherein, V$^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; V$^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

Y$^1$ represents a group represented by either one of the following formulae

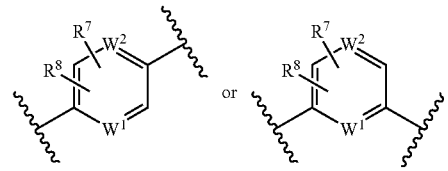

(wherein, R$^7$ and R$^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —CONV$^{d1}$V$^{d2}$ (wherein, V$^{d1}$ and V$^{d2}$ each independently represent a hydrogen atom or an optionally substituted $C_{1-6}$ alkyl group);

W$^1$ and W$^2$ each independently represent an optionally substituted carbon atom or nitrogen atom);

R$^3$ and R$^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and R$^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group].

[179] A kit characterized by a set of a therapeutic agent for undifferentiated gastric cancer comprising a compound represented by General Formula (I), a pharmacologically acceptable salt thereof or a solvate thereof and a formulation comprising a therapeutic substance for gastric cancer or a FGFR2 inhibitor:

General Formula (I)

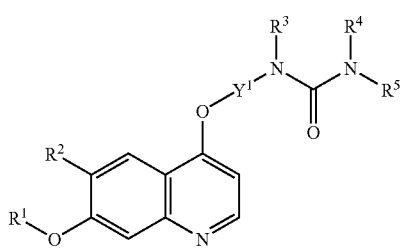

[wherein, $R^1$ represents a group represented by Formula $-V^1-V^2-V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula $-CONR^6-$, a group represented by Formula $-SO_2NR^6-$, a group represented by Formula $-NR^6SO_2-$, a group represented by Formula $-NR^6CO-$ or a group represented by Formula $-NR^6-$ (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

$R^2$ represents a cyano group, an optionally substituted $C_{1-6}$ alkoxy group, a carboxyl group, an optionally substituted $C_{2-7}$ alkoxycarbonyl group or a group represented by Formula $-CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

$Y^1$ represents a group represented by either one of the following formulae

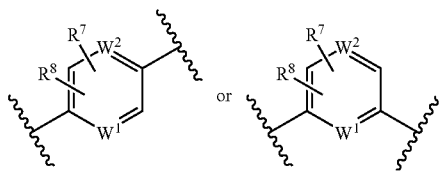

(wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula $-CONV^{d1}V^{d2}$ (wherein, $V^{d1}$ and $V^{d2}$ each independently represent a hydrogen atom or an optionally substituted $C_{1-6}$ alkyl group);

$W^1$ and $W^2$ each independently represent an optionally substituted carbon atom or nitrogen atom);

$R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group].

[180] A kit used for administration to a living organism comprising at least one selected from the group consisting of a cell overexpressing FGFR2 and a cell expressing mutant FGFR2, the kit characterized by a set of a formulation comprising a compound represented by General Formula (I), a pharmacologically acceptable salt thereof or a solvate thereof and a formulation comprising a therapeutic substance for gastric cancer or a FGFR2 inhibitor:

General Formula (I)

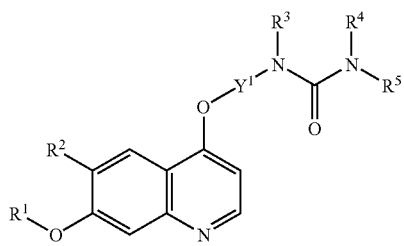

[wherein, $R^1$ represents a group represented by Formula $-V^1-V^2-V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula $-CONR^6-$, a group represented by Formula $-SO_2NR^6-$, a group represented by Formula $-NR^6SO_2-$, a group represented by Formula $-NR^6CO-$ or a group represented by Formula $-NR^6-$ (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

$R^2$ represents a cyano group, an optionally substituted $C_{1-6}$ alkoxy group, a carboxyl group, an optionally substituted $C_{2-7}$ alkoxycarbonyl group or a group represented by Formula $-CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

$Y^1$ represents a group represented by either one of the following formulae

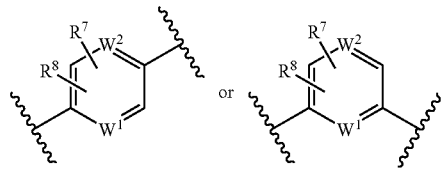

(wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —$CONV^{d1}V^{d2}$ (wherein, $V^{d1}$ and $V^{d2}$ each independently represent a hydrogen atom or an optionally substituted $C_{1-6}$ alkyl group);

$W^1$ and $W^2$ each independently represent an optionally substituted carbon atom or nitrogen atom);

$R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group].

[181] A therapeutic agent for undifferentiated gastric cancer comprising a compound represented by General Formula (I), a pharmacologically acceptable salt thereof or a solvate thereof characterized by administration to a living organism with a therapeutic substance for gastric cancer or a FGFR2 inhibitor:

General Formula (I)

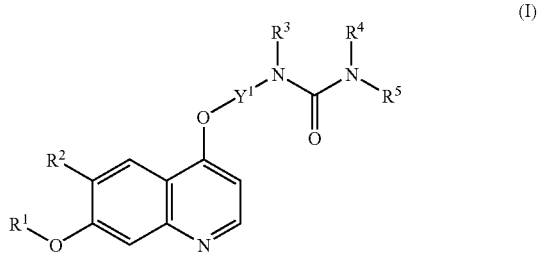

[wherein, $R^1$ represents a group represented by Formula —$V^1$—$V^2$—$V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula —$CONR^6$—, a group represented by Formula —$SO_2NR^6$—, a group represented by Formula —$NR^6SO_2$—, a group represented by Formula —$NR^6CO$— or a group represented by Formula —$NR^6$— (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

$R^2$ represents a cyano group, an optionally substituted $C_{1-6}$ alkoxy group, a carboxyl group, an optionally substituted $C_{2-7}$ alkoxycarbonyl group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

$Y^1$ represents a group represented by either one of the following formulae

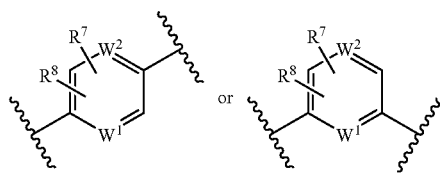

(wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —$CONV^{d1}V^{d2}$ (wherein, $V^{d1}$ and $V^{d2}$ each independently represent a hydrogen atom or an optionally substituted $C_{1-6}$ alkyl group);

$W^1$ and $W^2$ each independently represent an optionally substituted carbon atom or nitrogen atom);

$R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group].

[182] A pharmaceutical composition for administration to a living organism comprising at least one selected from the group consisting of a cell overexpressing FGFR2 and a cell expressing mutant FGFR2, the pharmaceutical composition comprising a compound represented by General Formula (I), a pharmacologically acceptable salt thereof or a solvate thereof characterized by administration to the living organism with a therapeutic substance for gastric cancer or a FGFR2 inhibitor:

General Formula (I)

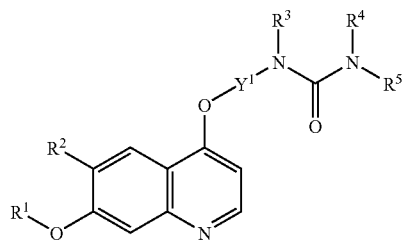

(I)

[wherein, $R^1$ represents a group represented by Formula —$V^1$—$V^2$—$V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula —$CONR^6$—, a group represented by Formula —$SO_2NR^6$—, a group represented by Formula —$NR^6SO_2$—, a group represented by Formula —$NR^6CO$— or a group represented by Formula —$NR^6$— (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

$R^2$ represents a cyano group, an optionally substituted $C_{1-6}$ alkoxy group, a carboxyl group, an optionally substituted $C_{2-7}$ alkoxycarbonyl group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

$Y^1$ represents a group represented by either one of the following formulae

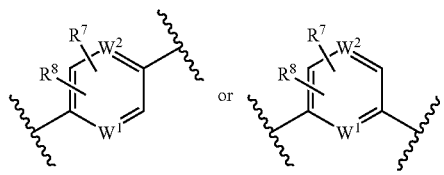

(wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —$CONV^{d1}V^{d2}$ (wherein, $V^{d1}$ and $V^{d2}$ each independently represent a hydrogen atom or an optionally substituted $C_{1-6}$ alkyl group);

$W^1$ and $W^2$ each independently represent an optionally substituted carbon atom or nitrogen atom);

$R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group].

According to (1) to (42) and [1] to [182] above, a compound represented by General Formula (I), a pharmacologically acceptable salt thereof or a solvate thereof is as follows. A compound represented by:

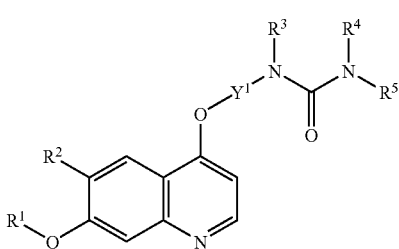

(I)

[wherein, $R^1$ represents a group represented by Formula —$V^1$—$V^2$—$V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula —$CONR^6$—, a group represented by Formula —$SO_2NR^6$—, a group represented by Formula —$NR^6SO_2$—, a group represented by Formula —$NR^6CO$— or a group represented by Formula —$NR^6$— (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);

$R^2$ represents a cyano group, an optionally substituted $C_{1-6}$ alkoxy group, a carboxyl group, an optionally substituted $C_{2-7}$ alkoxycarbonyl group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);

$Y^1$ represents a group represented by either one of the following formulae

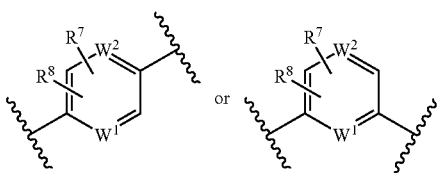

(wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —$CONV^{d1}V^{d2}$ (wherein, $V^{d1}$ and $V^{d2}$ each independently represent a hydrogen atom or an optionally substituted $C_{1-6}$ alkyl group);

$W^1$ and $W^2$ each independently represent an optionally substituted carbon atom or nitrogen atom);

$R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group], a pharmacologically acceptable salt thereof or a solvate thereof.

Furthermore, according to (1) to (42) above, the therapeutic substance for gastric cancer may be at least one selected from the group consisting of irinotecan, paclitaxel, carboquone, nimustine, 5-fluorouracil, tegafur, UFT, doxifluridine, carmofur, S-1, doxorubicin (Adriamycin), mitomycin C, aclarubicin, pirarubicin, epirubicin, docetaxel and cis-platinum (Cisplastin). A preferable therapeutic substance for gastric cancer is irinotecan, 5-fluorouracil or paclitaxel.

Moreover, according to (1) to (42) above, the FGFR2 inhibitor may comprise, for example, a compound that is not comprised in compounds represented by General Formula (I), and may include at least one compound selected from the group consisting of:

N-(3-trifluoromethyl-4-chlorophenyl)-N'-(4-(2-methylcarbamoylpyridine-4-yl)oxyphenyl)urea (BAY 43-9006);

6-[2-(methylcarbamoyl)phenylsulfanyl]-3-E-[2-(pyridine-2-yl)ethenyl]indazole (AG013736);

5-(5-fluoro-2-oxo-1,2-dihydroindole-3-ylidenemethyl)-2,4-dimethyl-1H-pyrrole-3-carboxylic acid(2-diethylaminoethyl)amide (SU11248); and N-{2-chloro-4-[(6,7-dimethoxy-4-quinolyl)oxy]phenyl}-N'-(5-methyl-3-isoxazolyl)urea (KRN951), a pharmacologically acceptable salt thereof or a solvate thereof.

The present invention provides a therapeutic agent, a kit and a therapeutic method for undifferentiated gastric cancer that show an excellent anti-tumor activity, use of a FGFR2 inhibitor for producing the therapeutic agent and a FGFR2 inhibitor for the therapeutic agent.

More specifically, there is provided a therapeutic agent, a kit and a therapeutic method for undifferentiated gastric cancer that show an excellent anti-tumor activity and that can be used for treating undifferentiated gastric cancer by combining:

(i) a FGFR2 inhibitor such as a compound represented by General Formula (I) and a therapeutic substance for gastric cancer;

(ii) a FGFR2 inhibitor such as a compound represented by General Formula (I) and a FGFR2 inhibitor that is not comprised in the compounds represented by General Formula (I); or (iii) a FGFR2 inhibitor such as a FGFR2 inhibitor that is not comprised in the compounds represented by General Formula (I) and a therapeutic substance for gastric cancer.

The present invention also provides a pharmaceutical composition and a kit for administration to a living organism comprising at least one selected from the group consisting of a cell overexpressing FGFR2 and a cell expressing mutant FGFR2, a method for treating a disease of the living organism, use of a FGFR2 inhibitor for producing the pharmaceutical composition and a FGFR2 inhibitor for the pharmaceutical composition.

More specifically, there is provided a pharmaceutical composition, a kit and a therapeutic method for the living organism, which show an excellent anti-tumor activity and that can be used for treating a disease by combining:

(i) a FGFR2 inhibitor such as a compound represented by General Formula (I) and a therapeutic substance for gastric cancer;

(ii) a FGFR2 inhibitor such as a compound represented by General Formula (I) and a FGFR2 inhibitor that is not comprised in the compounds represented by General Formula (I); or (iii) a FGFR2 inhibitor such as a FGFR2 inhibitor that is not comprised in the compounds represented by General Formula (I) and a therapeutic substance for gastric cancer.

BEST MODES FOR CARRYING OUT THE INVENTION

Figure 1:
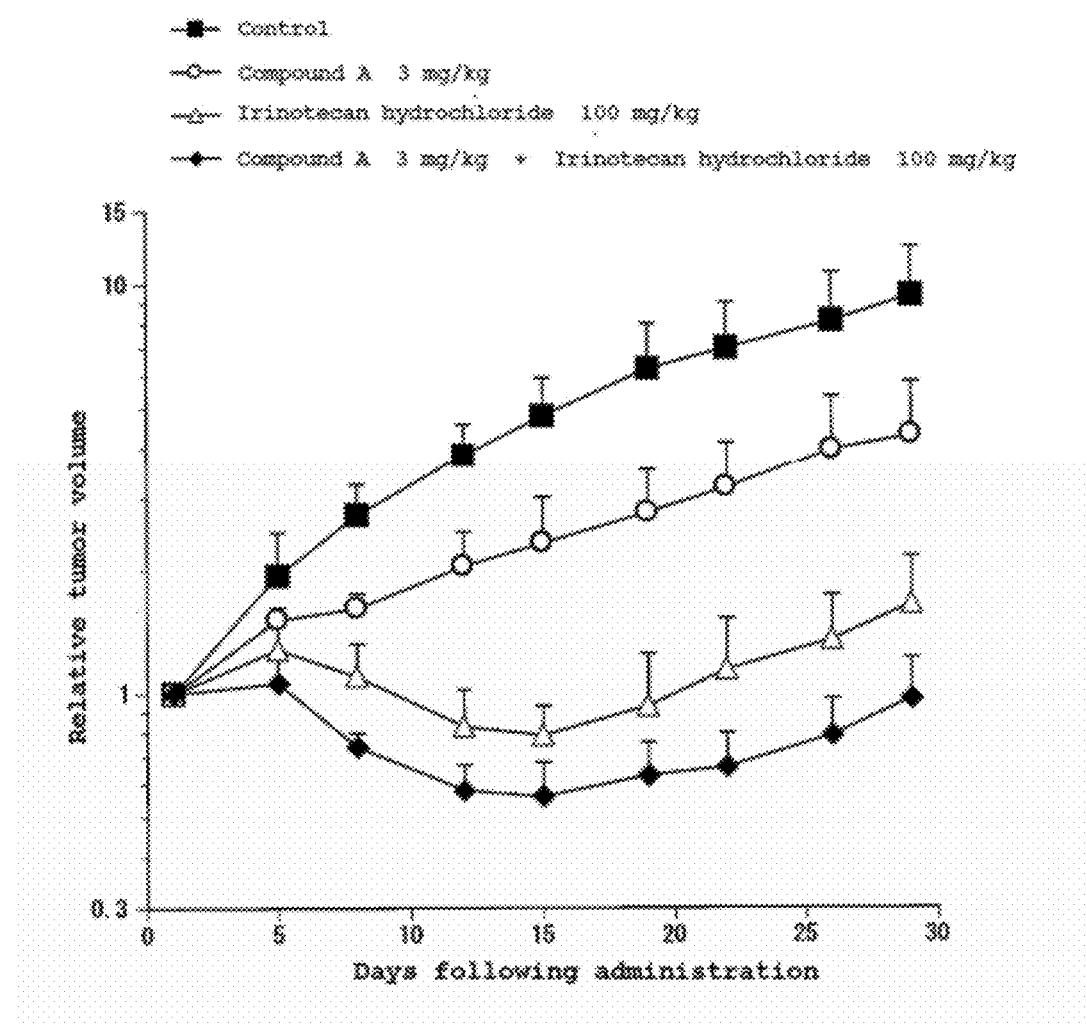
FIG. 1 shows the effect of combination use of 4-(3-chloro-4-(cyclopropylaminocarbonyl)aminophenoxy)-7-methoxy-6-quinolinecarboxamide (Compound A) (3 mg/kg) and irinotecan hydrochloride (100 mg/kg) on suppression of tumor growth in subcutaneous transplanted (xenograft) models (in vivo) of human scirrhous gastric cancer cell line (HSC-39).

Hereinafter, embodiments of the present invention will be described. The following embodiments are examples provided for illustrating the present invention, and the present invention is not intended to be limited thereto. The present invention may be carried out in various embodiments without departing from the spirit of the invention.

The publications, laid-open patent publications, patent publications and other patent documents cited herein are incorporated herein by reference. The present specification incorporates the disclosure of U.S. provisional application No. 60/887,006 (filed on 29 Jan., 2007) based on which the present application claims priority.

1. FGFR2 Inhibitor (1) FGFR2

According to the present invention, FGFR2 comprises a polypeptide including an amino acid sequence identical or substantially identical to the amino acid sequence represented by SEQ ID NO:2 (GenBank Accession No:NM_022970) or to the amino acids 22-822 of the amino acid sequence represented by SEQ ID NO:2. The polypeptide including the amino acid sequence represented by SEQ ID NO:2 is coded, for example, by a polynucleotide including the base sequence represented by SEQ ID NO:1. Usually, processing of the polypeptide comprising the amino acid sequence represented by SEQ ID NO:2 yields a mature form.

Examples of a polypeptide having an amino acid sequence substantially identical to the amino acid sequence (amino acids 22-822) represented by SEQ ID NO:2 include those selected from the group consisting of (a) to (d) below:

(a) a polypeptide comprising the amino acid sequence (amino acids 22-822) represented by SEQ ID NO:2;

(b) a polypeptide comprising an amino acid sequence having one or more (e.g., one or a few) amino acids deleted, substituted or added, or mutated by a combination thereof in the amino acid sequence (amino acids 22-822) represented by SEQ ID NO:2, and having substantially the same activity as FGFR2;

(c) a polypeptide encoded by a polynucleotide that hybridizes with a polynucleotide having a base sequence complementary to the base sequence represented by SEQ ID NO: 1 under stringent conditions, and having substantially the same activity as FGFR2; and (d) a polypeptide having an amino acid sequence having 90% or higher, preferably about 95% or higher and more preferably about 98% or higher identity (also referred to as "homology") to the amino acid sequence (amino acids 22-822) represented by SEQ ID NO:2, and having substantially the same activity as FGFR2.

Herein, the phrase "having substantially the same activity as FGFR2" means that at least one of the intracellular signals caused by ligand (e.g., FGF) binding is identical to one of the signals of a protein having the amino acid sequence (amino acids 22-822) represented by SEQ ID NO:2, and that the activation level of the intracellular signal is comparable to that of the protein having the amino acid sequence (amino acids 22-822) represented by SEQ ID NO:2. Furthermore, the term "comparable" means, for example, that the activation level of the intracellular signal caused by ligand (e.g., FGF) binding is at least 10%, preferably at least 30% of the activation level of the intracellular signal of a protein having the amino acid sequence (amino acids 22-822) represented by SEQ ID NO:2, which can be referred to as substantially the same activity. Examples of intracellular signals caused by ligand binding include: FGFR2 phosphorylation; Raf, MEK, ERK1 and ERK2 phosphorylation owing to FGFR2 phosphorylation; phosphorylation of phosphatidylinositol 3 kinase; Akt phosphorylation; phosphorylation of phospholipase-C-γ; increase in inositol 1,4,5-trisphosphate (IP3); and increase in diacylglycerol (DAG).

The activity of an intracellular signal caused by ligand binding can be measured by a conventional method such as immunoprecipitation method and western blotting.

Examples of amino acid sequences having one or more (e.g., one or a few) amino acids deleted, substituted or added, or mutated by a combination thereof in the amino acid sequence (amino acids 22-822) represented by SEQ ID NO:2 include:

(i) an amino acid sequence having 1-9 (e.g., 1-5, preferably 1-3, more preferably 1-2 and still more preferably one) amino acids deleted from the amino acid sequence (amino acids 22-822) represented by SEQ ID NO:2;

(ii) an amino acid sequence having 1-9 (e.g., 1-5, preferably 1-3, more preferably 1-2 and still more preferably one) amino acids added to the amino acid sequence (amino acids 22-822) represented by SEQ ID NO:2;

(iii) an amino acid sequence having 1-9 (e.g., 1-5, preferably 1-3, more preferably 1-2 and still more preferably one) amino acids substituted with other amino acids in the amino acid sequence (amino acids 22-822) represented by SEQ ID NO:2; and (iv) an amino acid sequence mutated by a combination of (i) to (iii) above.

As used herein, "deletion" of an amino acid refers to a mutation where one or more amino acid residues in the sequence are deleted, including deletion of amino acid residues from the end of the amino acid sequence and deletion in the middle of the amino acid sequence.

As used herein, "addition" of an amino acid refers to a mutation where one or more amino acid residues are added to the sequence, including addition of amino acid residues to the end of the amino acid sequence and addition in the middle of the amino acid sequence. Addition in the middle of the sequence may also be referred to as "insertion".

As used herein, "substitution" of an amino acid refers to a mutation where one or more amino acid residues in the sequence are substituted with different types of amino acid residues. When the amino acid sequence of FGFR2 is modified by such substitution, conservative substitution is preferable in order to retain the function of a protein. Conservative substitution means to alter a sequence to code an amino acid having similar property to the original amino acid. The property of amino acids can be classified, for example, into nonpolar amino acids (Ala, Ile, Leu, Met, Phe, Pro, Trp, Val), uncharged amino acids (Asn, Cys, Gln, Gly, Ser, Thr, Tyr), acidic amino acids (Asp, Glu), basic amino acids (Arg, His, Lys), neutral amino acids (Ala, Asn, Cys, Gln, Gly, Ile, Leu, Met, Phe, Pro, Ser, Thr, Trp, Tyr, Val), aliphatic amino acids (Ala, Gly), branched amino acids (Ile, Leu, Val), hydroxyamino acids (Ser, Thr), amide amino acids (Gln, Asn), sulfur-containing amino acids (Cys, Met), aromatic amino acids (His, Phe, Trp, Tyr), heterocyclic amino acids (His, Trp), imino acids (Pro, 4Hyp) and the like.

Thus, substitution, for example, between nonpolar amino acids or between uncharged amino acids, is preferable, among which, substitutions between Ala, Val, Leu and Ile, between Ser and Thr, between Asp and Glu, between Asn and Gln, between Lys and Arg, and between Phe and Tyr are favorable as substitution that retains the property of the protein. There is no limitation as to the number and the site of the amino acid to be mutated.

An example of a polypeptide having substantially the same amino acid sequence as the amino acid sequence (amino acids 22-822) represented by SEQ ID NO:2 includes a polypeptide encoded by a polynucleotide that hybridizes with a polynucleotide having a base sequence complementary to the base sequence represented by SEQ ID NO:1 under stringent conditions, and having substantially the same activity as FGFR2 as described above.

Herein, specific examples of polynucleotides that hybridize under stringent conditions include polynucleotides including base sequences having at least 90% or higher, preferably 95% or higher, more preferably 97% or higher, more preferably 98% or higher, or still more preferably 99% or higher identity with the base sequence represented by SEQ ID NO:1 when calculated using homology search software such as FASTA, BLAST, Smith-Waterman [Meth. Enzym., 164, 765 (1988)] with default (initial setting) parameters. Examples of such stringent conditions include "2×SSC, 0.1% SDS, 50° C.", "2×SSC, 0.1% SDS, 42° C.," and "1×SSC, 0.1% SDS, 37° C.", and for higher stringent conditions "2×SSC, 0.1% SDS, 65° C.," "0.5×SSC, 0.1% SDS, 42° C.," and "0.2×SSC, 0.1% SDS, 65° C.".

Hybridization can be carried out according to a known method. When a commercially available library is used, hybridization may be carried out according to the method described in the attached instruction.

Examples of polynucleotides that hybridize with a polynucleotide having a base sequence complementary to the base sequence represented by SEQ ID NO:1 under stringent conditions include polynucleotides comprising a base sequence having 90% or higher, preferably 95% or higher and more preferably 98% or higher identity with the base sequence represented by SEQ ID NO:1.

Examples of polynucleotides that hybridize with a polynucleotide having a base sequence complementary to the base sequence represented by SEQ ID NO:1 under stringent conditions include base sequences having one or more (e.g., one or several) nucleic acids mutated, for example, deleted, substituted or added in the base sequence represented by SEQ ID NO:1.

Examples of polynucleotides that hybridize with a polynucleotide having a base sequence complementary to the base sequence represented by SEQ ID NO:1 under stringent conditions include:

(i) a base sequence having 1-9 (e.g., 1-5, preferably 1-3, more preferably 1-2 and still more preferably one) nucleic acids deleted from the base sequence represented by SEQ ID NO:1;

(ii) a base sequence having 1-9 (e.g., 1-5, preferably 1-3, more preferably 1-2 and still more preferably one) nucleic acids added to the base sequence represented by SEQ ID NO:1;

(iii) a base sequence having 1-9 (e.g., 1-5, preferably 1-3, more preferably 1-2 and still more preferably one) nucleic acids substituted with other nucleic acids in the base sequence represented by SEQ ID NO:1; and (iv) a base sequence mutated by a combination of (i) to (iii) above.

Herein, the term "identity" (also referred to as "homology") of an amino acid sequence is used to indicate the degree of consistency of amino acid residues between the sequences to be compared. In order to calculate identity of a given amino acid sequence to an amino acid sequence to be compared, the presence of gaps and the property of the amino acids are considered (Wilbur, Natl. Acad. Sci. U.S.A. 80:726-730 (1983)). For the calculation of identity, a commercially available software BLAST (Altschul: J. Mol. Biol. 215:403-410 (1990)), FASTA (Peasron: Methods in Enzymology 183:63-69 (1990)) or the like can be used.

The "identity" value may be any value as long as it is obtained by using a homology search program known to those skilled in the art. For example, for such calculation, the default (initial setting) parameters can be used in homology algorithm BLAST (Basic local alignment search tool) http://www.ncbi.nlm.nih.gov/BLAST/ of the National Center for Biotechnology Information (NCBI).

According to the present invention, FGFR2 comprises mutant FGFR2 described below.

(2) Cell Overexpressing FGFR2

According to the present invention, a cell overexpressing FGFR2 comprises, for example, a cell expressing FGFR2 for a significant amount as compared to a normal cell. In addition, according to the present invention, a cell overexpressing FGFR2 comprises, for example, a cell expressing FGFR2 for at least 1.5 times higher, preferably at least 2 times higher, more preferably at least 3 times higher, still more preferably at least 4 times higher than a normal cell. Herein, according to the invention, a "normal cell" refers to, for example, cells other than cancer (e.g., undifferentiated gastric cancer) cells.

According to the present invention, a cell overexpressing FGFR2 is preferably undifferentiated gastric cancer cell, more preferably at least one cell selected from the group consisting of poorly differentiated adenocarcinoma, signet-ring cell carcinoma, mucinous carcinoma and scirrhous gastric cancer.

An expression level of FGFR2 may be analyzed, for example, by measuring the protein and/or the mRNA of FGFR2 expressed in the cell.

Protein can be measured, for example, by an immunochemical method (e.g., immunohistochemistry method, immunoprecipitation, western blotting, flow cytometry, ELISA, RIA, etc.), mass spectrometry or the like, preferably an immunochemical method, particularly preferably flow cytometry. These methods may be carried out according to conventional techniques.

On the other hand, mRNA can be measured, for example, by a method such as in situ hybridization, northern blot analysis, DNA microarray, RT-PCR, quantitative RT-PCR or the like, preferably RT-PCR or quantitative RT-PCR. These methods may be carried out according to conventional techniques.

(3) Cell Overexpressing Mutant FGFR2

According to the present invention, mutant FGFR2 comprises polypeptides comprising an amino acid sequence having one or a few amino acids deleted, substituted or added, or mutated by a combination thereof in a wild-type FGFR2 amino acid sequence such as the amino acid sequence (amino acids 22-822) represented by SEQ ID NO:2. Preferably, the mutant FGFR2 comprises polypeptides comprising an amino acid sequence having one or a few amino acids deleted, substituted or added, or mutated by a combination thereof in a wild-type FGFR2 amino acid sequence such as the amino acid sequence (amino acids 22-822) represented by SEQ ID NO:2, and having substantially the same activity as FGFR2. According to the present invention, a cell expressing mutant FGFR2 comprises cells expressing the above-mentioned polypeptides.

Examples of mutant FGFR2 include polypeptides comprising an amino acid sequence where serine at position 267 of the amino acid sequence (amino acids 22-822) represented by SEQ ID NO:2 is substituted by other amino acid, preferably proline (Cancer Research. 61, 3541-3543, 2001).

In addition, examples of mutant FGFR2 include polypeptides comprising a mutation site where a few amino acids at C-terminal are deleted in an amino acid sequence of wild-type FGFR2 such as amino acids 22-822 of the amino acid sequence represented by SEQ ID NO:2. Examples of mutant FGFR2 include polypeptides comprising an amino acid sequence where amino acids downstream from at least position 813, preferably at least position 784, more preferably at least position 780, and still more preferably at least position 769 are deleted from the amino acid sequence (amino acids 22-822) represented by SEQ ID NO:2.

Preferably, mutant FGFR2 is activating mutant FGFR2. Activating mutant FGFR2 refers to mutant FGFR2 that causes autophosphorylation in a ligand-independent manner and that activates intracellular signals.

The presence or the absence of FGFR2 mutation can be determined by analyzing the gene sequence of FGFR2 or the sequence of the transcript, i.e., mRNA, of FGFR2. An example of the method for analyzing a sequence includes dideoxynucleotide chain termination technique (Sanger et al., (1977) Proc. Natl. Acad. Sci. USA 74:5463). A sequence can also be analyzed by employing an appropriate DNA sequencer.

Furthermore, the presence or the absence of FGFR2 mutation can be analyzed, for example, by in situ hybridization, northern blot analysis, DNA microarray, RT-PCR, SSCP-PCR (Single-Strand Conformation Polymorphism-PCR) or the like. These methods may be carried out according to conventional techniques.

The presence or the absence of FGFR2 mutation can be analyzed, for example, by an immunochemical method (e.g., an immunohistochemistry method, immunoprecipitation, western blotting, flow cytometry, ELISA, RIA, etc.). These methods may be carried out according to conventional techniques.

According to the present invention, a cell expressing mutant FGFR2 is preferably an undifferentiated gastric cancer cell, more preferably at least one cell selected from the group consisting of poorly differentiated adenocarcinoma, signet-ring cell carcinoma, mucinous carcinoma and a scirrhous gastric cancer.

(4) FGFR2 Inhibitor of the Invention

Herein, a "halogen atom" refers to a fluorine atom, a chlorine atom, a bromine atom or an iodine atom.

Preferable examples of a "halogen atom" include a fluorine atom and a chlorine atom.

Herein, a "$C_{1-6}$ alkyl group" refers to a linear or branched alkyl group with a carbon number of 1-6, specific examples including a methyl group, an ethyl group, a 1-propyl group (n-propyl group), a 2-propyl group (i-propyl group), a 2-methyl-1-propyl group (i-butyl group), a 2-methyl-2-propyl group (t-butyl group), a 1-butyl group (n-butyl group), a 2-butyl group (s-butyl group), a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group and a 2,3-dimethyl-2-butyl group.

Preferable examples of a "$C_{1-6}$ alkyl group" include a methyl group, an ethyl group, a 1-propyl group, a 2-propyl group, a 2-methyl-1-propyl group, a 2-methyl-2-propyl group, a 1-butyl group and a 2-butyl group.

Herein, a "$C_{1-6}$ alkylene group" refers to a divalent group derived from a "$C_{1-6}$ alkyl group" defined above by removing any one hydrogen atom therefrom, specific examples including a methylene group, a 1,2-ethylene group, a 1,1-ethylene group, a 1,3-propylene group, a tetramethylene group, a pentamethylene group and a hexamethylene group.

Herein, a "$C_{2-6}$ alkenyl group" refers to a linear or branched alkenyl group having one double bond and a carbon number of 2-6, specific examples including an ethenyl group (vinyl group), a 1-propenyl group, a 2-propenyl group (allyl group), a 1-butenyl group, a 2-butenyl group, a 3-butenyl group, a pentenyl group and a hexenyl group.

Herein, a "$C_{2-6}$ alkynyl group" refers to a linear or branched alkynyl group having one triple bond and a carbon number of 2-6, specific examples including an ethinyl group, a 1-propynyl group, a 2-propynyl group, a 1-butynyl group, a 2-butynyl group, a 3-butynyl group, a pentynyl group and a hexynyl group.

Herein, a "$C_{3-8}$ cycloalkyl group" refers to a monocyclic or bicyclic saturated aliphatic hydrocarbon group with a carbon number of 3-8, specific examples including a cyclopropyl group, a cyclobutyl group, a cyclopentyl group, a cyclohexyl group, a cycloheptyl group, a cyclooctyl group, a bicyclo[2.1.0]pentyl group, a bicyclo[3.1.0]hexyl group, a bicyclo[2.1.1]hexyl group, a bicyclo[4.1.0]heptyl group, a bicyclo[2.2.1]heptyl group (norbornyl group), a bicyclo[3.3.0]octyl group, a bicyclo[3.2.1]octyl group and a bicyclo[2.2.2]octyl group.

Preferable examples of a "$C_{3-8}$ cycloalkyl group" include a cyclopropyl group, a cyclobutyl group and a cyclopentyl group.

Herein, a "$C_{6-10}$ aryl group" refers to an aromatic hydrocarbon cyclic group with a carbon number of 6-10, specific examples including a phenyl group, a 1-naphthyl group, a 2-naphthyl group, an indenyl group and an azulenyl group.

A preferable example of a "$C_{6-10}$ aryl group" includes a phenyl group.

Herein, a "heteroatom" refers to a nitrogen atom, an oxygen atom or a sulfur atom.

Herein, a "5-10-membered heteroaryl group" refers to an aromatic cyclic group having 5-10 atoms forming the ring and 1-5 heteroatoms included in the atoms forming the ring, specific examples including a furyl group, a thienyl group, a pyrrolyl group, an imidazolyl group, a triazolyl group, a tetrazolyl group, a thiazolyl group, a pyrazolyl group, an oxazolyl group, an isoxazolyl group, an isothiazolyl group, a furazanyl group, a thiadiazolyl group, an oxadiazolyl group, a pyridyl group, a pyrazinyl group, a pyridazinyl group, a pyrimidinyl group, a triazinyl group, a purinyl group, a pteridinyl group, a quinolyl group, an isoquinolyl group, a naphthridinyl group, a quinoxalinyl group, a cinnolinyl group, a quinazolinyl group, a phthalazinyl group, an imidazopyridyl group, an imidazothiazolyl group, an imidazoxazolyl group, a benzothiazolyl group, a benzoxazolyl group, a benzimidazolyl group, an indolyl group, an isoindolyl group, an indazolyl group, a pyrrolopyridyl group, a thienopyridyl group, a furopyridyl group, a benzothiadiazolyl group, a benzoxadiazolyl group, a pyridopyrimidinyl group, a benzofuryl group, a benzothienyl group and a thienofuryl group.

Preferable examples of a "5-10-membered heteroaryl group" include a furyl group, a thienyl group, a pyrrolyl group, an imidazolyl group, a thiazolyl group, a pyrazolyl group, an oxazolyl group, an isoxazolyl group, an isothiazolyl group, a pyridyl group and a pyrimidinyl group.

Herein, a "3-10-membered nonaromatic heterocyclic group":
(a) has 3-10 atoms forming the ring;
(b) has 1-2 heteroatoms included in the atoms forming the ring;
(c) may include 1-2 double bonds in the ring;
(d) may include 1-3 carbonyl groups, sulfinyl groups or sulfonyl groups in the ring; and
(e) is a nonaromatic monocyclic or bicyclic group where when a nitrogen atom is included in the atoms forming the ring, the nitrogen atom may have a chemical bond.

Specific examples include an aziridinyl group, an azetidinyl group, a pyrrolidinyl group, a piperidinyl group, an azepanyl group, an azocanyl group, a piperazinyl group, a diazepanyl group, a diazocanyl group, a diazabicyclo[2.2.1]heptyl group, a morpholinyl group, a thiomorpholinyl group, a 1,1-dioxothiomorpholinyl group, an oxiranyl group, an oxetanyl group, a tetrahydrofuryl group, a dioxolanyl group, a tetrahydropyranyl group, a dioxanyl group, a tetrahydrothienyl group, a tetrahydrothiopyranyl group, an oxazolidinyl group and a thiazolidinyl group.

Preferable examples of a "3-10-membered nonaromatic heterocyclic group" include an aziridinyl group, an azetidinyl group, a pyrrolidinyl group, a piperidinyl group, an azepanyl group, a piperazinyl group, a diazepanyl group, a morpholinyl group, a thiomorpholinyl group, a 1,1-dioxothiomorpholinyl group, a tetrahydrofuryl group and a tetrahydropyranyl group.

Herein, a "$C_{1-6}$ alkoxy group" refers to a group in which an oxygen atom is bound to the terminal of a "$C_{1-6}$ alkyl group" defined above, specific examples including a methoxy group, an ethoxy group, a 1-propoxy group (n-propoxy group), a 2-propoxy group (1-propoxy group), a 2-methyl-1-propoxy group (1-butoxy group), a 2-methyl-2-propoxy group (t-butoxy group), a 1-butoxy group (n-butoxy group), a 2-butoxy group (s-butoxy group), a 1-pentyloxy group, a 2-pentyloxy group, a 3-pentyloxy group, a 2-methyl-1-butoxy group, a 3-methyl-1-butoxy group, a 2-methyl-2-butoxy group, a 3-methyl-2-butoxy group, a 2,2-dimethyl-1-propoxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butoxy group, a 3,3-dimethyl-1-butoxy group, a 2,2-dimethyl-1-butoxy group, a 2-ethyl-1-butoxy group, a 3,3-dimethyl-2-butoxy group and a 2,3-dimethyl-2-butoxy group.

Preferable examples of a "$C_{1-6}$ alkoxy group" include a methoxy group, an ethoxy group, a 1-propoxy group, a 2-propoxy group, a 2-methyl-1-propoxy group, a 2-methyl-2-propoxy group, a 1-butoxy group and a 2-butoxy group.

Herein, a "$C_{1-6}$ alkylthio group" refers to a group in which a sulfur atom is bound to the terminal of a "$C_{1-6}$ alkyl group" defined above, specific examples including a methylthio group, an ethylthio group, a 1-propylthio group (n-propylthio group), a 2-propylthio group (i-propylthio group), a 2-methyl-1-propylthio group (1-butylthio group), a 2-methyl-2-propylthio group (t-butylthio group), a 1-butylthio group (n-butylthio group), a 2-butylthio group (s-butylthio group), a 1-pentylthio group, a 2-pentylthio group, a 3-pentylthio group, a 2-methyl-1-butylthio group, a 3-methyl-1-butylthio group, a 2-methyl-2-butylthio group, a 3-methyl-2-butylthio group, a 2,2-dimethyl-1-propylthio group, a 1-hexylthio group, a 2-hexylthio group, a 3-hexylthio group, a 2-methyl-1-pentylthio group, a 3-methyl-1-pentylthio group, a 4-methyl-1-pentylthio group, a 2-methyl-2-pentylthio group, a 3-methyl-2-pentylthio group, a 4-methyl-2-pentylthio group, a 2-methyl-3-pentylthio group, a 3-methyl-3-pentylthio group, a 2,3-dimethyl-1-butylthio group, a 3,3-dimethyl-1-butylthio group, a 2,2-dimethyl-1-butylthio group, a 2-ethyl-1-butylthio group, a 3,3-dimethyl-2-butylthio group and a 2,3-dimethyl-2-butylthio group.

Preferable examples of a "$C_{1-6}$ alkylthio group" include a methylthio group, an ethylthio group, a 1-propylthio group (n-propylthio group), a 2-propylthio group (1-propylthio group), a 2-methyl-1-propylthio group (1-butylthio group), a 2-methyl-2-propylthio group (t-butylthio group), a 1-butylthio group (n-butylthio group) and a 2-butylthio group (s-butylthio group).

Herein, a "$C_{3-8}$ cycloalkoxy group" refers to a group in which an oxygen atom is bound to the terminal of a "$C_{3-8}$ cycloalkyl group" defined above, specific examples including a cyclopropoxy group, a cyclobutoxy group, a cyclopentyloxy group, a cyclohexyloxy group, a cycloheptyloxy group, a cyclooctyloxy group, a bicyclo[2.1.0]pentyloxy group, a bicyclo[3.1.0]hexyloxy group, a bicyclo[2.1.1]hexyloxy group, a bicyclo[4.1.0]heptyloxy group, a bicyclo[2.2.1]heptyloxy group (norbornyloxy group), a bicyclo[3.3.0]octyloxy group, a bicyclo[3.2.1]octyloxy group and a bicyclo[2.2.2]octyloxy group.

Preferable examples of a "$C_{3-8}$ cycloalkoxy group" include a cyclopropoxy group, a cyclobutoxy group and a cyclopentyloxy group.

Herein, a "mono-$C_{1-6}$ alkylamino group" refers to a group in which a hydrogen atom in an amino group is substituted with a "$C_{1-6}$ alkyl group" defined above, specific examples including a methylamino group, an ethylamino group, a 1-propylamino group (n-propylamino group), a 2-propylamino group (i-propylamino group), a 2-methyl-1-propylamino group (1-butylamino group), a 2-methyl-2-propylamino group (t-butylamino group), a 1-butylamino group (n-butylamino group), a 2-butylamino group (s-butylamino group), a 1-pentylamino group, a 2-pentylamino group, a 3-pentylamino group, a 2-methyl-1-butylamino group, a 3-methyl-1-butylamino group, a 2-methyl-2-butylamino group, a 3-methyl-2-butylamino group, a 2,2-dimethyl-1-propylamino group, a 1-hexylamino group, a 2-hexylamino group, a 3-hexylamino group, a 2-methyl-1-pentylamino group, a 3-methyl-1-pentylamino group, a 4-methyl-1-pentylamino group, a 2-methyl-2-pentylamino group, a 3-methyl-2-pentylamino group, a 4-methyl-2-pentylamino group, a 2-methyl-3-pentylamino group, a 3-methyl-3-pentylamino group, a 2,3-dimethyl-1-butylamino group, a 3,3-dimethyl-1-butylamino group, a 2,2-dimethyl-1-butylamino group, a 2-ethyl-1-butylamino group, a 3,3-dimethyl-2-butylamino group and a 2,3-dimethyl-2-butylamino group.

Herein, a "di-$C_{1-6}$ alkylamino group" refers to a group in which two hydrogen atoms in an amino group are substituted with an identical or different "$C_{1-6}$ alkyl group" defined above, specific examples including a N,N-dimethylamino group, a N,N-diethylamino group, a N,N-di-n-propylamino group, a N,N-di-1-propylamino group, a N,N-di-n-butylamino group, a N,N-di-1-butylamino group, a N,N-di-s-butylamino group, a N,N-di-t-butylamino group, a N-ethyl-N-methylamino group, a N-n-propyl-N-methylamino group, a N-i-propyl-N-methylamino group, a N-n-butyl-N-methylamino group, a N-i-butyl-N-methylamino group, a N-s-butyl-N-methylamino group and a N-t-butyl-N-methylamino group.

Herein, a "$C_{2-7}$ acyl group" refers to a carbonyl group bound with a "$C_{1-6}$ alkyl group" defined above, specific examples including an acetyl group, a propionyl group, an isopropionyl group, a butyryl group, an isobutyryl group, a valeryl group, an isovaleryl group and a pivaloyl group.

Herein, a "$C_{2-7}$ alkoxycarbonyl group" refers to a carbonyl group bound with a "$C_{1-6}$ alkoxy group" defined above, specific examples including a methoxycarbonyl group, an ethoxycarbonyl group, a 1-propyloxycarbonyl group, a 2-propyloxycarbonyl group and a 2-methyl-2-propoxycarbonyl group.

Herein, "that may have a substituent" means "that may have one or more substituents in any combination at substitutable positions", specific examples of substituents including a halogen atom, a hydroxyl group, a thiol group, a nitro group, a cyano group, a formyl group, a carboxyl group, an amino group, a silyl group, a methanesulfonyl group, a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a 5-10-membered heteroaryl group, a 3-10-membered nonaromatic heterocyclic group, a $C_{1-6}$ alkoxy group, a $C_{1-6}$ alkylthio group, a $C_{3-8}$ cycloalkoxy group, a mono-$C_{1-6}$ alkylamino group, a di-$C_{1-6}$ alkylamino group, a $C_{2-7}$ acyl group and a $C_{2-7}$ alkoxycarbonyl group. In this case, the $C_{1-6}$ alkyl group, the $C_{2-6}$ alkenyl group, the $C_{2-6}$ alkynyl group, the $C_{3-8}$ cycloalkyl group, the $C_{6-10}$ aryl group, the 5-10-membered heteroaryl group, the 3-10-membered nonaromatic heterocyclic group, the $C_{1-6}$ alkoxy group, the $C_{1-6}$ alkylthio group, the $C_{3-8}$ cycloalkoxy group, the mono-$C_{1-6}$ alkylamino group, the di-$C_{1-6}$ alkylamino group, the $C_{2-7}$ acyl group and the $C_{2-7}$ alkoxycarbonyl group may each independently have 1-3 groups selected from the group consisting of the following substituent groups.

<Substituent Groups>

A halogen atom, a hydroxyl group, a thiol group, a nitro group, a cyano group, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5-10-membered heteroaryl group, a 3-10-membered nonaromatic heterocyclic group, a $C_{1-6}$ alkoxy group and a $C_{1-6}$ alkylthio group.

According to the present invention, an example of a FGFR2 inhibitor includes a compound represented by General formula (I).

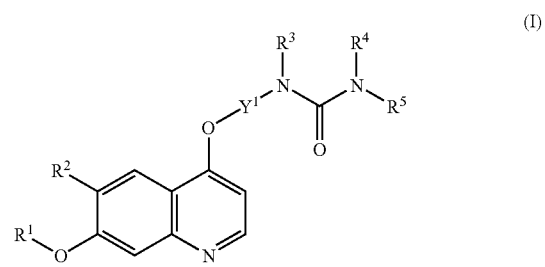

Hereinafter, a compound represented by General Formula (I) may also be referred to as a "FGFR2 inhibitor I".

(i) $R^1$ $R^1$ represents a group represented by Formula —$V^1$—$V^2$—$V^3$— (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula —$CONR^6$—, a group represented by Formula —$SO_2NR^6$—, a group represented by Formula —$NR^6SO_2$—, a group represented by Formula —$NR^6CO$— or a group represented by Formula —$NR^6$— (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group).

A preferable example of $R^1$ includes a $C_{1-6}$ alkyl group provided that $R^1$ may have a substituent selected from a 3-10-membered nonaromatic heterocyclic group, a hydroxyl group, a $C_{1-6}$ alkoxy group, an amino group, a mono-$C_{1-6}$ alkylamino group and a di-$C_{1-6}$ alkylamino group which may have a $C_{1-6}$ alkyl group.

More preferable examples of $R^1$ include a methyl group and a group represented by any one of the following formulae

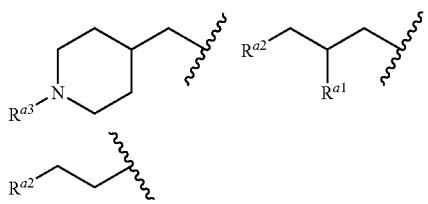

(wherein, $R^{a3}$ represents a methyl group; $R^{a1}$ represents a hydrogen atom or a hydroxyl group; $R^{a2}$ represents a methoxy group, an ethoxy group, a 1-pyrrolidinyl group, a 1-piperidinyl group, a 4-morpholinyl group, a dimethylamino group or a diethylamino group).

Still more preferable examples of $R^1$ include a methyl group and a 2-methoxyethyl group.

(ii) $R^2$ $R^2$ represents a cyano group, an optionally substituted $C_{1-6}$ alkoxy group, a carboxyl group, an optionally substituted $C_{2-7}$ alkoxycarbonyl group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group).

Preferable examples of $R^2$ include a cyano group or a group represented by Formula —$CONV^{a11}V^{a12}$ (wherein, $V^{a11}$ and $V^{a12}$ have the same meaning as defined above).

More preferable examples of $R^2$ include a cyano group or a group represented by Formula —$CONHV^{a16}$ (wherein, $V^{a16}$ represents a hydrogen atom, a $C_{1-6}$ alkyl group, a $C_{3-8}$ cycloalkyl group, a $C_{1-6}$ alkoxy group or a $C_{3-8}$ cycloalkoxy group, provided that $V^{a16}$ may have a substituent selected from a halogen atom, a cyano group, a hydroxyl group and a $C_{1-6}$ alkoxy group).

A still more preferable example of $R^2$ includes a group represented by Formula —$CONHV^{a17}$ (wherein, $V^{a17}$ represents a hydrogen atom, a $C_{1-6}$ alkyl group or a $C_{1-6}$ alkoxy group).

The most preferable example of $R^2$ includes a group represented by Formula —$CONHV^{a18}$ (wherein, $V^{a18}$ represents a hydrogen atom, a methyl group or a methoxy group).

(iii) $Y^1$ $Y^1$ represents a group represented by the following formula

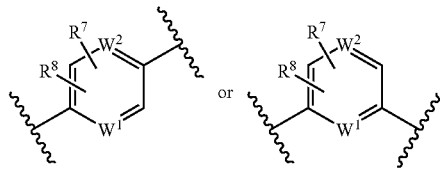

(wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —$CONV^{d1}V^{d2}$ (wherein, $V^{d1}$ and $V^{d2}$ each independently represent a hydrogen atom or an optionally substituted $C_{1-6}$ alkyl group);
$W^1$ and $W^2$ each independently represent an optionally substituted carbon atom or nitrogen atom).

A preferable example of $Y^1$ includes a group represented by the following formula

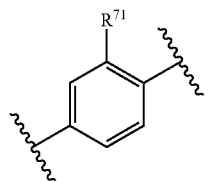

(wherein, $R^{71}$ represents a hydrogen atom or a halogen atom).

(iv) $R^3$ and $R^4$ $R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group.

A preferable example of $R^3$ and $R^4$ includes a hydrogen atom.

(v) $R^5$ $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted C$_{3-8}$ cycloalkyl group, an optionally substituted C$_{6-10}$ aryl group, an optionally substituted 5-10-membered heteroaryl group or an optionally substituted 3-10-membered nonaromatic heterocyclic group.

Preferable examples of R$^5$ include a hydrogen atom, an optionally substituted C$_{1-6}$ alkyl group, an optionally substituted C$_{2-6}$ alkenyl group, an optionally substituted C$_{2-6}$ alkynyl group, an optionally substituted C$_{3-8}$ cycloalkyl group, an optionally substituted C$_{6-10}$ aryl group and an optionally substituted 3-10-membered nonaromatic heterocyclic group.

More preferable examples of R$^5$ include a hydrogen atom, a C$_{1-6}$ alkyl group, a C$_{3-8}$ cycloalkyl group and a C$_{6-10}$ aryl group (provided that R$^5$ may have at least one substituent selected from the group consisting of a halogen atom and a methanesulfonyl group).

More preferable examples of R$^5$ include a methyl group, an ethyl group and a cyclopropyl group.

Furthermore, preferable examples of the compound represented by General Formula (I) include:

N-(4-(6-cyano-7-(2-methoxyethoxy)-4-quinolyl)oxy-2-fluorophenyl)-N'-(4-fluorophenyl)urea;

N-(2-chloro-4-((6-cyano-7-((1-methyl-4-piperidyl)methoxy)-4-quinolyl)oxy)phenyl)-N'-cyclopropyl urea;

N-(4-((6-cyano-7-(((2R)-3-(diethylamino)-2-hydroxypropyl)oxy)-4-quinolyl)oxy)phenyl)-N'-(4-fluorophenyl)urea;

N-(4-((6-cyano-7-(((2R)-2-hydroxy-3-(1-pyrrolidino)propyl)oxy)-4-quinolyl)oxy)phenyl)-N'-(4-fluorophenyl)urea;

4-(3-chloro-4-(cyclopropylaminocarbonyl)aminophenoxy)-7-methoxy-6-quinolinecarboxamide;

4-(3-chloro-4-(cyclopropylaminocarbonyl)aminophenoxy)-7-(2-methoxyethoxy)-6-quinolinecarboxamide;

N6-cyclopropyl-4-(3-chloro-4-(((cyclopropylamino)carbonyl)amino)phenoxy)-7-methoxy-6-quinolinecarboxamide;

N6-(2-methoxyethyl)-4-(3-chloro-4-(((cyclopropylamino)carbonyl)amino)phenoxy)-7-methoxy-6-quinolinecarboxamide;

N6-(2-fluoroethyl)-4-(3-chloro-4-(((cyclopropylamino)carbonyl)amino)phenoxy)-7-methoxy-6-quinolinecarboxamide;

N6-methoxy-4-(3-chloro-4-(((cyclopropylamino)carbonyl)amino)phenoxy)-7-methoxy-6-quinolinecarboxamide;

N6-methyl-4-(3-chloro-4-(((cyclopropylamino)carbonyl)amino)phenoxy)-7-methoxy-6-quinolinecarboxamide;

N6-ethyl-4-(3-chloro-4-(((cyclopropylamino)carbonyl)amino)phenoxy)-7-methoxy-6-quinolinecarboxamide;

4-(3-fluoro-4-(cyclopropylaminocarbonyl)aminophenoxy)-7-(2-methoxyethoxy)-6-quinolinecarboxamide;

4-(3-chloro-4-(cyclopropylaminocarbonyl)aminophenoxy)-7-(2-hydroxyethoxy)-6-quinolinecarboxamide;

4-(3-chloro-4-(cyclopropylaminocarbonyl)aminophenoxy)-7-((2S)-2,3-dihydroxypropyl)oxy-6-quinolinecarboxamide;

4-(3-chloro-4-(methylaminocarbonyl)aminophenoxy)-7-methoxy-6-quinolinecarboxamide;

4-(3-chloro-4-(ethylaminocarbonyl)aminophenoxy)-7-methoxy-6-quinolinecarboxamide;

N6-methoxy-4-(3-chloro-4-(((ethylamino)carbonyl)amino)phenoxy)-7-methoxy-6-quinolinecarboxamide;

4-(3-chloro-4-(cyclopropylaminocarbonyl)aminophenoxy)-7-(2-ethoxyethoxy)-6-quinolinecarboxamide;

4-(4-((cyclopropylamino)carbonyl)aminophenoxy)-7-(2-methoxyethoxy)-6-quinolinecarboxamide;

N-(2-fluoro-4-((6-carbamoyl-7-methoxy-4-quinolyl)oxy)phenyl)-N'-cyclopropyl urea;

N6-(2-hydroxyethyl)-4-(3-chloro-4-(((cyclopropylamino)carbonyl)amino)phenoxy)-7-methoxy-6-quinolinecarboxamide;

4-(3-chloro-4-(1-propylaminocarbonyl)aminophenoxy)-7-methoxy-6-quinolinecarboxamide;

4-(3-chloro-4-(cis-2-fluoro-cyclopropylaminocarbonyl)aminophenoxy)-7-methoxy-6-quinolinecarboxamide;

N6-methyl-4-(3-chloro-4-(((cyclopropylamino)carbonyl)amino)phenoxy)-7-(2-methoxyethoxy)-6-quinolinecarboxamide;

N6-methyl-4-(3-chloro-4-(((ethylamino)carbonyl)amino)phenoxy)-7-methoxy-6-quinolinecarboxamide;

4-(3-chloro-4-(cyclopropylaminocarbonyl)aminophenoxy)-7-(2-(4-morpholino)ethoxy)-6-quinolinecarboxamide;

4-(3-chloro-4-(2-fluoroethylaminocarbonyl)aminophenoxy)-7-methoxy-6-quinolinecarboxamide;

N6-((2R)tetrahydro-2-furanylmethyl)-4-(3-chloro-4-(((methylamino)carbonyl)amino)phenoxy)-7-methoxy-6-quinolinecarboxamide;

4-(3-fluoro-4-(ethylaminocarbonyl)aminophenoxy)-7-methoxy-6-quinolinecarboxamide;

4-(3-chloro-4-(((cyclopropylamino)carbonyl)amino)phenoxy)-7-((2R)-2-hydroxy-3-(1-pyrrolidino)propoxy)-6-quinolinecarboxamide;

N6-methyl-4-(3-chloro-4-(((methylamino)carbonyl)amino)phenoxy)-7-((2R)-3-diethylamino-2-hydroxypropoxy)-6-quinolinecarboxamide;

N6-methyl-4-(3-chloro-4-(((ethylamino)carbonyl)amino)phenoxy)-7-((2R)-3-diethylamino-2-hydroxypropoxy)-6-quinolinecarboxamide;

N6-methyl-4-(3-chloro-4-(((methylamino)carbonyl)amino)phenoxy)-7-((2R)-2-hydroxy-3-(1-pyrrolidino)propoxy)-6-quinolinecarboxamide;

N6-methyl-4-(3-chloro-4-(((ethylamino)carbonyl)amino)phenoxy)-7-((2R)-2-hydroxy-3-(1-pyrrolidino)propoxy)-6-quinolinecarboxamide;

N6-methyl-4-(3-chloro-4-(((methylamino)carbonyl)amino)phenoxy)-7-((1-methyl-4-piperidyl)methoxy)-6-quinolinecarboxamide;

N6-methyl-4-(3-chloro-4-(((ethylamino)carbonyl)amino)phenoxy)-7-((1-methyl-4-piperidyl)methoxy)-6-quinolinecarboxamide;

N-(4-(6-cyano-7-(2-methoxyethoxy)-4-quinolyl)oxy-2-fluorophenyl)-N'-cyclopropyl urea;

N-(4-(6-cyano-7-(3-(4-morpholino)propoxy)-4-quinolyl)oxyphenyl)-N'-(3-(methylsulfonyl)phenyl)urea;

4-(4-((cyclopropylamino)carbonyl)aminophenoxy)-7-methoxy-6-quinolinecarboxamide;

4-(3-fluoro-4-((2-fluoroethylamino)carbonyl)aminophenoxy)-7-methoxy-6-quinolinecarboxamide;

N6-(2-ethoxyethyl)-4-(3-chloro-4-(((methylamino)carbonyl)amino)phenoxy)-7-methoxy-6-quinolinecarboxamide;

4-(4-(3-ethylureido)-3-fluoro-phenoxy)-7-methoxyquinoline-6-carboxylic acid (2-cyanoethyl)amide; and N-(4-(6-(2-cyanoethyl)carbamoyl-7-methoxy-4-quinolyl)oxy-2-fluorophenyl)-N'-cyclopropyl urea.

More preferable examples of the compound represented by General Formula (I) include:

4-(3-chloro-4-(cyclopropylaminocarbonyl)aminophenoxy)-7-methoxy-6-quinolinecarboxamide;

4-(3-chloro-4-(ethylaminocarbonyl)aminophenoxy)-7-methoxy-6-quinolinecarboxamide;

N6-methoxy-4-(3-chloro-4-((cyclopropylamino)carbonyl)amino)phenoxy)-7-methoxy-6-quinolinecarboxamide;

4-(3-chloro-4-(methylaminocarbonyl)aminophenoxy)-7-methoxy-6-quinolinecarboxamide; and N6-methoxy-4-(3-chloro-4-(((ethylamino)carbonyl)amino)phenoxy)-7-methoxy-6-quinolinecarboxamide.

A still more preferable example of the compound represented by General Formula (I) includes 4-(3-chloro-4-(cyclopropylaminocarbonyl)aminophenoxy)-7-methoxy-6-quinolinecarboxamide (see Formula (II)).

The most preferable example of the FGFR2 inhibitor I includes methanesulfonate of 4-(3-chloro-4-(cyclopropylaminocarbonyl)aminophenoxy)-7-methoxy-6-quinolinecarboxamide.

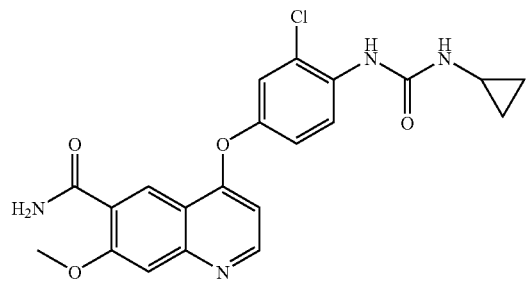

(II)

A compound represented by General formula (I) may be produced by a known method such as methods described in International Publications Nos. 02/32872 (WO02/32872) and 2005/063713 (WO2005/063713).

In addition, a FGFR2 inhibitor according to the present invention may not be a compound represented by General Formula (I) above (hereinafter, also referred to as a "FGFR2 inhibitor II") as long as it has an activity of inhibiting the kinase activity of FGFR2. Examples of FGFR2 inhibitors II include:

5-(5-fluoro-2-oxo-1,2-dihydroindole-3-ylidenemethyl)-2,4-dimethyl-1H-pyrrole-3-carboxylic acid (2-diethylaminoethyl)amide (hereinafter, also referred to as "SU11248"; Journal of Medicinal Chemistry., 46:1116-9, 2003, WO 01/060814) (see Formula (III)),

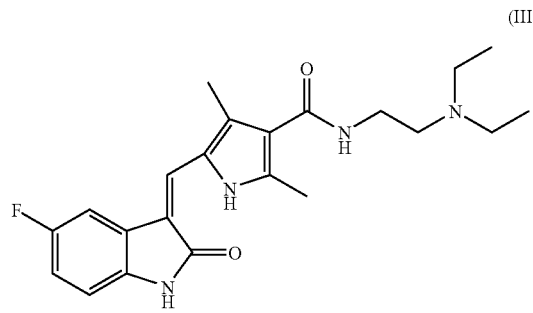 [SMILES: CCN(CC)CCNC(=O)c1c(C)[nH]c(/C=C2\C(=O)Nc3ccc(F)cc32)c1C]

(III)

N-(3-trifluoromethyl-4-chlorophenyl)-N'-(4-(2-methylcarbamoylpyridine-4-yl)oxyphenyl)urea (hereinafter, also referred to as "BAY 43-9006" or "sorafenib"; WO00/42012) (see Formula (IV)),

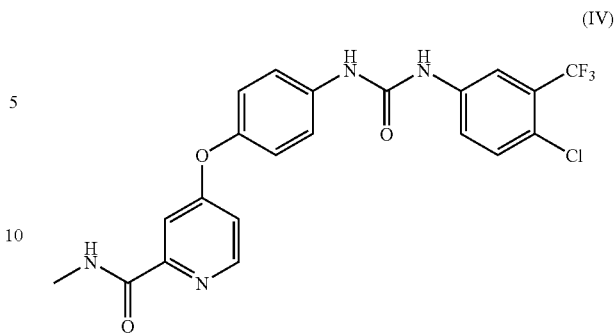

(IV)

6-[2-(methylcarbamoyl)phenylsulfanyl]-3-E-[2-(pyridine-2-yl)ethenyl]indazole (hereinafter, also referred to as "AG013736"; WO0/002369) (see Formula (V)), and

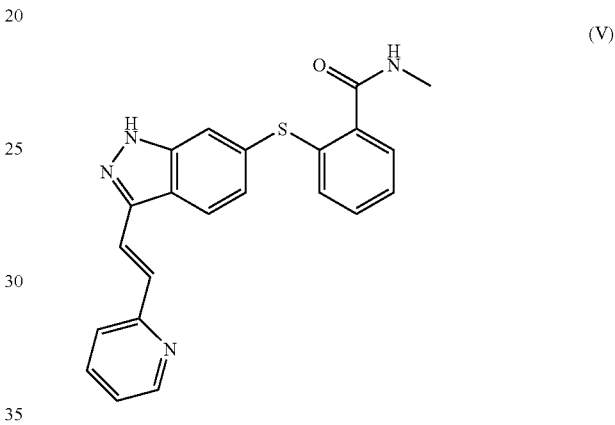

(V)

N-{2-chloro-4-[(6,7-dimethoxy-4-quinolyl)oxy]phenyl}-N'-(5-methyl-3-isoxazolyl)urea (hereinafter, also referred to as "KRN951"; WO02/088110) (see Formula (VI))

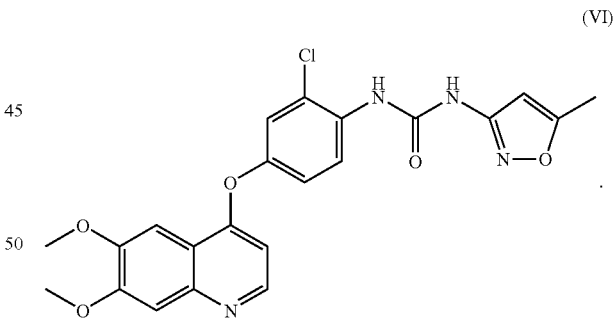

(VI)

SU11248, BAY 43-9006, AG013736 and KRN951 may be produced by a known method such as methods described in respective publications mentioned above.

According to the present invention, a FGFR2 inhibitor may form a pharmacologically acceptable salt with acid or base. The FGFR2 inhibitor of the invention also comprises such pharmacologically acceptable salts. Examples of salts formed with acids include inorganic acid salts such as hydrochloride salts, i salts, sulfate salts and phosphate salts, and organic acid salts such as formic acid, acetic acid, lactic acid, succinic acid, fumaric acid, maleic acid, citric acid, tartaric acid, stearic acid, benzoic acid, methanesulfonic acid, benzenesulfonic acid, p-toluenesulfonic acid and trifluoroacetic acid. Examples of salts formed with bases include alkali metal salts such as sodium salt and potassium salt, alkaline earth metal salts such as calcium salt and magnesium salt, organic base salts such as trimethylamine, triethylamine, pyridine, picoline, dicyclohexylamine, N,N'-dibenzyl ethylenediamine, arginine and lysine and ammonium salts.

Furthermore, according to the present invention, the FGFR2 inhibitor may exist as a solvate or an optical isomer. According to the present invention, the FGFR2 inhibitor comprises such solvates and optical isomers. Examples of solvates include hydrates and nonhydrates, preferably hydrates. Examples of solvents include water, alcohols (for example, methanol, ethanol and n-propanol) and dimethylformamide.

Moreover, according to the present invention, the FGFR2 inhibitor may be crystalline or amorphous. If a crystalline polymorph exists, it may exist as one type of any crystalline or mixture thereof.

According to the present invention, the FGFR2 inhibitor also comprises their metabolites generated by undergoing metabolism such as oxidation, reduction, hydrolysis and conjugation in vivo. According to the present invention, the FGFR2 inhibitor also comprises compounds that generate the FGFR2 inhibitor by undergoing metabolism such as oxidation, reduction and hydrolysis in vivo.

Preferably, the FGFR2 inhibitor of the invention is a substance that has an activity of inhibiting the FGFR2 kinase activity (hereinafter, also referred to as an "FGFR2 inhibitory activity"). Herein, an "FGFR2 kinase activity" refers to an activity of FGFR2 to phosphorylate a tyrosine residue of own protein or other protein.

Examples of methods for determining a FGFR2 inhibitory activity of the FGFR2 inhibitor include cell free kinase assay, western blotting, cell growth assay and viability assay. Examples of the cell growth assay include tritium thymidine uptake method, MTT method, XTT method (cell counting kit-8 (Dojindo Laboratories)), AlamarBlue technique, Neutral Red technique, BrdU technique, Ki67 staining and PCNA staining. Examples of the viability assay include TUNNEL staining, Caspase-3 cleavage detection and PARP cleavage detection. These methods may be carried out according to conventional techniques (Blood. 2005, 105, 2941-2948., Molecular Cancer Therapeutics. 2005, 4, 787-798).

Hereinafter, an exemplary method for determining a FGFR2 inhibitory activity will be described.

The FGFR2 inhibitory activity can be determined by cell free kinase assay.

FGFR2 can be prepared by a gene-engineering technique according to a conventional method. For example, according to the method of Baculovirus Expression System, human recombinant GST fusion protein, human recombinant histidine-tag fusion protein or the like may be expressed in an insect cell (*Spondoptea frugiperda* 9 (Sf9)). Furthermore, the expressed recombinant protein can be purified by affinity chromatography (e.g., GSH-agarose (Sigma) or Ni-NTH-agarose (Qiagen)). The purity and identification of the protein can be confirmed by SDS-PAGE, silver staining and western blotting using an antibody specific to FGFR2.

The cell free kinase assay may be carried out as follows.

First, to each well of a plate (e.g., 96-well, 384-well, etc.), 25 µl of a solution containing an ATP solution, a test substance, 5-10 mU of FGFR2 recombinant protein and 0.1 mg/ml Poly(Glu, Tyr)$_{4:1}$ may be added. To this mixture, MgATP is added to initiate reaction.

25 µl of this mixture may contain 8 mM MOPS (pH 7.0), 0.2 mM EDTA, 2.5 mM MnCl$_2$, 10 mM Mg acetate and the like. ATP used in this case may be labeled with a radioisotope such as [$\gamma$-$^{32}$P]-ATP and [$\gamma$-$^{33}$P]-ATP.

The reaction may be terminated by adding 5 µL of 3% phosphoric acid following incubation for a given period of time.

Each well may be subjected to an appropriate washing procedure.

A FGFR2 inhibitory activity can be assessed by determining the amount of ATP incorporation. When a radioactive isotope-labeled ATP mentioned above is used, the amount of ATP incorporation can be assessed by determination of the radioactivity captured on the plate with a scintillation counter. Alternatively, a certain amount of the reaction solution may be spotted onto a filter to measure the radioactivity thereof with a scintillation counter. The filter may be subjected to an appropriate washing procedure.

The FGFR2 inhibitory activity of the compound can be assessed by this method.

2. Therapeutic Substance for Gastric Cancer

According to the present invention, a therapeutic substance for gastric cancer is not particularly limited as long as it is a substance used for treating gastric cancer, a substance whose therapeutic use is suitable for gastric cancer or a substance having anti-tumor action against gastric cancer. In addition, the therapeutic substance for gastric cancer of the invention may be a therapeutic drug for gastric cancer obtained by formulating the compound as an active ingredient.

According to the present invention, examples of therapeutic substances for gastric cancer include carboquone, nimustine, 5-fluorouracil analogs (e.g., 5-fluorouracil, tegafur, UFT, doxifluridine and carmofur, S-1), doxorubicin (adriamycin), mitomycin C, aclarubicin, pirarubicin, epirubicin, irinotecan, paclitaxel analogs (e.g., docetaxel and paclitaxel), cis-platinum (Cisplatin)), preferably 5-fluorouracil, S-1, irinotecan, docetaxel, paclitaxel or cis-platinum, more preferably, irinotecan, 5-fluorouracil or paclitaxel. Therapeutic substances for gastric cancer may be produced according to a known method or they may be purchased.

Carboquone is available by purchasing Esquinon (Registered Trademark) (Sankyo).

Nimustine or nimustine hydrochloride is available by purchasing Nidran (Registered Trademark) (Sankyo).

5-Fluorouracil is available by purchasing 5-FU (Kyowa Hakko).

Tegafur is available by purchasing Futraful (Registered Trademark) (Taiho Pharmaceutical Co., Ltd.).

UFT refers to a combinational agent of tegafur and uracil. UFT is available by purchasing UFT (Registered Trademark) (Taiho Pharmaceutical Co., Ltd.).

Doxifluridine is available by purchasing Furtulon (Registered Trademark) (Chugai Pharmaceutical Co., Ltd.).

Carmofur is available by purchasing Mifurol (Registered Trademark) (Schering).

S-1 refers to a combinational agent of tegafur, gemeracil and oteracil potassium. S-1 is available by purchasing TS-1 (Registered Trademark) (Taiho Pharmaceutical Co., Ltd.).

Doxorubicin (adriamycin) or doxorubicin hydrochloride is available by purchasing Adriacin (Registered Trademark) (Kyowa Hakko).

Mitomycin C is available by purchasing mitomycin (Kyowa Hakko).

Aclarubicin or aclarubicin hydrochloride is available by purchasing Aclacinon (Registered Trademark) (Astellas Inc.).

Pirarubicin or pirarubicin hydrochloride is available by purchasing Pinorubin (Registered Trademark) (Nippon Kayaku Co., Ltd.) or Therarubicin (Registered Trademark) (Meiji Seika Kaisya, Ltd.).

Epirubicin or epirubicin hydrochloride is available by purchasing Farmorubicin (Registered Trademark) (Kyowa Hakko) or Epirubicin (Registered Trademark) (Nippon Kayaku Co., Ltd.).

Irinotecan or irinotecan hydrochloride is available by purchasing Campto (Registered Trademark) (Yakult). It is also available by purchasing Topotecin (Registered Trademark) (Daiichi Seiyaku).

Docetaxel or docetaxel hydrate is available by purchasing Taxoere (Registered Trademark) (Sanofi-aventis).

Paclitaxel is available by purchasing Taxol (Registered Trademark) (Bristol-Myers Squibb Company) or by purchasing Paclitaxel (Nippon Kayaku Co., Ltd.) or Paclitaxel (Calbiochem).

Cis-platinum (Cisplatin) is available by purchasing Randa (Registered Trademark) (Nippon Kayaku Co., Ltd.) or Briplatin (Registered Trademark) (Bristol-Myers Squibb Company).

Since a FGFR2 inhibitor of the present invention has an anti-tumor action against undifferentiated gastric cancer, it is also comprised in the therapeutic substances for gastric cancer. In this case, the therapeutic substance for gastric cancer is preferably a FGFR2 inhibitor I or II, and more preferably a FGFR inhibitor II.

According to the present invention, the therapeutic substance for gastric cancer may form a pharmacologically acceptable salt with acid or base. The therapeutic substance for gastric cancer according to the invention also comprises such pharmacologically acceptable salts. Examples of salts formed with acids include inorganic acid salts such as hydrochloride salts, hydrobromate salts, sulfate salts and phosphate salts, and organic acid salts such as formic acid, acetic acid, lactic acid, succinic acid, fumaric acid, maleic acid, citric acid, tartaric acid, stearic acid, benzoic acid, methanesulfonic acid, benzenesulfonic acid, p-toluenesulfonic acid and trifluoroacetic acid. Examples of salts formed with bases include alkali metal salts such as sodium salt and potassium salt, alkaline earth metal salts such as calcium salt and magnesium salt, organic base salts such as trimethylamine, triethylamine, pyridine, picoline, dicyclohexylamine, N,N'-dibenzyl ethylenediamine, arginine and lysine, and ammonium salts.

Furthermore, according to the present invention, the therapeutic substance for gastric cancer may exist as a solvate or an optical isomer. According to the present invention, the therapeutic substance for gastric cancer comprises such solvates and optical isomers. Examples of solvates include hydrates and nonhydrates, preferably hydrates. Examples of solvents include water, alcohols (for example, methanol, ethanol and n-propanol) and dimethylformamide.

Moreover, according to the present invention, the therapeutic substance for gastric cancer may be crystalline or amorphous. If a crystalline polymorph exists, it may exist as one type of any crystalline forms or mixture thereof.

According to the present invention, the therapeutic substance for gastric cancer also comprises their metabolites generated by undergoing metabolism such as oxidation, reduction, hydrolysis and conjugation in vivo. According to the present invention, the therapeutic substance for gastric cancer also comprises compounds that generate the therapeutic substance for gastric cancer by undergoing metabolism such as oxidation, reduction and hydrolysis in vivo.

3. Pharmaceutical Composition, Therapeutic Agent, Kit and Therapeutic Method

The present invention is characterized in that a FGFR2 inhibitor is combined with a therapeutic substance for gastric cancer. Specifically, the present invention relates to a therapeutic agent, a kit and a therapeutic method for undifferentiated gastric cancer characterized in that the followings are combined: (i) a FGFR2 inhibitor I and a therapeutic substance for gastric cancer; (ii) a FGFR2 inhibitor I and a FGFR2 inhibitor II; or (iii) a FGFR2 inhibitor II and a therapeutic substance for gastric cancer. Preferably, the therapeutic agent of the invention is used for a living organism comprising at least one selected from the group consisting of a cell overexpressing FGFR2 and a cell expressing mutant FGFR2.

Herein, undifferentiated gastric cancer comprises poorly differentiated adenocarcinoma, signet-ring cell carcinoma and mucinous carcinoma (Japanese Classification of Gastric Carcinoma "Igan-Toriatsukai Kiyaku" (13th ed.)). In the case of undifferentiated gastric cancer, cancer cells are likely to diffuse and likely to develop fibrosis that leads to scirrhous gastric cancer. Thus, the therapeutic agent of the invention is effective against at least one gastric cancer selected from the group consisting of poorly differentiated adenocarcinoma, signet-ring cell carcinoma, mucinous carcinoma and scirrhous gastric cancer.

The therapeutic agent of the invention may be administered to a mammal (e.g., human, rat, rabbit, sheep, pig, bovine, cat, dog, monkey, etc.).

The pharmaceutical composition of the invention comprises a FGFR2 inhibitor and a therapeutic substance for gastric cancer, specifically, (i) a FGFR2 inhibitor I and a therapeutic substance for gastric cancer; (ii) a FGFR2 inhibitor I and a FGFR2 inhibitor II; or (iii) a FGFR2 inhibitor II and a therapeutic substance for gastric cancer, which is administered to a living organism comprising at least one selected from the group consisting of a cell overexpressing FGFR2 and a cell expressing mutant FGFR2.

The pharmaceutical composition of the invention may be used as a therapeutic agent for a disease characterized by comprising at least one selected from the group consisting of a cell overexpressing FGFR2 and a cell expressing mutant FGFR2. An example of such a disease includes undifferentiated gastric cancer.

The pharmaceutical composition of the invention may be administered to a living organism, i.e., a mammal (e.g., human, rat, rabbit, sheep, pig, bovine, cat, dog, monkey, etc.). These living organisms of the present invention may comprise either a cell overexpressing FGFR2 or a cell expressing mutant FGFR2, or both of them.

According to the present invention, treatment comprises relieving symptoms of the disease, retarding progression of the disease, eliminating symptoms of the disease, improving prognosis of the disease and preventing recurrence of the disease.

According to the present invention, a therapeutic agent for cancer also comprises anti-tumor agents, agents for suppressing cancer metastasis, agents for improving cancer prognosis, agents for preventing of cancer recurrence and the like.

The effect of treatment may be confirmed by observation of an x-ray picture, CT or the like, by histopathological diagnosis by biopsy or according to tumor marker values.

According to the present invention, a FGFR2 inhibitor is as described in "1. FGFR2 inhibitor". The FGFR2 inhibitor of the invention is, for example, a FGFR2 inhibitor I such as a compound represented by General Formula (I), more preferably, 4-(3-chloro-4-(cyclopropylaminocarbonyl)aminophenoxy)-7-methoxy-6-quinolinecarboxamide, and more preferably methanesulfonate of 4-(3-chloro-4-(cyclopropylaminocarbonyl)aminophenoxy)-7-methoxy-6-quinolinecarboxamide.

On the other hand, the FGFR2 inhibitor of the invention is a FGFR2 inhibitor II, a substance that shows FGFR2 inhibitory activity and is not comprised in compounds represented by General Formula (I), which is preferably SU11248, BAY43-9006, AG013736 or KRN951.

According to the present invention, a therapeutic substance for gastric cancer is as described in "2. Therapeutic substance for gastric cancer", and it is preferably irinotecan, 5 or paclitaxel. Since a FGFR2 inhibitor has an anti-tumor activity against undifferentiated gastric cancer, it may be included in a therapeutic substance for gastric cancer.

Preferable embodiments of combinations of FGFR2 inhibitors and therapeutic substances for gastric cancer according to the present invention are described below.

(1) According to the present invention, when a FGFR2 inhibitor is a compound represented by General Formula (I), a pharmacologically acceptable salt thereof or a solvate thereof (a FGFR2 inhibitor I), it is preferably used in combination with a therapeutic substance for gastric cancer described in "2. Therapeutic substance for gastric cancer" above.

(2) According to the present invention, when a FGFR2 inhibitor is a compound represented by General Formula (I), a pharmacologically acceptable salt thereof or a solvate thereof (a FGFR2 inhibitor I), it is preferably used in combination with a FGFR2 inhibitor that is not comprised in compounds represented by General Formula (I) (FGFR2 inhibitors II) such as SU11248, BAY43-9006, AG03736, KRN951 or the like.

(3) According to the present invention, when a FGFR2 inhibitor is a FGFR2 inhibitor that is not comprised in compounds represented by General Formula (I) (FGFR2 inhibitors II), it is preferably used in combination with a therapeutic substance for gastric cancer described in "2. Therapeutic substance for gastric cancer" above.

According to the present invention, the phrase "in combination" refers to a combination of compounds for combination use, and includes both modes where separate substances are used in combination upon administration or where they are provided as a mixture.

The therapeutic agent of the invention is also provided in a form of a therapeutic agent for undifferentiated gastric cancer comprising a FGFR2 inhibitor I for administration to a patient in combination with a therapeutic substance for gastric cancer or a FGFR2 inhibitor II. Furthermore, the therapeutic agent of the invention is also provided in a form of a therapeutic agent for treating undifferentiated gastric cancer comprising a FGFR2 inhibitor II or in a form of a therapeutic agent for treating gastric cancer comprising a therapeutic substance for gastric cancer, for administration to a patient in combination with a therapeutic substance for gastric cancer or a FGFR2 inhibitor II.

Moreover, a pharmaceutical composition of the invention is also provided in a form of a pharmaceutical composition comprising a FGFR2 inhibitor I for administration to a patient in combination with a therapeutic substance for gastric cancer or a FGFR2 inhibitor II, for administration to a living organism comprising at least one selected from the group consisting of a cell overexpressing FGFR2 and a cell expressing mutant FGFR2. The pharmaceutical composition of the invention is also provided in a form of a pharmaceutical composition comprising a FGFR2 inhibitor II or a therapeutic substance for gastric cancer for administration to a patient in combination with a therapeutic substance for gastric cancer or a FGFR2 inhibitor II, for administration to the above-mentioned living organism.

A FGFR2 inhibitor I and a therapeutic substance for gastric cancer or a FGFR2 inhibitor II, or a FGFR2 inhibitor II and a therapeutic substance for gastric cancer may be administered simultaneously or separately. The term "simultaneously" means that they are administered at the same timing in a single administration schedule and does not necessarily mean that they are administered at exactly the same moment. The term "separately" means that they are administered at different timings in a single administration schedule.

The kit of the present invention is characterized by comprising a set of a formulation comprising a FGFR2 inhibitor I and a formulation comprising a therapeutic substance for gastric cancer or a FGFR2 inhibitor II. In addition, the kit of the present invention is characterized by comprising a set of a formulation comprising a FGFR2 inhibitor II and a formulation comprising a therapeutic substance for gastric cancer. The form of the formulations comprised in the kit of the invention is not particularly limited as long as they contain the substances mentioned above. The kit of the invention is useful as a kit for treating undifferentiated gastric cancer.

The formulations in the kit of the invention may be mixed together, or they may be kept separately and packed together. These formulations may be administered simultaneously or one after the other.

The therapeutic agent, the pharmaceutical composition, the kit or the method for treating undifferentiated gastric cancer of the invention may further include one or more other anti-tumor agents in combination. Such anti-tumor agents are not particularly limited as long as they have an anticancer activity.

The therapeutic agent, the pharmaceutical composition or the kit of the invention may be administered either orally or parenterally.

Upon use of the therapeutic agent, the pharmaceutical composition or the kit of the invention, the given dose of the FGFR2 inhibitor differs depending on the degree of the symptom, age, sex, weight and sensitivity difference of the patient, administration mode, administration period, administration interval, nature, prescription and type of the pharmaceutical formation and the type of the active ingredient. Usually, but without limitation, the dose is 0.1-1000 mg/day, preferably 0.5-100 mg/day and more preferably 1-30 mg/day for an adult (weight 60 kg), which may be usually administered once to three times a day.

Upon use of the therapeutic agent, the pharmaceutical composition or the kit of the invention, the given dose of the therapeutic substance for gastric cancer is usually, but without limitation, 0.1-6000 mg/day, preferably 10-4000 mg/day and more preferably 50-2000 mg/day for an adult (weight 60 kg), which may be usually administered once to three times a day.

The amount of the FGFR2 inhibitor I used is not particularly limited, and differs depending on the individual combination with a therapeutic substance for gastric cancer or a FGFR2 inhibitor II. For example, the amount of the FGFR2 inhibitor I is about 0.01-100 times (weight ratio), more preferably about 0.1-10 times (weight ratio) the amount of the therapeutic substance for gastric cancer or the FGFR2 inhibitor II.

Similarly, the amount of the FGFR2 inhibitor II used is not particularly limited, and differs depending on the combination with a therapeutic substance for gastric cancer. For example, the amount of the FGFR2 inhibitor II is about 0.01-100 times (weight ratio), more preferably about 0.1-10 times (weight ratio) the amount of the therapeutic substance for gastric cancer.

Although the pharmaceutical composition or the therapeutic agent of the invention may be used directly, they are generally made into formulations while mixing with appropriate additives.

A FGFR2 inhibitor or a therapeutic substance for gastric cancer contained in the kit of the invention may be made into a formulation while mixing with appropriate additives.

Examples of such additives include excipients, binders, lubricants, disintegrants, colorants, flavoring agents, emulsifiers, surfactants, solubilizing agents, suspending agents, tonicity agents, buffers, antiseptic agents, antioxidant agents, stabilizers, absorption promoters and the like that are generally used for medicine. If required, they may be used in combination. Examples of such additive are mentioned below.

Excipients: lactose, sucrose, glucose, cornstarch, mannitol, sorbitol, starch, alpha-starch, dextrin, crystalline cellulose, light anhydrous silicic acid, aluminum silicate, calcium silicate, magnesium aluminometasilicate and calcium hydrogen phosphate.

Binders: for example, polyvinyl alcohol, methyl cellulose, ethyl cellulose, gum arabic, tragacanth, gelatin, shellack, hydroxypropyl methylcellulose, hydroxypropylcellulose, carboxymethylcellulose sodium, polyvinylpyrrolidone and macrogol.

Lubricants: magnesium stearate, calcium stearate, sodium stearyl fumarate, talc, polyethyleneglycol and colloid silica.

Disintegrants: crystalline cellulose, agar, gelatin, calcium carbonate, sodium hydrogen carbonate, calcium citrate, dextrin, pectin, low substituted hydroxypropylcellulose, carboxymethylcellulose, carboxymethylcellulose calcium, croscarmellose sodium, carboxymethyl starch and carboxymethyl starch sodium.

Colorants: ferric oxide, yellow ferric oxide, carmine, caramel, beta-carotene, titanium oxide, talc, riboflavin sodium phosphate, yellow aluminum lake and the like that are approved as additives in drugs.

Flavoring agents: cocoa powder, menthol, aromatic acid, peppermint oil, camphor and cinnamon powder.

Emulsifiers and surfactants: stearyltriethanolamine, sodium lauryl sulfate, laurylaminopropionate, lecithin, glycerine monostearate, sucrose fatty acid ester and glycerine fatty acid ester.

Solubilizing agents: polyethyleneglycol, propylene glycol, benzyl benzoate, ethanol, cholesterol, triethanolamine, sodium carbonate, sodium citrate, Polysorbate 80 and nicotine acid amide.

Suspending agents: for example, in addition to the surfactants mentioned above, hydrophilic polymers such as polyvinyl alcohol, polyvinylpyrrolidone, methylcellulose, hydroxymethylcellulose, hydroxyethylcellulose, hydroxypropylcellulose and the like.

Tonicity agents: glucose, sodium chloride, mannitol and sorbitol.

Buffers: buffers such as phosphate, acetate, carbonate, citrate and the like.

Antiseptic agents: methylparaben, propylparaben, chlorobutanol, benzyl alcohol, phenethyl alcohol, dehydroacetic acid and sorbic acid.

Antioxidant agents: hydrosulfate, ascorbic acid and alpha-tocopherol.

Stabilizers: those generally used for medicine.

Absorption promoters: those generally used for medicine.

If required, components such as vitamins and amino acids may be blended.

Examples of the above-mentioned formulations include oral formulations such as tablets, powder, granule, fine granule, capsule, syrup, lozenge and inhaler; external formulations such as suppository, ointment, eye ointment, poultice strip, eye-drops, nasal drops, eardrops, skin patch and lotion; and injectable formulations.

The oral formulations mentioned above may be formulated by appropriately combining the additives mentioned above. If necessary, surface of these formulations may be coated.

The external formulations mentioned above may be formulated by appropriately combining the additives mentioned above, particularly excipients, binders, flavoring agents, emulsifiers, surfactants, solubilizing agents, suspending agent, tonicity agents, antiseptic agents, antioxidant agents, stabilizers and absorption promoters.

The injectable formulations mentioned above may be formulated by appropriately combining the additives mentioned above, particularly emulsifiers, surfactants, solubilizing agents, suspending agents, tonicity agents, buffers, antiseptic agents, antioxidant agents, stabilizers and absorption promoters. The injectable formulations may be used through means such as infusion, intramuscular injection, subcutaneous injection, intradermal injection and intravenous injection.

The therapeutic agent, the pharmaceutical composition or the kit of the invention can also comprise a packaging container, an instruction, a package insert or the like in addition to the FGFR2 inhibitor and/or the therapeutic substance for gastric cancer mentioned above. The packaging container, the instruction, the package insert or the like may be printed with description of a combination for using the compounds in combination, and description of usage and dose for using separate substances in combination upon administration or for use of them as a mixture. The usage and dose may be described by referring to the description above.

The kit of the invention may comprise: (a) at least one selected from the group consisting of a packaging container, an instruction and a package insert describing combination use of a FGFR2 inhibitor I with a therapeutic substance for gastric cancer or a FGFR2 inhibitor II; and (b) a therapeutic agent for undifferentiated gastric cancer comprising the FGFR2 inhibitor I. Moreover, the kit of the invention may comprise: (a)' at least one selected from the group consisting of a packaging container, an instruction and a package insert describing combination use of a FGFR2 inhibitor II with a therapeutic substance for gastric cancer; and (b)' a therapeutic agent for undifferentiated gastric cancer comprising the FGFR2 inhibitor II or a therapeutic agent for treating gastric cancer comprising the therapeutic substance for gastric cancer.

The kit of the invention may comprise: (a) above; and (b)'' a pharmaceutical composition comprising a FGFR2 inhibitor I for administration to a living organism comprising at least one selected from the group consisting of a cell overexpressing FGFR2 and a cell expressing mutant FGFR2. In addition, the kit of the invention may comprise: (a)' above; and (b)''' a pharmaceutical composition comprising a FGFR2 inhibitor II or a therapeutic substance for gastric cancer for administration to the above-mentioned living organism.

These kits are useful for treating undifferentiated gastric cancer. The packaging container, the instruction, the package insert of the like may be printed with description for using the substances in combination, and description of usage and dose for using separate substances in combination upon administration or for use of them as a mixture. The usage and dose may be determined by referring to the descriptions of the therapeutic agent, the pharmaceutical composition and the kit above.

The present invention also comprises a method for treating undifferentiated gastric cancer characterized by administering effective dosages of a FGFR2 inhibitor I and a therapeutic substance for gastric cancer or a FGFR2 inhibitor II to a patient. The present invention also comprises a method for treating undifferentiated gastric cancer characterized by administering effective dosages of a FGFR2 inhibitor II and a therapeutic substance for gastric cancer to a patient.

Furthermore, the present invention comprises a method for treating a disease characterized by administering effective dosages of a FGFR2 inhibitor I and a therapeutic substance for gastric cancer or a FGFR2 inhibitor II to a living organism comprising at least one selected from the group consisting of a cell overexpressing FGFR2 and a cell expressing mutant FGFR2. The present invention also comprises a method for treating a disease characterized by administering effective dosages of a FGFR2 inhibitor II and a therapeutic substance for gastric cancer to the living organism. According to the present invention, the disease is preferably undifferentiated gastric cancer.

According to the therapeutic method of the invention, the route and the method for administering the FGFR2 inhibitor are not particularly limited but reference may be made to the description of the pharmaceutical composition or the therapeutic agent of the invention above.

The present invention comprises use of a FGFR2 inhibitor I for producing a therapeutic agent for undifferentiated gastric cancer in combination with a therapeutic substance for gastric cancer or a FGFR2 inhibitor II. The present invention also comprises use of a FGFR2 inhibitor II or a therapeutic substance for gastric cancer for producing a therapeutic agent for undifferentiated gastric cancer in combination with a therapeutic substance for gastric cancer or a FGFR2 inhibitor II.

In addition, the present invention comprises use of a FGFR2 inhibitor I for producing a pharmaceutical composition in combination with a therapeutic substance for gastric cancer or a FGFR2 inhibitor II for administration to a living organism comprising at least one selected from the group consisting of a cell overexpressing FGFR2 and a cell expressing mutant FGFR2. The present invention also comprises use of a FGFR2 inhibitor II or a therapeutic substance for gastric cancer for producing a pharmaceutical composition in combination with a therapeutic substance for gastric cancer or a FGFR2 inhibitor II for administration to the above-mentioned living organism. According to the use of the invention, the pharmaceutical composition is useful as a therapeutic agent for undifferentiated gastric cancer.

The present invention comprises a FGFR2 inhibitor I for a therapeutic agent for undifferentiated gastric cancer in combination with a therapeutic substance for gastric cancer or a FGFR2 inhibitor II. The present invention also comprises a FGFR2 inhibitor II or a therapeutic substance for gastric cancer for a therapeutic agent for undifferentiated gastric cancer in combination with a therapeutic substance for gastric cancer or a FGFR2 inhibitor II.

Moreover, the present invention comprises a FGFR2 inhibitor I for a pharmaceutical composition in combination with a therapeutic substance for gastric cancer or a FGFR inhibitor II for administration to a living organism comprising at least one selected from the group consisting of a cell overexpressing FGFR2 and a cell expressing mutant FGFR2. The present invention also comprises a FGFR2 inhibitor II or a therapeutic substance for gastric cancer for a pharmaceutical composition in combination with a therapeutic substance for gastric cancer or a FGFR2 inhibitor II for administration to the above-mentioned living organism. According to the present invention, the pharmaceutical composition is useful as a therapeutic agent for undifferentiated gastric cancer.

Hereinafter, the present invention will be illustrated by way of specific examples, although the invention should not be limited thereto.

EXAMPLE 1

Combination Use of the Compound of the Invention and Irinotecan Hydrochloride in Subcutaneous Transplanted (Xenograft) Models (In Vivo) of Human Scirrhous Gastric Cancer Cell Line (HSC-39)

Human scirrhous gastric cancer cell line HSC-39 (purchased from Immuno-Biological Laboratories Co,. Ltd.) was cultured in RPMI1640 (containing 10% FBS) in a 5% carbon dioxide gas incubator at 37° C. to about 80% confluence, and then the cells were collected with trypsin-EDTA. A $5 \times 10^7$ cells/mL suspension was prepared with a phosphate buffer, and each 0.1 mL of the resulting cell suspension was subcutaneously transplanted to nude mice at the side of their bodies.

Twelve days after the transplantation, 4-(3-chloro-4-(cyclopropylaminocarbonyl)aminophenoxy)-7-methoxy-6-quinolinecarboxamide (3, 10 or 30 mg/kg, once a day for four weeks, oral) and irinotecan hydrochloride (Daiichi Seiyaku) (100 mg/kg, every four days for three times, intravenous) were administered alone or in combination. The major and minor axes of tumors were measured with Digimatic caliper (Mitsutoyo Corporation), and tumor volumes and relative tumor volumes were calculated according to the following formulae:

Tumor Volume (TV)=Major axis of tumor (mm)×(Minor axis of tumor)$^2$ (mm$^2$)/2

Relative Tumor Volume (RTV)=Tumor volume on measurement day/Tumor volume on the first administration day.

If statistically significant interaction was observed in the combination use group by two-way ANOVA, a synergistic effect was considered to exist.

Figure 2:
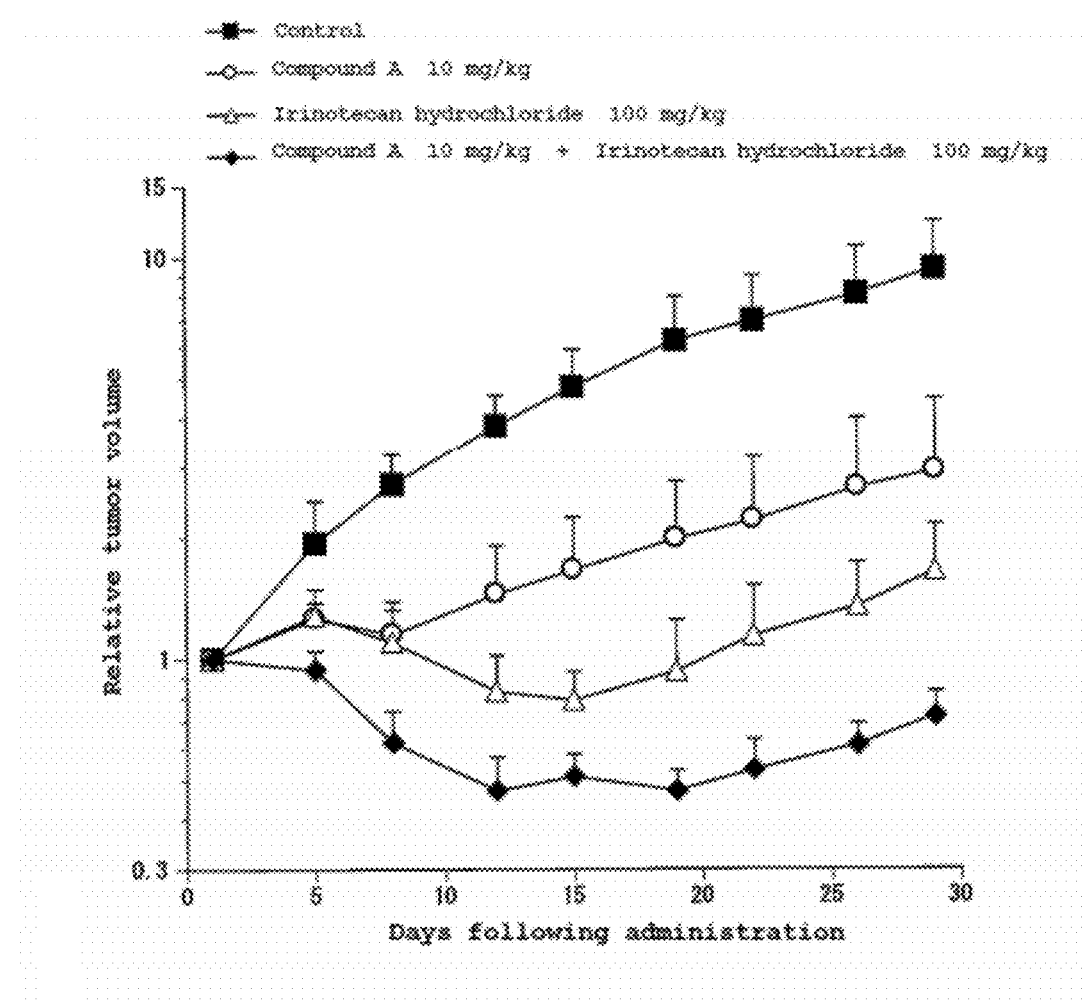
FIG. 2 shows the effect of combination use of 4-(3-chloro-4-(cyclopropylaminocarbonyl)aminophenoxy)-7-methoxy-6-quinolinecarboxamide (Compound A) (10 mg/kg) and irinotecan hydrochloride (100 mg/kg) on suppression of tumor growth in subcutaneous transplanted (xenograft) models (in vivo) of human scirrhous gastric cancer cell line (HSC-39).
Figure 3:
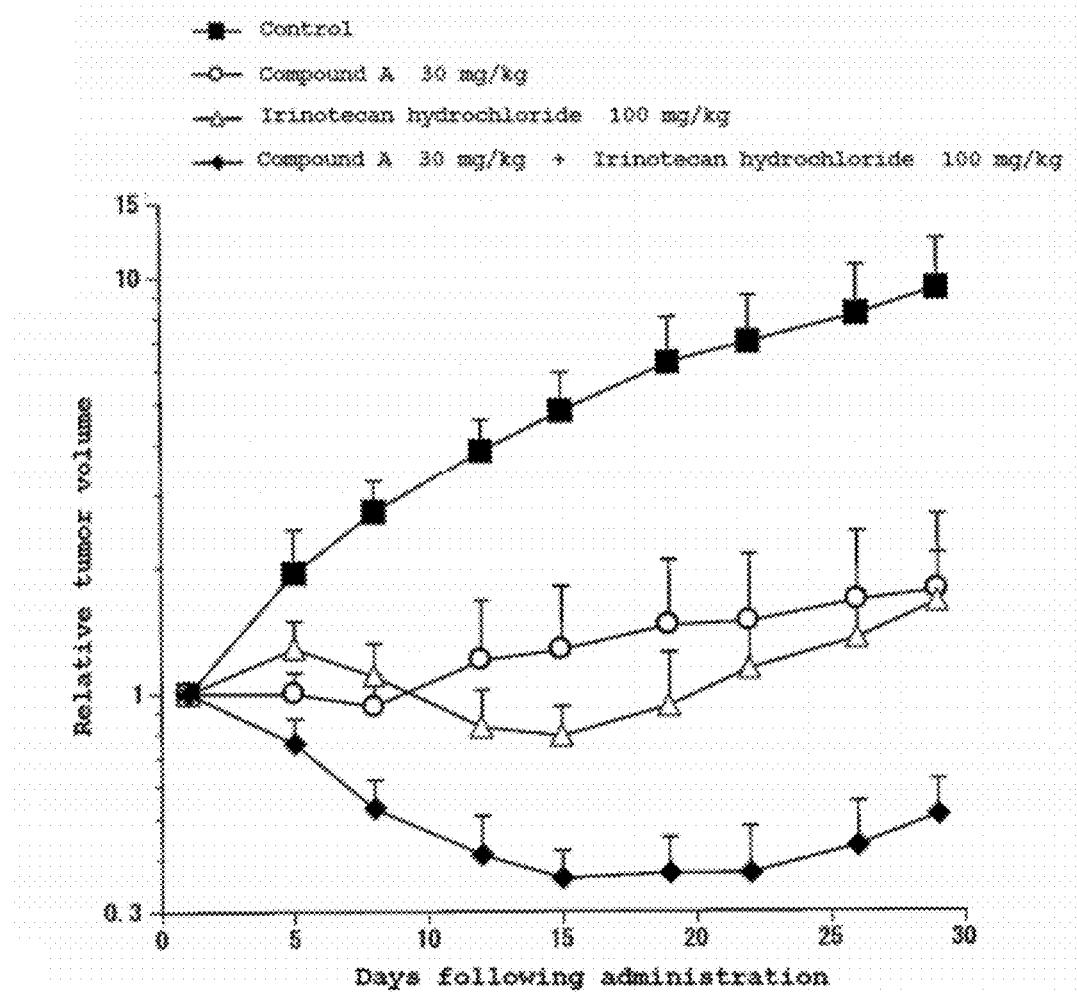
FIG. 3 shows the effect of combination use of 4-(3-chloro-4-(cyclopropylaminocarbonyl)aminophenoxy)-7-methoxy-6-quinolinecarboxamide (Compound A) (30 mg/kg) and irinotecan hydrochloride (100 mg/kg) on suppression of tumor growth in subcutaneous transplanted (xenograft) models (in vivo) of human scirrhous gastric cancer cell line (HSC-39).

As a result, 4-(3-chloro-4-(cyclopropylaminocarbonyl)aminophenoxy)-7-methoxy-6-quinolinecarboxamide (Compound A) showed an additive effect when used in combination with irinotecan hydrochloride, and their combination use showed a superior anti-tumor effect as compared with those obtained with 4-(3-chloro-4-(cyclopropylaminocarbonyl)aminophenoxy)-7-methoxy-6-quinolinecarboxamide or irinotecan hydrochloride alone (Tables 1, 2 and 3, and FIGS. 1, 2 and 3). In addition, combination use of 4-(3-chloro-4-(cyclopropylaminocarbonyl)aminophenoxy)-7-methoxy-6-quinolinecarboxamide and irinotecan hydrochloride also showed a remarkable anti-tumor effect that cannot be seen with irinotecan hydrochloride alone (Tables 1, 2 and 3, and FIGS. 1, 2 and 3).

TABLE 1

| Administered compound | Relative tumor volume on Day 29 Average ± standard deviation | Two-way ANOVA |
|---|---|---|
| Control (untreated) | 9.36 ± 2.97 | |
| Compound A 3 mg/kg | 4.29 ± 1.51 | |
| Irinotecan hydrochloride 100 mg/kg | 1.65 ± 0.51 | |
| Compound A 3 mg/kg + Irinotecan hydrochloride 100 mg/kg | 0.97 ± 0.25 | p = 0.320 Additive effect |

TABLE 2

| Administered compound | Relative tumor volume on Day 29 Average ± standard deviation | Two-way ANOVA |
|---|---|---|
| Control (untreated) | 9.36 ± 2.97 | |
| Compound A 10 mg/kg | 2.93 ± 1.55 | |
| Irinotecan hydrochloride 100 mg/kg | 1.65 ± 0.51 | |
| Compound A 10 mg/kg + Irinotecan hydrochloride 100 mg/kg | 0.72 ± 0.11 | p = 0.170 Additive effect |

TABLE 3

| Administered compound | Relative tumor volume on Day 29 Average ± standard deviation | Two-way ANOVA |
|---|---|---|
| Control (untreated) | 9.36 ± 2.97 | |
| Compound A 30 mg/kg | 1.76 ± 0.92 | |
| Irinotecan hydrochloride 100 mg/kg | 1.65 ± 0.51 | |
| Compound A 30 mg/kg + Irinotecan hydrochloride 100 mg/kg | 0.51 ± 0.11 | p = 0.0760 Additive effect |

Tables 1, 2 and 3 show anti-tumor effects obtained by the administration of 4-(3-chloro-4-(cyclopropylaminocarbonyl)aminophenoxy)-7-methoxy-6-quinolinecarboxamide (Compound A in Tables 1, 2 and 3) alone, the administration of irinotecan hydrochloride alone and the combination use of 4-(3-chloro-4-(cyclopropylaminocarbonyl)aminophenoxy)-7-methoxy-6-quinolinecarboxamide and irinotecan hydrochloride in HSC-39 subcutaneous transplanted (xenograft) models. The first day of administration was considered Day 1.

According to the obtained results, the combination of 4-(3-chloro-4-(cyclopropylaminocarbonyl)aminophenoxy)-7-methoxy-6-quinolinecarboxamide and irinotecan hydrochloride can provide a pharmaceutical composition and a kit that show a remarkable anti-tumor activity, which may be used for treating cancer.

EXAMPLE 2

Combination Use of the Compound of the Invention and 5-Fluorouracil in Subcutaneous Transplanted (Xenograft) Models (In Vivo) of Human Scirrhous Gastric Cancer Cell Line (HSC-39)

Human scirrhous gastric cancer cell line HSC-39 (purchased from Immuno-Biological Laboratories Co., Ltd.) was cultured in RPMI1640 (containing 10% FBS) in a 5% carbon dioxide gas incubator at 37° C. to about 80% confluence, and then the cells were collected with trypsin-EDTA. A $5\times10^7$ cells/mL suspension was prepared with a phosphate buffer, and each 0.1 mL of the resulting cell suspension was subcutaneously transplanted to nude mice at the side of their bodies.

Thirteen days after the transplantation, 4-(3-chloro-4-(cyclopropylaminocarbonyl)aminophenoxy)-7-methoxy-6-quinolinecarboxamide (3, 10 or 30 mg/kg, once a day for four weeks, oral) and 5-fluorouracil (Kyowa Hakko) (50 mg/kg, every four days for three times, intravenous) were administered alone or in combination. The major and minor axes of tumors were measured with Digimatic caliper (Mitsutoyo Corporation), and tumor volumes and relative tumor volumes were calculated according to the following formulae:

Tumor Volume (TV)=Major axis of tumor (mm)×(Minor axis of tumor)$^2$ (mm$^2$)/2

Relative Tumor Volume (RTV)=Tumor volume on measurement day/Tumor volume on the first administration day.

If statistically significant interaction was observed in the combination use group by two-way ANOVA, a synergistic effect was considered to exist.

Figure 4:
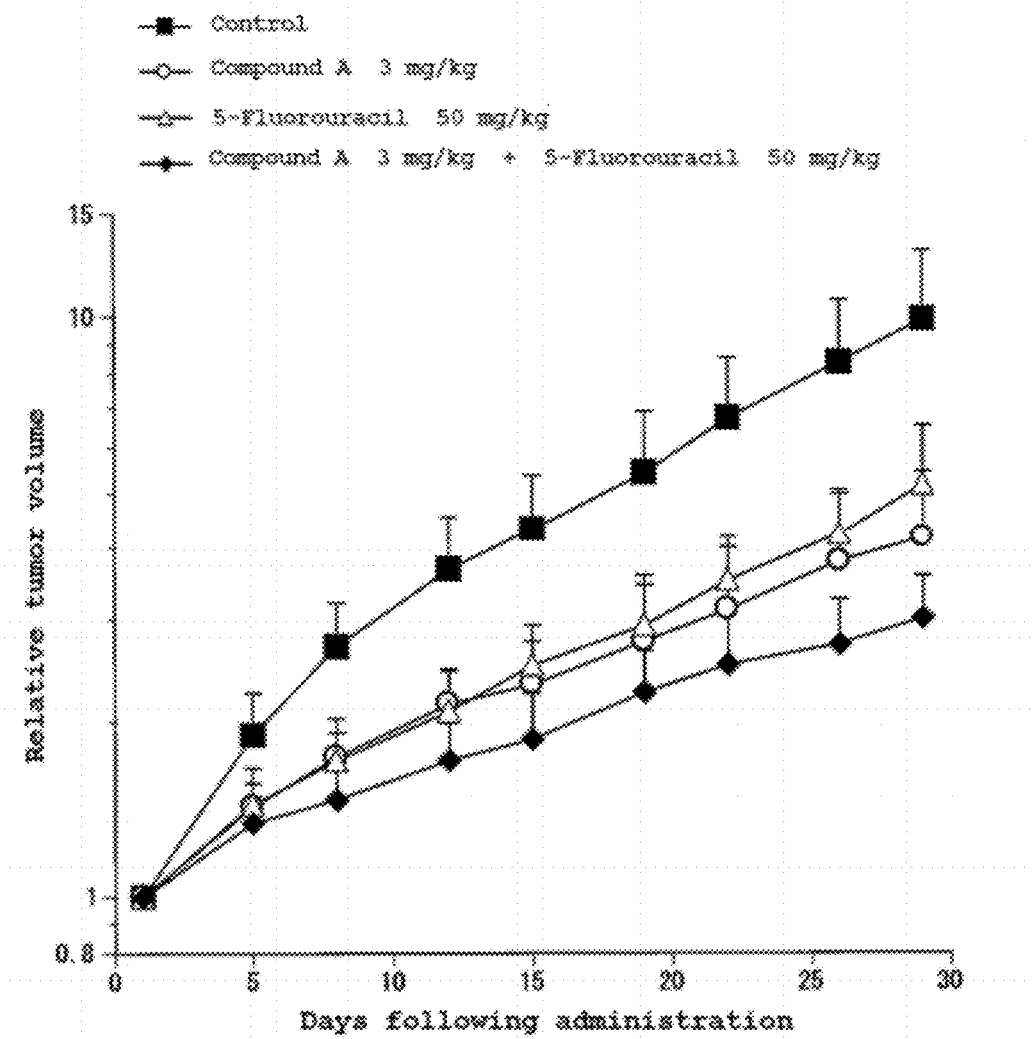
FIG. 4 shows the effect of combination use of 4-(3-chloro-4-(cyclopropylaminocarbonyl)aminophenoxy)-7-methoxy-6-quinolinecarboxamide (Compound A) (3 mg/kg) and 5-fluorouracil (50 mg/kg) on suppression of tumor growth in subcutaneous transplanted (xenograft) models (in vivo) of human scirrhous gastric cancer cell line (HSC-39).
Figure 5:
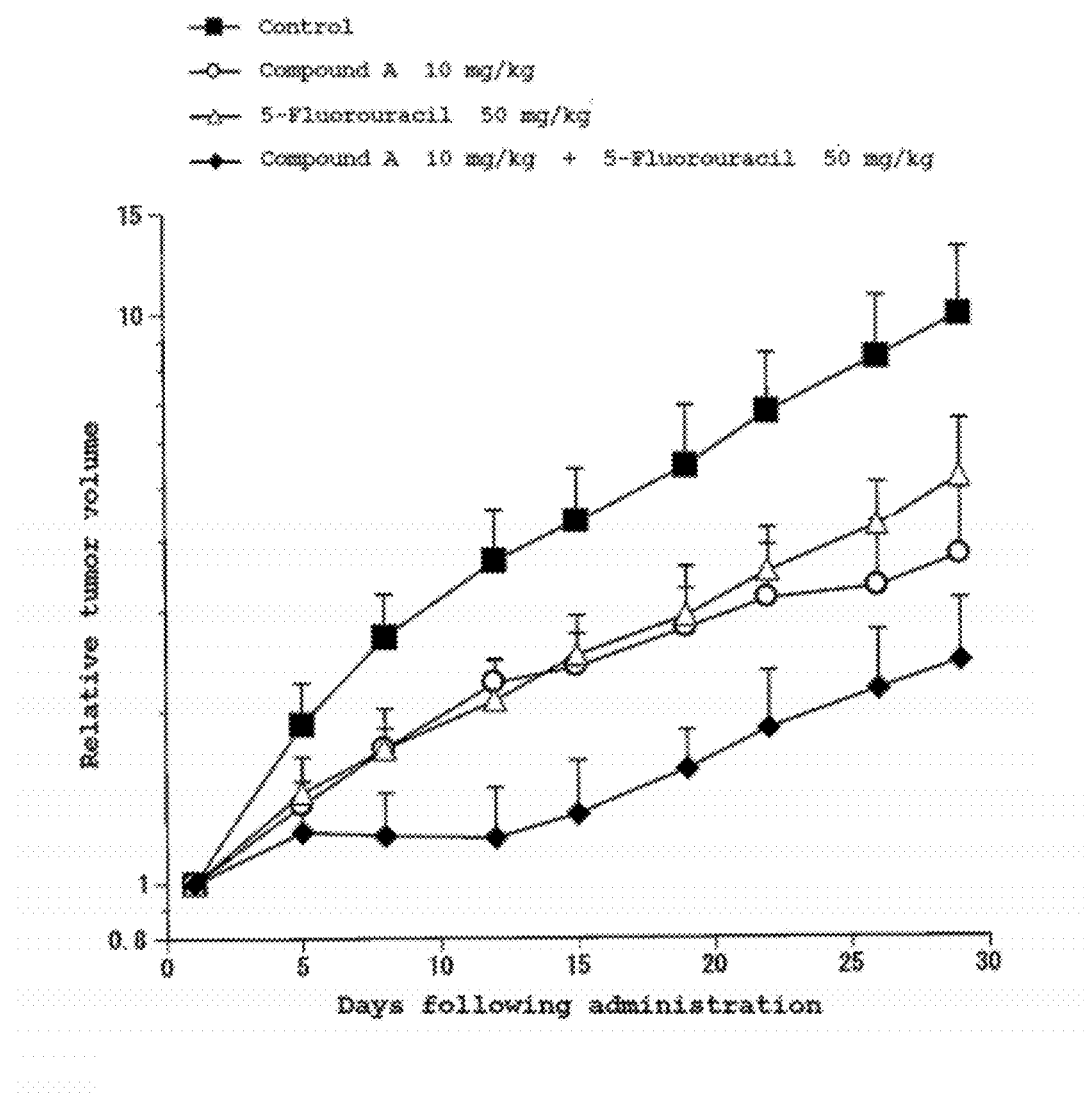
FIG. 5 shows the effect of combination use of 4-(3-chloro-4-(cyclopropylaminocarbonyl)aminophenoxy)-7-methoxy-6-quinolinecarboxamide (Compound A) (10 mg/kg) and 5-fluorouracil (50 mg/kg) on suppression of tumor growth in subcutaneous transplanted (xenograft) models (in vivo) of human scirrhous gastric cancer cell line (HSC-39).
Figure 6:
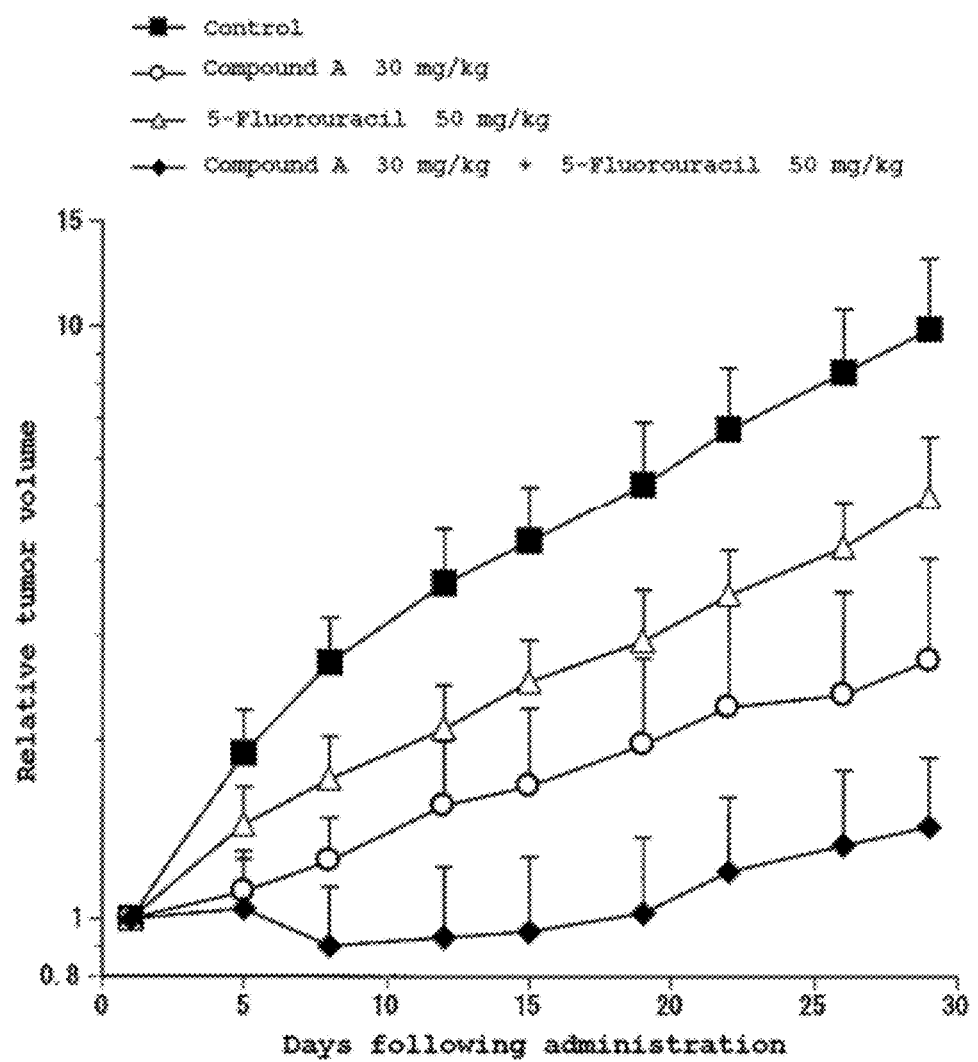
FIG. 6 shows the effect of combination use of 4-(3-chloro-4-(cyclopropylaminocarbonyl)aminophenoxy)-7-methoxy-6-quinolinecarboxamide (Compound A) (30 mg/kg) and 5-fluorouracil (50 mg/kg) on suppression of tumor growth in subcutaneous transplanted (xenograft) models (in vivo) of human scirrhous gastric cancer cell line (HSC-39).

As a result, 4-(3-chloro-4-(cyclopropylaminocarbonyl)aminophenoxy)-7-methoxy-6-quinolinecarboxamide (Compound A) showed an additive effect when used in combination with 5-fluorouracil, and their combination use showed a superior anti-tumor effect as compared with those obtained with 4-(3-chloro-4-(cyclopropylaminocarbonyl)aminophenoxy)-7-methoxy-6-quinolinecarboxamide or 5-fluorouracil alone (Tables 4, 5 and 6, and FIGS. 4, 5 and 6). In addition, combination use of 4-(3-chloro-4-(cyclopropylaminocarbonyl)aminophenoxy)-7-methoxy-6-quinolinecarboxamide and 5-fluorouracil also showed a remarkable anti-tumor effect that cannot be seen with 5-fluorouracil alone (Tables 4, 5 and 6, and FIGS. 4, 5 and 6).

TABLE 4

| Administered compound | Relative tumor volume on Day 29 Average ± standard deviation | Two-way ANOVA |
|---|---|---|
| Control (untreated) | 9.90 ± 3.12 | |
| Compound A 3 mg/kg | 4.16 ± 1.28 | |
| 5-Fluorouracil 50 mg/kg | 5.16 ± 1.37 | |
| Compound A 3 mg/kg + 5-Fluorouracil 50 mg/kg | 3.02 ± 0.55 | p = 0.150 Additive effect |

TABLE 5

| Administered compound | Relative tumor volume on Day 29 Average ± standard deviation | Two-way ANOVA |
|---|---|---|
| Control (untreated) | 9.90 ± 3.12 | |
| Compound A 10 mg/kg | 3.73 ± 1.21 | |
| 5-Fluorouracil 50 mg/kg | 5.16 ± 1.37 | |
| Compound A 10 mg/kg + 5-Fluorouracil 50 mg/kg | 2.44 ± 0.70 | p = 0.413 Additive effect |

TABLE 6

| Administered compound | Relative tumor volume on Day 29 Average ± standard deviation | Two-way ANOVA |
|---|---|---|
| Control (untreated) | 9.90 ± 3.12 | |
| Compound A 30 mg/kg | 2.72 ± 1.33 | |
| 5-Fluorouracil 50 mg/kg | 5.16 ± 1.37 | |
| Compound A 30 mg/kg + 5-Fluorouracil 50 mg/kg | 1.43 ± 0.44 | p = 0.887 Additive effect |

Tables 4, 5 and 6 show anti-tumor effects obtained by the administration of 4-(3-chloro-4-(cyclopropylaminocarbonyl)aminophenoxy)-7-methoxy-6-quinolinecarboxamide (Compound A in Tables 4, 5 and 6) alone, the administration of 5-fluorouracil alone and the combination use of 4-(3-chloro-4-(cyclopropylaminocarbonyl)aminophenoxy)-7-methoxy-6-quinolinecarboxamide and 5-fluorouracil in HSC-39 subcutaneous transplanted (xenograft) models. The first day of administration was considered Day 1.

According to the obtained results, the combination of 4-(3-chloro-4-(cyclopropylaminocarbonyl)aminophenoxy)-7-methoxy-6-quinolinecarboxamide and 5-fluorouracil can provide a pharmaceutical composition and a kit that show a remarkable anti-tumor activity, which may be used for treating cancer.

EXAMPLE 3

Combination Use of the Compound of the Invention and Paclitaxel in Subcutaneous Transplanted (Xenograft) Models (In Vivo) of Human Scirrhous Gastric Cancer Cell Line (HSC-39)

Human scirrhous gastric cancer cell line HSC-39 (purchased from Immuno-Biological Laboratories Co., Ltd.) was cultured in RPMI1640 (containing 10% FBS) in a 5% carbon dioxide gas incubator at 37° C. to about 80% confluence, and then the cells were collected with trypsin-EDTA. A $5 \times 10^7$ cells/mL suspension was prepared with a phosphate buffer, and each 0.1 mL of the resulting cell suspension was subcutaneously transplanted to nude mice at the side of their bodies.

Eleven days after the transplantation, 4-(3-chloro-4-(cyclopropylaminocarbonyl)aminophenoxy)-7-methoxy-6-quinolinecarboxamide (3, 10 or 30 mg/kg, once a day for four weeks, oral) and paclitaxel (Calbiochem) (14 mg/kg, once a day for five days, intravenous) were administered alone or in combination. The major and minor axes of tumors were measured with Digimatic caliper (Mitsutoyo Corporation), and tumor volumes and relative tumor volumes were calculated according to the following formulae:

Tumor Volume (TV)=Major axis of tumor (mm)×(Minor axis of tumor)$^2$ (mm$^2$)/2

Relative Tumor Volume (RTV)=Tumor volume on measurement day/Tumor volume on the first administration day.

If statistically significant interaction was observed in the combination use group by two-way ANOVA, a synergistic effect was considered to exist.

Figure 7:
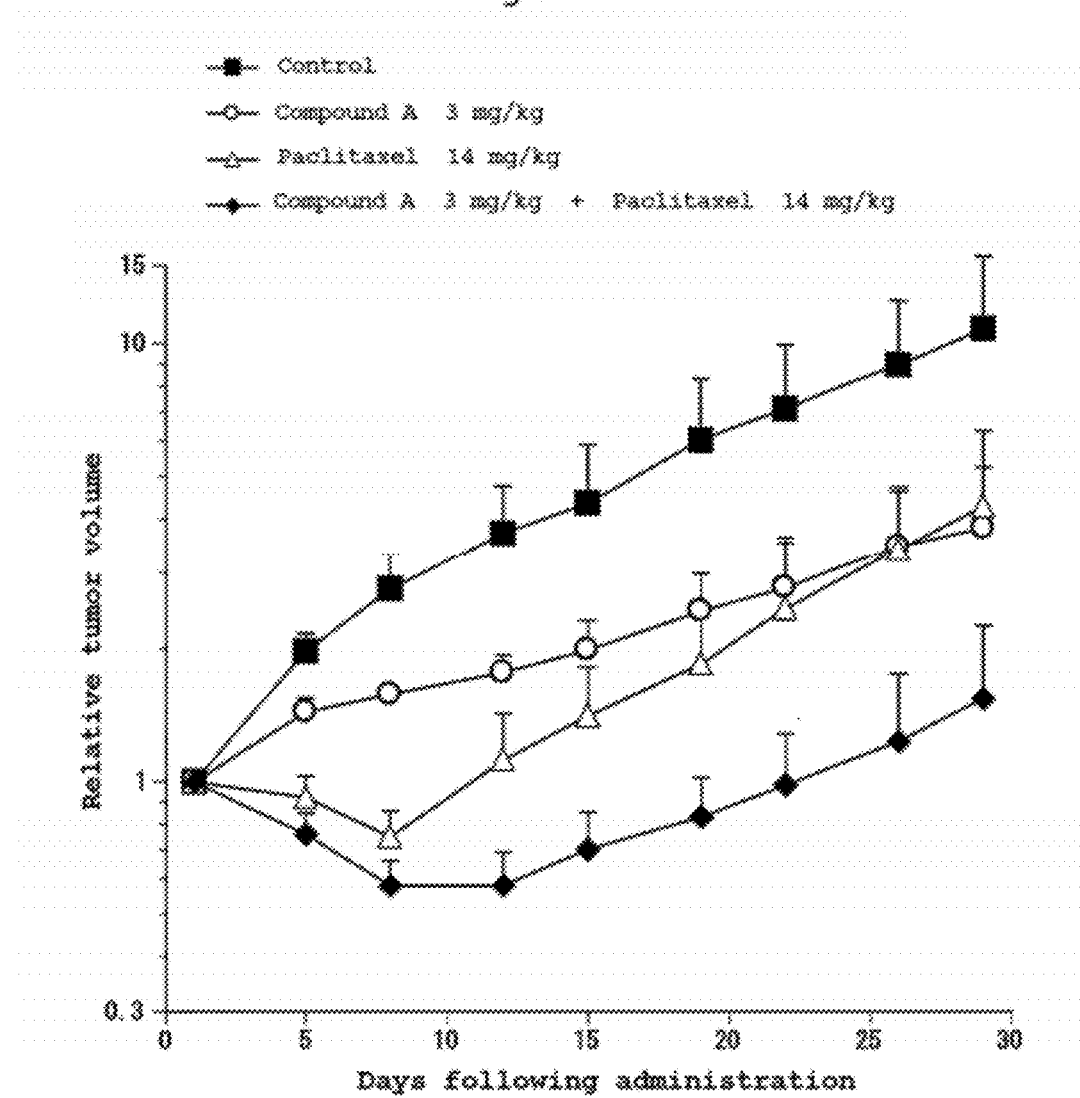
FIG. 7 shows the effect of combination use of 4-(3-chloro-4-(cyclopropylaminocarbonyl)aminophenoxy)-7-methoxy-6-quinolinecarboxamide (Compound A) (3 mg/kg) and paclitaxel (14 mg/kg) on suppression of tumor growth in subcutaneous transplanted (xenograft) models (in vivo) of human scirrhous gastric cancer cell line (HSC-39).
Figure 8:
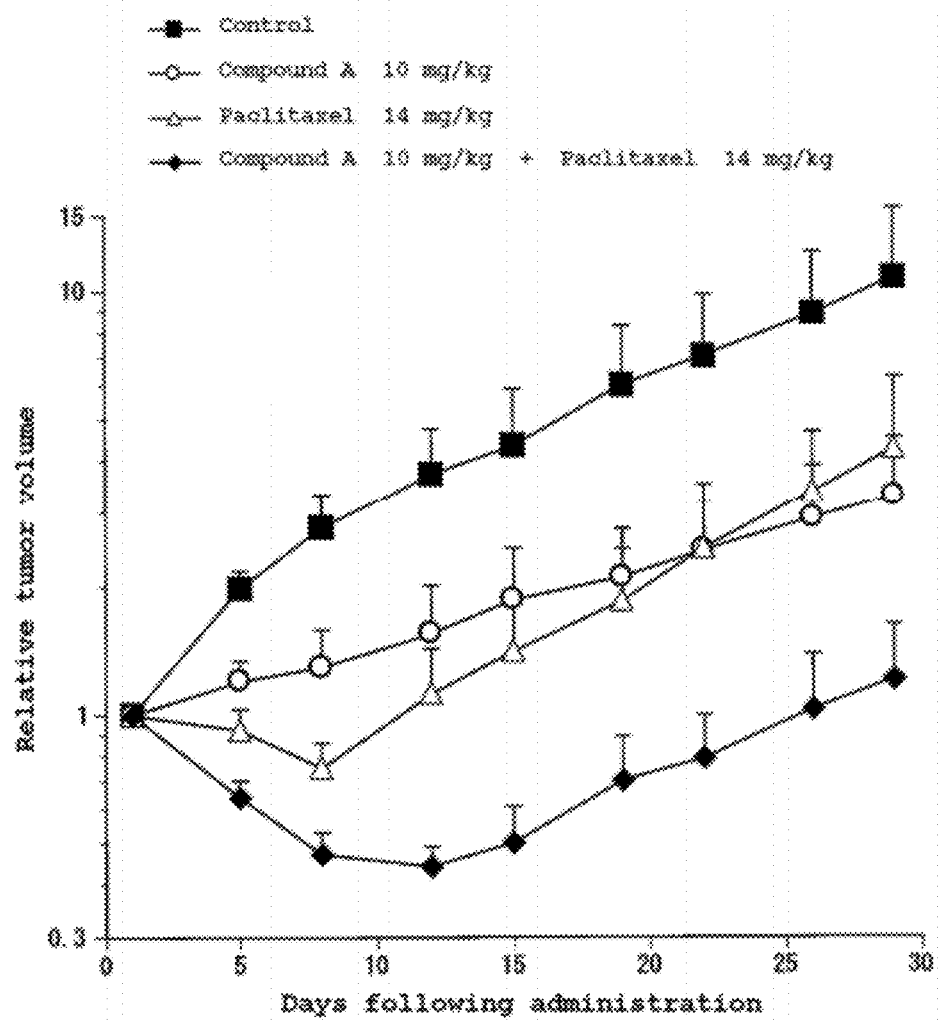
FIG. 8 shows the effect of combination use of 4-(3-chloro-4-(cyclopropylaminocarbonyl)aminophenoxy)-7-methoxy-6-quinolinecarboxamide (Compound A) (10 mg/kg) and paclitaxel (14 mg/kg) on suppression of tumor growth in subcutaneous transplanted (xenograft) models (in vivo) of human scirrhous gastric cancer cell line (HSC-39).
Figure 9:
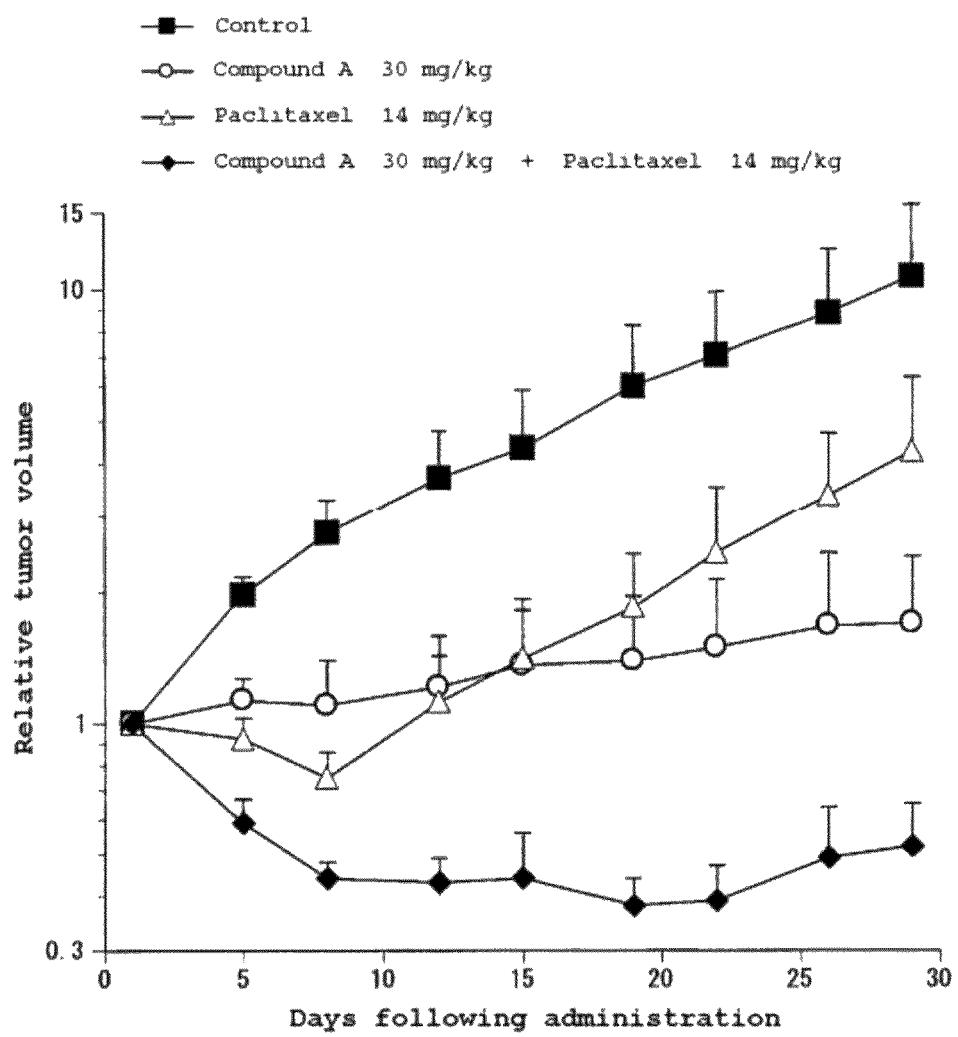
FIG. 9 shows the effect of combination use of 4-(3-chloro-4-(cyclopropylaminocarbonyl)aminophenoxy)-7-methoxy-6-quinolinecarboxamide (Compound A) (30 mg/kg) and paclitaxel (14 mg/kg) on suppression of tumor growth in subcutaneous transplanted (xenograft) models (in vivo) of human scirrhous gastric cancer cell line (HSC-39).

As a result, 4-(3-chloro-4-(cyclopropylaminocarbonyl) aminophenoxy)-7-methoxy-6-quinolinecarboxamide (Compound A) showed an additive effect when used in combination with paclitaxel, and their combination use showed a superior anti-tumor effect as compared with those obtained with 4-(3-chloro-4-(cyclopropylaminocarbonyl)aminophenoxy)-7-methoxy-6-quinolinecarboxamide or paclitaxel alone (Tables 7, 8 and 9, and FIGS. 7, 8 and 9). In addition, combination use of 4-(3-chloro-4-(cyclopropylaminocarbonyl)aminophenoxy)-7-methoxy-6-quinolinecarboxamide and paclitaxel also showed a remarkable anti-tumor effect that cannot be seen with paclitaxel alone (Tables 7, 8 and 9, and FIGS. 7, 8 and 9).

TABLE 7

| Administered compound | Relative tumor volume on Day 29 Average ± standard deviation | Two-way ANOVA |
|---|---|---|
| Control (untreated) | 10.75 ± 4.94 | |
| Compound A 3 mg/kg | 3.79 ± 1.43 | |
| Paclitaxel 14 mg/kg | 4.26 ± 2.06 | |
| Compound A 3 mg/kg + Paclitaxel 14 mg/kg | 1.54 ± 0.72 | p = 0.929 Additive effect |

TABLE 8

| Administered compound | Relative tumor volume on Day 29 Average ± standard deviation | Two-way ANOVA |
|---|---|---|
| Control (untreated) | 10.75 ± 4.94 | |
| Compound A 10 mg/kg | 3.27 ± 1.26 | |
| Paclitaxel 14 mg/kg | 4.26 ± 2.06 | |
| Compound A 10 mg/kg + Paclitaxel 14 mg/kg | 1.21 ± 0.42 | p = 0.918 Additive effect |

TABLE 9

| Administered compound | Relative tumor volume on Day 29 Average ± standard deviation | Two-way ANOVA |
|---|---|---|
| Control (untreated) | 10.75 ± 4.94 | |
| Compound A 30 mg/kg | 1.69 ± 0.72 | |
| Paclitaxel 14 mg/kg | 4.26 ± 2.06 | |
| Compound A 30 mg/kg + Paclitaxel 14 mg/kg | 0.52 ± 0.13 | p = 0.555 Additive effect |

Tables 7, 8 and 9 show anti-tumor effects obtained by the administration of 4-(3-chloro-4-(cyclopropylaminocarbonyl)aminophenoxy)-7-methoxy-6-quinolinecarboxamide (Compound A in Tables 7, 8 and 9) alone, the administration of paclitaxel alone and the combination use of 4-(3-chloro-4-(cyclopropylaminocarbonyl)aminophenoxy)-7-methoxy-6-quinolinecarboxamide and paclitaxel in HSC-39 subcutaneous transplanted (xenograft) models. The first day of administration was considered Day 1.

According to the obtained results, the combination of 4-(3-chloro-4-(cyclopropylaminocarbonyl)aminophenoxy)-7-methoxy-6-quinolinecarboxamide and paclitaxel can provide a pharmaceutical composition and a kit that show a remarkable anti-tumor activity, which may be used for treating cancer.

According to the results from these examples, a FGFR2 inhibitor, preferably 4-(3-chloro-4-(cyclopropylaminocarbonyl)aminophenoxy)-7-methoxy-6-quinolinecarboxamide, was found to show an excellent anti-tumor activity when used in combination with a therapeutic substance for gastric cancer, preferably irinotecan, 5-fluorouracil or paclitaxel.

INDUSTRIAL APPLICABILITY

According to the present invention, there is provided a therapeutic agent, a kit and a therapeutic method for undifferentiated gastric cancer that show an excellent anti-tumor activity, use of a FGFR2 inhibitor for producing said therapeutic agent, and a FGFR2 inhibitor for said therapeutic agent.

More particularly, there is provided a therapeutic agent, a kit and a therapeutic method for undifferentiated gastric cancer that show an excellent anti-tumor activity and that can be used for treating undifferentiated gastric cancer by combining:

(i) a FGFR2 inhibitor such as a compound represented by General Formula (I) and a therapeutic drug for gastric cancer;

(ii) a FGFR2 inhibitor such as a compound represented by General Formula (I) and a FGFR2 inhibitor that is not comprised in the compounds represented by General Formula (I); or (iii) a FGFR2 inhibitor such as a FGFR2 inhibitor that is not comprised in the compounds represented by General Formula (I) and a therapeutic drug for gastric cancer.

The present invention also provides a pharmaceutical composition and a kit for administration to a living organism comprising at least one selected from the group consisting of a cell overexpressing FGFR2 and a cell expressing mutant FGFR2, a method for treating a disease of said living organism, use of a FGFR2 inhibitor for producing said pharmaceutical composition and a FGFR2 inhibitor for said pharmaceutical composition.

More specifically, there is provided a pharmaceutical composition, a kit and a therapeutic method for said living organism that show an excellent anti-tumor activity and that can be used for treating a disease by combining:

(i) a FGFR2 inhibitor such as a compound represented by General Formula (I) and a therapeutic drug for gastric cancer;

(ii) a FGFR2 inhibitor such as a compound represented by General Formula (I) and a FGFR2 inhibitor that is not comprised in the compounds represented by General Formula (I); or (iii) a FGFR2 inhibitor such as a FGFR2 inhibitor that is not comprised in the compounds represented by General Formula (I) and a therapeutic drug for gastric cancer.

CROSS-REFERENCE TO PRIOR APPLICATION

This is a U.S. National Phase Application under 35 U.S.C §371 of International Patent Application No. PCT/JP2008/051697 filed Jan. 28, 2008, which claims the benefit of U.S. Provisional Application No. 60/887,006 filed Jan. 29, 2007, both of which are incorporated by reference herein. The International Application was published in Japanese on Aug. 7, 2008 as WO 2008/093855 A1 under PCT Article 21(2).

The invention claimed is:

1. A method for treating undifferentiated gastric cancer, characterized by administering effective dosages of 4(3-chloro-4-(cyclopropylaminocarbonyl)aminophenoxy)-7-methoxy-6-quinolinecarboxamide, or a pharmacologically acceptable salt thereof, and a therapeutic substance selected from the group consisting of irinotecan, paclitaxel, and pharmacologically acceptable salts thereof to a living organism.

* * * * *

UNITED STATES PATENT AND TRADEMARK OFFICE
CERTIFICATE OF CORRECTION

| | | |
|---|---|---|
| PATENT NO. | : 8,962,655 B2 | Page 1 of 1 |
| APPLICATION NO. | : 12/524754 | |
| DATED | : February 24, 2015 | |
| INVENTOR(S) | : Yuji Yamamoto | |

It is certified that error appears in the above-identified patent and that said Letters Patent is hereby corrected as shown below:

IN THE CLAIMS:

Column 99, claim 1

Line 42, delete "4(3-chloro-4-(cyclopropylaminocarbonyl)aminophenoxy)-7-methoxy-6-quinolinecarboxamide" and replace it with --4-(3-chloro-4-(cyclopropylaminocarbonyl)aminophenoxy-7-methoxy-6-quinolinecarboxamide--.

Signed and Sealed this
Eleventh Day of August, 2015

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 2469
<212> TYPE: DNA
<213> ORGANISM: Homo sapiens

<400> SEQUENCE: 1
atggtcagct ggggtcgttt catctgcctg gtcgtggtca ccatggcaac cttgtccctg      60
gcccggccct ccttcagttt agttgaggat accacattag agccagaaga gccaccaacc     120
aaataccaaa tctctcaacc agaagtgtac gtggctgcgc caggggagtc gctagaggtg     180
cgctgcctgt tgaaagatgc cgccgtgatc agttggacta aggatggggt gcacttgggg     240
cccaacaata ggacagtgct tattggggag tacttgcaga taaagggcgc cacgcctaga     300
gactccggcc tctatgcttg tactgccagt aggactgtag acagtgaaac ttggtacttc     360
atggtgaatg tcacagatgc catctcatcc ggagatgatg aggatgacac cgatggtgcg     420
gaagattttg tcagtgagaa cagtaacaac aagagagcac catactggac caacacagaa     480
aagatggaaa agcggctcca tgctgtgcct gcggccaaca ctgtcaagtt tcgctgccca     540 gccggggga acccaatgcc aaccatgcgg tggctgaaaa acgggaagga gtttaagcag     600
gagcatcgca ttggaggcta caaggtacga aaccagcact ggagcctcat tatggaaagt     660
gtggtcccat ctgacaaggg aaattatacc tgtgtagtgg agaatgaata cgggtccatc     720
aatcacacgt accacctgga tgttgtggag cgatcgcctc accggcccat cctccaagcc     780
ggactgccgg caaatgcctc cacagtggtc ggaggagacg tagagtttgt ctgcaaggtt     840
tacagtgatg cccagcccca catccagtgg atcaagcacg tggaaaagaa cggcagtaaa     900
tacgggcccg acgggctgcc ctacctcaag gttctcaagc actcggggat aaatagttcc     960
aatgcagaag tgctggctct gttcaatgtg accgaggcgg atgctgggga atatatatgt    1020
aaggtctcca attatatagg gcaggccaac cagtctgcct ggctcactgt cctgccaaaa    1080
cagcaagcgc ctggaagaga aaaggagatt acagcttccc cagactacct ggagatagcc    1140
atttactgca tagggtctt cttaatcgcc tgtatggtgg taacagtcat cctgtgccga    1200
atgaagaaca cgaccaagaa gccagacttc agcagccagc cggctgtgca caagctgacc    1260
aaacgtatcc ccctgcggag acaggtaaca gtttcggctg agtccagctc ctccatgaac    1320
tccaacaccc cgctggtgag gataacaaca cgcctctctt caacggcaga cacccccatg    1380
ctggcagggg tctccgagta tgaacttcca gaggaccaa aatgggagtt tccaagagat    1440
```

-continued

```
aagctgacac tgggcaagcc cctgggagaa ggttgctttg ggcaagtggt catggcggaa    1500
gcagtgggaa ttgacaaaga caagcccaag gaggcggtca ccgtggccgt gaagatgttg    1560
aaagatgatg ccacagagaa agacctttct gatctggtgt cagagatgga gatgatgaag    1620
atgattggga aacacaagaa tatcataaat cttcttggag cctgcacaca ggatgggcct    1680
ctctatgtca tagttgagta tgcctctaaa ggcaacctcc gagaatacct ccgagcccgg    1740
aggccacccg ggatggagta ctcctatgac attaaccgtg ttcctgagga gcagatgacc    1800
ttcaaggact tggtgtcatg cacctaccag ctggccagag gcatggagta cttggcttcc    1860
caaaaatgta ttcatcgaga tttagcagcc agaaatgttt tggtaacaga aaacaatgtg    1920
atgaaaatag cagactttgg actcgccaga gatatcaaca atatagacta ttacaaaaag    1980
accaccaatg gcggcttcc agtcaagtgg atggctccag aagccctgtt tgatagagta    2040
tacactcatc agagtgatgt ctggtccttc ggggtgttaa tgtgggagat cttcactta    2100 gggggctcgc cctacccagg gattcccgtg gaggaacttt ttaagctgct gaaggaagga    2160
cacagaatgg ataagccagc caactgcacc aacgaactgt acatgatgat gagggactgt    2220
tggcatgcag tgcctccca gagaccaacg ttcaagcagt tggtagaaga cttggatcga    2280
attctcactc tcacaaccaa tgaggaatac ttggacctca gccaacctct cgaacagtat    2340
tcacctagtt accctgacac aagaagttct tgttcttcag gagatgattc tgttttttct    2400
ccagacccca tgccttacga accatgcctt cctcagtatc cacacataaa cggcagtgtt    2460
aaaacatga                                                            2469
```

<210> SEQ ID NO 2
<211> LENGTH: 822
<212> TYPE: PRT
<213> ORGANISM: Homo sapiens

<400> SEQUENCE: 2

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
```

```
                180                 185                 190
Lys Asn Gly Lys Glu Phe Lys Gln Glu His Arg Ile Gly Gly Tyr Lys
                195                 200                 205

Val Arg Asn Gln His Trp Ser Leu Ile Met Glu Ser Val Pro Ser
        210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
                260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
        290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
                340                 345                 350

Ala Trp Leu Thr Val Leu Pro Lys Gln Gln Ala Pro Gly Arg Glu Lys
                355                 360                 365

Glu Ile Thr Ala Ser Pro Asp Tyr Leu Glu Ile Ala Ile Tyr Cys Ile
        370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
                420                 425                 430

Ala Glu Ser Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
        450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
                500                 505                 510

Val Thr Val Ala Val Lys Met Leu Lys Asp Asp Ala Thr Glu Lys Asp
        515                 520                 525

Leu Ser Asp Leu Val Ser Glu Met Glu Met Met Lys Met Ile Gly Lys
        530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
                580                 585                 590

Arg Val Pro Glu Glu Gln Met Thr Phe Lys Asp Leu Val Ser Cys Thr
                595                 600                 605
```

-continued

```
Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
    755                 760                 765

Glu Tyr Leu Asp Leu Ser Gln Pro Leu Glu Gln Tyr Ser Pro Ser Tyr
770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815

Asn Gly Ser Val Lys Thr
                820
```